(12) United States Patent
Tanaka et al.

(10) Patent No.: US 7,935,700 B2
(45) Date of Patent: May 3, 2011

(54) MORPHOLINE COMPOUND

(75) Inventors: Yoshihito Tanaka, Tokyo (JP); Shuzo Takeda, Tokyo (JP); Hidemitsu Higashi, Tokyo (JP); Mamoru Matsuura, Tokyo (JP); Fujio Kobayashi, Tokyo (JP); Maiko Hamada, Tokyo (JP); Minoru Tanaka, Tokyo (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 900 days.

(21) Appl. No.: 11/662,228

(22) PCT Filed: Sep. 8, 2005

(86) PCT No.: PCT/JP2005/017002
§ 371 (c)(1),
(2), (4) Date: Apr. 13, 2007

(87) PCT Pub. No.: WO2006/028284
PCT Pub. Date: Mar. 16, 2006

(65) Prior Publication Data
US 2007/0265257 A1 Nov. 15, 2007

(30) Foreign Application Priority Data
Sep. 8, 2004 (JP) .................. 2004-261655

(51) Int. Cl.
*A61K 31/535* (2006.01)
*C07D 417/12* (2006.01)
(52) U.S. Cl. .................... 514/236.8; 544/133
(58) Field of Classification Search .......... 544/133; 514/236.8
See application file for complete search history.

(56) References Cited

U.S. PATENT DOCUMENTS

| 4,870,074 A | 9/1989 | Kon et al. |
| 2004/0014775 A1 | 1/2004 | Du Bois et al. |
| 2004/0058923 A1 | 3/2004 | Ancliff et al. |

FOREIGN PATENT DOCUMENTS

| EP | 1 389 616 | 2/2004 |
| JP | 63-264467 | 11/1988 |
| JP | 2004-509952 | 4/2004 |
| WO | 00/53600 | 9/2000 |
| WO | 03/082294 | 10/2003 |
| WO | 2004/004731 | 1/2004 |

OTHER PUBLICATIONS

Byrn et al., Solid-State Chemistry of Drugs, Second Edition, 1999, pp. 233-247.*
Registry No. 852165-28-7, Jun. 13, 2005.*
Pease et al., Expert Opin. Ther. Patents (2009) 19(1), 39-58.*
Heidi Heath et al., "Chemokine Receptor Usage by Human Eosinophils", J. Clin. Invest., vol. 99, No. 2, pp. 178-184, Jan. 1997.
Hiroshi Ochi et al., "T Helper Cell Type 2 Cytokine-mediated Comitogenic Responses and CCR3 Expression During Differentiation of Human Mast Cells In Vitro", J. Exp. Med., vol. 190, No. 2, pp. 267-280, Jul. 19, 1999.
Mariagrazia Uguccioni et al., "High Expression of the Chemokine Receptor CCR3 in Human Blood Basophils", J. Clin. Invest., vol. 100, No. 5, pp. 1137-1143, Sep. 1997.
Federica Sallusto et al., "Selective Expression of the Eotaxin Receptor CCR3 by Human T Helper 2 Cells", Science, vol. 277, 5334, pp. 2005-2007, Sep. 26, 1997.
Phillip M. Murphy et al., "International Union of Pharmacology. XXII. Nomenclature for Chemokine Receptors", Pharmacological Reviews, vol. 52, No. 1, pp. 145-176, 2000.
Weilie Ma et al. "CCR3 is essential for skin eosinophilia and airway hyperresponsiveness in a murine model of allergic skin inflammation", The Journal of Clinical Investigation, vol. 109, No. 5, pp. 621-628, Mar. 2002.
Frode L. Jahnsen et al., "Glucocorticosteroids Inhibit mRNA Expression for Eotaxin, Eotaxin-2, and Monocyte-Chemotactic Protein-4 in Human Airway Inflammation with Eosinophilia", The Journal of Immunology, vol. 163, No. 3, pp. 1545-1551, 1999.
Kenneth J. Katschke, Jr. et al., "Differential Expression of Chemokine Receptors on Peripheral Blood, Synovial Fluid, and Synovial Tissue Monocytes/Macrophages in Rheumatoid Arthritis", Arthritis & Rheumatism, vol. 44, No. 5, pp. 1022-1032, May 2001.
Supplementary European Search Report issued Sep. 9, 2010 in European Application No. 05 78 3689 corresponding to the present US Application.

* cited by examiner

*Primary Examiner* — Rebecca L Anderson
(74) *Attorney, Agent, or Firm* — Wenderoth, Lind & Ponack, L.L.P.

(57) ABSTRACT

A compound represented by the formula (1)

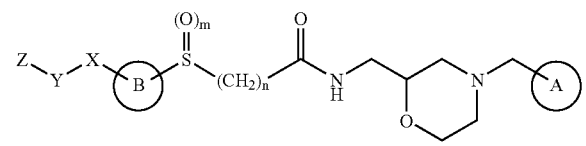

(1)

wherein ring A is aryl optionally having substituent(s) and the like; ring B is arylene optionally having substituent(s) and the like; m=0-2; n=1-5; X is a bond and the like; Y is a bond and the like; and Z is hydrogen atom and the like or a pharmaceutically acceptable salt thereof, and a hydrate or solvate thereof have affinity for CCR3, and can be pharmaceutical products for the treatment and/or prophylaxis of immune or inflammatory diseases.

24 Claims, No Drawings

MORPHOLINE COMPOUND

TECHNICAL FIELD

The present invention relates to a novel morpholine compounds having affinity for CCR3. The compound and a salt thereof are useful as a drug for the treatment and/or prophylaxis of a disease wherein a cell having CCR3 plays an important role in the onset, progress and retention of pathology, such as asthma, sinusitis, atopic dermatitis, allergic rhinitis, allergic conjunctivitis, allergic myelitis, ulcerative colitis, Crohn's disease, rheumatoid arthritis and the like.

BACKGROUND ART

As chemotactic substances that induce chemotaxis and topical infiltration of leukocytes such as neutrophil, monocyte and the like, there are classical chemotactic factors such as complement catabolites C3a and C5a, arachidonate metabolites such as leukotriene $B_4$ and the like, platelet-activating factor, bacterium-derived formyl peptide and the like. These are secondary products mainly associated with tissue lesions. On the other hand, the presence of a series of cytokines that are produced by new expression of gene and responsible for the induction and activation of particular leukocyte, namely, chemokines, was verified by interleukin (IL-8) (CXCL8) purified and gene cloned by Matsushima et al. in 1987 (see. e.g., Proc. Natl. Acad. Sci. USA, 84, 9223-9237 (1987) and J. Exp. Med., 167, 1883-1893 (1988)).

There are 42 chemokines identified to the present, and chemokines are classified into four subgroups based on the characteristics of their amino acid sequences. That is, C chemokine, CC chemokine, CXC chemokine and $CX_3C$ chemokine.

XCL1 belonging to C chemokine shows chemotactic activity for T cells and NK cells.

CC chemokine shows chemotactic activity for monocytes other than neutrophils, lymphocytes, Langerhans cells, dendritic cells, eosinophils, mast cells and basophils. Furthermore, CXC chemokine mainly acts on chemotaxis of neutrophils as represented by the action of CXCL8, and $CX_3C$ chemokine mainly acts on chemotaxis of NK cells. These chemokines exhibits their actions by binding to G-protein-coupled receptors (chemokine receptors) and 18 chemokine receptors have been identified to the present (see e.g., CELL TECHNOLOGY, 17, 1022-1029 (1998) and Immunity, 12, 121-127 (2000)).

Therefore, a substance that inhibits the binding between chemokine and its receptor suppresses selective chemotaxis and activation of leukocytes, and is considered to be useful as a pharmaceutical product for the prophylaxis or treatment of acute and chronic inflammatory diseases including allergic diseases and the like.

Particularly, one of the pathological characteristics of asthma, sinusitis, atopic dermatitis, allergic rhinitis, allergic conjunctivitis, allergic myelitis, ulcerative colitis, Crohn's disease, rheumatoid arthritis and the like is eosinophil infiltration into the inflammatory tissue. Therefore, eosinophils are considered to play a key role in the onset, progress and retention of these diseases.

It is known that CCR3, one of the CC chemokine receptors, plays an important role in the chemotaxis to inflammatory lesion and activation and the like of eosinophils, and CCR3 is expressed not only in eosinophils but also in inflammatory cells such as mast cells, basophils, dendritic cells, Th2 cells and the like (J. Clin. Invest., 99(2), 178-184 (1997), J. Exp. Med., 190(2), 267-280 (1999), J. Clin. Invest., 100(5), 1137-1143 (1997), Science, 277, 5334, 2005-2007 (1997), and Pharmacol. Rev., 52(1), 145-176 (2000)). In asthma and atopic dermatitis models of CCR3 gene knockout mouse, eosinophils infiltration into the lung and skin, and airway hypersensitivity are suppressed as compared to wild-type mouse (J. Clin. Invest., 109(5), 621-628 (2002)).

It is also known that infiltration of activated eosinophils is observed in nasal polyp tissue extract of sinusitis, and CCL11, CCL13 and CCL24, which are selective and strong ligands of CCR3, significantly increase therein (J. Immunol., 163(3), 1545-1551 (1999)). Moreover, CCR3 positive mononuclear cells significantly increase in peripheral blood and synovial fluid of rheumatoid arthritis patients as compared to healthy subjects (Arthritis Rheum., 44(5), 1022-1032 (2001)).

In consideration of the above, a compound having affinity for CCR3 is expected to be useful as a pharmaceutical product for the prophylaxis or treatment of immune and inflammatory diseases.

In addition, for example, the following patent references regarding therapeutic agents for immune and inflammatory diseases, which show affinity for chemokine receptors, have been published. WO97/24325 discloses diphenylmethane derivatives and WO98/25617 discloses arylpiperazine derivatives, as compounds having affinity for chemokine receptors, WO98/02151, WO98/04554 and WO00/34278 disclose tricyclic heteroaromatic derivatives and the like having affinity for chemokine receptors, WO99/55324 and WO99/55330 disclose phenylalanine derivatives and the like having affinity for chemokine receptors, WO00/58305 discloses piperazine derivatives and the like having affinity for chemokine receptors, and WO00/31033, WO00/53600, WO01/14333, WO02/66460 and WO02/88111 disclose piperidine derivatives and the like having affinity for chemokine receptors. In addition, WO02/18335 discloses cyclic amine derivatives having a CCR3 antagonistic action. In addition, WO02/26722, WO02/26723, WO03/82292, WO03/82294, WO03/82861, WO03/82862, WO03/82295, WO03/82863, WO03/99287 and WO03/99798 disclose morpholine derivatives and the like having affinity for chemokine receptors. However, these compounds do not have the structural characteristics that the compound of the present invention to be mentioned below shows as a preferable embodiment (i.e., compounds having sulfur atom on alkylene chain having morpholine ring via methylene amide).

Since a clinically effective low-molecular-weight compound having CCR3 affinity has not bee reported to date, a CCR3 antagonist having a different structure is expected to be a pharmaceutical product for the treatment or prophylaxis of acute and chronic inflammatory diseases and the like, including immune and allergic diseases.

EP243959A discloses a racemate of the formula (26) shown below, which is useful as a synthetic intermediate for the compound of the present invention.

DISCLOSURE OF THE INVENTION

The present invention aims at provision of a pharmaceutical product having affinity for CCR3, which is used for the treatment and/or prophylaxis of immune and inflammatory diseases.

In view of the above-mentioned situation, the present inventors have conducted intensive studies in an attempt to find a nonpeptidic compound having a CCR3 antagonistic action and found that a morpholine compound or a pharmaceutically acceptable salt thereof, or a hydrate or solvate thereof inhibits CCR3 ligand from binding to CCR3 and acts as an antagonist. Thus, they have found that the compound of the present invention can be a pharmaceutical product for the treatment or prophylaxis of acute and chronic inflammatory diseases including immune and allergic diseases, which resulted in the completion of the present invention.

Accordingly, the gist of the present invention is as follows.

[1] A compound represented by the formula (1)

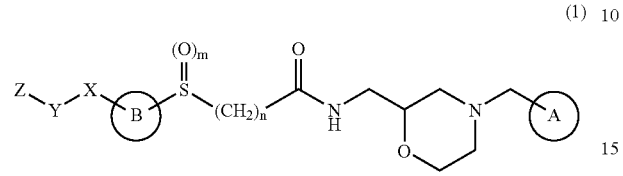

(1)

wherein ring A is aryl optionally having substituent(s), or heteroaryl optionally having substituent(s), ring B is arylene optionally having substituent(s), divalent heterocyclic group optionally having substituent(s), or $C_{3-8}$ cycloalkylene optionally having substituent (s), m is an integer of 0 to 2, n is an integer of 1 to 5, X is a bond, —NH—, —NR$^1$— wherein R$^1$ is $C_{1-6}$ alkyl optionally having substituent(s), —CO—, —CO$_2$—, —OCO—, —CONR$^a$— wherein R$^a$ is hydrogen atom or $C_{1-6}$ alkyl optionally having substituent(s), hereinafter the same, —NR$^a$CO—, —NR$^2$CONR$^3$— wherein R$^2$ and R$^3$ may be the same or different and each is hydrogen atom or $C_{1-6}$ alkyl optionally having substituent(s), or R$^2$ and R$^3$ in combination optionally form, together with the atoms bonded thereto, a ring optionally having substituent(s), oxygen atom, sulfur atom, —SO—, —SO$_2$—, —NR$^a$SO$_2$—, —SO$_2$NR$^a$—, $C_{1-6}$ alkylene optionally having substituent(s), $C_{2-6}$ alkenylene optionally having substituent(s), $C_{2-6}$ alkynylene optionally having substituent (s), —O—X$^a$— wherein X$^a$ is $C_{1-6}$ alkylene optionally having substituent(s), hereinafter the same, —X$^a$—O—, —CO—X$^a$—, —X$^a$—CO—, —CONR$^a$—X$^a$—, —X$^a$—CONR$^a$—, —NR$^a$CO—X$^a$—, —X$^a$—NR$^a$CO—, —S—X$^a$—, —X$^a$—S—, —SO—X$_a$—, —X$^a$—SO—, —NR$^a$—X$^a$—, —X$^a$—NR$^a$—, —SO$_2$—X$^a$—, —X$^a$—SO$_2$—, —C(=N—CO$_2$—R$^1$)—, —C(=N—SO$_2$—R$^1$)—, —C(=N—SO$_2$NH$_2$)—, —C(=CH—NO$_2$)— or —C(=N—CN)— or $C_{3-8}$ cycloalkylidene group optionally having substituent(s), Y is a bond, —NH—, —NR$^4$— wherein R$^4$ is $C_{1-6}$ alkyl optionally having substituent(s), hereinafter the same, —CO—, —CO$_2$—, —OCO—, —CONR$^b$— wherein R$^b$ is hydrogen atom or $C_{1-6}$ alkyl optionally having substituent(s), hereinafter the same, —NR$^b$CO—, —NR$^5$CONR$^6$— wherein R$^5$ and R$^6$ may be the same or different and each is hydrogen atom or $C_{1-6}$ alkyl optionally having substituent(s), or R$^5$ and R$^6$ in combination optionally form, together with the atoms bonded thereto, a ring optionally having substituent(s), oxygen atom, sulfur atom, —SO—, —SO$_2$—, —NR$^b$SO$_2$—, —SO$_2$NR$^b$—, $C_{1-6}$ alkylene optionally having substituent(s), $C_{2-6}$ alkenylene optionally having substituent(s), $C_{2-6}$ alkynylene optionally having substituent(s), —O—X$^b$— wherein X$^b$ is $C_{1-6}$ alkylene optionally having substituent(s), hereinafter the same, —X$^b$—O—, —CO—X$^b$—, —X$^b$—CO—, —CONR$^b$—X$^b$—, —X$^b$—CONR$^b$—, —NR$^b$CO—X$^b$—, —X$^b$—NR$^b$CO—, —S—X$^b$—, —X$^b$—S—, —SO—X$^b$—, —X$^b$—SO—, —NR$^b$—X$^b$—, —X$^b$—NR$^b$—, —SO$_2$—X$^b$—, —X$^b$—SO$_2$—, —C(=N—CO$_2$—R$^4$)—, —C(=N—SO$_2$—R$^4$)—, —C(=N—SO$_2$NH$_2$)—, —C(=CH—NO$_2$)— or —C(=N—CN)—, and Z is hydrogen atom, halogen atom, $C_{1-6}$ alkyl optionally having substituent(s), $C_{3-8}$ cycloalkyl optionally having substituent(s), aryl optionally having substituent(s), heterocyclic group optionally having substituent(s), hydroxy, nitro, amino, cyano, $C_{1-6}$ alkoxy optionally having substituent(s), mono- or di-$C_{1-6}$ alkylamino optionally having substituent(s), $C_{1-7}$ acylamino optionally having substituent(s), sulfonylamino optionally having substituent(s), hydrazino optionally having substituent(s), guanidino optionally having substituent(s) or amidino optionally having substituent(s), or a pharmaceutically acceptable salt thereof, or a hydrate or solvate thereof.

[2] The compound described in [1] above, wherein ring B is arylene optionally having substituent(s), or divalent heterocyclic group optionally having substituent(s), and X is a bond, —NH—, —NR$^1$— wherein R$^1$ is $C_{1-6}$ alkyl optionally having substituent(s), —CO—, —CO$_2$—, —OCO—, —CONR$^a$— wherein R$^a$ is hydrogen atom or $C_{1-6}$ alkyl optionally having substituent(s), hereinafter the same, —NR$^a$CO—, —NR$^2$CONR$^3$— wherein R$^2$ and R$^3$ may be the same or different and each is hydrogen atom or $C_{1-6}$ alkyl optionally having substituent(s), or R$^2$ and R$^3$ in combination optionally form, together with the atoms bonded thereto, a ring optionally having substituent(s), oxygen atom, sulfur atom, —SO—, —SO$_2$—, —NR$^a$SO$_2$—, —SO$_2$NR$^a$—, $C_{1-6}$ alkylene optionally having substituent(s), $C_{2-6}$ alkenylene optionally having substituent(s), $C_{2-6}$ alkynylene optionally having substituent(s), —O—X$^a$— wherein X$^a$ is $C_{1-6}$ alkylene optionally having substituent(s), hereinafter the same, —X$^a$—O—, —CO—X$^a$—, —X$^a$—CO—, —CONR$^a$—X$^a$—, —X$^a$—CONR$^a$—, —NR$^a$CO—X$^a$—, —X$^a$—NR$^a$CO—, —S—X$^a$—, —X$^a$—S—, —SO—X$^a$—, —X$^a$—SO—, —NR$^a$—X$^a$—, —X$^a$—NR$^a$—, —SO$_2$—X$^a$—, —X$^a$—SO$_2$—, —C(=N—CO$_2$—R$^1$)—, —C(=N—SO$_2$—R$^1$)—, —C(=N—SO$_2$NH$_2$)—, —C(=CH—NO$_2$)— or —C(=N—CN)—, or a pharmaceutically acceptable salt thereof, or a hydrate or solvate thereof.

[3] The compound described in [1] or [2] above, wherein, in the formula (1), m is 0 or 2, or a pharmaceutically acceptable salt thereof, or a hydrate or solvate thereof.

[4] The compound described in any one of [1] to [3] above, wherein, in the formula (1), m is 0, or a pharmaceutically acceptable salt thereof, or a hydrate or solvate thereof.

[5] The compound described in any one of [1] to [4] above, wherein, in the formula (1), X is a bond, —NH—, —NR$^1$— wherein R$^1$ is $C_{1-6}$ alkyl optionally having substituent(s), —CO—, —CO$_2$—, —OCO—, —CONR$^a$— wherein R$^a$ is hydrogen atom or $C_{1-6}$ alkyl optionally having substituent(s), hereinafter the same, —NR$^a$CO—, —NR$^2$CONR$^3$— wherein R$^2$ and R$^3$ may be the same or different and each is hydrogen atom or $C_{1-6}$ alkyl optionally having substituent(s), oxygen atom, sulfur atom, —SO—, —SO$_2$—, —NR$^a$SO$_2$—, —SO$_2$NR$^a$—, $C_{2-6}$ alkenylene optionally having substituent(s), —CO—X$^a$— wherein X$^a$ is $C_{1-6}$ alkylene optionally having substituent(s), hereinafter the same, —X$^a$—CO—, —CONR$^a$—X$^a$—, —X$^a$—CONR$^a$—, —NR$^a$CO—X$^a$—, —X$^a$—NR$^a$CO— or $C_{3-8}$ cycloalkylidene optionally having substituent(s), or a pharmaceutically acceptable salt thereof, or a hydrate or solvate thereof.

[6] The compound described in any one of [1] to [5] above, wherein, in the formula (1), X is a bond, —CO—, —CONR$^a$— wherein R$^a$ is hydrogen atom or $C_{1-6}$ alkyl optionally having substituent(s), hereinafter the same, —NR$^a$CO—, —CO—X$^a$— wherein X$^a$ is C$_{1-6}$ alkylene optionally having substituent(s), hereinafter the same, —X$^a$—CO—, —CONR$^a$—X$^a$—, —X$^a$—CONR$^a$—, —NR$^a$CO—X$^a$— or —X$^a$—NR$^a$CO—, or a pharmaceutically acceptable salt thereof, or a hydrate or solvate thereof.

[7] The compound described in any one of [1] to [6] above, wherein, in the formula (1), Y is a bond, —NH—, —NR$^4$— wherein R$^4$ is C$_{1-6}$ alkyl optionally having substituent(s), —CO—, —CO$_2$—, —OCO—, —CONR$^b$— wherein R$^b$ is hydrogen atom or C$_{1-6}$ alkyl optionally having substituent(s), hereinafter the same, —NR$^b$CO—, —NR$^5$CONR$^6$— wherein R$^5$ and R$^6$ may be the same or different and each is hydrogen atom or C$_{1-6}$ alkyl optionally having substituent(s), oxygen atom, sulfur atom, —SO—, —SO$_2$—, —NR$^b$SO$_2$—, —SO$_2$NR$^b$—, —CO—X$^b$— wherein X$^b$ is C$_{1-6}$ alkylene optionally having substituent(s), hereinafter the same, —X$^b$—CO—, —CONR$^b$—X$^b$—, —X$^b$—CONR$^b$—, —NR$^b$CO—X$^b$— or —X$^b$—NR$^b$CO—, or a pharmaceutically acceptable salt thereof, or a hydrate or solvate thereof.

[8] The compound described in any one of [1] to [7] above, wherein, in the formula (1), Y is a bond, —CO—, —CONR$^b$— wherein R$^b$ is hydrogen atom or C$_{1-6}$ alkyl optionally having substituent(s), hereinafter the same, —NR$^b$CO—, —CO—X$^b$— wherein X$^b$ is C$_{1-6}$ alkylene optionally having substituent(s), hereinafter the same, —X$^b$—CO, —CONR$^b$—X$^b$—, —X$^b$—CONR$^b$—, —NR$^b$CO—X$^b$— or —X$^b$—NR$^b$CO—, or a pharmaceutically acceptable salt thereof, or a hydrate or solvate thereof.

[9] The compound described in any one of [1] to [8] above, wherein, in the formula (1), Z is hydrogen atom, halogen atom, C$_{1-6}$ alkyl optionally having substituent(s), C$_{3-8}$ cycloalkyl optionally having substituent(s), aryl optionally having substituent(s), heterocyclic group optionally having substituent(s), hydroxy, nitro, amino, cyano, C$_{1-6}$ alkoxy optionally having substituent(s), mono- or di-C$_{1-6}$ alkylamino optionally having substituent(s), C$_{1-7}$ acylamino optionally having substituent(s), sulfonylamino optionally having substituent(s), hydrazino optionally having substituent(s), guanidino optionally having substituent(s), or amidino optionally having substituent(s), or a pharmaceutically acceptable salt thereof, or a hydrate or solvate thereof.

[10] The compound described in any one of [1] to [9] above, wherein, in the formula (1), Z is hydrogen atom, hydroxy, amino, C$_{1-6}$ alkyl optionally having substituent(s), C$_{1-6}$ alkoxy optionally having substituent(s), aryl optionally having substituent(s) or heterocyclic group optionally having substituent(s), or a pharmaceutically acceptable salt thereof, or a hydrate or solvate thereof.

[11] The compound described in [1] above, which is represented by the formula (1a)

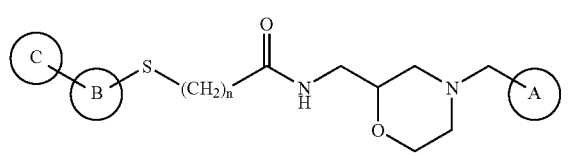

(1a)

wherein ring C is aryl optionally having substituent(s) or heteroaryl and other symbols are as defined in the above-mentioned [1], or a pharmaceutically acceptable salt thereof, or a hydrate or solvate thereof.

[12] The compound described in any one of [1] to [11] above, wherein, in the formula (1), ring A is phenyl optionally having substituent(s), or a pharmaceutically acceptable salt thereof, or a hydrate or solvate thereof.

[13] The compound described in any one of [1] to [12] above, wherein, in the formula (1), n is 1 to 3, or a pharmaceutically acceptable salt thereof, or a hydrate or solvate thereof.

[14] The compound described in any one of [1] to [13] above, wherein, in the formula (1), the absolute configuration at the 2-position of morpholine is S configuration, or a pharmaceutically acceptable salt thereof, or a hydrate or solvate thereof.

[15] The compound described in [1] above, which is selected from the group consisting of (2S)-[4-(carboxymethyl)thiazol-2-ylthio]-N-{[4-(3,4-dichlorobenzyl)morpholin-2-yl]methyl}acetamide, (2S)-[4-(3-aminophenyl)thiazol-2-ylthio]-N-{[4-(3,4-dichlorobenzyl)morpholin-2-yl]methyl}acetamide, (2S)-[4-(3-carbamoyl-4-hydroxyphenyl)thiazol-2-ylthio]-N-{[4-(3,4-dichlorobenzyl)morpholin-2-yl]methyl}acetamide, (2S)-N-{[4-(3,4-dichlorobenzyl)morpholin-2-yl]methyl}-[4-(pyridin-4-yl)thiazol-2-ylthio]acetamide, (2S)-N-{[4-(3,4-dichlorobenzyl)morpholin-2-yl]methyl}-[4-(3,4-dimethoxyphenyl)thiazol-2-ylthio]acetamide, (2S)-(4-carbamoylthiazol-2-ylthio)-N-{[4-(3,4-dichlorobenzyl)morpholin-2-yl]methyl}acetamide, (2S)-{4-[(2-amino-2-oxoethyl)aminocarbonyl]thiazol-2-ylthio}-N-{[4-(3,4-dichlorobenzyl)morpholin-2-yl]methyl}acetamide, (2S)-N-{[4-(3,4-dichlorobenzyl)morpholin-2-yl]methyl}-[4-(5-methyl-1,2,4-oxadiazol-3-yl)thiazol-2-ylthio]acetamide, (2S)-(5-amino-8H-indeno[1,2-d]thiazol-2-ylthio)-N-{[4-(3,4-dichlorobenzyl)morpholin-2-yl]methyl}acetamide, (2S)-(4-carboxyphenylthio)-N-{[4-(3,4-dichlorobenzyl)morpholin-2-yl]methyl}acetamide, (2S)-{4-[(2-amino-2-oxoethyl)aminocarbonyl]phenylthio}-N-{[4-(3,4-dichlorobenzyl)morpholin-2-yl]methyl}acetamide, (2S)-{4-[(2-carboxyethyl)aminocarbonyl]thiazol-2-ylthio}-N-{[4-(3,4-dichlorobenzyl)morpholin-2-yl]methyl}acetamide, (2S)-(5-acetamino-1,3,4-thiadiazol-2-ylthio)-N-{[4-(3,4-dichlorobenzyl)morpholin-2-yl]methyl}acetamide, (2S)-4-(4-carbamoylthiazol-2-ylthio)-N-{[4-(3,4-dichlorobenzyl)morpholin-2-yl]methyl}butyramide, (2S)-N-{[4-(3,4-dichlorobenzyl)morpholin-2-yl]methyl}-[4-(1H-tetrazol-5-yl)thiazol-2-ylthio]acetamide, (2S)-N-{[4-(3,4-dichlorobenzyl)morpholin-2-yl]methyl}-([1,3]thiazolo[5,4-b]pyridin-2-ylthio)acetamide, (2S)-(E)-[4-(2-carbamoylethen-1-yl)thiazol-2-ylthio]-N-{[4-(3,4-dichlorobenzyl)morpholin-2-yl]methyl}acetamide, (2S)-[4-(carbamoylmethyl)thiazol-2-ylthio]-N-{[4-(3,4-difluorobenzyl)morpholin-2-yl]methyl}acetamide, (2S)-[4-(carbamoylmethyl)thiazol-2-ylthio]-N-{[4-(4-fluorobenzyl)morpholin-2-yl]methyl}acetamide, (2S)-(4-carboxy-5-methylthiazol-2-ylthio)-N-{[4-(3,4-dichlorobenzyl)morpholin-2-yl]methyl}acetamide, (2S)-(4-carbamoyl-5-methylthiazol-2-ylthio)-N-{[4-(3,4-dichlorobenzyl)morpholin-2-yl]methyl}acetamide, (2S)-(4-carbamoylthiazol-2-ylthio)-N-{[4-(3-chloro-4-fluorobenzyl)morpholin-2-yl]methyl}acetamide, (2S)-[4-(2-amino-2-oxoethyl)aminocarbonylthiazol-2-ylthio]-N-{[4-(3,4-difluorobenzyl)morpholin-2-yl]methyl}acetamide, (2S)-(5-amino-1,3,4-thiadiazol-2-ylthio)-N-{[4-(3-chlorobenzyl)morpholin-2-yl]methyl}acetamide, (2S)-(5-amino-1,3,4-thiadiazol-2-ylthio)-N-{[4-(3,4-difluorobenzyl)morpholin-2-yl]

methyl}acetamide, (2S)-N-{[4-(3,4-dichlorobenzyl)morpholin-2-yl]methyl}-(pyrimidin-2-ylthio)acetamide, (2S)-(3-acetyl-2-oxo-2H-chromen-6-ylthio)-N-{[4-(3,4-dichlorobenzyl)morpholin-2-yl]methyl}acetamide, (2S)-N-{[4-(3,4-difluorobenzyl)morpholin-2-yl]methyl}-(6-oxo-1,6-dihydropyridazin-3-ylthio)acetamide, (2S)-[6-(carbamoylmethyl)pyrazin-2-ylthio]-N-{[4-(3,4-dichlorobenzyl)morpholin-2-yl]methyl}acetamide, and (2S)-4-(cyclopentanesulfonyl)-N-{[4-(3-chloro-4-fluorobenzyl)morpholin-2-yl]methyl}butyramide, or a pharmaceutically acceptable salt thereof, or a hydrate or solvate thereof.

[16] A CCR3 antagonist comprising, as an active ingredient, the compound described in any one of [1] to [15] above, or a pharmaceutically acceptable salt thereof, or a hydrate or solvate thereof.

[17] A pharmaceutical composition comprising the compound described in any one of [1] to [15] above, or a pharmaceutically acceptable salt thereof, or a hydrate or solvate thereof, and a pharmaceutically acceptable carrier.

[18] The pharmaceutical composition described in [17] above, which is an agent for the prophylaxis and/or treatment of asthma, sinusitis, allergic rhinitis, atopic dermatitis, allergic conjunctivitis, allergic myelitis, ulcerative colitis, Crohn's disease or rheumatoid arthritis.

[19] A method for the prophylaxis and/or treatment of a disease involving CCR3, which comprises administering an effective amount of the compound described in any one of [1] to [15] above, or a pharmaceutically acceptable salt thereof, or a hydrate or solvate thereof to an animal.

[20] The method described in [19] above, wherein the disease involving CCR3 is asthma, sinusitis, allergic rhinitis, atopic dermatitis, allergic conjunctivitis, allergic myelitis, ulcerative colitis, Crohn's disease or rheumatoid arthritis.

[21] Use of the compound described in any one of [1] to [15] above, or a pharmaceutically acceptable salt thereof, or a hydrate or solvate thereof for the production of an agent for the prophylaxis and/or treatment of a disease involving CCR3.

[22] Use described in [21] above, wherein the disease involving CCR3 is asthma, sinusitis, allergic rhinitis, atopic dermatitis, allergic conjunctivitis, allergic myelitis, ulcerative colitis, Crohn's disease or rheumatoid arthritis.

[23] A compound represented by the formula (26)

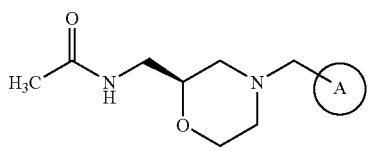

(26)

wherein A is aryl optionally having substituent(s) or heteroaryl optionally having substituent(s), or a salt thereof.

[24] A production method of a compound represented by the formula (1)

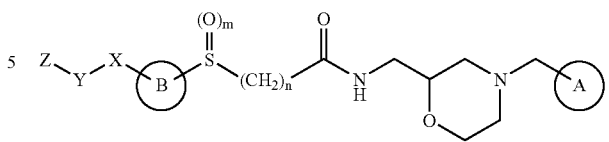

(1)

wherein ring A is aryl optionally having substituent(s), or heteroaryl optionally having substituent(s), ring B is arylene optionally having substituent(s), divalent heterocyclic group optionally having substituent(s), or $C_{3-8}$ cycloalkylene optionally having substituent(s), m is an integer of 0 to 2, n is an integer of 1 to 5, X is a bond, —NH—, —NR$^1$— wherein R$^1$ is $C_{1-6}$ alkyl optionally having substituent(s), —CO—, —CO$_2$—, —OCO—, —CONR$^a$— wherein R$^a$ is hydrogen atom or $C_{1-6}$ alkyl optionally having substituent(s), hereinafter the same, —NR$^a$CO—, —NR$^2$CONR$^a$— wherein R$^2$ and R$^3$ may be the same or different and each is hydrogen atom or $C_{1-6}$ alkyl optionally having substituent(s), or R$^2$ and R$^3$ in combination optionally form, together with the atoms bonded thereto, a ring optionally having substituent(s), oxygen atom, sulfur atom, —SO—, —SO$_2$—, —NR$^a$SO$_2$—, —SO$_2$NR$^a$—, $C_{1-6}$ alkylene optionally having substituent(s), $C_{2-6}$ alkenylene optionally having substituent(s), $C_{2-6}$ alkynylene optionally having substituent(s), —O—X$^a$— wherein X$^a$ is $C_{1-6}$ alkylene optionally having substituent(s), hereinafter the same, —X$^a$—O—, —CO—X$^a$—, —X$^a$—CO—, —CONR$^a$—X$^a$—, —X$^a$—CONR$^a$—, —NR$^a$CO—X$^a$—, —X$^a$—NR$^a$CO—, —S—X$^a$—, —X$^a$—S—, —SO—X$^a$—, —X$^a$—SO—, —NR$^a$—X$^a$—, —X$^a$—NR$^a$—, —SO$_2$—X$^a$—, —X$^a$—SO$_2$—, —C(=N—CO$_2$—R$^1$)—, —C(=N—SO$_2$—R$^1$)—, —C(=N—SO$_2$NH$_2$)—, —C(=CH—NO$_2$)—, —C(=N—CN)— or $C_{3-8}$ cycloalkylidene optionally having substituent(s), Y is a bond, —NH—, —NR$^4$— wherein R$^4$ is $C_{1-6}$ alkyl optionally having substituent(s), hereinafter the same, —CO—, —CO$_2$—, —OCO—, —CONR$^b$— wherein R$^b$ is hydrogen atom or $C_{1-6}$ alkyl optionally having substituent(s), hereinafter the same, —NR$^b$CO—, —NR$^5$CONR$^6$— wherein R$^5$ and R$^6$ may be the same or different and each is hydrogen atom or $C_{1-6}$ alkyl optionally having substituent(s), or R$^5$ and R$^6$ in combination optionally form, together with the atoms bonded thereto, a ring optionally having substituent(s), oxygen atom, sulfur atom, —SO—, —SO$_2$—, —NR$^b$SO$_2$—, —SO$_2$NR$^b$—, $C_{1-6}$ alkylene optionally having substituent(s), $C_{2-6}$ alkenylene optionally having substituent(s), $C_{2-6}$ alkynylene optionally having substituent(s), —O—X$^b$— wherein X$^b$ is $C_{1-6}$ alkylene optionally having substituent(s), hereinafter the same, —X$^b$—O—, —CO—X$^b$—, —X$^b$—CO—, —CONR$^b$—X$^b$—, —X$^b$—CONR$^b$—, —NR$^b$CO—X$^b$—, —X$^b$—NR$^b$CO—, —S—X$^b$—, —X$^b$—S—, —SO—X$^b$—, —X$^b$—SO—, —NR$^b$—X$^b$—, —X$^b$—NR$^b$—, —SO$_2$—X$^b$—, —X$^b$—SO$_2$—, —C(=N—CO$_2$—R$^4$)—, —C(=N—SO$_2$—R$^4$)—, —C(=N—SO$_2$NH$_2$)—, —C(=CH—NO$_2$)— or —C(=N—CN)—, and Z is hydrogen atom, halogen atom, $C_{1-6}$ alkyl optionally having substituent(s), $C_{3-8}$ cycloalkyl optionally having substituent(s), aryl optionally having substituent(s), heterocyclic group optionally having substituent(s), hydroxy, nitro, amino, cyano, $C_{1-6}$ alkoxy optionally having substituent(s), mono- or di-$C_{1-6}$ alkylamino optionally having substituent(s), $C_{1-7}$ acylamino optionally having substituent(s), sulfonylamino optionally having substituent(s), hydrazino optionally having substituent(s), guanidino optionally having substituent(s) or amidino optionally having substituent(s), or a salt thereof, which comprises reacting a compound represented by the formula (6)

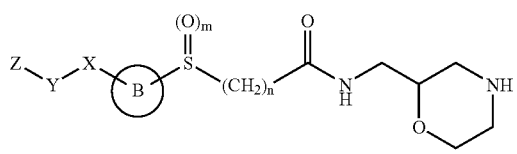
(6)

wherein each symbol is as defined above, or a salt thereof, with a compound represented by the formula (8)

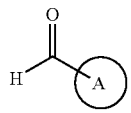
(8)

wherein ring A is as defined above, or a salt thereof.

According to the present invention, the diseases in which a cell having CCR3 plays an important role in the onset, progress and retention of pathology, such as asthma, sinusitis, allergic rhinitis, atopic dermatitis, allergic conjunctivitis, allergic myelitis, ulcerative colitis, Crohn's disease, rheumatoid arthritis and the like can be treated and/or prevented.

BEST MODE FOR EMBODYING THE INVENTION

The terms and symbols used in the present specification are defined as follows.

As the "halogen atom", for example, fluorine atom, chlorine atom, bromine atom and iodine atom can be mentioned.

The "aryl" of the "aryl optionally having substituent(s)" means monocyclic to tricyclic $C_{6-14}$ aryl, and, for example, phenyl, naphthyl, anthryl, indenyl and the like can be mentioned. Preferable examples thereof include phenyl, naphthyl and the like, and more preferable examples include phenyl.

The "aryl" may be partially hydrogenated. The position of hydrogenation is not particularly limited. As the partially hydrogenated aryl, for example, tetrahydronaphthyl, indanyl and the like can be mentioned.

When the "aryl" has a "substituent", the kind and number thereof are not particularly limited, and aryl has 1 to 4 substituents selected from the "substituents" defined below at substitutable position(s). Preferable examples of the substituents that aryl may have include halogen atom, cyano, nitro, $C_{1-6}$ alkyl, $C_{1-6}$ haloalkyl, $C_{1-6}$ alkoxy, hydroxy, amino, mono- or di-($C_{1-11}$ acyl)amino, carboxy, $C_{1-6}$ alkoxy-carbonyl, carbamoyl, hydroxyamidino and the like, more preferable examples thereof include chlorine atom, fluorine atom, cyano, nitro, methyl, trifluoromethyl, methoxy, hydroxy, amino, acetylamino, carboxy, methoxycarbonyl, carbamoyl and hydroxyamidino, still more preferable examples thereof include fluorine atom, chlorine atom, methyl and trifluoromethyl, and yet more preferable examples thereof include fluorine atom and chlorine atom.

The "heteroaryl" of the "heteroaryl optionally having substituent(s)" means a 5- to 7-membered aromatic heterocyclic (monocyclic) group containing, as a ring atom besides carbon atom, 1 to 3 kinds of 1 to 4 hetero atoms selected from nitrogen atom, sulfur atom and oxygen atom and, for example, furyl, thienyl, pyrrolyl, thiazolyl, pyrazolyl, oxazolyl, isoxazolyl, isothiazolyl, imidazolyl, 1,2,4-oxadiazolyl, 1,3,4-oxadiazolyl, 1,2,3-triazolyl, 1,2,4-triazolyl, 1,2,4-thiadiazolyl, 1,3,4-thiadiazolyl, tetrazolyl, pyridyl, pyrimidinyl, pyrazinyl, pyridazinyl, 1,3,5-triazinyl, azepinyl, diazepinyl and the like can be mentioned. In addition, the "heteroaryl" also includes groups derived from an aromatic heterocycle (bicyclic or above) obtained by condensing a 5- to 7-membered aromatic heterocycle containing, as a ring atom besides carbon atom, 1 to 3 kinds of 1 to 4 hetero atoms selected from nitrogen atom, sulfur atom and oxygen atom and a benzene ring or the above-mentioned aromatic heterocyclic (monocyclic) group and, for example, indolyl, isoindolyl, benzo[b]furyl, benzo[b]thienyl, benzimidazolyl, benzoxazolyl, benzoisoxazolyl, benzothiazolyl, benzoisothiazolyl, quinolyl, isoquinolyl and the like can be mentioned.

The "heteroaryl" may be partially hydrogenated. The position of hydrogenation is not particularly limited. As the partially hydrogenated heteroaryl, for example, tetrahydrobenzimidazolyl, tetrahydroquinolyl, tetrahydroisoquinolyl and the like can be mentioned.

Preferable examples of heteroaryl include furyl, thienyl, thiazolyl, pyridyl, indolyl, benzo[b]furyl, benzo[b]thienyl, benzoxazolyl, benzothiazolyl, quinolyl and isoquinolyl, and more preferable examples include furyl, thienyl, thiazolyl and pyridyl.

When "heteroaryl" has "substituent(s)", the kind and number thereof are not particularly limited, and heteroaryl has 1 to 4 substituents selected from the "substituents" defined below at substitutable position(s). Preferable examples of the substituent that heteroaryl may have include halogen atom, cyano and nitro, and more preferable examples include halogen atom.

The "arylene" of the "arylene optionally having substituent(s)" means a divalent group further having a bond at any position of the above-mentioned "aryl" and, for example, divalent groups such as phenylene, naphthylene, indenylene and the like can be mentioned.

The "arylene" may be partially hydrogenated. The position of hydrogenation is not particularly limited. As the partially hydrogenated arylene, for example, tetrahydronaphthylene, indanylene and the like can be mentioned.

Preferable examples of arylene include phenylene, naphthylene, indanylene and the like, and more preferable examples thereof include phenylene and the like.

When "arylene" has substituent(s), the kind and number thereof are not particularly limited, and arylene has 1 to 3 substituents selected from the "substituents" defined below at substitutable position(s). Preferable examples of the substituent that arylene may have include $C_{1-6}$ alkyl, $C_{1-6}$ alkoxy, hydroxy, oxo and the like, and more preferable examples thereof include oxo.

The "heterocyclic group" of the "divalent heterocyclic group optionally having substituent(s)" for ring B and "heterocyclic group optionally having substituent(s)" for Z means a 5- to 14-membered monocyclic to tricyclic heterocyclic group containing, as a ring atom besides carbon atom, 1 to 3 kinds of 1 to 4 hetero atoms selected from nitrogen atom, sulfur atom and oxygen atom. The "heterocyclic group" encompasses a saturated ring, an aromatic ring (encompassing "heteroaryl" defined above), and a partially hydrogenated ring group thereof. As the partially hydrogenated heteroaryl, for example, dihydrofuryl, dihydrothienyl, pyrrolinyl, thiazolinyl, pyrazolinyl, oxazolinyl, isoxazolinyl, isothiazolinyl, imidazolinyl, 1,2,4-oxadiazolinyl, 1,3,4-oxadiazolinyl, 1,2,3-triazolinyl, 1,2,4-triazolinyl, 1,2,4-thiadiazolinyl, 1,3,4-thiadiazolinyl, dihydropyridazinyl, tetrahydrobenzimidazolyl, tetrahydroquinolyl, tetrahydroisoquinolyl and the like can be mentioned.

As the "saturated heterocyclic group", for example, pyrrolidinyl, piperidyl, piperazinyl, tetrahydrofuranyl, morpholinyl, thiazolidinyl, thiomorpholinyl, homopiperazinyl and the like can be mentioned. In addition, the "heterocyclic group" encompasses a "crosslinked heterocyclic group" containing, as a ring atom besides carbon atom, 1 to 4 hetero atoms selected from oxygen atom, sulfur atom and nitrogen atom, and as the crosslinked ring group, for example, 3-azabicyclo[3.2.2]nonan-3-yl, 8-azabicyclo[3.2.1]octan-8-yl and the like can be mentioned.

When the "heterocyclic group" has "substituent(s)", the kind and number thereof are not particularly limited, and heterocyclic group has 1 to 4 substituents selected from the "substituents" defined below at substitutable position(s). Preferable examples of the substituent(s) that the heterocyclic group may have include $C_{1-6}$ alkyl, hydroxy, nitro, amino, cyano, carboxy, $C_{1-6}$ alkoxy-carbonyl, carbamoyl, oxo and the like, and methyl, ethoxycarbonyl, carbamoyl and oxo are more preferable.

Preferable examples of the "heterocyclic group" include pyridyl, pyrazinyl, pyrimidinyl, pyridazinyl, imidazolyl, pyrrolyl, pyrrolidinyl, morpholinyl, thienyl, furyl, thiazolyl, pyrazolyl, isothiazolyl, oxazolyl, isoxazolyl, quinolyl, isoquinolyl, tetrahydroquinolyl, tetrahydroisoquinolyl, quinolizinyl, quinazolyl, quinoxalinyl, cinnolinyl, phthalazinyl, 1,8-naphthyridinyl, acrydinyl, purinyl, pteridinyl, 1,2,4-oxadiazolyl, 1,2,4-oxadiazolinyl, 1,3,4-oxadiazolyl, 1,2,3-triazolyl, 1,2,4-triazolyl, 1,3,5-triazinyl, 1,2,4-thiadiazolyl, 1,3,4-thiadiazolyl, tetrazolyl, piperidyl, piperazinyl, azepinyl, azepanyl, diazepanyl, diazepinyl, tetrahydrofuranyl, morpholinyl, indolyl, isoindolyl, indolinyl, isoindolinyl, indazolyl, indolizinyl, carbazolyl, tetrahydrobenzimidazolyl, chromanyl, isochromanyl, chromenyl, isochromenyl, [1,3]thiazolo[5,4-b]pyridyl, 4,5,6,7-tetrahydro[1,3]thiazolo[5,4-c]pyridyl, 1H-benzo[b]azepinyl, 2,3-dihydro-1H-benzo[b]azepinyl, thieno[3,2-c]pyridyl, 3-azabicyclo[3.2.2]nonan-3-yl, 8-azabicyclo[3.2.1]octan-8-yl, benzo[b]furyl, benzo[b]thienyl, benzimidazolyl, benzoxazolyl, benzoisoxazolyl, benzothiazolyl, benzoisothiazolyl, 8H-indeno[1,2-d]thiazolyl, 4,5-dihydro-naphto[1,2-d]thiazolyl and the like, and more preferable examples include pyridyl, pyrazinyl, pyrimidinyl, pyridazinyl, thienyl, furyl, thiazolyl, pyrazolyl, isothiazolyl, oxazolyl, isoxazolyl, 1,2,4-oxadiazolyl, 1,3,4-oxadiazolyl, 1,2,3-triazolyl, 1,2,4-triazolyl, 1,3,5-triazinyl, 1,2,4-thiadiazolyl, 1,3,4-thiadiazolyl, benzo[b]furyl, benzo[b]thienyl, benzimidazolyl, benzoxazolyl, benzoisoxazolyl, benzothiazolyl, benzoisothiazolyl, 8H-indeno[1,2-d]thiazolyl, 4,5-dihydro-naphto[1,2-d]thiazolyl, more preferable examples thereof include thiazolyl, 1,3,4-thiadiazolyl, pyridyl, pyrimidinyl, pyridazinyl, pyrazinyl, thienyl, and still more preferable examples thereof include thiazolyl, 1,3,4-thiadiazolyl, pyridazinyl and pyrazinyl.

The "divalent heterocyclic group optionally having substituent(s)" means a divalent group having a bond at any position of the above-mentioned "heterocyclic group". The position of the bond is not particularly limited and it can be appropriately determined depending on the kind of the group. Preferable examples of the "divalent heterocyclic group" include pyrrolyl, thienyl, furyl, thiazolyl, pyrazolyl, isothiazolyl, oxazolyl, isoxazolyl, 1,2,4-oxadiazolyl, 1,3,4-oxadiazolyl, 1,2,4-triazolyl, 1,2,4-thiadiazolyl, 1,3,4-thiadiazolyl, pyridyl, pyrazinyl, pyrimidinyl, pyridazinyl which may be partially hydrogenated, indenothiazolyl which may be partially hydrogenated, naphtothiazolyl which may be partially hydrogenated, quinazolyl, chromenyl, thiazolopyridyl which may be partially hydrogenated, benzoazepinyl, thienopyridyl, benzothiazolyl, imidazolyl, tetrazolyl and the like, and more preferable examples include thienyl, thiazolyl, 1,3,4-thiadiazolyl, pyridyl, pyrimidinyl, pyridazinyl, pyrazinyl and the like, and more preferable examples thereof include thiazolyl, 1,3,4-thiadiazolyl, pyridazinyl and pyrazinyl.

When the "divalent heterocyclic group" has "substituent(s)", the kind and number thereof are not particularly limited, and divalent heterocyclic group has 1 to 3 substituents selected from the "substituents" defined below at substitutable position(s). Preferable examples of the substituent(s) that the divalent heterocyclic group may have include $C_{1-6}$ alkyl, $C_{1-6}$ haloalkyl, $C_{1-6}$ alkoxy, hydroxy, halogen atom, oxo, thioxo and the like, more preferable examples thereof include methyl and oxo, wherein oxo is more preferable.

The "C3-B cycloalkylene" of the "$C_{3-8}$ cycloalkylene optionally having substituent(s)" means monocyclic to tricyclic cycloalkylene (including "crosslinked cycloalkylene") having 3 to 8 carbon atoms and, for example, cyclopropylene, cyclobutylene, cyclopentylene, cyclohexylene, cycloheptylene, cyclooctylene, norbornylene, bicyclo[2.2.1]heptylene or bicyclo[2.2.2]octylene and the like can be mentioned, and preferably, cyclopropylene, cyclobutylene, cyclopentylene and cyclohexylene can be mentioned.

When "$C_{3-8}$ cycloalkylene" has "substituent(s)", the kind and number thereof are not particularly limited, and $C_{3-8}$ cycloalkylene has 1 to 4 substituents selected from the "substituents" defined below at substitutable position(s). Preferable examples of the substituent(s) that the $C_{3-8}$ cycloalkylene may have include $C_{1-6}$ alkyl, $C_{1-6}$ alkoxy, hydroxy, amino, halogen atom, $C_{1-6}$ haloalkyl, $C_{1-6}$ haloalkoxy and the like.

The "$C_{1-6}$ alkyl" of "$C_{1-6}$ alkyl optionally having substituent(s)" means straight chain or branched chain alkyl having 1 to 6 carbon atoms and, for example, methyl, ethyl, n-propyl, isopropyl, n-butyl, isobutyl, sec-butyl, tert-butyl, pentyl, isopentyl, neopentyl, tertiary pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl and the like can be mentioned.

Preferable examples of "$C_{1-6}$ alkyl" include methyl, ethyl, n-propyl, isopropyl, n-butyl, isobutyl and the like, and more preferable examples thereof include methyl, ethyl and the like.

When "$C_{1-6}$ alkyl" has substituent(s), the kind and number thereof are not particularly limited, and $C_{1-6}$ alkyl has 1 to 4 substituents selected from the "substituents" defined below at substitutable position(s) and the kind and number thereof are not particularly limited. Preferable examples of the substituent(s) that "$C_{1-6}$ alkyl" may have include $C_{1-6}$ alkoxy, hydroxy, halogen atom and the like.

As the "ring" of the "ring optionally having substituent(s) formed by $R^2$ and $R^3$ together with the atoms bond thereto" in —$NR^2CONR^3$— wherein $R^2$ and $R^3$ may be the same or different and each is hydrogen atom or alkyl, or $R^2$ and $R^3$ in combination optionally form a ring together with the atoms bonded thereto for X, "nitrogen-containing saturated heterocycle" (e.g., 1,3-imidazolidin-2-one, 3,4,5,6-tetrahydro-2

(1H)-pyrimidinone and the like) included in the "heterocyclic group" defined above can be mentioned.

When the "ring" has "substituent(s)", the kind and number thereof are not particularly limited, and ring has 1 to 3 substituents selected from the "substituents" defined below at substitutable position(s). Preferable examples of the substituent(s) that the "ring" may have include $C_{1-6}$ alkyl, $C_{1-6}$ alkoxy, hydroxy, halogen atom and the like.

The "$C_{1-6}$ alkylene" of the "$C_{1-6}$ alkylene optionally having substituent(s)" means an alkylene chain having 1 to 6 carbon atoms and, for example, methylene, ethylene, trimethylene, tetramethylene, pentamethylene, hexamethylene and the like can be mentioned.

Preferable examples of "$C_{1-6}$ alkylene" include methylene, ethylene and trimethylene, and more preferable examples thereof include methylene and ethylene.

When "$C_{1-6}$ alkylene" has "substituent(s)", the kind and number thereof are not particularly limited, and $C_{1-6}$ alkylene has 1 to 3 substituents selected from the "substituents" defined below at substitutable position(s). Preferable examples of the substituent(s) that "$C_{1-6}$ alkylene" may have include $C_{1-6}$ alkyl, $C_{1-6}$ alkoxy, hydroxy, carboxy, carbamoyl and the like, and methyl, isobutyl and carboxy are more preferable.

When "$C_{1-6}$ alkylene" is substituted by one or more $C_{1-6}$ alkyl mentioned above, it means a branched alkylene chain (e.g., methylmethylene, dimethylmethylene, 1-methylethylene, 2-methylethylene, 1,1-dimethylethylene, 2,2-dimethylethylene, ethylmethylene, diethylmethylene, 1-ethylethylene, 2-ethylethylene, 1-methyltrimethylene, 1,1-dimethyltrimethylene, 2-methyltrimethylene, 2,2-dimethyltrimethylene, 3-methyltrimethylene, 3,3-dimethyltrimethylene, 1-ethyltrimethylene, 2-ethyltrimethylene, 3-ethyltrimethylene etc.).

The "$C_{2-6}$ alkenylene" of "$C_{2-6}$ alkenylene optionally having substituent(s)" is straight chain or branched chain alkenylene having 2 to 6 carbon atoms, which has double bond(s) at any position of the above-mentioned "$C_{1-6}$ alkylene". The position and number of the double bond is not particularly limited. As "$C_{2-6}$ alkenylene", vinylene, 1-propenylene, 2-propenylene, 1-butenylene, 2-butenylene, 3-butenylene, 1-pentenylene and the like can be mentioned, and vinylene, 1-propenylene and 2-propenylene can be preferably mentioned. When "$C_{2-6}$ alkenylene" has "substituent(s)", the kind and number thereof are not particularly limited, and $C_{2-6}$ alkenylene has 1 to 3 substituents selected from the "substituents" defined below at substitutable position(s). Preferable examples of the substituent(s) that "$C_{2-6}$ alkenylene" may have include $C_{1-6}$ alkyl, $C_{1-6}$ alkoxy, hydroxy, halogen atom and the like.

The "$C_{2-6}$ alkynylene" of the "$C_{2-6}$ alkynylene optionally having substituent(s)" is straight chain or branched chain alkynylene having 2 to 6 carbon atoms, which has triple bond(s) at any position of the above-mentioned "$C_{1-6}$ alkylene". The position and number of the triple bond are not particularly limited. As "$C_{2-6}$ alkynylene", ethynylene, 1-propynylene, 2-propynylene, 1-butynylene, 2-butynylene, 3-butynylene, 1-pentynylene and the like can be mentioned, and ethynylene, 1-propynylene and 2-propynylene can be preferably mentioned. When "$C_{2-6}$ alkynylene" has "substituent(s)", the kind and number thereof are not particularly limited, and $C_{2-6}$ alkynylene has 1 to 3 substituents selected from the "substituents" defined below at substitutable position(s). Preferable examples of the substituent(s) that "$C_{2-6}$ alkynylene" may have include $C_{1-6}$ alkyl, $C_{1-6}$ alkoxy, hydroxy, halogen atom and the like.

The "$C_{3-8}$ cycloalkylidene" of the "$C_{3-8}$ cycloalkylidene optionally having substituent(s)" means monocyclic to tricyclic cycloalkylidene (including "crosslinked cycloalkylidene") having 3 to 8 carbon atoms and, for example, cyclopropylidene, cyclobutylidene, cyclopentylidene, cyclohexylidene, cycloheptylidene, cyclooctylidene, norbornylidene, bicyclo[2.2.1]heptylidene or bicyclo[2.2.2]octylidene and the like can be mentioned, and cyclopropylidene, cyclobutylidene, cyclopentylidene and cyclohexylidene can be preferably mentioned.

When "$C_{3-8}$ cycloalkylidene" has "substituent(s)", the kind and number thereof are not particularly limited, and $C_{3-8}$ cycloalkylidene has 1 to 4 substituents selected from the "substituents" defined below at substitutable position(s). Preferable examples of the substituent(s) that $C_{3-8}$ cycloalkylidene may have include $C_{1-6}$ alkyl, $C_{1-6}$ alkoxy, hydroxy, amino, halogen atom, $C_{1-6}$ haloalkyl, $C_{1-6}$ haloalkoxy and the like.

As the "ring" of the "ring optionally having substituent(s) formed by $R^5$ and $R^6$ together with the atoms bonded thereto" in —$NR^5CONR^6$— wherein $R^5$ and $R^6$ may be the same or different and each is hydrogen atom or alkyl, or $R^5$ and $R^6$ in combination optionally form a ring together with the atoms bonded thereto, for Y, "nitrogen-containing saturated heterocycle" (e.g., 1,3-imidazolidin-2-one, 3,4,5,6-tetrahydro-2 (1H)-pyrimidinone and the like) included in the "heterocyclic group" defined above can be mentioned.

When the "ring" has "substituent(s)", the kind and number thereof are not particularly limited, and ring has 1 to 3 substituents selected from the "substituents" defined below at substitutable position(s). Preferable examples of the substituent(s) that the "ring" may have include $C_{1-6}$ alkyl, $C_{1-6}$ alkoxy, hydroxy, halogen atom and the like.

"$C_{3-8}$ cycloalkyl" of the "$C_{3-8}$ cycloalkyl optionally having substituent(s)" means monocyclic to tricyclic cycloalkyl (including "crosslinked cycloalkyl") having 3 to 8 carbon atoms and, for example, cyclopropyl, cyclobutyl, cyclopentyl, cyclohexyl, cycloheptyl, cyclooctyl, norbornyl, bicyclo[2.2.1]heptyl or bicyclo[2.2.2]octyl and the like can be mentioned, and cyclopropyl, cyclobutyl, cyclopentyl and cyclohexyl can be preferably mentioned.

When "$C_{3-8}$ cycloalkyl" has "substituent(s)", the kind and number thereof are not particularly limited, and $C_{3-8}$ cycloalkyl has 1 to 4 substituents selected from the "substituents" defined below at substitutable position(s). Preferable examples of the substituent(s) that the $C_{3-8}$ cycloalkyl may have include $C_{1-6}$ alkyl, $C_{1-6}$ alkoxy, hydroxy, halogen atom and the like.

The "$C_{1-6}$ alkoxy" of the "$C_{1-6}$ alkoxy optionally having substituent(s)" means straight chain or branched chain alkoxy having 1 to 6 carbon atoms and, for example, methoxy, ethoxy, n-propoxy, isopropoxy, n-butoxy, isobutoxy, secondary butoxy, tertiary butoxy, pentoxy, isopentoxy, neopentoxy, tertiary pentoxy, 1-methylbutoxy, 2-methylbutoxy, 1,2-dimethylpropoxy, 1-ethylpropoxy, hexyloxy, isohexyloxy, 1-methylpentoxy, 2-methylpentoxy, 3-methylpentoxy, 1,1-dimethylbutoxy, 1,2-dimethylbutoxy, 2,2-dimethylbutoxy, 1-ethylbutoxy, 1,1,2-trimethylpropoxy, 1,2,2-trimethylpropoxy, 1-ethyl-2-methylpropoxy, 1-ethyl-1-methylpropoxy and the like can be mentioned.

Preferable examples of "$C_{1-6}$ alkoxy" include methoxy, ethoxy, n-propoxy, isopropoxy, n-butoxy and the like, and more preferable examples include methoxy, ethoxy and the like.

When "$C_{1-6}$ alkoxy" has substituent(s), the kind and number thereof are not particularly limited, and $C_{1-6}$ alkoxy has 1 to 4 substituents selected from the "substituents" defined below at substitutable position(s), and the kind and number of the substituent are not particularly limited. Preferable examples of the substituent(s) that the "$C_{1-6}$ alkoxy" may have include $C_{1-6}$ alkyl, $C_{1-6}$ alkoxy, hydroxy, halogen atom and the like.

The "mono- or di-$C_{1-6}$ alkylamino" of the "mono- or di-$C_{1-6}$ alkylamino optionally having substituent(s)" is alkylamino mono- or di-substituted by linear or branched chain alkyl having 1 to 6 carbon atoms (total carbon number of dialkylamino is 2 to 12), and shows methylamino, dimethylamino, ethylamino, diethylamino, methylethylamino, propylamino, dipropylamino, isopropylamino, diisopropylamino, butylamino, dibutylamino, isobutylamino, sec-butylamino, tert-butylamino, pentylamino, hexylamino and the like.

Preferable examples of "mono- or di-$C_{1-6}$ alkylamino" include methylamino, dimethylamino, ethylamino, diethylamino, methylethylamino, propylamino, dipropylamino, isopropylamino, diisopropylamino and the like, and more preferable examples include methylamino, dimethylamino, ethylamino, diethylamino, methylethylamino, propylamino and the like.

When "mono- or di-$C_{1-6}$ alkylamino" has "substituent(s)", the kind and number thereof are not particularly limited, and mono- or di-$C_{1-6}$ alkylamino has 1 to 4 substituents selected from the "substituents" defined below at substitutable position(s). Preferable examples of the substituent(s) that the mono- or di-$C_{1-6}$ alkylamino may have include $C_{1-6}$ alkyl, $C_{1-6}$ alkoxy, hydroxy, halogen atom and the like.

The "$C_{1-7}$ acylamino" of the "$C_{1-7}$ acylamino optionally having substituent(s)" is acylamino wherein the acyl moiety is alkanoyl having 1 to 7 carbon atoms (e.g., formyl, acetyl, propionyl, butyryl, valeryl, pivaloyl etc.), alkenoyl having 3 to 7 carbon atoms (e.g., acryloyl, methacryloyl, crotonoyl etc.), alkynoyl having 3 to 7 carbon atoms (e.g., propioloyl etc.), benzoyl and the like, and shows acetylamino, propionylamino, butyrylamino, valerylamino, pivaloylamino, benzoylamino and the like.

Preferable examples of "$C_{1-7}$ acylamino" include acetylamino, propionylamino, butyrylamino, valerylamino, pivaloylamino, benzoylamino and the like, and more preferable examples thereof include acetylamino, propionylamino, benzoylamino and the like.

When "$C_{1-7}$ acylamino" has "substituent(s)", the kind and number thereof are not particularly limited, and $C_{1-7}$ acylamino has 1 to 4 substituents selected from the "substituents" defined below at substitutable position(s). Preferable examples of the substituent(s) that the $C_{1-7}$ acylamino may have include $C_{1-6}$ alkyl, $C_{1-6}$ alkoxy, hydroxy, halogen atom and the like.

When "sulfonylamino optionally having substituent(s)" has "substituent(s)", the kind and number thereof are not particularly limited, and sulfonylamino has substituent(s) selected from the "substituents" defined below at the amino group. Preferable examples of the substituent(s) that the sulfonylamino may have include amino, $C_{1-6}$ alkyl, aryl, heteroaryl and the like.

When "hydrazino optionally having substituent(s)" has "substituent(s)", the kind and number thereof are not particularly limited, and hydrazino has 1 to 3 substituents selected from the "substituents" defined below at substitutable position(s). Preferable examples of the substituent(s) that hydrazino may have include $C_{1-6}$ alkyl, aryl, heteroaryl and the like. Examples of aryl and heteroaryl are as mentioned above.

When "guanidino optionally having substituent(s)" has "substituent(s)", the kind and number thereof are not particularly limited, and guanidino has 1 to 3 substituents selected from the "substituents" defined below at substitutable position(s). Preferable examples of the substituent(s) that guanidino may have include hydroxy, nitro, cyano and the like.

When "amidino optionally having substituent(s)" has "substituent(s)", the kind and number thereof are not particularly limited, and amidino has 1 to 3 substituents selected from the "substituents" defined below at substitutable position(s). Preferable examples of the substituent(s) that amidino may have include hydroxy, nitro, cyano and the like.

The "substituent" of each of the above-mentioned groups optionally having substituents is not particularly limited and, for example, halogen atom (e.g., fluorine atom, chlorine atom, bromine atom, iodine atom), $C_{1-6}$ alkyl (e.g., straight chain or branched chain alkyl group having 1 to 6 carbon atoms such as methyl, ethyl, n-propyl, isopropyl, n-butyl, isobutyl, sec-butyl, tert-butyl, pentyl, isopentyl, neopentyl, tertiary pentyl, 1-methylbutyl, 2-methylbutyl, 1,2-dimethylpropyl, 1-ethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl and the like), $C_{3-8}$ cycloalkyl (e.g., cyclopropyl, cyclobutyl, cyclopentyl, cyclohexyl, cycloheptyl, cyclooctyl, norbornyl, bicyclo[2.2.1]heptyl or bicyclo[2.2.2]octyl etc.), $C_{3-8}$ cycloalkyloxy (e.g., cyclopropyloxy, cyclobutyloxy, cyclopentyloxy, cyclohexyloxy, cycloheptyloxy, cyclooctyloxy, norbornyloxy, bicyclo[2.2.1]heptyloxy or bicyclo[2.2.2]octyloxy etc.), $C_{1-6}$ haloalkyl (e.g., the above-mentioned $C_{1-6}$ alkyl having at least one halogen atom mentioned above such as trifluoromethyl and the like), $C_{1-6}$ alkoxy (e.g., straight chain or branched chain alkoxy having 1 to 6 carbon atoms such as methoxy, ethoxy, n-propoxy, isopropoxy, n-butoxy, isobutoxy, secondary butoxy, tertiary butoxy, pentoxy, isopentoxy, neopentoxy, tertiary pentoxy, 1-methylbutoxy, 2-methylbutoxy, 1,2-dimethylpropoxy, 1-ethylpropoxy, hexyloxy, isohexyloxy, 1-methylpentoxy, 2-methylpentoxy, 3-methylpentoxy, 1,1-dimethylbutoxy, 1,2-dimethylbutoxy, 2,2-dimethylbutoxy, 1-ethylbutoxy, 1,1,2-trimethylpropoxy, 1,2,2-trimethylpropoxy, 1-ethyl-2-methylpropoxy, 1-ethyl-1-methylpropoxy and the like), $C_{1-6}$ haloalkoxy (e.g., the above-mentioned $C_{1-6}$ alkoxy having at least one of the above-mentioned halogen atoms such as trifluoromethoxy and the like), $C_{6-14}$ aryl (e.g., phenyl, naphthyl, anthryl etc.), $C_{6-14}$ aryloxy (e.g., phenyloxy, naphthyloxy, anthryloxy etc.), hydroxy, nitro, amino, mono- or di-$C_{1-6}$ alkylamino (e.g., methylamino, ethylamino, dimethylamino, diethylamino, propylamino, isopropylamino, butylamino, diisopropylamino etc.), mono- or di-($C_{3-8}$ cycloalkyl)amino (e.g., cyclopropylamino, cyclobutylamino, cyclopentylamino, cyclohexylamino, cycloheptylamino, cyclooctylamino, norbornylamino, bicyclo[2.2.1]heptylamino, bicyclo[2.2.2]octylamino, dicyclopropylamino, dicyclobutylamino, dicyclopentylamino, dicyclohexylamino, dicycloheptylamino, dicyclooctylamino, dinorbornylamino, di(bicyclo[2.2.1]heptyl)amino, di(bicyclo[2.2.2]octyl)amino etc.), mono- or di-($C_{6-14}$ aryl)amino (e.g., phenylamino, naphthylamino, anthrylamino, diphenylamino etc.), $C_{1-11}$ acyl [for example, $C_{1-7}$ alkanoyl (e.g., formyl, acetyl, propionyl, butyryl, isobutyryl, valeryl, isovaleryl, pivaloyl etc.), $C_{3-7}$ alkenoyl (e.g., acryloyl, methacryloyl, crotonoyl etc.), $C_{3-7}$ alkynoyl (e.g., propioloyl etc.), $C_{7-11}$ aroyl (e.g., benzoyl, 1-naphthoyl, 2-naphthoyl etc.) etc.], mono- or di-($C_{1-11}$ acyl)amino (e.g., amino having the above-mentioned $C_{1-11}$ acyl such as acetylamino, benzoylamino and the like), mono- or di-($C_{1-6}$ alkoxy-carbonyl)amino (e.g., methoxycarbonylamino, ethoxycarbonylamino etc.), sulfonylamino, amino-$C_{1-6}$ alkyl (e.g., aminomethyl, aminoethyl etc.), mono- or di-($C_{1-6}$ alkyl)amino-$C_{1-6}$ alkyl (e.g., methylaminomethyl, ethylaminomethyl etc.), $C_{3-8}$ cyclic amino (e.g., aziridino, azetidino, pyrrolidino, piperidino etc.), hydrazino, guanidino, amidino, hydroxyamidino, $C_{1-6}$ alkoxyamidino (e.g., methoxyamidino, ethoxyamidino etc.), aminomethyleneamino, imino, carboxy, $C_{1-6}$ alkoxy-carbonyl (e.g., methoxycarbonyl, ethoxycarbonyl, propoxycarbonyl, isopropoxycarbonyl, butoxycarbonyl, isobutoxycarbonyl, tertiary butoxycarbonyl, pentyloxycarbonyl etc.), carbamoyl, mono- or di-($C_{1-6}$ alkyl)aminocarbonyl (e.g., methylaminocarbonyl, ethylaminocarbonyl, propylaminocarbonyl, isopropylaminocarbonyl, butylaminocarbonyl, sec-butylaminocarbonyl, tert-butylaminocarbonyl, dimethylaminocarbonyl, diethylaminocarbonyl, ethylmethylaminocarbonyl, dipropylaminocarbonyl, methylpropylaminocarbonyl, diisopropylaminocarbonyl etc.), mono- or di-($C_{6-14}$ aryl)aminocarbonyl (e.g., phenylaminocarbonyl, naphthylaminocarbonyl etc.), cyano, $C_{7-13}$ aralkyl (e.g., $C_{1-3}$ alkyl having $C_{6-10}$ aryl such as benzyl, 1-phenylethyl, 2-phenylethyl, 1-phenylpropyl, 3-phenylpropyl, 1-phenylbutyl, 4-phenylbutyl, 1-naphthylmethyl, 2-naphthylmethyl, 1-(1-naphthyl)ethyl, 2-(1-naphthyl)ethyl, 1-(2-naphthyl)ethyl, 2-(2-naphthyl)ethyl and the like), mono- or di-($C_{7-13}$ aralkyl) aminocarbonyl (e.g., benzylaminocarbonyl, 2-phenylethylaminocarbonyl etc.), heteroaryl (e.g., pyrrolyl, furyl, thienyl, imidazolyl, pyrazolyl, thiazolyl, isothiazolyl, oxazolyl, isoxazolyl, triazolyl, oxadiazolyl, thiadiazolyl, pyridyl, pyrazinyl, pyrimidinyl, pyridazinyl, azepinyl, diazepinyl etc.), heteroaryl-$C_{1-3}$ alkyl (e.g., the above-mentioned $C_{1-3}$ alkyl having the above-mentioned heteroaryl such as 2-pyridylmethyl, 3-pyridylmethyl, 4-pyridylmethyl, 1-(2-pyridyl)ethyl, 1-(3-pyridyl)ethyl, 1-(4-pyridyl)ethyl, 2-(2-pyridyl)ethyl, 2-(3-pyridyl)ethyl, 2-(4-pyridyl)ethyl, 3-(2-pyridyl)propyl and the like), mono- or di-(heteroaryl-$C_{1-3}$ alkyl)aminocarbonyl (e.g., 2-pyridylmethylaminocarbonyl, 3-pyridylmethylaminocarbonyl etc.), hydroxy, mercapto, $C_{1-6}$ alkylthio (e.g., methylthio, ethylthio etc.), $C_{6-14}$ arylthio (e.g., phenylthio, naphthylthio etc.), —$SO_3H$, —$SO_2NH_2$, sulfonamide, oxo or thioxo and the like can be mentioned.

In the formula (1), ring A is aryl optionally having substituent(s), or heteroaryl optionally having substituent(s), and is preferably phenyl optionally having substituent(s).

As the substituent of ring A, halogen atom (e.g., fluorine atom, chlorine atom etc., particularly chlorine atom), $C_{1-6}$ alkyl optionally having substituent(s) (e.g., $C_{1-6}$ alkyl optionally substituted by halogen atom(s), particularly methyl, trifluoromethyl) or $C_{1-6}$ alkoxy optionally having substituent(s) (e.g., $C_{1-6}$ alkoxy optionally substituted by halogen atom(s), particularly methoxy) and the like are preferable.

The ring A is particularly preferably phenyl substituted by 1 or 2 fluorine atoms or chlorine atoms, more preferably phenyl substituted by fluorine atom(s) or chlorine atom(s) at the 3-position and/or the 4-position, more preferably 3,4-dichlorophenyl or 3,4-difluorophenyl.

Ring B is arylene optionally having substituent(s), divalent heterocyclic group optionally having substituent(s), $C_{3-8}$ cycloalkylene optionally having substituent(s), preferably arylene optionally having substituent(s), or heteroarylene optionally having substituent(s). Preferable examples of ring B include phenylene, thienylene, pyridylene, thiazolylene optionally substituted by methyl, 1,3,4-thiadiazolylene, pyridazinylene which is optionally substituted by oxo, and optionally partially hydrogenated, indenothiazolylene, naphtothiazolylene, thiazolopyridylene and benzothiazolylene, thiazolopyridylene optionally partially hydrogenated, isoxazolylene, pyrimidinylene, chromenylene optionally substituted by oxo, quinazolinylene, benzoazepinylene, thienopyridylene, indanylene optionally substituted by oxo, furylene, naphthylene, imidazolylene, pyrazinylene, cyclopentylene and tetrazolylene, more preferable examples thereof include phenylene, thienylene, thiazolylene, 1,3,4-thiadiazolylene, and pyridazinylene which is optionally substituted by oxo and optionally partially hydrogenated. As a more preferable embodiment, thiazolylene can be mentioned. As a still more preferable other embodiment, 1,3,4-thiadiazolylene can be mentioned. As a yet more preferable other embodiment, optionally partially hydrogenated pyridazinylene, which is optionally substituted by oxo, can be mentioned. As the substituent of ring B, $C_{1-6}$ alkyl, oxo and the like are preferable, and methyl is more preferable.

m is an integer of 0 to 2, preferably 0 or 2, and more preferably 0.

n is an integer of 1 to 5, preferably 1 to 3, and more preferably 1.

X is a bond, —NH—, —$NR^1$— wherein $R^1$ is $C_{1-6}$ alkyl optionally having substituent(s), hereinafter the same, —CO—, —$CO_2$—, —OCO—, —$CONR^a$— wherein $R^a$ is hydrogen atom or $C_{1-6}$ alkyl optionally having substituent(s), hereinafter the same, —$NR^aCO$—, —$NR^2CONR^3$— wherein $R^2$ and $R^3$ may be the same or different and each is hydrogen atom or $C_{1-6}$ alkyl optionally having substituent(s). Alternatively, $R^2$ and $R^3$ in combination optionally form, together with the atoms bonded thereto, a ring optionally having substituent(s), hereinafter the same, oxygen atom, sulfur atom, —SO—, —$SO_2$—, —$NR^aSO_2$—, —$SO_2NR^a$—, $C_{1-6}$ alkylene optionally having substituent(s), $C_{2-6}$ alkenylene optionally having substituent(s), $C_{2-6}$ alkynylene optionally having substituent(s), —O—$X^a$— wherein $X^a$ is $C_{1-6}$ alkylene optionally having substituent(s), hereinafter the same, —$X^a$—O—, —CO—$X^a$, —$X^a$—CO—, —$CONR^a$—$X^a$—, —$X^a$—$CONR^a$—, —$NR^aCO$—$X^a$—, —$X^a$—$NR^aCO$—, —S—$X^a$—, —$X^a$—S—, —SO—$X^a$—, —$X^a$—SO—, —$NR^a$—$X^a$—, —$X^a$—$NR^a$—, —$SO_2$—$X^a$—, —$X^a$—$SO_2$—, —C(=N—$CO_2$—$R^1$)—, —C(=N—$SO_2$—$R^1$)—, —C(=N—$SO_2NH_2$)—, —C(=CH—$NO_2$)—, —C(=N—CN)—, or $C_{3-8}$ cycloalkylidene optionally having substituent(s); preferably a bond, —NH—, —$NR^1$—, —CO—, —$CO_2$—, —OCO—, —$CONR^a$—, —$NR^aCO$—, —$NR^2CONR^3$—, oxygen atom, sulfur atom, —SO—, —$SO_2$—, —$NR^aSO_2$—, —$SO_2NR^a$, $C_{2-6}$ alkenylene optionally having substituent(s), —CO—$X^a$—, —$X^a$—CO—, —$CONR^a$—$X^a$—, —$X^a$—$CONR^a$—, —$NR^aCO$—$X^a$—, —$X^a$—$NR^aCO$— or $C_{3-8}$ cycloalkylidene optionally having substituent(s); more preferably a bond, —CO—, —$CONR^a$—, —$NR^aCO$—, —CO—$X^a$—, —$X^a$—CO—, —$CONR^a$—$X^a$—, —$X^a$—$CONR^a$—, —$NR^aCO$—$X^a$— or —$X^a$—$NR^aCO$—. Still more preferably, it is a bond, —CO—, —CO—$X^a$—, —$X^a$—CO—, —$NR^aCO$—$X^a$— or —$X^a$—$NR^aCO$—, yet more preferably a bond, —CO—, —CO—$X^a$—, and further more preferably —CO—$X^a$— or —$X^a$—CO—.

$R^1$ is $C_{1-6}$ alkyl optionally having substituent(s), preferably $C_{1-3}$ alkyl; $R^2$ and $R^3$ may be the same or different and each is hydrogen atom or $C_{1-6}$ alkyl optionally having substituent(s), preferably hydrogen atom or $C_{1-3}$ alkyl; $R^a$ is hydrogen atom or $C_{1-6}$ alkyl optionally having substituent(s), preferably hydrogen atom or $C_{1-3}$ alkyl; $X^a$ is $C_{1-6}$ alkylene optionally having substituent(s), preferably $C_{1-3}$ alkylene.

Y is a bond, —NH—, —$NR^4$— wherein $R^4$ is $C_{1-6}$ alkyl optionally having substituent(s), hereinafter the same, —CO—, —$CO_2$—, —OCO—, —$CONR^b$— wherein $R^b$ is hydrogen atom or $C_{1-6}$ alkyl optionally having substituent(s), hereinafter the same, —$NR^bCO$—, —$NR^5CONR^6$— wherein R⁵ and R⁶ may be the same or different and each is hydrogen atom or $C_{1-6}$ alkyl optionally having substituent(s). Or, R⁵ and R⁶ in combination optionally form, together with the atoms bonded thereto, a ring optionally having substituent (s), hereinafter the same, oxygen atom, sulfur atom, —SO—, —SO$_2$—, —NR$^b$SO$_2$—, —SO$_2$NR$^b$—, $C_{1-6}$ alkylene optionally having substituent(s), $C_{2-6}$ alkenylene optionally having substituent(s), $C_{2-6}$ alkynylene optionally having substituent (s), —O—X$^b$— wherein X$^b$ is $C_{1-6}$ alkylene optionally having substituent(s), hereinafter the same, —X$^b$—O—, —CO—X$^b$—, —X$^b$—CO—, —CONR$^b$—X$^b$—, —X$^b$—CONR$^b$—, —NR$^b$CO—X$^b$—, —X$^b$—NR$^b$CO—, —S—X$^b$—, —X$^b$—S—, —SO—X$^b$—, —X$^b$—SO—, —NR$^b$—X$^b$—, —X$^b$—NR$^b$—, —SO$_2$—X$^b$—, —X$^b$—SO$_2$—, —C(=N—CO$_2$—R⁴)—C(=N—SO$_2$—R⁴)—, —C(=N—SO$_2$NH$_2$)—, —C(=CH—NO$_2$)— or —C(=N—CN)—; preferably a bond, —NH—, —NR⁴—, —CO—, —CO$_2$—, —OCO—, —CONR$^b$—, —NR$^b$CO—, —NR⁵CONR⁵—, oxygen atom, sulfur atom, —SO—, —SO$_2$—, —NR$^b$SO$_2$—, —SO$_2$NR$^b$—, —CO—X$^b$—, —X$^b$—CO—, —CONR$^b$—X$^b$—, —X$^b$—CONR$^b$—, —NR$^b$CO—X$^b$— or —X$^b$—NR$^b$CO—; more preferably, a bond, —CO—, —CONR$^b$—, —NR$^b$CO—, —CO—X$^b$—, —X$^b$CO—, —CONR$^b$—X$^b$—, —X$^b$—CONR$^b$—, —NR$^b$CO—X— or —X$^b$—NR$^b$CO—. Y is more preferably a bond, —CO—, —CO—X$^b$—, —X$^b$—CO—, —NR$^b$CO—X$^b$— or —X$^b$—NR$^b$CO—, still more preferably a bond, —CO—, —CO—X$^b$— or —X$^b$—CO—, yet more preferably a bond, —CO—X$^b$— or —X$^b$—CO—, further more preferably a bond.

R⁴ is $C_{1-6}$ alkyl optionally having substituent(s), preferably $C_{1-3}$ alkyl; R⁵ and R⁶ may be the same or different and each is hydrogen atom or $C_{1-6}$ alkyl optionally having substituent(s), preferably hydrogen atom or $C_{1-3}$ alkyl; R$^b$ is hydrogen atom or $C_{1-6}$ alkyl optionally having substituent(s), preferably hydrogen atom or $C_{1-3}$ alkyl; X$^b$ is $C_{1-6}$ alkylene optionally having substituent(s), preferably $C_{1-3}$ alkylene.

Z is hydrogen atom, halogen atom, $C_{1-6}$ alkyl optionally having substituent(s), $C_{3-8}$ cycloalkyl optionally having substituent(s), aryl optionally having substituent(s), heterocyclic group optionally having substituent(s), hydroxy, nitro, amino, cyano, $C_{1-6}$ alkoxy optionally having substituent(s), mono- or di-$C_{1-6}$ alkylamino optionally having substituent (s), $C_{1-7}$ acylamino optionally having substituent(s), sulfonylamino optionally having substituent(s), hydrazino optionally having substituent(s), guanidino optionally having substituent(s), or amidino optionally having substituent(s);
preferably hydrogen atom, halogen atom, $C_{1-6}$ alkyl optionally having substituent(s), $C_{3-8}$ cycloalkyl optionally having substituent(s), aryl optionally having substituent(s), heterocyclic group optionally having substituent(s), hydroxy, nitro, amino, cyano, $C_{1-6}$ alkoxy optionally having substituent(s), mono- or di-$C_{1-6}$ alkylamino optionally having substituent (s), $C_{1-7}$ acylamino optionally having substituent(s), sulfonylamino optionally having substituent(s), hydrazino optionally having substituent(s), guanidino optionally having substituent(s), or amidino optionally having substituent(s);
more preferably, hydrogen atom, hydroxy, amino, $C_{1-6}$ alkyl optionally having substituent(s), $C_{1-6}$ alkoxy optionally having substituent(s), aryl optionally having substituent(s) or a heterocyclic group optionally having substituent(s). More preferably, Z is hydrogen atom, hydroxy or amino, still more preferably hydroxy or amino. As a still more preferable embodiment, hydroxy can be mentioned. As a yet more preferable other embodiment, amino can be mentioned.

Preferable examples of the group represented by Z-Y—X— include hydrogen atom, carboxyl, carboxymethyl, amino, carbamoyl, carbamoylmethyl, (2-amino-2-oxoethyl) aminocarbonyl and the like.

As the compound represented by the formula (1), a compound represented by the formula (1a)

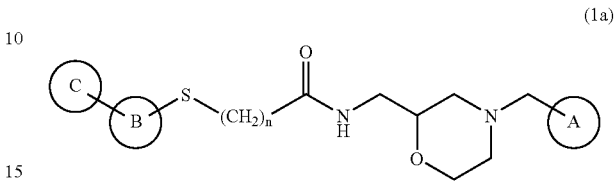

(1a)

wherein ring C is aryl optionally having substituent(s) or heteroaryl, and other symbols are as defined above, is also preferable.

In the formula (1a), ring C is preferably phenyl, pyridyl, 1,2,4-oxadiazolyl which may be partially hydrogenated, 1,2, 4-triazolyl, tetrazolyl, isoxazolyl and the like.

As the substituent of ring C, $C_{1-6}$ alkyl, $C_{1-6}$ alkoxy, hydroxy, nitro, amino, cyano, carboxy, $C_{1-6}$ alkoxy-carbonyl, carbamoyl, oxo and the like are preferable, and methoxy, hydroxy, amino, carboxy, methyl, carbamoyl and oxo are more preferable.

More preferable specific compounds of the formula (1) include (2S)-[4-(carboxymethyl)thiazol-2-ylthio]-N-{[4-(3, 4-dichlorobenzyl)morpholin-2-yl]methyl}acetamide, (2S)-[4-(3-aminophenyl)thiazol-2-ylthio]-N-{[4-(3,4-dichlorobenzyl)morpholin-2-yl]methyl}acetamide, (2S)-[4-(3-carbamoyl-4-hydroxyphenyl)thiazol-2-ylthio]-N-{[4-(3,4-dichlorobenzyl)morpholin-2-yl]methyl}acetamide, (2S)-N-{[4-(3,4-dichlorobenzyl)morpholin-2-yl]methyl}-[4-(pyridin-4-yl)thiazol-2-ylthio]acetamide, (2S)-N-{[4-(3,4-dichlorobenzyl)morpholin-2-yl]methyl}-[4-(3,4-dimethoxyphenyl)thiazol-2-ylthio]acetamide, (2S)-(4-carbamoylthiazol-2-ylthio)-N-{[4-(3,4-dichlorobenzyl) morpholin-2-yl]methyl}acetamide, (2S)-{4-[(2-amino-2-oxoethyl)aminocarbonyl]thiazol-2-ylthio}-N-{[4-(3,4-dichlorobenzyl)morpholin-2-yl]methyl}acetamide, (2S)-N-{[4-(3,4-dichlorobenzyl)morpholin-2-yl]methyl}-[4-(5-methyl-1,2,4-oxadiazol-3-yl)thiazol-2-ylthio]acetamide hydrochloride, (2S)-(5-amino-8H-indeno[1,2-d]thiazol-2-ylthio)-N-{[4-(3,4-dichlorobenzyl)morpholin -2-yl] methyl}acetamide, (2S)-(4-carboxyphenylthio)-N-{[4-(3,4-dichlorobenzyl)morpholin-2-yl]methyl}acetamide, (2S)-{4-[(2-amino-2-oxoethyl)aminocarbonyl]phenylthio}-N-{[4-(3,4-dichlorobenzyl)morpholin-2-yl]methyl}acetamide, (2S)-{4-[(2-carboxyethyl)aminocarbonyl]thiazol-2-ylthio}-N-{[4-(3,4-dichlorobenzyl)morpholin-2-yl] methyl}acetamide hydrochloride, (2S)-(5-acetamino-1,3,4-thiadiazol-2-ylthio)-N-{[4-(3,4-dichlorobenzyl)morpholin-2-yl]methyl}acetamide, (2S)-4-(4-carbamoylthiazol-2-ylthio)-N-{[4-(3,4-dichlorobenzyl)morpholin-2-yl] methyl}butyramide hydrochloride, (2S)-N-{[4-(3,4-dichlorobenzyl)morpholin-2-yl]methyl}-[4-(1H-tetrazol-5-yl)thiazol-2-ylthio]acetamide, (2S)-N-{[4-(3,4-dichlorobenzyl)morpholin-2-yl]methyl}-([1,3]thiazolo[5,4-b]pyridin-2-ylthio)acetamide, (2S)-(E)-[4-(2-carbamoylethen-1-yl)thiazol-2-ylthio]-N-{[4-(3,4-dichlorobenzyl)morpholin-2-yl]methyl}acetamide, (2S)-[4-(carbamoylmethyl)thiazol-2-ylthio]-N-{[4-(3,4-difluorobenzyl)morpholin-2-yl]methyl}acetamide, (2S)-[4-(carbamoylmethyl)thiazol-2-ylthio]-N-{[4-(4-fluorobenzyl)

morpholin-2-yl]methyl}acetamide, (2S)-(4-carboxy-5-methylthiazol-2-ylthio)-N-{[4-(3,4-dichlorobenzyl)morpholin-2-yl]methyl}acetamide, (2S)-(4-carbamoyl-5-methylthiazol-2-ylthio)-N-{[4-(3,4-dichlorobenzyl)morpholin-2-yl]methyl}acetamide, (2S)-(4-carbamoylthiazol-2-ylthio)-N-{[4-(3-chloro-4-fluorobenzyl)morpholin-2-yl]methyl}acetamide, (2S)-[4-(2-amino-2-oxoethyl)aminocarbonylthiazol-2-ylthio]-N-{[4-(3,4-difluorobenzyl)morpholin-2-yl]methyl}acetamide, (2S)-(5-amino-1,3,4-thiadiazol-2-ylthio)-N-{[4-(3-chlorobenzyl)morpholin-2-yl]methyl}acetamide, (2S)-(5-amino-1,3,4-thiadiazol-2-ylthio)-N-{[4-(3,4-difluorobenzyl)morpholin-2-yl]methyl}acetamide, (2S)-N-{[4-(3,4-dichlorobenzyl)morpholin-2-yl]methyl}-(pyrimidin-2-ylthio)acetamide, (2S)-(3-acetyl-2-oxo-2H-chromen-6-ylthio)-N-{[4-(3,4-dichlorobenzyl)morpholin-2-yl]methyl}acetamide, (2S)-N-{[4-(3,4-difluorobenzyl)morpholin-2-yl]methyl}-(6-oxo-1,6-dihydropyridazin-3-ylthio)acetamide, (2S)-[6-(carbamoylmethyl)pyrazin-2-ylthio]-N-{[4-(3,4-dichlorobenzyl)morpholin-2-yl]methyl}acetamide, and (2S)-4-(cyclopentanesulfonyl)-N-{[4-(3-chloro-4-fluorobenzyl)morpholin-2-yl]methyl}butyramide.

Since the compound of the formula (1) and a pharmaceutically acceptable salt thereof may be present in the form of a hydrate or a solvate (e.g., ethanol solvate etc.), hydrates and solvates thereof are also encompassed in the present invention. In addition, since the compound of the formula (1) has an asymmetric atom, at least two kinds of optical isomers are present. The optical isomer and racemate thereof are encompassed in the present invention.

The compound of the formula (1) can be synthesized by the following methods (1) to (11), a method according to the method, a method known to those of ordinary skill in the art in the organic synthesis, and a method according to the method described in WO97/24325, WO98/25617, WO98/02151, WO98/04554, WO00/34278, WO99/55324, WO99/55330, WO00/58305, WO00/31033, WO00/53600, WO01/14333, WO02/66460, WO02/88111, WO02/18335, WO02/26722, WO02/26723, WO03/82292, WO03/82294, WO03/82861, WO03/82862, WO03/82295, WO03/82863, WO03/99287, WO03/99798 (these references are incorporated into the present specification by reference).

The following methods (1) to (11) show examples of the production method of the compound (the compound of the formula (1)) of the present invention, which are not to be construed as limitative.

The compounds of the formulas (2) to (26) to be used for the following methods (1) to (11) can be synthesized by a method known to those of ordinary skill in the art in the organic synthesis, and a method according to the methods described in the above-mentioned references and the like.

The term "substituent necessary for construction of heteroaryl (including heteroarylene)" used for the explanation of the following synthetic methods means a substituent necessary for construction of heteroaryl, with an acidic or basic catalyst, light, heat and the like and, in most cases, by an addition reaction or a condensation reaction accompanying elimination of water, alcohol, acid, halogenated hydrogen and the like.

As specific "substituent necessary for construction of heteroaryl" mentioned above, any of the combinations of bromoacetyl and thioamide for the construction of thiazole, any of the combinations of hydroxyamidine and carboxylic acid for the construction of 1,2,4-oxadiazole, any of the combinations of hydrazide and carboxylic acid for the construction of 1,3,4-oxadiazole, any of the combinations of S-methylthioamide and hydrazide for the construction of 1,2,4-triazole, any of the combinations of imidate and hydrazide and the like can be mentioned.

The term "under ice-cooling or at room temperature" used for the explanation of the following synthetic methods means 0° C. to 30° C.

Method (1)

By reacting a compound represented by the formula (2)

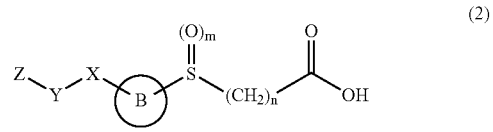

wherein each symbol is as defined above, or an acid addition salt thereof,
with a compound represented by the formula (3)

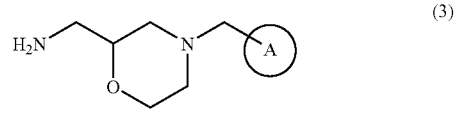

wherein each symbol is as defined above, or an acid addition salt thereof, in a suitable solvent that does not inhibit the reaction (e.g., tetrahydrofuran (hereinafter to be abbreviated as THF), dichloromethane, N,N-dimethylformamide (hereinafter to be abbreviated as DMF) or a mixed solvent thereof etc.), in the presence of a tertiary amine such as triethylamine, diisopropylethylamine and the like, and using a condensation agent [for example, dicyclohexylcarbodiimide (hereinafter to be abbreviated as DCC), N-(3-dimethylaminopropyl)-N'-ethylcarbodiimide (hereinafter to be abbreviated as EDC) or a hydrochloride thereof, 2-ethoxy-1-ethoxycarbonyl-1,2-dihydroxyquinoline (hereinafter to be abbreviated as EEDQ), carbodiimidazole (hereinafter to be abbreviated as CDI), diethylphosphoryl cyamide, benzotriazol-1-yloxy tripyrrolidinophosphonium hexafluorophosphate (hereinafter to be abbreviated as PyBOP), diphenylphosphoryl azide (hereinafter to be abbreviated as DPPA), isobutyl chloroformate, diethylacetyl chloride, trimethylacetyl chloride and the like] alone, or in combination with an additive such as N-hydroxysuccinimide (hereinafter to be abbreviated as HONSu), hydroxybenzotriazole (hereinafter to be abbreviated as HOBT), or 3-hydroxy-4-oxo-3,4-dihydro-1,2,3-benzotriazine (hereinafter to be abbreviated as HOOBT), or 4-dimethylaminopyridine (hereinafter to be abbreviated as DMAP) and the like, at a temperature of generally −30° C. to 80° C., preferably −10° C. to 25° C., for 1-24 hrs,
a compound represented by the formula (1)

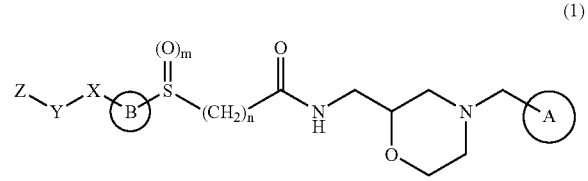

wherein each symbol is as defined above, can be obtained.

In addition, by carrying out the similar reaction using a reactive derivative of a compound of the formula (2) (e.g., acid chloride, acylimidazole etc.), a compound represented by the formula (1) can be obtained.

Generally, this reaction is carried out in a suitable solvent that does not inhibit the reaction (e.g., THF, dichloromethane, chloroform, benzene or a mixed solvent thereof etc.), in the presence of tertiary amine such as triethylamine and the like or pyridine and the like, under ice-cooling or at room temperature for 1-24 hr.

Method (2)

By reacting a compound represented by the formula (2)

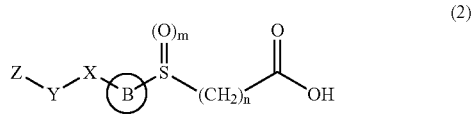
(2)

wherein each symbol is as defined above, or an acid addition salt thereof, with a compound represented by the formula (4)

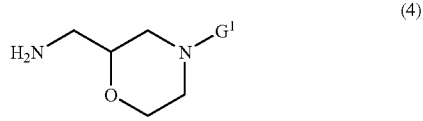
(4)

wherein $G^1$ is a protecting group (e.g., tert-butoxycarbonyl (Boc), benzyloxycarbonyl (Cbz), or an acid addition salt thereof, in a suitable solvent that does not inhibit the reaction (THF, dichloromethane, DMF or a mixed solvent thereof etc.), in the presence of a tertiary amine such as triethylamine, diisopropylethylamine and the like, and a condensation agent (same as the condensation agent described in method (1)) under ice-cooling or at room temperature for 1-24 hrs, a compound represented by the formula (5)

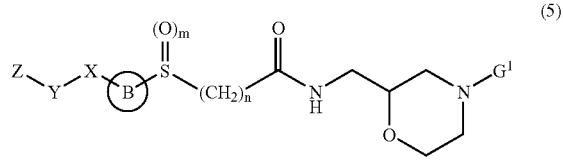
(5)

wherein each symbol is as defined above, can be obtained. The compound is deprotected, when the protecting group is a Boc group, for example, by reaction in an inert solvent such as acetonitrile, THF, 1,4-dioxane, ethyl acetate and the like, using an acid such as hydrogen chloride or trifluoroacetic acid (hereinafter to be abbreviated as TFA) and the like, generally at −30° C. to 60° C. for 10 min-24 hrs, and when the protecting group is a Cbz group, for example, by hydrogenation in an inert solvent such as methanol, ethanol, ethyl acetate and the like, in the presence of a catalyst such as palladium carbon and the like, or reaction using hydrogen bromide-acid (e.g., acetic acid and the like) for generally −30° C. to 60° C. for 10 min to 24 hrs, whereby a compound represented by the formula (6)

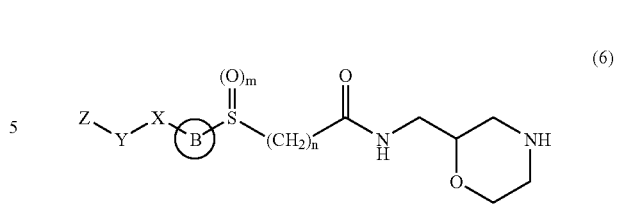
(6)

wherein each symbol is as defined above, can be obtained.

By reacting this compound with a compound represented by the formula (7)

(7)

wherein $L^1$ is a leaving group such as chlorine, bromine, iodine, methanesulfonyloxy, p-toluenesulfonyloxy, trifluoromethanesulfonyloxy and the like, and other symbols are as defined above, in a suitable solvent that does not inhibit the reaction (THF, dichloromethane, DMF or a mixed solvent thereof etc.), in the presence of a base such as triethylamine, pyridine, DMAP, potassium carbonate, sodium hydrogen carbonate, sodium hydroxide and the like, under ice-cooling or at room temperature for 1-24 hrs, a compound represented by the formula (1)

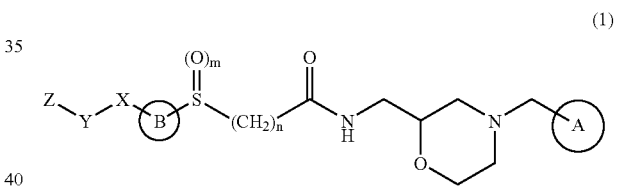
(1)

wherein each symbol is as defined above, can be obtained.

In addition, by reacting a compound of the formula (6) with an aldehyde compound represented by the formula (8)

(8)

wherein each symbol is as defined above, in the presence of sodium borohydride, sodium cyanoborohydride, sodium triacetoxyborohydride and the like, in a suitable solvent that does not inhibit the reaction (methanol, ethanol, dichloromethane, THF, acetonitrile, 1,4-dioxane etc.), using, where necessary, an acidic catalyst such as acetic acid, p-toluenesulfonic acid, boron trifluoride-diethyl ether complex and the like, generally at 0° C. to 100° C. for 10 min to 24 hrs, a compound represented by the formula (1)

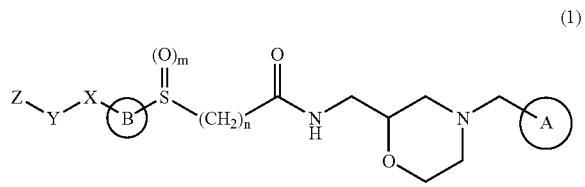

wherein each symbol is as defined above, can be obtained.

Method (3)

A compound of the formula (1), wherein X is —CONH—$(CH_2)_q$— wherein q is an integer of 0 to 6, can also be synthesized by the following method.

That is, by reacting a compound represented by the formula (9)

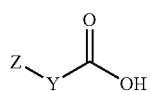

wherein each symbol is as defined above, or an acid addition salt thereof, with a compound represented by the formula (10)

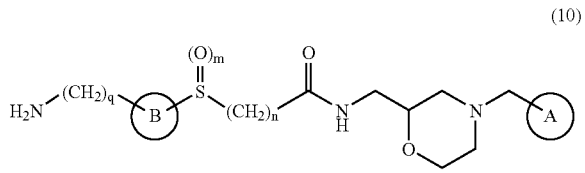

wherein q is an integer of 0 to 6, and other symbols are as defined above, or an acid addition salt thereof, in a suitable solvent that does not inhibit the reaction (e.g., THF, dichloromethane, DMF or a mixed solvent thereof etc.), in the presence of a tertiary amine such as triethylamine, diisopropylethylamine and the like and a condensation agent (same as the condensation agent described in method (1)) under ice-cooling or at room temperature for 1-24 hrs, a compound represented by the formula (1)

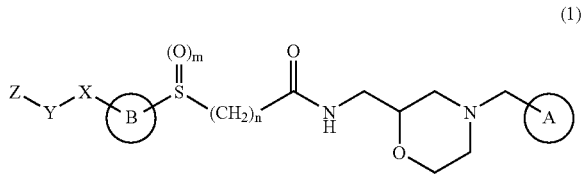

wherein each symbol is as defined above and X is —CONH—$(CH_2)_q$— wherein q is an integer of 0 to 6, can be obtained.

In addition, by carrying out the similar reaction using a reactive derivative of the compound of the formula (9) (acid chloride, acyl imidazole etc.), a compound represented by the formula (1) can be obtained.

Method (4)

A compound of the formula (1), wherein X is —NHCO—$(CH_2)_q$— wherein q is an integer of 0 to 6, can also be synthesized by the following method.

That is, by reacting a compound represented by the formula (11)

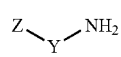

wherein each symbol is as defined above, or an acid addition salt thereof, with a compound represented by the formula (12)

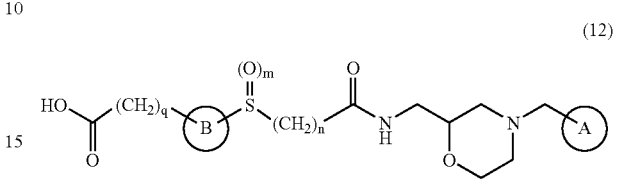

wherein q is an integer of 0 to 6, and other symbols are as defined above, or an acid addition salt thereof, in a suitable solvent that does not inhibit the reaction (e.g., THF, dichloromethane, DMF or a mixed solvent thereof etc.), in the presence of a tertiary amine such as triethylamine, diisopropylethylamine and the like, and a condensation agent (same as the condensation agent described in method (2)) under ice-cooling or at room temperature for 1-24 hrs, a compound represented by the formula (1)

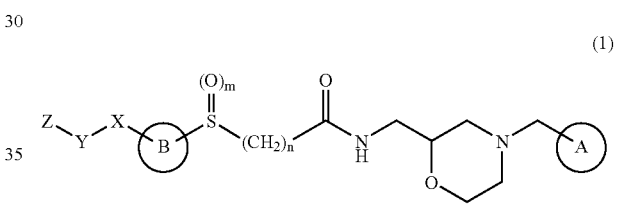

wherein each symbol is as defined above, and X is —NHCO—$(CH_2)_q$— wherein q is an integer of 0 to 6, can be obtained.

In addition, by carrying out the similar reaction using a reactive derivative of a compound of the formula (12) (acid chloride, acyl imidazole etc.), a compound represented by the formula (1) can be obtained.

Method (5)

A compound of the formula (1), wherein m=0 can also be synthesized by the following method.

That is, by reacting a compound represented by the formula (13)

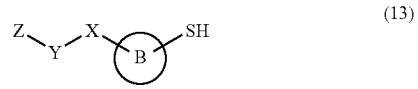

wherein each symbol is as defined above, or an acid addition salt thereof, in a suitable solvent that does not inhibit the reaction (e.g., dichloromethane, chloroform, dichloroethane, diethyl ether, dimethylformamide, water or a mixed solvent thereof etc.), with a compound represented by the formula (14)

(14)

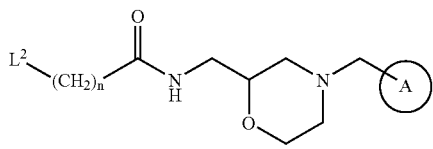

wherein L² is a leaving group such as chlorine, bromine, iodine, methanesulfonyloxy, p-toluenesulfonyloxy, trifluoromethanesulfonyloxy and the like, and other symbols are as defined above, or an acid addition salt thereof, in the presence of a base such as triethylamine, pyridine, DMAP, potassium carbonate, sodium hydrogen carbonate, sodium hydroxide and the like, under ice-cooling or at room temperature for 1-24 hrs,
a compound represented by the formula (1)

(1)

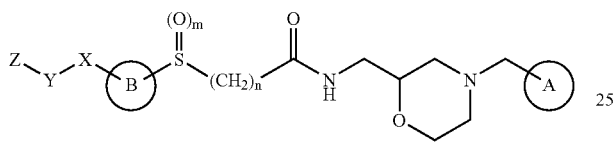

wherein each symbol is as defined above and m=0, can be obtained.

Of the compounds represented by the formula (14), a compound represented by the following formula, wherein n is 1, which is an optically active form

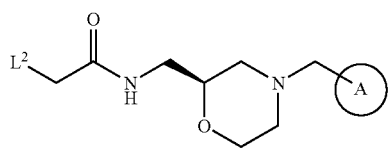

wherein each symbol is as defined above, or an acid addition salt thereof, can be obtained by reacting a compound represented by the formula (26)

(26)

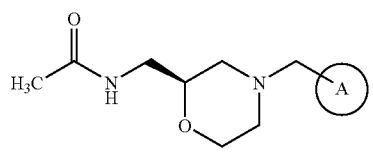

wherein each symbol is as defined above, or an acid addition salt thereof, with a halogenated agent such as chlorine, bromine, pyridinium tribromide, trimethylphenylammonium tribromide, iodine and the like, in a suitable solvent that does not inhibit the reaction (e.g., dichloromethane, chloroform, dichloroethane, acetic acid or a mixed solvent thereof etc.) at 0° C. to 100° C. for 10 min-24 hrs.

A compound represented by the formula (26) and an acid addition salt thereof are novel compounds, and can be produced by acetylating an optically active form of a compound represented by the above-mentioned formula (3) by a conventional method.
Method (6)

A compound of the formula (1), wherein m=0 can also be synthesized by the following method.

That is, by reacting a compound represented by the formula (15)

(15)

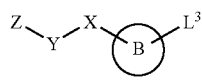

wherein L³ is a leaving group such as chlorine, bromine, iodine, methanesulfonyloxy, p-toluenesulfonyloxy, trifluoromethanesulfonyloxy and the like, and other symbols are as defined above, or an acid addition salt thereof, in a suitable solvent that does not inhibit the reaction (e.g., dichloromethane, chloroform, dichloroethane, diethyl ether, dimethylformamide, water or a mixed solvent thereof etc.), with a compound represented by the formula (16)

(16)

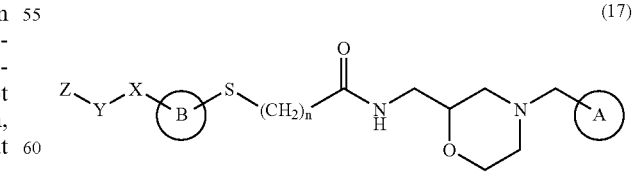

wherein each symbol is as defined above, or an acid addition salt thereof, in the presence of a base such as triethylamine, pyridine, DMAP, potassium carbonate, sodium hydrogen carbonate, sodium hydroxide and the like, under ice-cooling or at room temperature for 1-24 hrs, a compound represented by the formula (1)

(1)

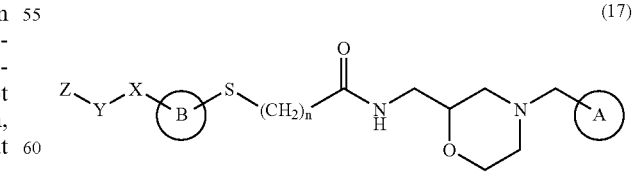

wherein each symbol is as defined above and m=0, can be obtained.
Method (7)

A compound of the formula (1), wherein m=1 or 2 can also be synthesized by the following method.

That is, by reacting a compound represented by the formula (17)

(17)

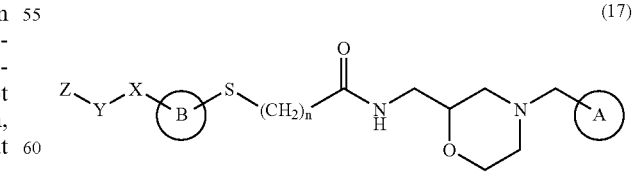

wherein each symbol is as defined above, or an acid addition salt thereof, using an oxidant such as m-chloroperbenzoic acid and the like in a suitable solvent that does not inhibit the reaction (e.g., halogenated hydrocarbons such as dichloromethane, dichloroethane, chloroform and the like or a mixed solvent thereof etc.), or using an oxidant such as aqueous hydrogen peroxide and the like in a carboxylic acid solvent such as acetic acid, trifluoroacetic acid, formic acid and the like, at a temperature of generally −30° C. to 80° C., preferably −10° C. to 60° C. for 0.5-24 hrs, a compound represented by the formula (1)

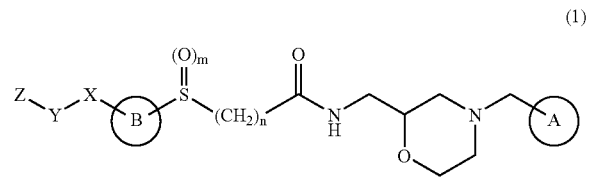
(1)

wherein each symbol is as defined above and m=1 or 2, can be obtained.

When, in the above-mentioned reaction, an amino group and the like irrelevant to the reaction are present in the reaction substances, the substituent may be protected with a suitable protecting group, followed by the reaction and the protecting group may be eliminated after the reaction. As the amino-protecting group used at that time, carbamates such as tertiary butoxycarbonyl, benzyloxycarbonyl and the like, amides such as formyl, acetyl, trifluoroacetyl, benzoyl and the like, arylalkyl such as benzyl, p-methoxybenzyl, trityl and the like, and the like can be mentioned. The protecting groups can be eliminated, for example, by solvolysis using an acid such as hydrochloric acid, formic acid, trifluoroacetic acid and the like or a base such as sodium hydroxide, potassium hydroxide and the like, reduction using metal hydride complex and the like, hydrogenation using palladium-carbon catalyst, Raney-nickel and the like, oxidization using 2,3-dichloro-5,6-dicyano-p-benzoquinone and the like, and the like.

Method (8)

A compound of the formula (1), wherein ring B is heteroarylene optionally having substituent(s) can also be synthesized by the following method. That is, by reacting a compound represented by the formula (18)

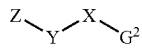
(18)

wherein $G^2$ is a substituent necessary for the construction of heteroaryl, and other symbols are as defined above, or an acid addition salt thereof, with a compound represented by the formula (19)

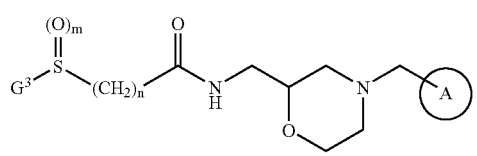
(19)

wherein $G^3$ is a substituent necessary for the construction of heteroaryl, and other symbols are as defined above, or an acid addition salt thereof, a compound represented by the formula (1)

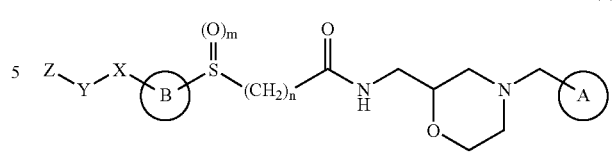
(1)

wherein ring B is heteroarylene optionally having substituent(s), and other symbols are as defined above, can be obtained.

Method (9)

A compound of the formula (1), wherein Z is heteroaryl optionally having substituent(s), can also be synthesized by the following method. That is, by reacting a compound represented by the formula (20)

$$G^4 \qquad (20)$$

wherein $G^4$ is a substituent necessary for construction of heteroaryl, or an acid addition salt thereof, with a compound represented by the formula (21)

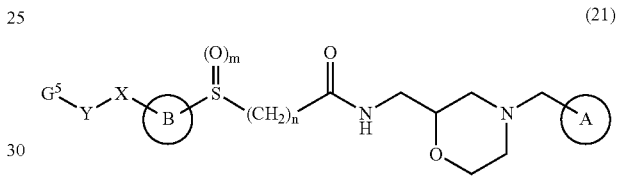
(21)

wherein $G^5$ is a substituent necessary for the construction of heteroaryl, and other symbols are as defined above, or an acid addition salt thereof, a compound represented by the formula (1)

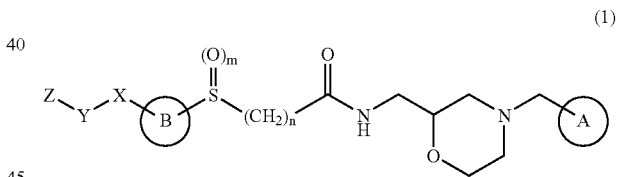
(1)

wherein Z is heteroaryl optionally having substituent(s), and other symbols are as defined above, can be obtained.

Method (10)

A compound of the formula (1), wherein X is $-Q_1-(CH_2)_q-$ wherein $Q_1$ is $-NH-$, $-NR^7-$ wherein $R^7$ is $C_{1-6}$ alkyl optionally having substituent(s), oxygen atom or sulfur atom, and q is an integer of 0 to 6, can also be synthesized by the following method.

That is, by reacting a compound represented by the formula (22)

(22)

wherein $G^6$ is $-NH_2$, $-NHR^7$ wherein $R^7$ is $C_{1-6}$ alkyl optionally having substituent(s), $-OH$ or $-SH$, and other symbols are as defined above, or an acid addition salt thereof, with a compound represented by the formula (23)

(23)

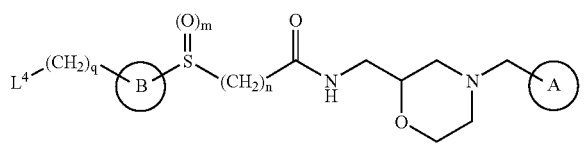

wherein $L^4$ is a leaving group such as chlorine, bromine, iodine, methanesulfonyloxy, p-toluenesulfonyloxy, trifluoromethanesulfonyloxy and the like, and other symbols are as defined above, or an acid addition salt thereof, in a suitable solvent that does not inhibit the reaction (e.g., dichloromethane, chloroform, dichloroethane, diethyl ether, water or a mixed solvent thereof etc.), in the presence of a base (e.g., triethylamine, pyridine, DMAP, potassium carbonate, sodium hydrogen carbonate, sodium hydroxide etc.) under ice-cooling or at room temperature for 1-24 hrs, a compound represented by the formula (1)

(1)

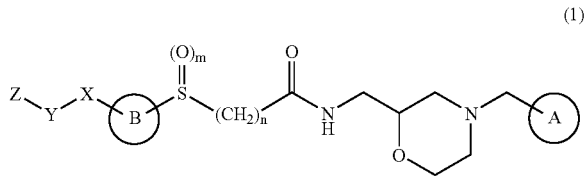

wherein X is $-Q_1-(CH_2)_q-$ wherein $Q_1$ is $-NH-$, $-NR^7-$ wherein $R^7$ is $C_{1-6}$ alkyl optionally having substituent(s), oxygen atom or sulfur atom, and q is an integer of 0 to 6, can be obtained.

Method (11)

A compound of the formula (1), wherein X is $-Q_2-(CH_2)_q-$ wherein $Q_2$ is $-NH-$, $-NR^7-$ wherein $R^7$ is $C_{1-6}$ alkyl optionally having substituent(s), oxygen atom or sulfur atom, and q is an integer of 0 to 6, can also be synthesized by the following method.

That is, by reacting a compound represented by the formula (24)

(24)

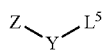

wherein $L^5$ is a leaving group such as chlorine, bromine, iodine, methanesulfonyloxy, p-toluenesulfonyloxy, trifluoromethanesulfonyloxy and the like, and other symbols are as defined above, or an acid addition salt thereof, with a compound represented by the formula (25)

(25)

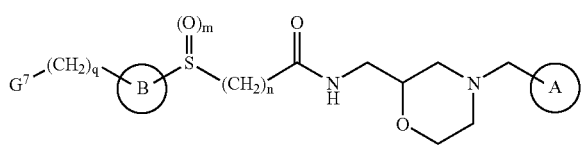

wherein $G^7$ is $-NH_2$, $-NHR^7$ wherein $R^7$ is $C_{1-6}$ alkyl optionally having substituent(s), $-OH$ or $-SH$, and other symbols are as defined above, or an acid addition salt thereof, in a suitable solvent that does not inhibit the reaction (e.g., dichloromethane, chloroform, dichloroethane, diethyl ether, water or a mixed solvent thereof etc.) in the presence of a base such as triethylamine, pyridine, DMAP, potassium carbonate, sodium hydrogen carbonate, sodium hydroxide and the like, under ice-cooling or at room temperature for 1-24 hrs, a compound represented by the formula (1)

(1)

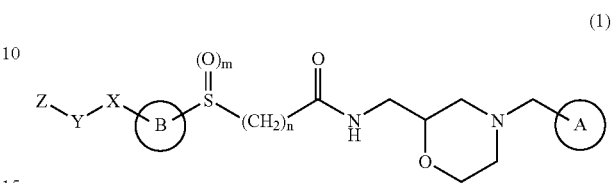

wherein X is $-Q_2-(CH_2)_q-$ wherein $Q_2$ is $-NH-$, $-NR^7-$ wherein $R^7$ is $C_{1-6}$ alkyl optionally having substituent(s), oxygen atom or sulfur atom, and q is an integer of 0 to 6, can be obtained.

As a pharmaceutically acceptable salt of the compound of the formula (1), acid addition salts with inorganic acid and organic acid can be mentioned, and the compound of the formula (1) can be converted to salt by treating with an inorganic acid or an organic acid by a conventional method. In addition, hydrate and solvate of the compound of the formula (1) are also encompassed in the present invention, and can be produced by a well-known method.

The compound of the present invention thus obtained can be isolated and purified by a conventional method such as recrystallization, column chromatography and the like. When the obtained resultant product is a racemate, for example, it can be resolved into a desired optically active form by fractional recrystallization of a salt with an optically active acid, or by passing through a column packed with an optically active carrier. Each of the diastereomers can be separated by fractional recrystallization, column chromatography and the like. They can also be obtained by the use of an optically active starting material compound and the like. In addition, the stereoisomer can be isolated by recrystallization, column chromatography and the like.

When the morpholine compound of the present invention, or a pharmaceutically acceptable salt thereof, or a hydrate or solvate thereof is used as a pharmaceutical agent, the compound of the present invention can be mixed with a pharmaceutically acceptable carrier (e.g., excipient, binder, disintegrant etc.) and the obtained pharmaceutical composition or preparation (e.g., tablet, liquid etc.) can be administered orally or parenterally. A pharmaceutical composition can be formed according to a conventional method.

The dose is determined in consideration of age, body weight, general health condition, sex, diet, administration time, administration method, clearance rate, combination of drugs, the severity of the disease state of patients under treatment at that time, and other factors. While the daily dose of the compound of the present invention varies depending on the condition and body weight of patients, the kind of compound, administration route and the like, for example, oral dose is 0.01-1000 mg/kg body weight/day, which is administered in one to several portions a day, and parenteral dose is about 0.001-100 mg/kg body weight/day, which is administered in one to several portions a day.

As a disease to be the target of the treatment and/or prophylaxis, for example, diseases wherein a cell having CCR3 plays an important role in the onset, progress and retention of pathology, such as asthma, sinusitis, allergic rhinitis, atopic dermatitis, allergic conjunctivitis, allergic myelitis, ulcerative colitis, Crohn's disease, rheumatoid arthritis and the like can be mentioned. Here, the treatment in the present invention means administration of the compound of the present invention for the purpose of cure of disease, amelioration of disease, or prevention of aggravation of disease, prevention of fit and the like in the individual already suffering from the disease (e.g., mammals including human), and the prophylaxis means administration of the compound of the present invention for the purpose of preventing the onset of a disease in a healthy individual free of a disease (e.g., mammals including human).

EXAMPLES

The present invention is explained in detail in the following by referring to Examples and Experimental Examples, which are not to be construed as limitative.

$^1$H-NMR spectrum of the compounds was measured at 300 MHz or 400 MHz. The chemical shift of $^1$H-NMR is shown by parts per million (ppm) of relative delta (δ) value, using tetramethylsilane (TMS) as the internal standard. The coupling constant is shown in hertz (Hz), and the obvious multiplicity is shown by s (singlet), d (doublet), t (triplet), q (quartet), m (multiplet), dd (doublet of doublets), brs (broad singlet) and the like. Column chromatography was performed using silica gel manufactured by Fuji-Silysia Chemical Ltd. Preparative isolation by HPLC was performed using a column manufactured by WATERS or Shiseido Co., Ltd., and a mixed solvent of 0.05% aqueous TFA solution and 0.05% TFA-acetonitrile solution as an eluent.

The term "room temperature" used in the explanation of the following Examples means 10° C. to 30° C.

Example 1

Synthesis of (2S)-(4-carboxythiazol-2-ylthio)-N-{[4-(3,4-dichlorobenzyl)morpholin-2-yl]methyl}acetamide

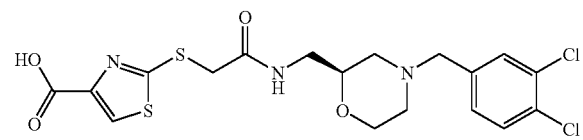

(1-1) Synthesis of (2S)-N-{[4-(3,4-dichlorobenzyl)morpholin-2-yl]methyl}chloroacetamide (2S)-2-Aminomethyl-4-(3,4-dichlorobenzyl)morpholine dihydrochloride (30.5 g) was added to chloroform (400 mL) and saturated aqueous sodium hydrogen carbonate solution (400 mL). After dropwise addition of chloroacetyl chloride (7.7 mL) under ice-cooling, and the mixture was stirred at room temperature for 3 hrs. After completion of the reaction, the mixture was extracted with chloroform. The extract was washed with saturated brine, dried over anhydrous sodium sulfate, and the solvent was evaporated under reduced pressure to give the title compound (31.6 g) as a colorless oil.

(1-2) Synthesis of (2S)-N-{[4-(3,4-dichlorobenzyl)morpholin-2-yl]methyl}chloroacetamide hydrochloride The resultant product (31.0 g) of (1-1) was dissolved in ethyl acetate (100 mL), and a 4 mol/L hydrogen chloride-ethyl acetate solution (22.5 mL) was added dropwise under ice-cooling. Ethanol was further added for dissolution, and the mixture was left standing overnight and the resulting solid was collected by filtration, washed with ethyl acetate, and dried to give the title compound (29.8 g) as white crystals.

(1-3) Synthesis of 4-ethoxycarbonyl-2-mercaptothiazole

Ethyl bromopyruvate (90%, 100 g) was completely dissolved in ethanol (1000 mL), ammonium dithiocarbamate (55.9 g) was added, and the mixture was stirred at room temperature for 2.5 hrs and heated under reflux for 1 hr. After completion of the reaction, the solvent was evaporated under reduced pressure, water was added to the obtained residue. The solid was collected by filtration, washed with water and isopropyl ether, and dried to give the title compound (63.3 g) as a yellow powder.

(1-4) Synthesis of (2S)-N-{[4-(3,4-dichlorobenzyl)morpholin-2-yl]methyl}-[4-(ethoxycarbonyl)thiazol-2-ylthio]acetamide The resultant product (776 mg) of (1-2) and the resultant product (379 mg) of (1-3) were dissolved in dimethylformamide (6 mL), potassium carbonate (829 mg) was added, and the mixture was stirred overnight at room temperature. The reaction mixture was poured into water, and the mixture was extracted with ethyl acetate. The extract was washed with saturated brine, dried over anhydrous sodium sulfate, and the solvent was evaporated under reduced pressure. The obtained residue was purified by silica gel column chromatography using a mixed solvent of chloroform and methanol as an eluent. The solvent was evaporated from the eluent to give the title compound (850 mg) as a pale-yellow oil.

(1-5) Synthesis of (2S)-(4-carboxythiazol-2-ylthio)-N-{[4-(3,4-dichlorobenzyl)morpholin-2-yl]methyl}acetamide The resultant product (850 mg) of (1-4) was dissolved in methanol (4 mL) and tetrahydrofuran (4 mL), 1 mol/L aqueous sodium hydroxide solution (4 mL) was added, and the mixture was stirred overnight at room temperature. 1 mol/L hydrochloric acid was added to the reaction mixture, and the organic solvent alone was evaporated under reduced pressure. Saturated brine was added to the obtained residue, and the mixture was extracted with a mixed solvent of chloroform-methanol. The extract was dried over anhydrous sodium sulfate, and the solvent was evaporated under reduced pressure. The obtained residue was purified by silica gel column chromatography using a mixed solvent of chloroform and methanol as an eluent. The solvent was evaporated from the eluent to give the title compound (479 mg) as a white solid.

$^1$H-NMR (DMSO-d$_6$) δ 1.80 (1H, t, J=10.5 Hz), 1.99-2.10 (1H, m), 2.55 (1H, d, J=10.8 Hz), 2.65 (1H, d, J=10.8 Hz), 3.13 (2H, t, J=5.7 Hz), 3.36-3.52 (4H, m), 3.75 (1H, d, J=10.8 Hz), 3.99 (2H, s), 7.29 (1H, dd, J=1.2, 8.1 Hz), 7.53-7.59 (2H, m), 8.31-8.35 (2H, m), 12.3 (1H, brs).

MS (ESI) m/z: 476 [M+H].

Example 2

Synthesis of (2S)-[4-(carboxymethyl)thiazol-2-ylthio]-N-{[4-(3,4-dichlorobenzyl)morpholin-2-yl]methyl}acetamide

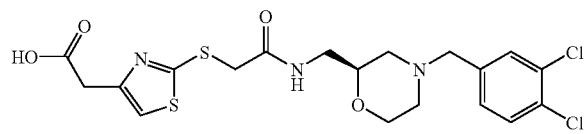

(2-1) Synthesis of 4-ethoxycarbonylmethyl-2-mercaptothiazole

By a similar method as in (1-3), the title compound (40.1 g) was obtained as white crystals from ethyl 4-chloroacetoacetate (47.0 g) and ammonium dithiocarbamate (34.6 g).

(2-2) Synthesis of (2S)-N-{[4-(3,4-dichlorobenzyl)morpholin-2-yl]methyl}-[4-(ethoxycarbonylmethyl)thiazol-2-ylthio]acetamide By a similar method as in (1-4), the title compound (21.3 g) was obtained as a pale-yellow oil from the resultant product (15.5 g) of (1-2) and the resultant product (8.94 g) of (2-1).

(2-3) Synthesis of (2S)-[4-(carboxymethyl)thiazol-2-ylthio]-N-{[4-(3,4-dichlorobenzyl)morpholin-2-yl]methyl}acetamide By a similar method as in (1-5), the title compound (18.0 g) was obtained as a white amorphous solid from the resultant product (21.3 g) of (2-2).

$^1$H-NMR (DMSO-$d_6$) δ 1.79 (1H, t, J=10.8 Hz), 2.00-2.11 (1H, m), 2.56 (1H, d, J=11.1 Hz), 2.65 (1H, d, J=11.1 Hz), 3.13 (2H, t, J=5.7 Hz), 3.34-3.52 (4H, m), 3.67 (2H, s), 3.77 (1H, d, J=11.1 Hz), 3.92 (2H, s), 7.29 (1H, dd, J=1.8, 11.1 Hz), 7.38 (1H, s), 7.54-7.60 (2H, m), 8.29-8.32 (1H, m), 12.3 (1H, brs).

MS (ESI) m/z: 490 [M+H].

Example 3

Synthesis of (2S)-[4-(3-cyanophenyl)thiazol-2-ylthio]-N-{[4-(3,4-dichlorobenzyl)morpholin-2-yl]methyl}acetamide

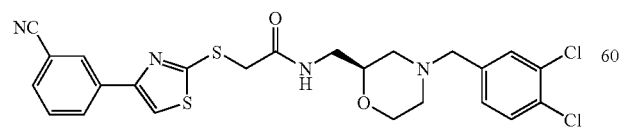

(3-1) Synthesis of 4-(3-cyanophenyl)-2-mercaptothiazole

By a similar method as in (1-3), the title compound (4.07 g) was obtained as a yellow pale solid from 3'-cyano-2-bromoacetophenone (8.96 g) and ammonium dithiocarbamate (4.41 g).

(3-2) Synthesis of (2S)-[4-(3-cyanophenyl)thiazol-2-ylthio]-N-{[4-(3,4-dichlorobenzyl)morpholin-2-yl]methyl}acetamide By a similar method as in (1-4), the title compound (264 mg) was obtained as a brown amorphous solid from the resultant product (352 mg) of (1-1) and the resultant product (218 mg) of (3-1).

$^1$H-NMR (DMSO-$d_6$) δ 1.75 (1H, t, J=10.8 Hz), 1.91-1.99 (1H, m), 2.48 (1H, d, J=9.9 Hz), 2.59 (1H, d, J=9.9 Hz), 3.15 (2H, t, J=5.7 Hz), 3.33-3.52 (4H, m), 3.71 (1H, d, J=10.5 Hz), 4.05 (2H, s), 7.20 (1H, dd, J=1.8, 8.1 Hz), 7.43 (1H, d, J=1.8 Hz), 7.55 (1H, d, J=8.4 Hz), 7.65 (1H, t, J=7.8 Hz), 7.81 (1H, d, J=7.8 Hz), 8.25-8.29 (2H, m), 8.39-8.41 (2H, m).

MS (ESI) m/z: 533 [M+H].

Example 4

Synthesis of (2S)-[4-(4-cyanophenyl)thiazol-2-ylthio]-N-{[4-(3,4-dichlorobenzyl)morpholin-2-yl]methyl}acetamide

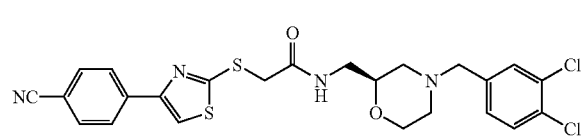

(4-1) Synthesis of 4-(4-cyanophenyl)-2-mercaptothiazole

By a similar method as in (1-3), the title compound (4.24 g) was obtained as a yellow solid from 4'-cyano-2-bromoacetophenone (5.17 g) and ammonium dithiocarbamate (2.54 g).

(4-2) Synthesis of (2S)-[4-(4-cyanophenyl)thiazol-2-ylthio]-N-{[4-(3,4-dichlorobenzyl)morpholin-2-yl]methyl}acetamide By a similar method as in (1-4), the title compound (469 mg) was obtained as a yellow amorphous solid from the resultant product (352 mg) of (1-1) and the resultant product (218 mg) of (4-1).

$^1$H-NMR (DMSO-$d_6$) δ 1.75 (1H, t, J=10.8 Hz), 1.91-2.00 (1H, m), 2.50 (1H, d, J=11.1 Hz), 2.60 (1H, d, J=11.1 Hz), 3.15 (2H, t, J=5.7 Hz), 3.33-3.55 (4H, m), 3.71 (1H, d, J=11.7 Hz), 4.05 (2H, s), 7.22 (1H, d, J=8.1 Hz), 7.44 (1H, s), 7.56 (1H, d, J=8.1 Hz), 7.91 (2H, d, J=8.5 Hz), 8.14 (2H, d, J=8.5 Hz), 8.32-8.40 (2H, m).

MS (ESI) m/z: 533 [M+H].

Example 5

Synthesis of (2S)-N-{[4-(3,4-dichlorobenzyl)morpholin-2-yl]methyl}-[4-(4-methoxycarbonylphenyl)thiazol-2-ylthio]acetamide

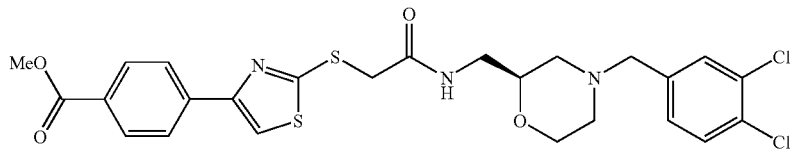

(5-1) Synthesis of 2-mercapto-4-(4-methoxycarbonylphenyl)thiazole

By a similar method as in (1-3), the title compound (4.81 g) was obtained as a pale-yellow solid from 4'-methoxycarbonyl-2-chloroacetophenone (7.64 g) and ammonium dithiocarbamate (3.96 g).

(5-2) Synthesis of (2S)-N-{[4-(3,4-dichlorobenzyl)morpholin-2-yl]methyl}-[4-(4-methoxycarbonylphenyl)thiazol-2-ylthio]acetamide By a similar method as in (1-4), the title compound (650 mg) was obtained as a pale-yellow amorphous solid from the resultant product (422 mg) of (1-1) and the resultant product (302 mg) of (5-1).

$^1$H-NMR (DMSO-$d_6$) δ 1.76 (1H, t, J=10.8 Hz), 1.91-2.01 (1H, m), 2.50 (1H, d, J=11.1 Hz), 2.60 (1H, d, J=11.1 Hz), 3.15 (2H, t, J=6.0 Hz), 3.33-3.55 (4H, m), 3.71 (1H, d, J=9.3 Hz), 3.86 (3H, s), 4.05 (2H, s), 7.22 (1H, d, J=8.1 Hz), 7.44 (1H, s), 7.55 (1H, d, J=8.1 Hz), 8.01 (2H, d, J=8.4 Hz), 8.09 (2H, d, J=8.4 Hz), 8.25 (1H, s), 8.35-8.39 (1H, m).

MS (ESI) m/z: 566 [M+H].

Example 6

Synthesis of (2S)-N-{[4-(3,4-dichlorobenzyl)morpholin-2-yl]methyl}-[4-(3-nitrophenyl)thiazol-2-ylthio]acetamide

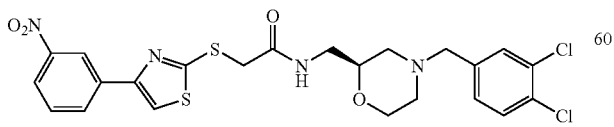

(6-1) Synthesis of 2-mercapto-4-(3-nitrophenyl)thiazole

By a similar method as in (1-3), the title compound 21.1 g) was obtained as a yellow solid from 3'-nitro-2-bromoacetophenone (25.0 g) and ammonium dithiocarbamate (11.3 g).

(6-2) Synthesis of (2S)-N-{[4-(3,4-dichlorobenzyl)morpholin-2-yl]methyl}-[4-(3-nitrophenyl)thiazol-2-ylthio]acetamide By a similar method as in (1-4), the title compound (4.94 g) was obtained as a yellow amorphous solid from the resultant product (3.52 g) of (1-1) and the resultant product (2.38 g) of (6-1).

$^1$H-NMR (DMSO-$d_6$) δ 1.76 (1H, t, J=10.8 Hz), 1.91-2.01 (1H, m), 2.48 (1H, d, J=9.9 Hz), 2.61 (1H, d, J=10.8 Hz), 3.16 (2H, t, J=5.7 Hz), 3.33-3.52 (4H, m), 3.71 (1H, d, J=10.5 Hz), 4.05 (2H, s), 7.21 (1H, d, J=8.1 Hz), 7.44 (1H, s), 7.55 (1H, d, J=8.4 Hz), 7.74 (1H, t, J=7.8 Hz), 8.19 (1H, d, J=7.5 Hz), 8.33-8.43 (3H, m), 8.71 (1H, s).

MS (ESI) m/z: 553 [M+H].

Example 7

Synthesis of (2S)-[4-(4-carboxyphenyl)thiazol-2-ylthio]-N-{[4-(3,4-dichlorobenzyl)morpholin-2-yl]methyl}acetamide

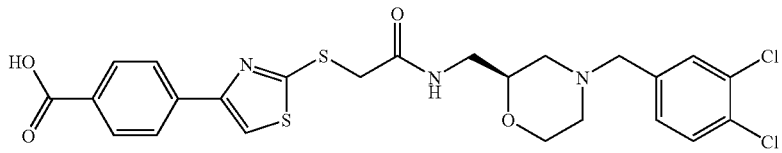

By a similar method as in (1-5), the title compound (388 mg) was obtained as a pale-yellow solid from the resultant product (580 mg) of (5-2).

$^1$H-NMR (DMSO-$d_6$) δ 1.76 (1H, t, J=10.8 Hz), 1.91-2.01 (1H, m), 2.50 (1H, d, J=11.1 Hz), 2.61 (1H, d, J=11.1 Hz), 3.15 (2H, t, J=5.7 Hz), 3.33-3.55 (4H, m), 3.71 (1H, d, J=10.8 Hz), 4.05 (2H, s), 7.22 (1H, dd, J=1.8, 8.1 Hz), 7.45 (1H, d, J=1.8 Hz), 7.55 (1H, d, J=8.1 Hz), 7.99 (2H, d, J=8.4 Hz), 8.07 (2H, d, J=8.4 Hz), 8.22 (1H, s), 8.36 (1H, t, J=5.7 Hz), 13.0 (1H, brs).

MS (ESI) m/z: 552 [M+H].

Example 8

Synthesis of (2S)-[4-(4-carbamoylphenyl)thiazol-2-ylthio]-N-{[4-(3,4-dichlorobenzyl)morpholin-2-yl]methyl}-acetamide

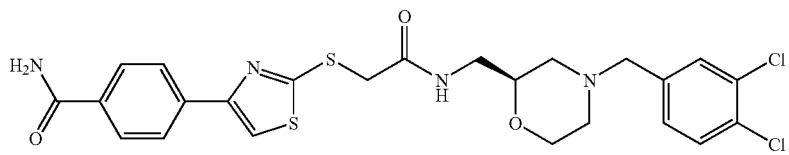

The resultant product (276 mg) of Example 7 was dissolved in tetrahydrofuran (2.5 mL), triethylamine (77 μL) and isobutyl chloroformate (72 μL) were added, and the mixture was stirred at room temperature for 2.5 hrs. A 7 mol/L ammonia-methanol solution (2 mL) was added to the reaction mixture, and the mixture was stirred at room temperature for 40 min. A saturated aqueous sodium hydrogen carbonate solution was added to the reaction mixture, and the mixture was extracted with ethyl acetate. The extract was washed with saturated brine, dried over anhydrous sodium sulfate, and the solvent was evaporated under reduced pressure. The obtained residue was purified by silica gel column chromatography using a mixed solvent of chloroform and ethanol as an eluent. The solvent was evaporated from the eluent to give the title compound (202 mg) as a white amorphous solid.

$^1$H-NMR (DMSO-$d_6$) δ 1.76 (1H, t, J=10.5 Hz), 1.91-2.02 (1H, m), 2.50 (1H, d, J=11.1 Hz), 2.61 (1H, d, J=11.1 Hz), 3.15 (2H, t, J=5.6 Hz), 3.33-3.55 (4H, m), 3.72 (1H, d, J=11.4 Hz), 4.04 (2H, s), 7.22 (1H, dd, J=1.4, 8.2 Hz), 7.40 (1H, brs), 7.46 (1H, d, J=1.4 Hz), 7.55 (1H, d, J=8.2 Hz), 7.94 (2H, d, J=8.3 Hz), 8.02 (3H, m), 8.17 (1H, s), 8.36 (1H, t, J=5.7 Hz).

MS (ESI) m/z: 551 [M+H].

Example 9

Synthesis of (2S)-[4-(3-aminophenyl)thiazol-2-ylthio]-N-{[4-(3,4-dichlorobenzyl)morpholin-2-yl]methyl}acetamide

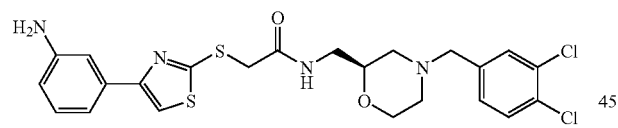

A solution of the resultant product (4.65 g) of (6-2) in tetrahydrofuran (24 mL) and methanol (16 mL) was added dropwise to an aqueous (16 mL) suspension of ammonium chloride (2.25 g) and iron powder (1.41 g) at 60° C. The reaction mixture was heated under reflux for 3.5 hrs. After allowing to cool, the reaction mixture was filtered through celite. A 1 mol/L aqueous sodium hydroxide solution was added to the filtrate, and the organic solvent alone was evaporated under reduced pressure. The residue was extracted with ethyl acetate, the extract was washed with saturated brine, dried over anhydrous sodium sulfate, and the solvent was evaporated under reduced pressure. The obtained residue was purified by silica gel column chromatography using a mixed solvent of chloroform and methanol as an eluent. The solvent was evaporated from the eluent to give the title compound (3.87 g) as a pale-yellow amorphous solid.

$^1$H-NMR (DMSO-$d_6$) δ 1.77 (1H, t, J=10.5 Hz), 1.91-2.02 (1H, m), 2.52 (1H, d, J=11.1 Hz), 2.62 (1H, d, J=11.1 Hz), 3.15 (2H, t, J=5.7 Hz), 3.37-3.53 (4H, m), 3.73 (1H, d, J=11.4 Hz), 3.99 (2H, s), 5.13 (2H, s), 6.53 (1H, m), 7.05 (2H, m), 7.14 (1H, s), 7.24 (1H, dd, J=1.5, 8.4 Hz), 7.49 (1H, d, J=1.5 Hz), 7.56 (1H, d, J=8.4 Hz), 7.79 (1H, s), 8.31 (1H, t, J=5.7 Hz).

MS (ESI) m/z: 523 [M+H].

Example 10

Synthesis of (2S)-[4-(3-carbamoyl-4-hydroxyphenyl)thiazol-2-ylthio]-N-{[4-(3,4-dichlorobenzyl)morpholin-2-yl]methyl}acetamide

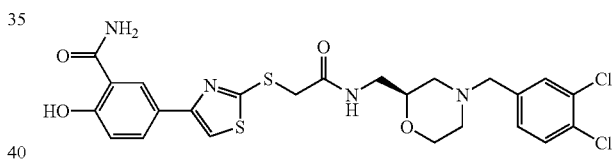

(10-1) Synthesis of 4-(3-carbamoyl-4-hydroxyphenyl)-2-mercaptothiazole

By a similar method as in (1-3), the title compound (24.0 g) was obtained as a white solid from 3'-carbamoyl-4'-hydroxy-2-bromoacetophenone (25.8 g) and ammonium dithiocarbamate (12.1 g).

(10-2) Synthesis of (2S)-[4-(3-carbamoyl-4-hydroxyphenyl)thiazol-2-ylthio]-N-{[4-(3,4-dichlorobenzyl)morpholin-2-yl]methyl}acetamide By a similar method as in (1-4), the title compound (10.0 g) was obtained as a white amorphous solid from the resultant product (7.03 g) of (1-1) and the resultant product (5.05 g) of (10-1).

$^1$H-NMR (DMSO-$d_6$) δ 1.74 (1H, t, J=10.8 Hz), 1.90-2.02 (1H, m), 2.50 (1H, d, J=11.1 Hz), 2.59 (1H, d, J=11.1 Hz), 3.14 (2H, m), 3.33-3.52 (4H, m), 3.70 (1H, d, J=11.1 Hz), 4.03 (2H, s), 6.95 (1H, d, J=8.7 Hz), 7.21 (1H, d, J=8.1 Hz), 7.45 (1H, s), 7.55 (1H, d, J=8.1 Hz), 7.82 (1H, s), 7.94-8.04 (2H, m), 8.32-8.39 (2H, m), 8.51 (1H, brs), 13.2 (1H, s)

MS (ESI) m/z: 567 [M+H].

Example 11

Synthesis of (2S)-N-{[4-(3,4-dichlorobenzyl)morpholin-2-yl]methyl}-[4-(pyridin-4-yl)thiazol-2-ylthio]acetamide

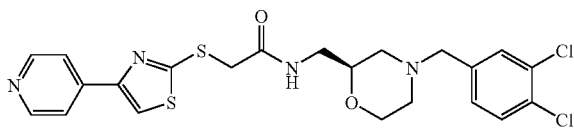

(11-1) Synthesis of 2-mercapto-4-(pyridine-4-yl)thiazole

By a similar method as in (1-3), the title compound (1.60 g) was obtained as a brown solid from 4-(bromoacetyl)pyridine hydrobromide (9.06 g) and ammonium dithiocarbamate (10.7 g).

(11-2) Synthesis of (2S)-N-{[4-(3,4-dichlorobenzyl)morpholin-2-yl]methyl}-[4-(pyridin-4-yl)thiazol-2-ylthio]acetamide By a similar method as in (1-4), the title compound (512 mg) was obtained as a white solid from the resultant product (535 mg) of (1-1) and the resultant product (295 mg) of (11-1).

$^1$H-NMR (DMSO-$d_6$) δ 1.76 (1H, t, J=10.5 Hz), 1.90-2.02 (1H, m), 2.50 (1H, d, J=11.1 Hz), 2.61 (1H, d, J=11.1 Hz), 3.15 (2H, t, J=5.7 Hz), 3.33-3.51 (4H, m), 3.72 (1H, d, J=11.1 Hz), 4.05 (2H, s), 7.22 (1H, d, J=8.4 Hz), 7.47 (1H, s), 7.56 (1H, d, J=8.4 Hz), 7.89 (2H, d, J=5.7 Hz), 8.34-8.40 (2H, m), 8.63 (2H, d, J=5.7 Hz).

MS (ESI) m/z: 509 [M+H].

Example 12

Synthesis of (2S)-N-{[4-(3,4-dichlorobenzyl)morpholin-2-yl]methyl}-[4-(pyridin-3-yl)thiazol-2-ylthio]acetamide

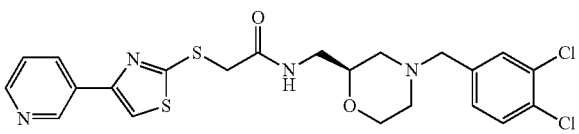

(12-1) Synthesis of 2-mercapto-4-(pyridin-3-yl)thiazole

By a similar method as in (1-3), the title compound (3.26 g) was obtained as pale-yellow crystals from 3-(dibromoacetyl)pyridine hydrobromide (10.8 g) and ammonium dithiocarbamate (13.2 g).

(12-2) Synthesis of (2S)-N-{[4-(3,4-dichlorobenzyl)morpholin-2-yl]methyl}-[4-(pyridin-3-yl)thiazol-2-ylthio]acetamide By a similar method as in (1-4), the title compound (283 mg) was obtained as a pale-yellow amorphous solid from the resultant product (352 mg) of (1-1) and the resultant product (194 mg) of (12-1).

$^1$H-NMR (DMSO-$d_6$) δ 1.75 (1H, t, J=10.5 Hz), 1.90-2.00 (1H, m), 2.50 (1H, d, J=11.1 Hz), 2.61 (1H, d, J=11.1 Hz), 3.15 (2H, t, J=5.7 Hz), 3.33-3.52 (4H, m), 3.71 (1H, d, J=11.1 Hz), 4.05 (2H, s), 7.21-7.24 (1H, m), 7.42-7.49 (2H, m), 7.56 (1H, d, J=8.1 Hz), 8.21 (1H, s), 8.26-8.28 (1H, m), 8.31-8.39 (1H, m), 8.53-8.56 (1H, m), 9.16-9.18 (1H, m).

MS (ESI) m/z: 509 [M+H].

Example 13

Synthesis of (2S)-N-{[4-(3,4-dichlorobenzyl)morpholin-2-yl]methyl}-[4-(3,4-dimethoxyphenyl)thiazol-2-ylthio]acetamide

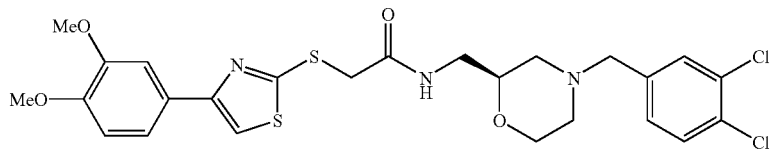

(13-1) Synthesis of 4-(3,4-dimethoxyphenyl)-2-mercapto-thiazole

By a similar method as in (1-3), the title compound (6.08 g) was obtained as a yellow solid from 3',4'-dimethoxy-2-bromoacetophenone (24.0 g) and ammonium dithiocarbamate (6.72 g).

(13-2) Synthesis of (2S)-N-{[4-(3,4-dichlorobenzyl)morpholin-2-yl]methyl}-[4-(3,4-dimethoxyphenyl)thiazol-2-ylthio]acetamide By a similar method as in (1-4), the title compound (180 mg) was obtained as a pale-yellow solid from the resultant product (352 mg) of (1-1) and the resultant product (253 mg) of (13-1).

$^1$H-NMR (DMSO-$d_6$) δ 1.75 (1H, t, J=10.5 Hz), 1.90-2.02 (1H, m), 2.50 (1H, d, J=11.1 Hz), 2.60 (1H, d, J=11.1 Hz), 3.15 (2H, t, J=5.7 Hz), 3.33-3.51 (4H, m), 3.72 (1H, d, J=11.1 Hz), 3.78 (3H, s), 3.82 (3H, s), 4.00 (2H, s), 6.99 (1H, d, J=9.0 Hz), 7.22 (1H, d, J=8.1 Hz), 7.44-7.50 (3H, m), 7.55 (1H, d, J=8.1 Hz), 7.91 (1H, s), 8.32 (1H, t, J=5.7 Hz).

MS (ESI) m/z: 568 [M+H].

Example 14

Synthesis of (2S)-[4-(3-acetaminophenyl)thiazol-2-ylthio]-N-{[4-(3,4-dichlorobenzyl)morpholin-2-yl]methyl}acetamide

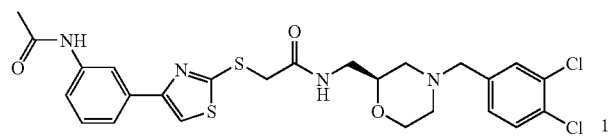

To a solution of the resultant product (262 mg) of Example 9 in pyridine (2 mL) was added dropwise acetic anhydride (57 μL). The reaction mixture was stirred overnight at room temperature. The reaction mixture was poured into water, and the mixture was extracted with ethyl acetate. The extract was washed with saturated brine, dried over anhydrous sodium sulfate, and the solvent was evaporated under reduced pressure. The obtained residue was purified by silica gel column chromatography using a mixed solvent of chloroform and methanol as an eluent. The solvent was evaporated from the eluent to give the title compound (279 mg) as a white amorphous solid.

$^1$H-NMR (DMSO-$d_6$) δ 1.76 (1H, t, J=10.5 Hz), 1.90-2.02 (1H, m), 2.05 (3H, s), 2.50-2.62 (2H, m), 3.15 (2H, t, J=5.7 Hz), 3.33-3.50 (4H, m), 3.72 (1H, m), 4.00 (2H, s), 7.24 (1H, dd, J=2.1, 8.4 Hz), 7.34 (1H, t, J=8.1 Hz), 7.48 (1H, d, J=2.1 Hz), 7.54-7.61 (3H, m), 7.92 (1H, s), 8.09 (1H, s), 8.30-8.34 (1H, m), 10.0 (1H, s).

MS (ESI) m/z: 565 [M+H].

Example 15

Synthesis of (2S)-(4-carbamoylthiazol-2-ylthio)-N-{[4-(3,4-dichlorobenzyl)morpholin-2-yl]methyl}acetamide

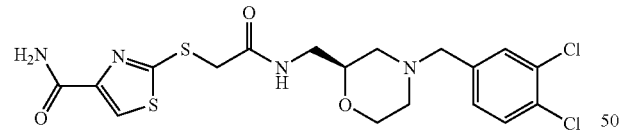

By a similar method as in Example 8, the title compound (4.07 g) was obtained as a white amorphous solid from the resultant product (4.76 g) of (1-5).

$^1$H-NMR (DMSO-$d_6$) δ 1.73 (1H, t, J=10.6 Hz), 1.92-2.07 (1H, m), 2.52 (1H, d, J=11.0 Hz), 2.58 (1H, d, J=11.0 Hz), 3.13 (2H, t, J=5.7 Hz), 3.39-3.52 (4H, m), 3.74 (1H, d, J=11.4 Hz), 3.96 (1H, d, J=14.7 Hz), 4.03 (1H, d, J=14.7 Hz), 7.28 (1H, dd, J=1.5, 8.1 Hz), 7.51-7.56 (2H, m), 7.64 (1H, brs), 7.75 (1H, brs), 8.13 (1H, s), 8.31 (1H, t, J=6.5 Hz).

MS (ESI) m/z: 475 [M+H].

Example 16

Synthesis of (2S)-N-{[4-(3,4-dichlorobenzyl)morpholin-2-yl]methyl}-[4-(ethylaminocarbonyl)thiazol-2-ylthio]acetamide hydrochloride

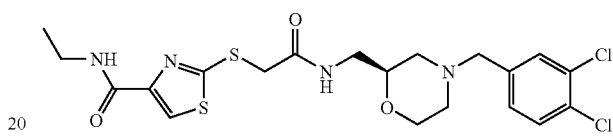

The resultant product (476 mg) of (1-5) and ethylamine hydrochloride (98 mg) were dissolved in dimethylformamide (2 mL), then 1-(3-dimethylaminopropyl)-3-ethylcarbodiimide hydrochloride (288 mg), hydroxybenzotriazole hydrate (230 mg) and triethylamine (167 μL) were added, and the mixture was stirred overnight at room temperature. A saturated aqueous sodium hydrogen carbonate solution was added to the reaction mixture, and the mixture was extracted with ethyl acetate. The extract was washed with saturated brine, dried over anhydrous sodium sulfate, and the solvent was evaporated under reduced pressure. The obtained residue was purified by silica gel column chromatography using a mixed solvent of chloroform and methanol as an eluent. The solvent was evaporated from the eluent to give the title compound (free form, 441 mg) as a pale-yellow amorphous solid. By a similar method as in (1-2), the title compound (357 mg) was obtained as pale-yellow crystals from the obtained residue.

$^1$H-NMR (DMSO-$d_6$) δ 1.10 (3H, t, J=7.2 Hz), 2.60-2.79 (1H, m), 2.89-3.06 (1H, m), 3.08-3.31 (6H, m), 3.70-4.04 (5H, m), 4.31 (2H, brs), 7.57 (1H, d, J=8.1 Hz), 7.74 (1H, d, J=8.1 Hz), 7.91 (1H, brs), 8.13 (1H, s), 8.37-8.42 (1H, m), 8.56 (1H, brs), 11.4 (1H, brs).

MS (ESI) m/z: 503 [M+H].

Example 17

Synthesis of (2S)-{4-[(2-amino-2-oxoethyl)aminocarbonyl]thiazol-2-ylthio}-N-{[4-(3,4-dichlorobenzyl)morpholin-2-yl]methyl}acetamide

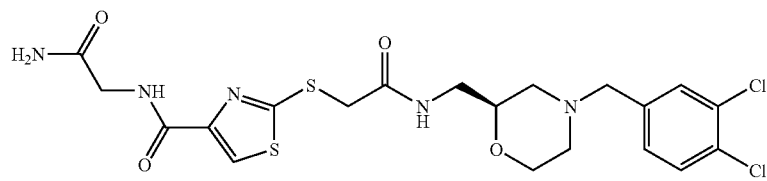

By a similar method as in Example 16, the title compound (286 mg) was obtained as a pale-yellow solid from the resultant product (476 mg) of (1-5) and glycinamide hydrochloride (133 mg).

¹H-NMR (DMSO-$d_6$) δ 1.75 (1H, t, J=10.5 Hz), 1.92-2.05 (1H, m), 2.52 (1H, d, J=11.1 Hz), 2.61 (1H, d, J=11.1 Hz), 3.13 (2H, t, J=5.7 Hz), 3.36-3.50 (4H, m), 3.70 (1H, d, J=11.4 Hz), 3.83 (2H, d, J=6.0 Hz), 4.02 (2H, s), 7.09 (1H, brs), 7.28 (1H, dd, J=1.8, 8.1 Hz), 7.40 (1H, brs), 7.53 (1H, d, J=1.8 Hz), 7.58 (1H, d, J=8.1 Hz), 8.18 (1H, s), 8.34 (1H, t, J=5.7 Hz), 8.41 (1H, t, J=6.0 Hz).

MS (ESI) m/z: 532 [M+H].

Example 18

Synthesis of (2S)-[4-(carbamoylmethyl)thiazol-2-ylthio]-N-{[4-(3,4-dichlorobenzyl)morpholin-2-yl]methyl}acetamide

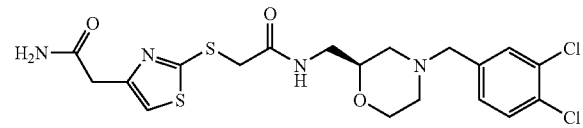

By a similar method as in Example 8, the title compound (318 mg) was obtained as a white amorphous solid from the resultant product (490 mg) of (2-3).

¹H-NMR (DMSO-$d_6$) δ 1.78 (1H, t, J=10.5 Hz), 1.94-2.09 (1H, m), 2.55 (1H, d, J=11.1 Hz), 2.64 (1H, d, J=11.1 Hz), 3.13 (2H, t, J=5.7 Hz), 3.38-3.52 (6H, m), 3.76 (1H, d, J=11.4 Hz), 3.91 (1H, s), 6.97 (1H, brs), 7.27-7.31 (2H, m), 7.38 (1H, brs), 7.53-7.60 (2H, m), 8.28 (1H, t, J=5.7 Hz).

MS (ESI) m/z: 489 [M+H].

Example 19

Synthesis of (2S)-N-{[4-(3,4-dichlorobenzyl)morpholin-2-yl]methyl}-[4-(ethylaminocarbonylmethyl)thiazol-2-ylthio]acetamide hydrochloride

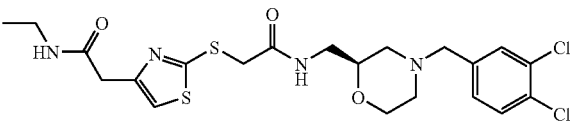

By a similar method as in Example 16, the title compound (425 mg) was obtained as white crystals from the resultant product (490 mg) of (2-3) and ethylamine hydrochloride (98 mg).

¹H-NMR (DMSO-$d_6$) δ 1.02 (3H, t, J=7.5 Hz), 2.60-2.80 (1H, m), 2.86-3.28 (7H, m), 3.51 (2H, s), 3.63-4.01 (5H, m), 4.32 (2H, brs), 7.30 (1H, s), 7.55 (1H, d, J=8.1 Hz), 7.74 (1H, d, J=8.1 Hz), 7.89 (1H, s), 8.01 (1H, m), 8.46 (1H, m), 11.1 (1H, brs).

MS (ESI) m/z: 517 [M+H].

Example 20

Synthesis of (2S)-{4-[(2-amino-2-oxoethyl)aminocarbonylmethyl]thiazol-2-ylthio}-N-{[4-(3,4-dichlorobenzyl)morpholin-2-yl]methyl}acetamide

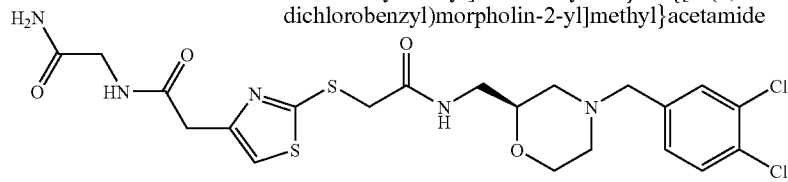

By a similar method as in Example 16, the title compound (465 mg) was obtained as a white amorphous solid from the resultant product (49.0 mg) of (2-3) and glycinamide hydrochloride (133 mg).

¹H-NMR (DMSO-$d_6$) δ 1.78 (1H, t, J=10.5 Hz), 1.96-2.09 (1H, m), 2.55 (1H, d, J=10.8 Hz), 2.64 (1H, d, J=10.8 Hz), 3.13 (2H, t, J=5.7 Hz), 3.39-3.50 (4H, m), 3.60 (2H, s), 3.66 (2H, d, J=5.6 Hz), 3.75 (1H, d, J=11.4 Hz), 3.92 (2H, s), 7.07 (1H, brs), 7.28-7.38 (3H, m), 7.53-7.60 (2H, m), 8.19 (1H, t, J=5.6 Hz), 8.28 (1H, t, J=5.7 Hz).

MS (ESI) m/z: 546 [M+H].

Example 21

Synthesis of (2S)-{4-[(3-amino-3-oxopropyl)aminocarbonyl]thiazol-2-ylthio}-N-{[4-(3,4-dichlorobenzyl)morpholin-2-yl]methyl}acetamide

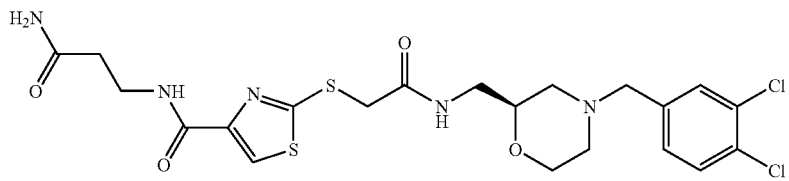

By a similar method as in Example 16, the title compound (384 mg) was obtained as a white amorphous solid from the resultant product (476 mg) of (1-5) and β-alaninamide hydrochloride (149 mg).

$^1$H-NMR (DMSO-$d_6$) δ 1.74 (1H, t, J=10.5 Hz), 1.93-2.04 (1H, m), 2.35 (2H, t, J=7.2 Hz), 2.52 (1H, d, J=10.5 Hz), 2.59 (1H, d, J=10.5 Hz), 3.14 (2H, t, J=5.7 Hz), 3.36-3.51 (6H, m), 3.74 (1H, d, J=10.8 Hz), 3.98 (1H, d, J=14.0 Hz), 4.02 (1H, d, J=14.0 Hz), 6.85 (1H, brs), 7.28 (1H, dd, J=1.5, 8.4 Hz), 7.37 (1H, brs), 7.52 (1H, d, J=1.5 Hz), 7.57 (1H, d, J=8.4 Hz), 8.14 (1H, s), 8.26-8.39 (2H, m).

MS (ESI) m/z: 546 [M+H].

Example 22

Synthesis of (2S)-N-{[4-(3,4-dichlorobenzyl)morpholin-2-yl]methyl}-[4-(N$^2$-hydroxyamidino)thiazol-2-ylthio]acetamide

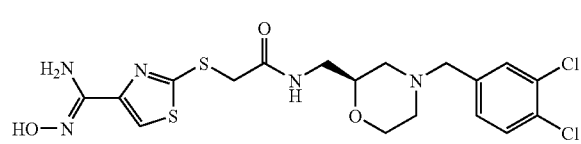

(22-1) Synthesis of (2S)-(4-cyanothiazol-2-ylthio)-N-{[4-(3,4-dichlorobenzyl)morpholin-2-yl]methyl}acetamide The resultant product (3.45 g) of Example 15 was dissolved in tetrahydrofuran (15 mL), and pyridine (1.76 mL) was added. After dropwise addition of trifluoroacetic anhydride (2.05 mL) under ice-cooling, the reaction mixture was stirred overnight at room temperature. The reaction mixture was poured into water, and the mixture was extracted with ethyl acetate. The extract was washed with saturated brine, dried over anhydrous sodium sulfate, and the solvent was evaporated under reduced pressure. The obtained residue was purified by silica gel column chromatography using a mixed solvent of chloroform and methanol as an eluent. The solvent was evaporated from the eluent to give the title compound (2.85 g) as a colorless oil.

(22-2) Synthesis of (2S)-N-{[4-(3,4-dichlorobenzyl)morpholin-2-yl]methyl}-[4-(N$^2$-hydroxyamidino)thiazol-2-ylthio]acetamide The resultant product (2.85 g) of (22-1) was dissolved in ethanol (30 mL), potassium carbonate (2.58 g) and hydroxylamine hydrochloride (603 mg) were added, and the reaction mixture was stirred overnight at room temperature. Water was added to the reaction mixture, and the resultant solid was collected by filtration to give the title compound (2.32 g) as white crystals.

$^1$H-NMR (DMSO-$d_6$) δ 1.75 (1H, t, J=10.5 Hz), 1.92-2.08 (1H, m), 2.52 (1H, d, J=11.7 Hz), 2.61 (1H, d, J=11.7 Hz), 3.12 (2H, t, J=5.7 Hz), 3.39-3.50 (4H, m), 3.75 (1H, d, J=12.0 Hz), 3.95 (1H, d, J=14.7 Hz), 4.01 (1H, d, J=14.7 Hz), 5.77 (2H, s), 7.29 (1H, dd, J=1.8, 8.1 Hz), 7.53 (1H, d, J=1.8 Hz), 7.57 (1H, d, J=8.1 Hz), 7.72 (1H, s), 8.32 (1H, t, J=5.7 Hz), 9.54 (1H, brs).

MS (ESI) m/z: 490 [M+H].

Example 23

Synthesis of (2S)-N-{[4-(3,4-dichlorobenzyl)morpholin-2-yl]methyl}-[4-(5-methyl-1,2,4-oxadiazol-3-yl)thiazol-2-ylthio]acetamide hydrochloride

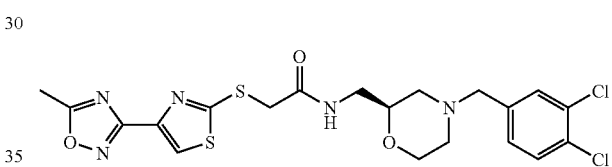

The resultant product (490 mg) of (22-2) was dissolved in xylene (6 mL) and pyridine (1 mL). After dropwise addition of acetic anhydride (104 μL), the mixture was heated under reflux for 2 hrs. After allowing to cool, acetic anhydride (28 μL) was added dropwise, and the mixture was further heated under reflux for 4 hrs. Ethyl acetate was added to the reaction mixture, and the mixture was washed with saturated brine, dried over anhydrous sodium sulfate, and the solvent was evaporated under reduced pressure. The obtained residue was purified by silica gel column chromatography using a mixed solvent of chloroform and methanol as an eluent. The solvent was evaporated from the eluent to give the title compound (free form, 457 mg) as a pale-yellow oil. By a similar method as in (1-2), the title compound (275 mg) was obtained as white crystals from the obtained residue.

$^1$H-NMR (DMSO-$d_6$) δ 2.65 (3H, s), 2.67-2.89 (1H, m), 2.90-3.09 (1H, m), 3.10-3.41 (4H, m), 3.72-4.04 (3H, m), 4.09 (2H, s), 4.32 (2H, brs), 7.56 (1H, d, J=8.1 Hz), 7.74 (1H, d, J=8.1 Hz), 7.90 (1H, brs), 8.34 (1H, s), 8.51-8.58 (1H, m), 11.3 (1H, brs).

MS (ESI) m/z: 514 [M+H]

Example 24

Synthesis of (2S)-N-{[4-(3,4-dichlorobenzyl)morpholin-2-yl]methyl}-[4-(5-ethoxycarbonyl-1,2,4-oxadiazol-3-yl)thiazol-2-ylthio]acetamide

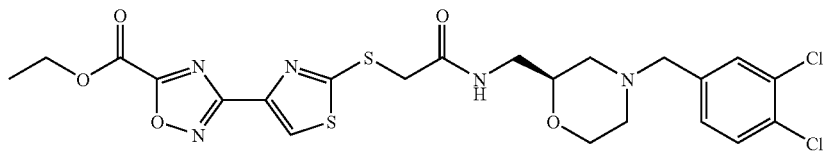

By a similar method as in Example 23, the title compound (223 mg) was obtained as a pale-yellow amorphous solid from the resultant product (1.66 g) of (22-2) and ethyl chloroglyoxylate (451 μL).

$^1$H-NMR (DMSO-$d_6$) δ 1.37 (3H, t, J=6.9 Hz), 1.80 (1H, t, J=10.6 Hz), 1.97-2.09 (1H, m), 2.53 (1H, d, J=11.0 Hz), 2.65 (1H, d, J=11.0 Hz), 3.15 (2H, t, J=5.7 Hz), 3.40-3.55 (4H, m), 3.75 (1H, d, J=11.3 Hz), 4.08 (1H, s), 4.45 (1H, q, J=7.2 Hz), 7.29 (1H, dd, J=1.7, 8.3 Hz), 7.51 (1H, d, J=1.7 Hz), 7.57 (1H, d, J=8.3 Hz), 8.40 (1H, t, J=5.6 Hz), 8.52 (1H, s).

MS (ESI) m/z: 572 [M+H].

Example 25

Synthesis of (2S)-[4-(5-carbamoyl-1,2,4-oxadiazol-3-yl)thiazol-2-ylthio]-N-{[4-(3,4-dichlorobenzyl)morpholin-2-yl]methyl}acetamide

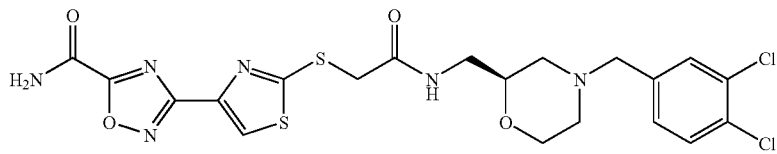

A 7 mol/L ammonia-methanol solution (2 mL) was added to the resultant product (175 mg) of Example 24, and the mixture was stirred at room temperature for 1.5 hrs. The resultant solid was collected by filtration to give the title compound (40 mg) as a white solid.

$^1$H-NMR (DMSO-$d_6$) δ 1.79 (1H, t, J=10.6 Hz), 1.98-2.09 (1H, m), 2.54 (1H, d, J=11.1 Hz), 2.65 (1H, d, J=11.1 Hz), 3.15 (2H, t, J=5.7 Hz), 3.38-3.53 (4H, m), 3.75 (1H, d, J=11.2 Hz), 4.07 (1H, s), 7.27 (1H, dd, J=1.4, 8.3 Hz), 7.29 (1H, d, J=1.4 Hz), 7.57 (1H, d, J=8.3 Hz), 8.34-8.40 (2H, m), 8.45 (1H, brs), 8.80 (1H, brs).

MS (ESI) m/z: 543 [M+H].

Example 26

Synthesis of (2S)-N-{[4-(3,4-dichlorobenzyl)morpholin-2-yl]methyl}-(5-nitro-8H-indeno[1,2-d]thiazol-2-ylthio)acetamide

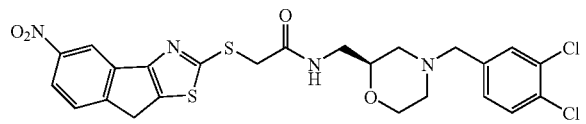

(26-1) Synthesis of 5-nitro-8H-2-mercapto-indeno[1,2-d]thiazole

By a similar method as in (1-3), the title compound (3.4 g) was obtained as a yellow powder from 2-bromo-6-nitro-1-indanone (7.4 g) and ammonium dithiocarbamate (6 g).

(26-2) Synthesis of (2S)-N-{[4-(3,4-dichlorobenzyl)morpholin-2-yl]methyl}-(5-nitro-8H-indeno[1,2-d]thiazol-2-ylthio)acetamide By a similar method as in (1-4), the title compound (520 mg) was obtained as a pale-yellow powder from the resultant product (500 mg) of (26-1) and the resultant product (700 mg) of (1-1).

$^1$H-NMR (DMSO-$d_6$) δ 1.75-1.83 (1H, m), 1.95-2.03 (1H, m), 2.49-2.52 (1H, m), 2.62-2.68 (1H, m), 3.14-3.19 (2H, m), 3.33 (2H, s), 3.40-3.51 (2H, m), 3.69-3.75 (1H, m), 4.03 (2H, s), 4.12 (2H, s), 7.17-7.22 (1H, m), 7.41 (1H, d, J=2.4 Hz), 7.52 (1H, d, J=8.0 Hz), 7.82 (1H, d, J=8.0 Hz), 8.13-8.18 (1H, m), 8.31-8.36 (2H, m).

MS (ESI) m/z: 565 [M+H].

Example 27

Synthesis of (2S)-(5-amino-8H-indeno[1,2-d]thiazol-2-ylthio)-N-{[4-(3,4-dichlorobenzyl)morpholin-2-yl]methyl}acetamide By a similar method as in Example 9, the title compound (180 mg) was obtained as a white powder from the resultant product (270 mg) of (26-2).

$^1$H-NMR (DMSO-$d_6$) δ 1.72-1.78 (1H, m), 1.94-2.01 (1H, m), 2.50-2.54 (1H, m), 2.59-2.64 (1H, m), 3.13-3.17 (2H, m), 3.35 (2H, s), 3.43-3.50 (2H, m), 3.68-3.75 (3H, m), 3.98 (2H, s), 5.08 (2H, s), 6.45-6.49 (1H, m), 6.87-6.89 (1H, m), 7.16 (1H, d, J=8.0 Hz), 7.20-7.23 (1H, m), 7.45-7.47 (1H, m), 7.54 (1H, d, J=8.0 Hz), 8.24-8.29 (1H, m).

MS (ESI) m/z: 535 [M+H].

Example 28

Synthesis of (2S)-N-{[4-(3,4-dichlorobenzyl)morpholin-2-yl]methyl}-(4,5-dihydro-8-nitronaphto[1,2-d]thiazol-2-ylthio)acetamide

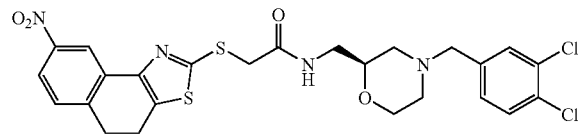

(28-1) Synthesis of 4,5-2-mercapto-8-nitronaphto[1,2-d]thiazole

By a similar method as in (1-3), the title compound (0.95 g) was obtained as a yellow powder from 2-bromo-7-nitro-1-tetralone (4.5 g) and ammonium dithiocarbamate (3.3 g).

(28-2) Synthesis of (2S)-N-{[4-(3,4-dichlorobenzyl)morpholin-2-yl]methyl}-(4,5-dihydro-8-nitronaphto[1,2-d]thiazol-2-ylthio)acetamide By a similar method as in (1-4), the title compound (800 mg) was obtained as a white amorphous solid from the resultant product (500 mg) of (28-1) and the resultant product (670 mg) of (1-1).

$^1$H-NMR (DMSO-$d_6$) δ 1.70-1.81 (1H, m), 1.95-2.02 (1H, m), 2.49-2.52 (1H, m), 2.61-2.66 (1H, m), 3.03-3.19 (6H, m), 3.35 (2H, s), 3.41-3.52 (2H, m), 3.69-3.73 (1H, m), 4.02 (2H, s), 7.21 (1H, dd, J=1.6, 8.0 Hz), 7.44 (1H, d, J=1.6 Hz), 7.52-7.60 (2H, m), 8.07 (1H, dd, J=2.4, 8.0 Hz), 8.34-8.39 (1H, m), 8.44 (1H, d, J=2.4 Hz).

MS (ESI) m/z: 579 [M+H].

Example 29

Synthesis of (2S)-(8-amino-4,5-dihydronaphto[1,2-d]thiazol-2-ylthio)-N-{[4-(3,4-dichlorobenzyl)morpholin-2-yl]methyl}acetamide

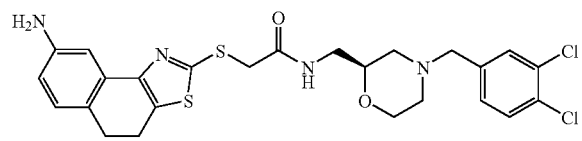

By a similar method as in Example 9, the title compound (570 mg) was obtained as a white amorphous solid from the resultant product (600 mg) of (28-2).

$^1$H-NMR (DMSO-$d_6$) δ 1.74-1.81 (1H, m), 1.96-2.04 (1H, m), 2.51-2.54 (1H, m), 2.61-2.65 (1H, m), 2.79 (2H, t, J=7.6 Hz), 2.88 (2H, t, J=7.6 Hz), 3.12-3.17 (2H, m), 3.38 (2H, s), 3.40-3.52 (2H, m), 3.71-3.74 (1H, m), 3.94 (2H, s), 4.96 (2H, s), 6.42 (1H, dd, J=1.6, 8.0 Hz), 6.90 (1H, d, J=8.0 Hz), 7.06 (1H, d, J=1.6 Hz), 7.24 (1H, dd, J=1.6, 8.0 Hz), 7.48 (1H, d, J=1.6 Hz), 7.55 (1H, d, J=8.0 Hz), 8.24-8.27 (1H, m).

MS (ESI) m/z: 549 [M+H].

Example 30

Synthesis of (2S)-N-{[4-(3,4-dichlorobenzyl)morpholin-2-yl]methyl}-(thiophen-2-ylthio)acetamide

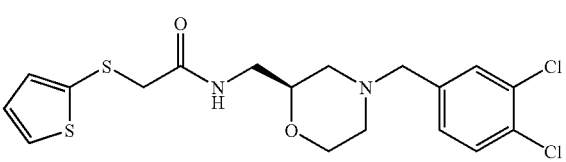

By a similar method as in (1-4), the title compound (4.2 g) was obtained as a brown oil from 2-mercaptothiophene (1 mL) and the resultant product (3.7 g) of (1-1).

$^1$H-NMR (DMSO-$d_6$) δ 1.74-1.81 (1H, m), 2.02-2.10 (1H, m), 2.53-2.65 (2H, m), 3.07-3.13 (2H, m), 3.40-3.50 (6H, m), 3.72-3.80 (1H, m), 7.00-7.05 (1H, m), 7.15-7.18 (1H, m), 7.28-7.34 (1H, m), 7.53-7.62 (3H, m), 8.04-8.08 (1H, m).

MS (ESI) m/z: 431 [M+H].

Example 31

Synthesis of (2S)-(2-bromothiophen-5-ylthio)-N-{[4-(3,4-dichlorobenzyl)morpholin-2-yl]methyl}acetamide

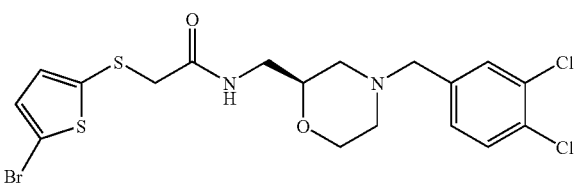

The resultant product (2.0 g) of Example 30 was dissolved in acetic acid (40 mL), pyridinium tribromide (1.5 g) was added, and the mixture was stirred at 60° C. for 1 hr. The reaction mixture was poured into water, and the mixture was extracted with ethyl acetate. The extract was washed with saturated brine, dried over anhydrous sodium sulfate, and the solvent was evaporated under reduced pressure. The obtained residue was purified by silica gel column chromatography using a mixed solvent of chloroform and methanol as an eluent. The solvent was evaporated from the eluent to give the title compound (2.0 g) as a white powder.

$^1$H-NMR (DMSO-$d_6$) δ 1.75-1.80 (1H, m), 2.02-2.10 (1H, m), 2.54-2.66 (2H, m), 3.06-3.13 (2H, m), 3.40-3.52 (6H, m), 3.74-3.79 (1H, m), 7.03 (1H, d, J=4.0 Hz), 7.15 (1H, d, J=4.0 Hz), 7.28-7.33 (1H, m), 7.53-7.55 (1H, m), 7.57 (1H, d, J=8.0 Hz), 8.07-8.13 (1H, m).

Example 32

Synthesis of (2S)-N-{[4-(3,4-dichlorobenzyl)morpholin-2-yl]methyl}-[5-(pyridin-4-yl)thiophen-2-ylthio]acetamide

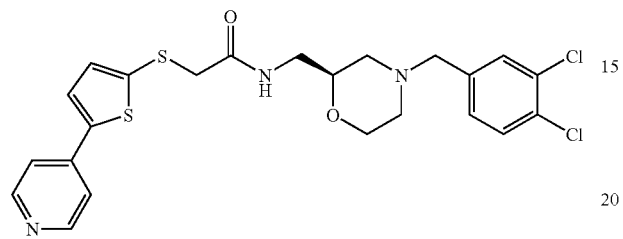

The resultant product (500 mg) of Example 31 and 4-pyridylboronic acid (250 mg) were dissolved in a mixed solvent of ethylene glycol dimethyl ether (25 mL) and water (5 mL), sodium hydrogen carbonate (500 mg) and tetrakistriphenylphosphine palladium (60 mg) were added, and the mixture was stirred overnight at 100° C. The reaction mixture was poured into water, and the mixture was extracted with ethyl acetate. The extract was washed with saturated brine, dried over anhydrous sodium sulfate, and the solvent was evaporated under reduced pressure. The obtained residue was purified by silica gel column chromatography using a mixed solvent of chloroform and methanol as an eluent. The solvent was evaporated from the eluent, and the obtained residue was recrystallized from ethyl acetate to give the title compound (90 mg) as a pale-brown powder.

$^1$H-NMR (DMSO-$d_6$) δ 1.72-1.80 (1H, m), 1.97-2.06 (1H, m), 2.51-2.54 (1H, m), 2.60-2.64 (1H, m), 3.08-3.13 (2H, m), 3.37-3.47 (4H, m), 3.59 (2H, s), 3.71-3.76 (1H, m), 7.21-7.27 (2H, m), 7.47-7.49 (1H, m), 7.52-7.59 (3H, m), 7.71 (1H, d, J=8.0 Hz), 8.12-8.16 (1H, m), 8.53-8.57 (2H, m).

MS (ESI) m/z: 508 [M+H].

Example 33

Synthesis of (2S)-N-{[4-(3,4-dichlorobenzyl)morpholin-2-yl]methyl}-[5-(3-nitrophenyl)thiophen-2-ylthio]acetamide

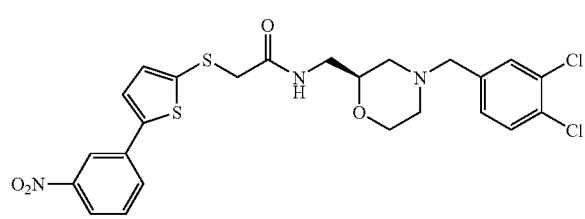

By a similar method as in Example 32, the title compound (350 mg) was obtained as a yellow powder from the resultant product (630 mg) of Example 31 and 3-nitrophenylboronic acid (210 mg).

$^1$H-NMR (DMSO-$d_6$) δ 1.74-1.81 (1H, m), 1.96-2.05 (1H, m), 2.50-2.55 (1H, m), 2.59-2.64 (1H, m), 3.08-3.14 (2H, m), 3.36-3.47 (4H, m), 3.58 (2H, s), 3.71-3.76 (1H, m), 7.20-7.25 (2H, m), 7.43-7.45 (1H, m), 7.52 (1H, d, J=8.0 Hz), 7.65-7.72 (2H, m), 8.05 (1H, d, J=8.0 Hz), 8.11-8.17 (2H, m), 8.32-8.35 (1H, m).

MS (ESI) m/z: 552 [M+H]

Example 34

Synthesis of (2S)-[5-(3-aminophenyl)thiophen-2-ylthio]-N-{[4-(3,4-dichlorobenzyl)morpholin-2-yl]methyl}acetamide

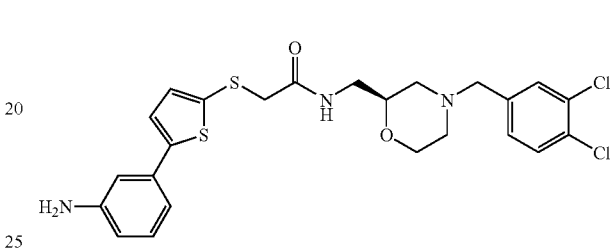

By a similar method as in Example 9, the title compound (190 mg) was obtained as a white powder from the resultant product (300 mg) of Example 33.

$^1$H-NMR (DMSO-$d_6$) δ 1.74-1.79 (1H, m), 1.98-2.05 (1H, m), 2.51-2.54 (1H, m), 2.60-2.65 (1H, m), 3.08-3.13 (2H, m), 3.37-3.52 (6H, m), 3.71-3.76 (1H, m), 5.19 (2H, brs), 6.51 (1H, d, J=8.0 Hz), 6.74 (1H, d, J=8.0 Hz), 6.78 (1H, s), 7.02 (1H, t, J=8.0 Hz), 7.11 (1H, d, J=4.0 Hz), 7.22 (1H, d, J=4.0 Hz), 7.26 (1H, s), 7.49 (1H, s), 7.55 (1H, d, J=8.0 Hz), 8.05-8.10 (1H, m).

MS (ESI) m/z: 522 [M+H].

Example 35

Synthesis of (2S)-[5-(3-cyanophenyl)thiophen-2-ylthio]-N-{[4-(3,4-dichlorobenzyl)morpholin-2-yl]methyl}acetamide

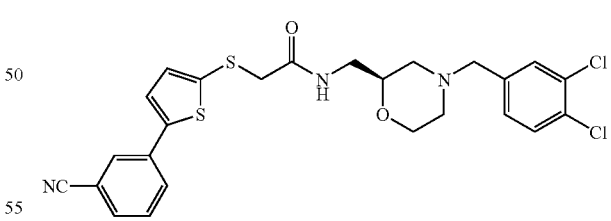

By a similar method as in Example 32, the title compound (150 mg) was obtained as a white powder from the resultant product (560 mg) of Example 31 and 3-cyanophenylboronic acid (170 mg).

$^1$H-NMR (DMSO-$d_6$) δ 1.73-1.81 (1H, m), 1.97-2.05 (1H, m), 2.51-2.54 (1H, m), 2.59-2.64 (1H, m), 3.08-3.13 (2H, m), 3.36-3.48 (4H, m), 3.56 (2H, s), 3.71-3.77 (1H, m), 7.18-7.26 (2H, m), 7.45 (1H, s), 7.54 (1H, d, J=8.0 Hz), 7.57-7.64 (2H, m), 7.74 (1H, d, J=8.0 Hz), 7.90 (1H, d, J=8.0 Hz), 8.12 (2H, brs).

MS (ESI) m/z: 532 [M+H].

Example 36

Synthesis of (2S)-N-{[4-(3,4-dichlorobenzyl)morpholin-2-yl]methyl}-{5-[3-(N²-hydroxyamidino)phenyl]thiophen-2-ylthio}acetamide

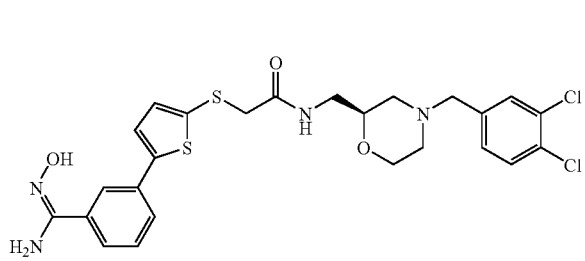

By a similar method as in (22-2), the title compound (210 mg) was obtained as a white powder from the resultant product (500 mg) of Example 35.

¹H-NMR (DMSO-d₆) δ 1.74-1.79 (1H, m), 1.97-2.05 (1H, m), 2.51-2.54 (1H, m), 2.60-2.65 (1H, m), 3.09-3.14 (2H, m), 3.38-3.48 (4H, m), 3.54 (2H, s), 3.71-3.76 (1H, m), 5.89 (2H, s), 7.18 (1H, d, J=3.6 Hz), 7.23 (1H, d, J=8.4 Hz), 7.39 (1H, t, J=7.6 Hz), 7.45 (1H, d, J=3.6 Hz), 7.48 (1H, s), 7.54 (1H, d, J=8.4 Hz), 7.59-7.64 (2H, m), 7.90 (1H, s), 8.08-8.13 (1H, m), 9.69 (1H, s).

MS (ESI) m/z: 565 [M+H].

Example 37

Synthesis of (2S)-(4-carboxyphenylthio)-N-{[4-(3,4-dichlorobenzyl)morpholin-2-yl]methyl}acetamide

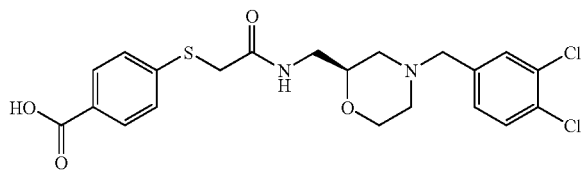

By a similar method as in (1-4), the title compound (1.2 g) was obtained as a white amorphous solid from 4-mercaptobenzoic acid (500 mg) and the resultant product (1.1 g) of (1-1).

¹H-NMR (DMSO-d₆) δ 1.70-1.78 (1H, m), 1.97-2.06 (1H, m), 2.51-2.61 (2H, m), 3.10-3.15 (2H, m), 3.37-3.49 (4H, m), 3.73-3.79 (3H, m), 7.24-7.28 (1H, m), 7.40 (2H, d, J=8.4 Hz), 7.50 (1H, s), 7.56 (1H, d, J=8.4 Hz), 7.83 (2H, d, J=8.4 Hz), 8.22-8.26 (1H, m), 12.85 (1H, brs).

MS (ESI) m/z: 469 [M+H].

Example 38

Synthesis of (2S)-(4-carbamoylphenylthio)-N-{[4-(3,4-dichlorobenzyl)morpholin-2-yl]methyl}acetamide

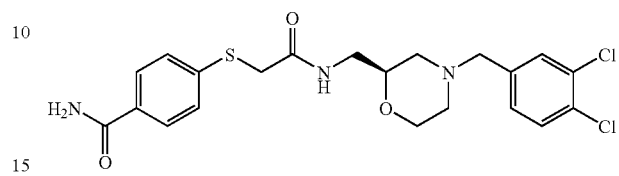

By a similar method as in Example 8, the title compound (330 mg) was obtained as a white powder from the resultant product (520 mg) of Example 37.

¹H-NMR (DMSO-d₆) δ 1.70-1.76 (1H, m), 1.96-2.04 (1H, m), 2.51-2.61 (2H, m), 3.09-3.14 (2H, m), 3.37-3.48 (4H, m), 3.70-3.79 (3H, m), 7.25-7.33 (2H, m), 7.36 (2H, d, J=8.4 Hz), 7.50-7.52 (1H, m), 7.56 (1H, d, J=8.4 Hz), 7.80 (2H, d, J=8.4 Hz), 7.91 (1H, brs), 8.17-8.22 (1H, m).

MS (ESI) m/z: 468 [M+H].

Example 39

Synthesis of (2S)-(4-acetaminophenylthio)-N-{[4-(3,4-dichlorobenzyl)morpholin-2-yl]methyl}acetamide

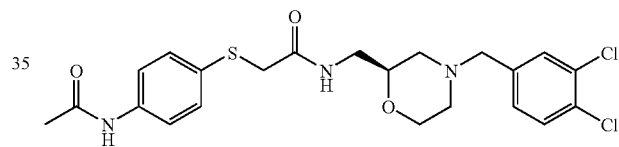

(39-1) Synthesis of (2S)-(4-aminophenylthio)-N-{[4-(3,4-dichlorobenzyl)morpholin-2-yl]methyl}acetamide By a similar method as in (1-4), the title compound (130 mg) was obtained as a white amorphous solid from 4-mercaptoaniline (300 mg) and the resultant product (850 mg) of (1-1).

(39-2) Synthesis of (2S)-(4-acetaminophenylthio)-N-{[4-(3,4-dichlorobenzyl)morpholin-2-yl]methyl}acetamide By a similar method as in Example 14, the title compound (130 mg) was obtained as a white amorphous solid from the resultant product (120 mg) of (39-1).

¹H-NMR (DMSO-d₆) δ 1.68-1.75 (1H, m), 1.96-2.05 (4H, m), 2.51-2.60 (2H, m), 3.06-3.12 (2H, m), 3.37-3.47 (4H, m), 3.53-3.56 (2H, m), 3.71-3.78 (1H, m), 7.25-7.32 (3H, m), 7.50-7.58 (4H, m), 8.04-8.09 (1H, m), 9.93 (1H, s).

MS (ESI) m/z: 482 [M+H].

Example 40

Synthesis of (2S)-{4-[(2-amino-2-oxoethyl)aminocarbonyl]phenylthio}-N-{[4-(3,4-dichlorobenzyl)morpholin-2-yl]methyl}acetamide

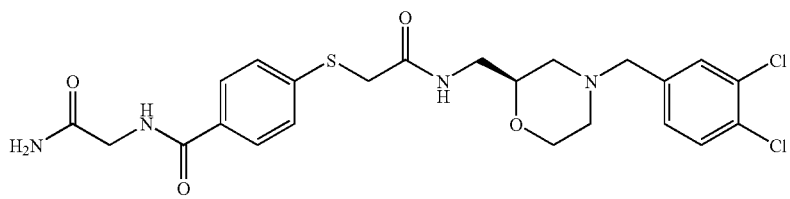

By a similar method as in Example 16, the title compound (390 mg) was obtained as a white powder from the resultant product (400 mg) of Example 37 and glycinamide hydrochloride (100 mg).

$^1$H-NMR (DMSO-$d_6$) δ 1.71-1.77 (1H, m), 1.98-2.06 (1H, m), 2.51-2.63 (2H, m), 3.09-3.15 (2H, m), 3.38-3.50 (4H, m), 3.71-3.83 (5H, m), 7.00 (1H, brs), 7.25-7.30 (1H, m), 7.33 (1H, brs), 7.38 (2H, d, J=8.0 Hz), 7.51 (1H, s), 7.56 (1H, d, J=8.0 Hz), 7.81 (2H, d, J=8.0 Hz), 8.18-8.24 (1H, m), 8.58-8.63 (1H, m).

MS (ESI) m/z: 525 [M+H].

Example 41

Synthesis of (2S)-{3-[(2-amino-2-oxoethyl)aminocarbonyl]phenylthio}-N-{[4-(3,4-dichlorobenzyl)morpholin-2-yl]methyl}acetamide

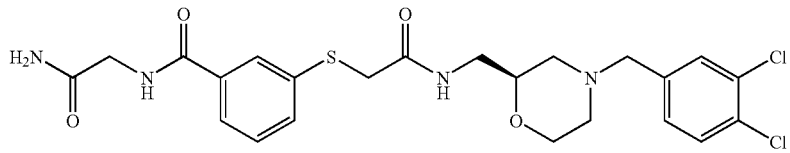

(41-1) Synthesis of (2S)-N-{[4-(3,4-dichlorobenzyl)morpholin-2-yl]methyl}-(3-methoxycarbonylphenylthio)acetamide 3-mercaptobenzoic acid (840 mg) and the resultant product (2.1 g) of (1-2) were dissolved in dimethylformamide (50 mL), potassium carbonate (2.1 g) was added, and the mixture was stirred at room temperature for 4 hrs. Methyl iodide (0.34 mL) was added, and the mixture was further stirred for 1 hr. Water was poured into the reaction mixture, and the mixture was extracted with ethyl acetate. The extract was washed with saturated brine, dried over anhydrous sodium sulfate, and the solvent was evaporated under reduced pressure. The obtained residue was purified by silica gel column chromatography using a mixed solvent of chloroform and methanol as an eluent. The solvent was evaporated from the eluent to give the title compound (2.0 g) as a white amorphous solid.

(41-2) Synthesis of (2S)-(3-carboxyphenylthio)-N-{[4-(3,4-dichlorobenzyl)morpholin-2-yl]methyl}acetamide By a similar method as in (1-5), the title compound (800 mg) was obtained as a white amorphous solid from the resultant product (2.0 g) of (41-1).

(41-3) Synthesis of (2S)-{3-[(2-amino-2-oxoethyl)aminocarbonyl]phenylthio}-N-{[4-(3,4-dichlorobenzyl)morpholin-2-yl]methyl}acetamide By a similar method as in Example 16, the title compound (210 mg) was obtained as a white powder from the resultant product (310 mg) of (41-2) and glycinamide hydrochloride (90 mg).

$^1$H-NMR (DMSO-$d_6$) δ 1.70-1.76 (1H, m), 1.97-2.03 (1H, m), 2.51-2.61 (2H, m), 3.08-3.13 (2H, m), 3.36-3.48 (4H, m), 3.70-3.82 (5H, m), 7.06 (1H, s), 7.28 (1H, d, J=8.0 Hz), 7.38-7.43 (2H, m), 7.47-7.59 (3H, m), 7.66-7.70 (1H, m), 7.83 (1H, s), 8.19-8.24 (1H, m), 8.67-8.74 (1H, m).

MS (ESI) m/z: 525 [M+H].

Example 42

Synthesis of (2S)-N-{[4-(3,4-dichlorobenzyl)morpholin-2-yl]methyl}-[4-(hydrazinocarbonyl)thiazol-2-ylthio]acetamide

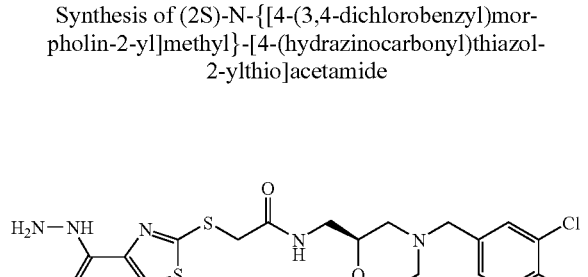

(42-1) Synthesis of (2S)-[4-(N'-tert-butoxycarbonylhydrazinocarbonyl)thiazol-2-ylthio]-N-{[4-(3,4-dichlorobenzyl)morpholin-2-yl]methyl}acetamide By a similar method as in Example 16, the title compound (4.01 g) was obtained as white crystals from the resultant product (8.45 g) of (1-5) and tert-butoxycarbonyl hydrazide (2.81 g).

(42-2) Synthesis of (2S)-N-{[4-(3,4-dichlorobenzyl)morpholin-2-yl]methyl}-[4-(hydrazinocarbonyl)thiazol-2-ylthio]acetamide The resultant product (4.01 g) of (42-1) was dissolved in methylene chloride (30 mL), trifluoroacetic acid (10 mL) was added, and the mixture was stirred overnight. The reaction mixture was concentrated under reduced pressure, a 1 mol/L aqueous sodium hydroxide solution was added to the residue, and the mixture was extracted with chloroform. The extract was washed with saturated brine, dried over anhydrous sodium sulfate, and the solvent was evaporated under reduced pressure. The obtained residue was recrystallized from a mixed solvent of ethyl acetate and methanol to give the title compound (453 mg) as white crystals.

$^1$H-NMR (DMSO-d$_6$) δ 1.73 (1H, t, J=10.5 Hz), 1.92-2.07 (1H, m), 2.52 (1H, d, J=11.1 Hz), 2.58 (1H, d, J=11.1 Hz), 3.13 (2H, t, J=5.7 Hz), 3.36-3.49 (4H, m), 3.75 (1H, d, J=11.4 Hz), 4.01 (1H, d, J=14.7 Hz), 4.06 (1H, d, J=14.7 Hz), 4.40-4.90 (2H, brs), 7.28 (1H, dd, J=1.8, 8.1 Hz), 7.53 (1H, d, J=1.8 Hz), 7.58 (1H, d, J=8.1 Hz), 8.13 (1H, s), 8.34 (1H, t, J=5.7 Hz), 9.62 (1H, s).

MS (ESI) m/z: 490 [M+H].

Example 43

Synthesis of (2S)-N-{[4-(3,4-dichlorobenzyl)morpholin-2-yl]methyl}-[4-(5-methyl-1,2,4-triazol-3-yl)thiazol-2-ylthio]acetamide hydrochloride

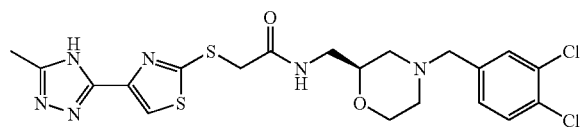

The resultant product (490 mg) of (42-2) and ethyl imidoacetate hydrochloride (148 mg) were suspended in ethanol (5 mL), triethylamine (167 μL) was added, and the mixture was heated under reflux for 5 hrs. Ethyl imidoacetate hydrochloride (148 mg) and triethylamine (167 μL) were added to the reaction mixture, and the mixture was further heated under reflux for 6 hrs. Ethyl acetate was added to the reaction mixture, and the mixture was washed with saturated brine, dried over anhydrous sodium sulfate, and the solvent was evaporated under reduced pressure. The obtained residue was purified by silica gel column chromatography using a mixed solvent of chloroform and ethanol as an eluent. The solvent was evaporated from the eluent to give a white amorphous solid. Purification by HPLC gave trifluoroacetic acid salt of the title compound as a colorless oil. By a similar method as in (1-2), the title compound (141 mg) was obtained as a white powder from the obtained residue.

$^1$H-NMR (DMSO-d$_6$) δ 2.43 (3H, s), 2.72-2.82 (1H, m), 2.90-3.07 (1H, m), 3.10-3.36 (4H, m), 3.72-4.08 (6H, m), 4.31 (2H, brs), 7.57 (1H, d, J=8.1 Hz), 7.73 (1H, d, J=8.1 Hz), 7.92 (1H, s), 8.15 (1H, s), 8.56-8.61 (1H, m), 11.6 (1H, brs).

MS (ESI) m/z: 513 [M+H].

Example 44

Synthesis of (2S)-{4-[((1S)-2-amino-1-hydroxymethyl-2-oxoethyl)aminocarbonyl]thiazol-2-ylthio}-N-{[4-(3,4-dichlorobenzyl)morpholin-2-yl]methyl}acetamide

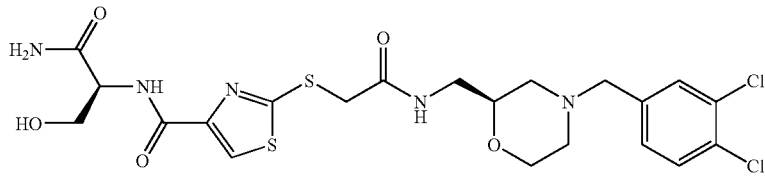

By a similar method as in Example 16, the title compound (203 mg) was obtained as a white solid from the resultant product (476 mg) of (1-5) and L-serinamide hydrochloride (169 mg).

$^1$H-NMR (DMSO-d$_6$) δ 1.77 (1H, t, J=10.8 Hz), 1.95-2.07 (1H, m), 2.54 (1H, d, J=10.5 Hz), 2.63 (1H, d, J=10.5 Hz), 3.15 (2H, t, J=5.7 Hz), 3.36-3.50 (4H, m), 3.59-3.79 (3H, m), 4.01 (2H, s), 4.34-4.42 (1H, m), 5.06 (1H, t, J=5.7 Hz), 7.21 (1H, brs), 7.29 (1H, dd, J=1.8, 8.4 Hz), 7.49 (1H, brs), 7.54 (1H, d, J=1.8 Hz), 7.58 (1H, d, J=8.4 Hz), 8.03 (1H, d, J=8.1 Hz), 8.21 (1H, s), 8.37 (1H, t, J=5.7 Hz).

MS (ESI) m/z: 562 [M+H].

Example 45

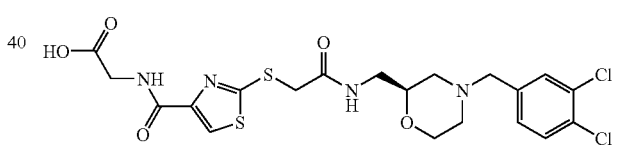

Synthesis of (2S)-[4-(carboxymethylaminocarbonyl)thiazol-2-ylthio]-N-{[4-(3,4-dichlorobenzyl)morpholin-2-yl]methyl}acetamide hydrochloride (45-1) Synthesis of (2S)-[4-(tert-butoxycarbonylmethylaminocarbonyl)thiazol-2-ylthio]-N-{[4-(3,4-dichlorobenzyl)morpholin-2-yl]methyl}acetamide By a similar method as in Example 16, the title compound (592 mg) was obtained as a white amorphous solid from the resultant product (476 mg) of (1-5) and glycine-tert-butyl ester hydrochloride (201 mg).

(45-2) Synthesis of (2S)-[4-(carboxymethylaminocarbonyl)thiazol-2-ylthio]-N-{[4-(3,4-dichlorobenzyl)morpholin-2-yl]methyl}acetamide hydrochloride By a similar method as in (42-2), trifluoroacetic acid salt of the title compound was obtained as a colorless oil from the resultant product (592 mg) of (45-1). By a similar method as in (1-2), the title compound (512 mg) was obtained as a white powder from the obtained residue.

$^1$H-NMR (DMSO-$d_6$) δ 2.62-2.80 (1H, m), 2.88-3.07 (1H, m), 3.10-3.30 (4H, m), 3.64-4.08 (7H, m), 4.29 (2H, brs), 7.53 (1H, d, J=8.1 Hz), 7.74 (1H, d, J=8.1 Hz), 7.86 (1H, s), 8.20 (1H, s), 8.51-8.55 (1H, m), 8.60 (1H, t, J=6.0 Hz), 11.0 (1H, brs), 12.6 (1H, brs).

MS (ESI) m/z: 533 [M+H].

Example 46

Synthesis of (2S)-{4-[(2-carboxyethyl)aminocarbonyl]thiazol-2-ylthio}-N-{[4-(3,4-dichlorobenzyl)morpholin-2-yl]methyl}acetamide hydrochloride

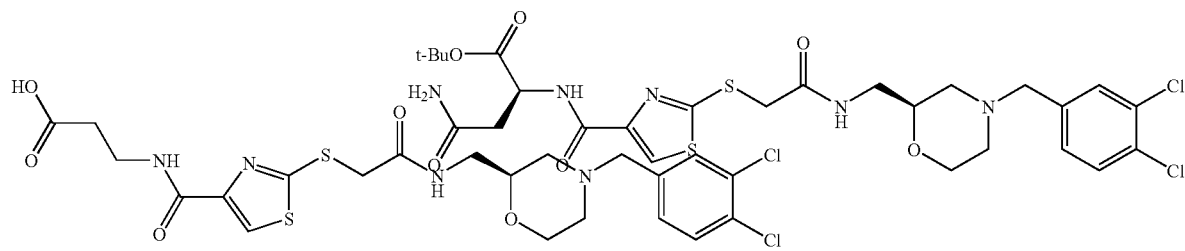

(46-1) Synthesis of (2S)-{4-[(2-tert-butoxycarbonylethyl)aminocarbonyl]thiazol-2-ylthio}-N-{[4-(3,4-dichlorobenzyl)morpholin-2-yl]methyl}acetamide By a similar method as in Example 16, the title compound (614 mg) was obtained as a colorless oil from the resultant product (476 mg) of (1-5) and β-alanine-tert-butyl ester hydrochloride (218 mg).

(46-2) Synthesis of (2S)-{4-[(2-carboxyethyl)aminocarbonyl]thiazol-2-ylthio}-N-{[4-(3,4-dichlorobenzyl)morpholin-2-yl]methyl}acetamide hydrochloride By a similar method as in (42-2), trifluoroacetic acid salt of the title compound was obtained as a colorless oil from the resultant product (592 mg) of (46-1). By a similar method as in (1-2), the title compound (531 mg) was obtained as a white powder from the obtained residue.

$^1$H-NMR (DMSO-$d_6$) δ 2.62-2.81 (1H, m), 2.88-3.07 (1H, m), 3.10-3.35 (4H, m), 3.42-3.50 (2H, m), 3.62-4.11 (7H, m), 4.31 (2H, brs), 7.57 (1H, d, J=8.1 Hz), 7.74 (1H, d, J=8.1 Hz), 7.92 (1H, s), 8.16 (1H, s), 8.39 (1H, t, J=5.7 Hz), 8.55 (1H, t, J=5.7 Hz), 11.5 (1H, brs), 12.4 (1H, brs).

MS (ESI) m/z: 547 [M+H].

Example 47

Synthesis of (2S)-{4-[((1S)-3-amino-1-(tert-butoxycarbonyl)-3-oxopropyl)aminocarbonyl]thiazol-2-ylthio}-N-{[4-(3,4-dichlorobenzyl)morpholin-2-yl]methyl}acetamide By a similar method as in Example 16, the title compound (625 mg) was obtained as a white amorphous solid from the resultant product (476 mg) of (1-5) and L-asparagine-tert-butyl ester hydrochloride (270 mg).

$^1$H-NMR (DMSO-$d_6$) δ 1.39 (9H, s), 1.78 (1H, t, J=10.5 Hz), 1.95-2.07 (1H, m), 2.51-2.70 (4H, d, J=10.5 Hz), 3.14 (2H, t, J=5.7 Hz), 3.38-3.50 (4H, m), 3.75 (1H, d, J=10.8 Hz), 4.00 (2H, s), 4.60-4.67 (1H, m), 6.97 (1H, brs), 7.29 (1H, d, J=8.4 Hz), 7.46 (1H, brs), 7.53-7.59 (2H, m), 8.21 (1H, s), 8.27-8.33 (1H, m), 8.47 (1H, d, J=8.1 Hz).

MS (ESI) m/z: 646 [M+H].

Example 48

Synthesis of (2S)-{4-[((1S)-3-amino-1-carboxy-3-oxopropyl)aminocarbonyl]thiazol-2-ylthio}-N-{[4-(3,4-dichlorobenzyl)morpholin-2-yl]methyl}acetamide hydrochloride

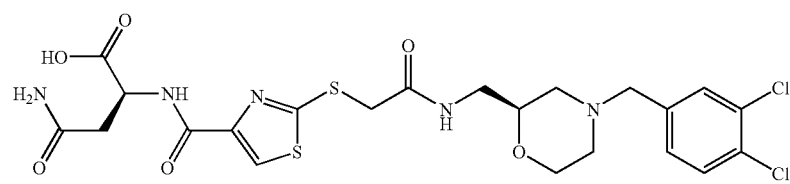

By a similar method as in (42-2), trifluoroacetic acid salt of the title compound was obtained as a colorless oil from the resultant product (561 mg) of Example 47. By a similar method as in (1-2), the title compound (491 mg) was obtained as a white powder from the obtained residue.

¹H-NMR (DMSO-d₆) δ 2.60-2.82 (3H, m), 2.88-3.07 (1H, m), 3.09-3.35 (4H, m), 3.72-4.12 (5H, m), 4.32 (2H, brs), 4.62-4.74 (1H, m), 6.98 (1H, brs), 7.51 (1H, brs), 7.59 (1H, dd, J=1.8, 8.1 Hz), 7.73 (1H, d, J=8.1 Hz), 7.94 (1H, d, J=1.8 Hz), 8.21 (1H, s), 8.42-8.58 (2H, m), 11.6 (1H, brs).

MS (ESI) m/z: 590 [M+H].

Example 49

Synthesis of (2S)-{4-[(((1S)-1-carbamoyl-3-methyl)butyl)aminocarbonyl]thiazol-2-ylthio}-N-{[4-(3,4-dichlorobenzyl)morpholin-2-yl]methyl}acetamide

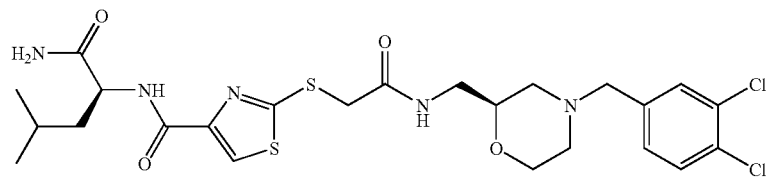

By a similar method as in Example 16, the title compound (562 mg) was obtained as a white amorphous solid from the resultant product (476 mg) of (1-5) and L-leucinamide hydrochloride (200 mg).

¹H-NMR (DMSO-d₆) δ 0.82-0.92 (6H, m), 1.49-1.69 (3H, m), 1.74 (1H, t, J=10.8 Hz), 1.93-2.07 (1H, m), 2.53 (1H, d, J=10.5 Hz), 2.60 (1H, d, J=10.5 Hz), 3.08-3.18 (2H, m), 3.36-3.50 (4H, m), 3.70-3.76 (1H, m), 3.97-4.08 (2H, m), 4.38-4.52 (1H, m), 7.11 (1H, brs), 7.28 (1H, dd, J=1.8, 8.1 Hz), 7.49-7.59 (3H, m), 8.04 (1H, d, J=9.0 Hz), 8.19 (1H, s), 8.35 (1H, t, J=5.7 Hz).

MS (ESI) m/z: 588 [M+H].

Example 50

Synthesis of (2S)-{4-[(((1S)-1-carboxy-3-methyl)butyl)aminocarbonyl]thiazol-2-ylthio}-N-{[4-(3,4-dichlorobenzyl)morpholin-2-yl]methyl}acetamide hydrochloride

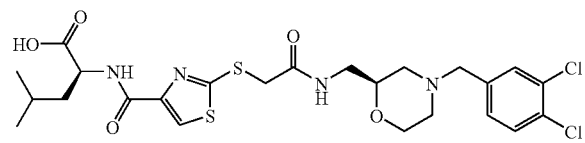

(50-1) Synthesis of (2S)-N-{[4-(3,4-dichlorobenzyl)morpholin-2-yl]methyl}-{4-[((1S)-1-methoxycarbonyl-3-methyl)butylaminocarbonyl]thiazol-2-ylthio}-acetamide By a similar method as in Example 16, the title compound (559 mg) was obtained as a pale-yellow amorphous solid from the resultant product (476 mg) of (1-5) and L-leucine methyl ester hydrochloride (218 mg).

(50-2) Synthesis of (2S)-{4-[(((1S)-1-carboxy-3-methyl)butyl)aminocarbonyl]thiazol-2-ylthio}-N-{[4-(3,4-dichlorobenzyl)morpholin-2-yl]methyl}acetamide hydrochloride By a similar method as in (1-5), a free form of the title compound was obtained as a colorless oil form the resultant product (500 mg) of (50-1). By a similar method as in (1-2), the title compound (470 mg) was obtained as a white powder from the obtained residue.

¹H-NMR (DMSO-d₆) δ 0.80-0.99 (6H, m), 1.51-1.70 (2H, m), 1.71-1.87 (1H, m), 2.62-2.80 (1H, m), 2.88-3.07 (1H, m), 3.10-3.30 (4H, m), 3.74-4.13 (5H, m), 4.32 (2H, brs), 4.40-4.52 (1H, m), 7.58 (1H, d, J=8.4 Hz), 7.74 (1H, d, J=8.4 Hz), 7.93 (1H, s), 8.21 (1H, s), 8.32 (1H, d, J=8.7 Hz), 8.57 (1H, t, J=5.7 Hz), 11.5 (1H, brs), 12.7 (1H, brs).

MS (ESI) m/z: 589 [M+H].

Example 51

Synthesis of (2S)-{4-[((1S)-1-carboxyethyl)aminocarbonyl]thiazol-2-ylthio}-N-{[4-(3,4-dichlorobenzyl)morpholin-2-yl]methyl}acetamide hydrochloride

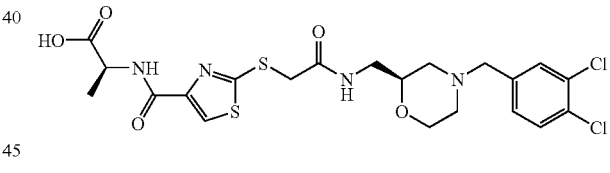

(51-1) Synthesis of (2S)-{4-[((1S)-1-benzyloxycarbonylethyl)aminocarbonyl]thiazol-2-ylthio}-N-{[4-(3,4-dichlorobenzyl)morpholin-2-yl]methyl}acetamide By a similar method as in Example 16, the title compound (677 mg) was obtained as a pale-yellow oil from the resultant product (476 mg) of (1-5) and L-alanine benzyl ester tosylate (422 mg).

(51-2) Synthesis of (2S)-{4-[((1S)-1-carboxyethyl)aminocarbonyl]thiazol-2-ylthio}-N-{[4-(3,4-dichlorobenzyl)morpholin-2-yl]methyl}acetamide By a similar method as in (1-5), a free form of the title compound was obtained as a colorless oil from the resultant product (677 mg) of (51-1). By a similar method as in (1-2), the title compound (480 mg) was obtained as a white powder from the obtained residue.

¹H-NMR (DMSO-d₆) δ 1.40 (3H, d, J=7.2 Hz), 2.64-2.81 (1H, m) 2.88-3.07 (1H, m), 3.10-3.30 (4H, m), 3.71-4.13 (5H, m), 4.31 (2H, brs), 4.39-4.51 (1H, m), 7.57 (1H, d, J=8.4 Hz), 7.74 (1H, d, J=8.4 Hz), 7.91 (1H, s), 8.20 (1H, s), 8.37 (1H, d, J=7.8 Hz), 8.55 (1H, t, J=5.4 Hz), 11.4 (1H, brs), 12.7 (1H, brs).

MS (ESI) m/z: 547 [M+H].

Example 52

Synthesis of (2S)-(5-amino-1,3,4-thiadiazol-2-ylthio)-N-{[4-(3,4-dichlorobenzyl)morpholin-2-yl]methyl}acetamide

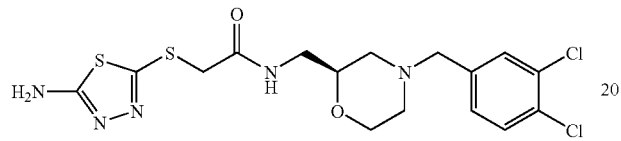

By a similar method as in (1-4), the title compound (760 mg) was obtained as white crystals from the resultant product (776 mg) of (1-2) and 2-amino-5-mercapto-1,3,4-thiadiazole (266 mg).

$^1$H-NMR (DMSO-$d_6$) δ 1.79 (1H, t, J=10.5 Hz), 1.99-2.10 (1H, m), 2.55 (1H, d, J=11.1 Hz), 2.65 (1H, d, J=11.1 Hz), 3.11 (2H, t, J=5.7 Hz), 3.41-3.52 (4H, m), 3.70-3.81 (3H, m), 7.21-7.33 (3H, m), 7.53-7.59 (2H, m), 8.20 (1H, t, J=5.7 Hz).

MS (ESI) m/z: 448 [M+H].

Example 53

Synthesis of (2S)-(5-acetamino-1,3,4-thiadiazol-2-ylthio)-N-{[4-(3,4-dichlorobenzyl)morpholin-2-yl]methyl}acetamide

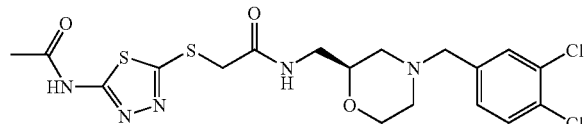

By a similar method as in Example 14, the title compound (447 mg) was obtained as white crystals from the resultant product (448 mg) of Example 52.

$^1$H-NMR (DMSO-$d_6$) δ 1.78 (1H, t, J=10.5 Hz), 1.96-2.09 (1H, m), 2.16 (3H, s), 2.54 (1H, d, J=10.8 Hz), 2.64 (1H, d, J=10.8 Hz), 3.13 (2H, t, J=5.7 Hz), 3.38-3.52 (4H, m), 3.75 (1H, d, J=11.1 Hz), 3.94 (2H, s), 7.29 (1H, dd, J=1.5, 8.1 Hz), 7.53 (1H, d, J=1.5 Hz), 7.58 (1H, d, J=8.1 Hz), 8.28 (1H, t, J=5.7 Hz), 12.6 (1H, s).

MS (ESI) m/z: 490 [M+H].

Example 54

Synthesis of (2S)-N-{[4-(3,4-dichlorobenzyl)morpholin-2-yl]methyl}-(4-methyl-5-carboxythiazol-2-ylthio)acetamide hydrochloride

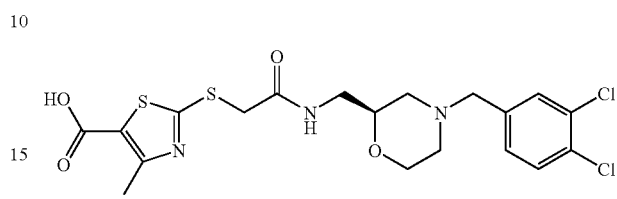

(54-1) Synthesis of 4-methyl-5-ethoxycarbonyl-2-mercaptothiazole

By a similar method as in (1-3), the title compound (63.9 g) was obtained as a pale-yellow solid from ethyl 2-chloroacetoacetate (100 g) and ammonium dithiocarbamate (73.6 g).

(54-2) Synthesis of (2S)-N-{[4-(3,4-dichlorobenzyl)morpholin-2-yl]methyl}-(4-methyl-5-ethoxycarbonylthiazol-2-ylthio)acetamide By a similar method as in (1-4), the title compound (975 mg) was obtained as a pale-yellow oil from the resultant product (776 mg) of (1-2) and the resultant product (407 mg) of (54-1).

(54-3) Synthesis of (2S)-N-{[4-(3,4-dichlorobenzyl)morpholin-2-yl]methyl}-(4-methyl-5-carboxythiazol-2-ylthio)acetamide The resultant product (975 mg) of (54-2) was reacted by a similar method as in (1-5), and purified by HPLC to give trifluoroacetic acid salt of the title compound as a colorless oil. By a similar method as in (1-2), the title compound (120 mg) was obtained as a white solid from the obtained residue.

$^1$H-NMR (DMSO-$d_6$) δ 2.55 (3H, s), 2.70-2.82 (1H, m), 2.90-3.07 (1H, m), 3.10-3.34 (4H, m), 3.76-4.13 (6H, m), 4.32 (2H, brs), 7.57 (1H, dd, J=1.5, 8.4 Hz), 7.74 (1H, d, J=8.4 Hz), 7.93 (1H, d, J=1.5 Hz), 8.56 (1H, d, J=5.7 Hz), 11.5 (1H, brs)

MS (ESI) m/z: 490 [M+H].

Example 55

Synthesis of (2S)-4-(4-carbamoylthiazol-2-ylthio)-N-{[4-(3,4-dichlorobenzyl)morpholin-2-yl]methyl}butyramide hydrochloride

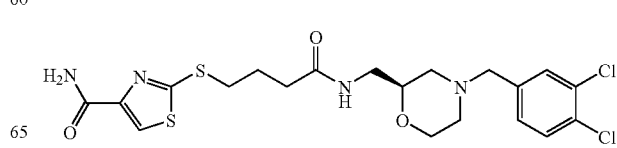

(55-1) Synthesis of benzyl 4-[4-(ethoxycarbonyl)thiazol-2-ylthio]butyrate

By a similar method as in (1-4), the title compound (11.1 g) was obtained as a pale-yellow oil from the resultant product (8.33 g) of (1-3) and benzyl 4-bromobutyrate (10.3 g).

(55-2) Synthesis of 4-[4-(ethoxycarbonyl)thiazol-2-ylthio]butyric acid

The resultant product (10.7 g) of (55-1) was dissolved in trifluoroacetic acid (30 mL), thioanisole (10.3 mL) was added, and the reaction mixture was stirred overnight at room temperature. The reaction mixture was concentrated under reduced pressure, the residue was dissolved in ethyl acetate, washed with water, dried over anhydrous sodium sulfate, and the solvent was evaporated under reduced pressure. The obtained residue was purified by silica gel column chromatography using a mixed solvent of hexane and ethyl acetate as an eluent. The solvent was evaporated from the eluent to give the title compound (5.81 g) as a white solid.

(55-3) Synthesis of (2S)-N-{[4-(3,4-dichlorobenzyl)morpholin-2-yl]methyl}-4-[4-(ethoxycarbonyl)thiazol-2-ylthio]butyramide By a similar method as in Example 16, the title compound (2.61 g) was obtained as a colorless oil from the resultant product (3.03 g) of (55-2) and (2S)-2-aminomethyl-4-(3,4-dichlorobenzyl)morpholine dihydrochloride (3.48 g).

(55-4) Synthesis of (2S)-4-(4-carbamoylthiazol-2-ylthio)-N-{[4-(3,4-dichlorobenzyl)morpholin-2-yl]methyl}butyramide hydrochloride By a similar method as in Example 25, a free form of the title compound was obtained as a colorless oil from the resultant product (533 mg) of (55-3). By a similar method as in (1-2), the title compound (397 mg) was obtained as a white solid from the obtained residue.

$^1$H-NMR (DMSO-$d_6$) δ 1.90-1.99 (2H, m), 2.26 (2H, t, J=7.2 Hz), 2.60-2.89 (1H, m), 2.90-3.07 (1H, m), 3.08-3.31 (6H, m), 3.70-4.01 (3H, m), 4.33 (2H, brs), 7.56-7.60 (2H, m), 7.72-7.75 (2H, m), 7.92 (1H, brs), 8.10-8.15 (2H, m), 11.4 (1H, brs)

MS (ESI) m/z: 503 [M+H].

Example 56

Synthesis of (2S)-4-[4-(carbamoylmethyl)thiazol-2-ylthio]-N-{[4-(3,4-dichlorobenzyl)morpholin-2-yl]methyl}butyramide hydrochloride

(56-1) Synthesis of benzyl 4-[4-(ethoxycarbonylmethyl)thiazol-2-ylthio]butyrate By a similar method as in (1-4), the title compound (2.17 g) was obtained as a pale-yellow oil from the resultant product (1.57 g) of (2-1) and benzyl 4-bromobutyrate (1.80 g).

(56-2) Synthesis of 4-[4-(ethoxycarbonylmethyl)thiazol-2-ylthio]butyric acid By a similar method as in (55-2), the title compound (0.82 g) was obtained as a colorless oil from the resultant product (2.08 g) of (56-1).

(56-3) Synthesis of (2S)-N-{[4-(3,4-dichlorobenzyl)morpholin-2-yl]methyl}-4-[4-(ethoxycarbonylmethyl)thiazol-2-ylthio]butyramide By a similar method as in Example 16, the title compound (1.32 g) was obtained as a colorless oil from the resultant product (796 mg) of (56-2) and (2S)-2-aminomethyl-4-(3,4-dichlorobenzyl)morpholine dihydrochloride (870 mg).

(56-4) Synthesis of (2S)-4-[4-(carbamoylmethyl)thiazol-2-ylthio]-N-{[4-(3,4-dichlorobenzyl)morpholin-2-yl]methyl}butyramide hydrochloride By a similar method as in Example 25, trifluoroacetic acid salt of the title compound was obtained as a colorless oil from the resultant product (1.32 g) of (56-3). By a similar method as in (1-2), the title compound (181 mg) was obtained as a white solid from the obtained residue.

$^1$H-NMR (DMSO-$d_6$) δ 1.90-1.97 (2H, m), 2.24 (2H, t, J=7.2 Hz), 2.63-2.82 (1H, m), 2.88-3.29 (7H, m), 3.50 (2H, s), 3.79-4.01 (3H, m), 4.34 (2H, brs), 6.98 (1H, brs), 7.32 (1H, s), 7.45 (1H, brs), 7.62 (1H, dd, J=1.5, 8.1 Hz), 7.74 (1H, d, J=8.1 Hz), 7.97 (1H, d, J=1.5 Hz), 8.12 (1H, d, J=5.7 Hz) 11.8 (1H, brs)

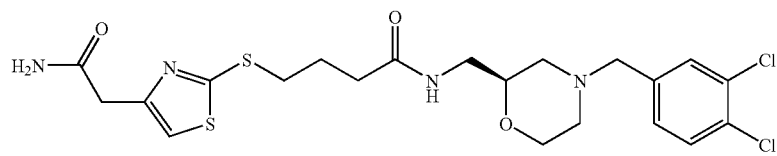

MS (ESI) m/z: 517 [M+H].

Example 57

Synthesis of (2S)-4-(4-carboxythiazol-2-ylthio)-N-{[4-(3,4-dichlorobenzyl)morpholin-2-yl]methyl}butyramide

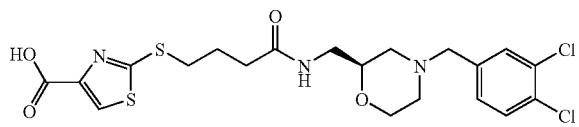

By a similar method as in (1-5), the title compound (1.31 g) was obtained as a white amorphous solid from the resultant product (1.34 g) of (55-3).

$^1$H-NMR (DMSO-$d_6$) δ 1.70-1.99 (3H, m), 2.00-2.11 (1H, m), 2.23 (2H, t, J=7.2 Hz), 2.52 (1H, d, J=11.1 Hz), 2.61 (1H, d, J=11.1 Hz), 3.05-3.11 (2H, m), 3.20 (2H, t, J=7.2 Hz), 3.40-3.61 (4H, m), 3.74 (1H, d, J=1H), 7.29 (1H, dd, J=1.8, 8.4 Hz), 7.52-7.59 (2H, m), 7.95 (1H, dd, J=6.0, 6.0z), 8.35 (1H, s).
MS (ESI) m/z: 504 [M+H].

Example 58

Synthesis of (2S)-4-[4-(2-amino-2-oxoethyl)aminocarbonylthiazol-2-ylthio]-N-{[4-(3,4-dichlorobenzyl)morpholin-2-yl]methyl}butyramide

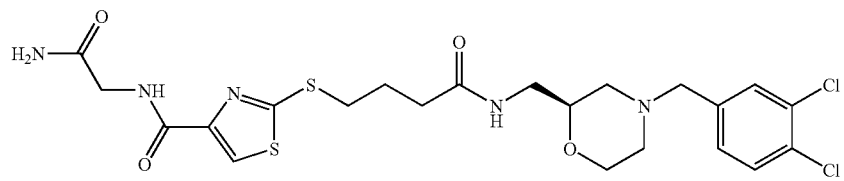

By a similar method as in Example 16, the title compound (1.12 g) was obtained as a white amorphous solid from the resultant product (1.01 g) of Example 57 and glycinamide hydrochloride (265 mg).

$^1$H-NMR (DMSO-$d_6$) δ 1.75-2.10 (4H, m), 2.24 (2H, t, J=7.2 Hz), 2.54 (1H, d, J=11.1 Hz), 2.64 (1H, d, J=11.1 Hz), 3.06-3.12 (2H, m), 3.23 (2H, t, J=7.3 Hz), 3.40-3.52 (4H, m), 3.70-3.83 (3H, m), 7.06 (1H, brs), 7.28 (1H, dd, J=1.7, 8.3 Hz), 7.39 (1H, brs), 7.53 (1H, d, J=1.7 Hz), 7.57 (1H, d, J=8.3 Hz), 7.98 (1H, dd, J=5.7, 5.7 Hz), 8.18 (1H, s), 8.42 (1H, t, J=5.8 Hz).

MS (ESI) m/z: 560 [M+H].

Example 59

Synthesis of (2S)-N-{[4-(3,4-dichlorobenzyl)morpholin-2-yl]methyl}-[4-(1H-tetrazol-5-yl)thiazol-2-ylthio]acetamide

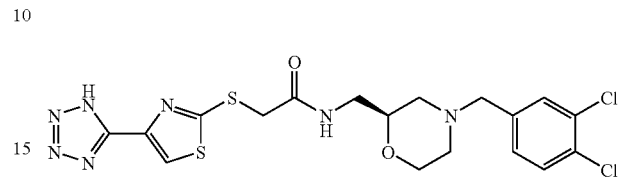

The resultant product (457 mg) of (22-1), sodium azide (78 mg) and ammonium chloride (525 mg) were suspended in dimethylformamide (3 mL), and the mixture was heated under reflux for 4 hrs. Water was added to the reaction mixture, and the mixture was extracted with ethyl acetate. The extract was washed with saturated brine, dried over anhydrous sodium sulfate, and the solvent was evaporated under reduced pressure. The obtained residue was purified by silica gel column chromatography using a mixed solvent of chloroform and methanol as an eluent. The solvent was evaporated from the eluent to give the title compound (193 mg) as an orange powder.

$^1$H-NMR (DMSO-$d_6$) δ 1.82-1.96 (1H, m), 2.02-2.18 (1H, m), 2.66 (1H, d, J=11.4 Hz), 2.78 (1H, d, J=11.4 Hz), 3.12-3.18 (2H, m), 3.39-3.57 (4H, m), 3.72 (1H, d, J=11.7 Hz), 3.92 (1H, d, J=15.0 Hz), 4.00 (1H, d, J=15.0 Hz), 7.24 (1H, d, J=8.1 Hz), 7.49 (1H, s), 7.54 (1H, d, J=8.1 Hz), 8.31 (1H, dd, J=5.7, 5.7 Hz), 8.34 (1H, s).
MS (ESI) m/z: 500 [M+H].

Example 60

Synthesis of (2S)-(5-carboxymethyl-4-methylthiazol-2-ylthio)-N-{[4-(3,4-dichlorobenzyl)morpholin-2-yl]methyl}acetamide

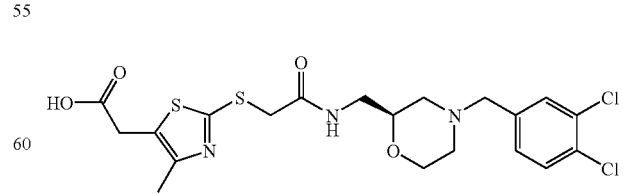

By a similar method as in (1-4), the title compound (316 mg) was obtained as a pale-yellow amorphous solid from the resultant product (388 mg) of (1-2) and 5-carboxymethyl-4-methyl-2-mercaptothiazole (189 mg).

¹H-NMR (DMSO-d₆) δ 1.73-1.87 (1H, m), 1.97-2.09 (1H, m), 2.21 (3H, s), 2.55 (1H, d, J=11.1 Hz), 2.66 (1H, d, J=11.1 Hz), 3.10-3.16 (2H, m), 3.39-3.52 (4H, m), 3.74 (2H, s), 3.76 (1H, d, J=11.1 Hz), 3.88 (2H, s), 7.29 (1H, d, J=8.1 Hz), 7.53-7.60 (2H, m), 8.28 (1H, dd, J=5.7, 5.7 Hz).

MS (ESI) m/z: 504 [M+H].

Example 61

Synthesis of (2S)-N-{[4-(3,4-dichlorobenzyl)morpholin-2-yl]methyl}-[4-methyl-5-(1-oxoethyl)thiazol-2-ylthio]acetamide hydrochloride

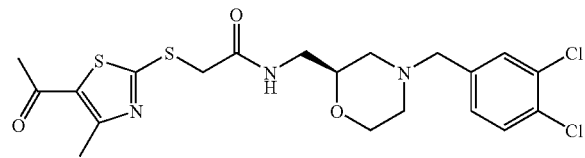

(61-1) Synthesis of 4-methyl-5-(1-oxoethyl)-2-mercaptothiazole

By a similar method as in (1-3), the title compound (25.0 g) was obtained as an orange solid from 3-chloroacetylacetone (23.7 g) and ammonium dithiocarbamate (21.4 g).

(61-2) Synthesis of (2S)-N-{[4-(3,4-dichlorobenzyl)morpholin-2-yl]methyl}-[4-methyl-5-(1-oxoethyl)thiazol-2-ylthio]acetamide hydrochloride By a similar method as in (1-4), the title compound (free form, 455 mg) was obtained as a pale-yellow oil from the resultant product (388 mg) of (1-2) and the resultant product (173 mg) of (61-1). By a similar method as in (1-2), the title compound (420 mg) was obtained as a white solid from the obtained residue.

¹H-NMR (DMSO-d₆) δ 2.50 (3H, s), 2.60 (3H, s), 2.70-2.89 (1H, m), 2.90-3.07 (1H, m), 3.09-3.38 (4H, m), 3.76-4.08 (5H, m), 4.32 (2H, brs), 7.56 (1H, d, J=8.4 Hz), 7.75 (1H, d, J=8.4 Hz), 7.91 (1H, s), 8.56 (1H, dd, J=5.4, 5.4 Hz), 11.3 (1H, brs).

MS (ESI) m/z: 488 [M+H].

Example 62

Synthesis of (2S)-(5-carbamoylmethyl-4-methylthiazol-2-ylthio)-N-{[4-(3,4-dichlorobenzyl)morpholin-2-yl]methyl}acetamide

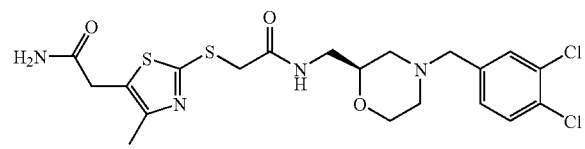

By a similar method as in Example 16, the title compound (217 mg) was obtained as a white solid from the resultant product (409 mg) of Example 60 and ammonium chloride (321 mg).

¹H-NMR (DMSO-d₆) δ 1.72-1.86 (1H, m), 1.97-2.09 (1H, m), 2.22 (3H, s), 2.55 (1H, d, J=10.5 Hz), 2.66 (1H, d, J=10.5 Hz), 3.10-3.16 (2H, m), 3.39-3.52 (6H, m), 3.76 (1H, d, J=9.6 Hz), 3.87 (2H, s), 7.07 (1H, brs), 7.29 (1H, d, J=8.4 Hz), 7.53-7.62 (3H, m), 8.27 (1H, dd, J=5.7, 5.7 Hz).

MS (ESI) m/z: 503 [M+H].

Example 63

Synthesis of (2S)-(5-carbamoyl-4-methylthiazol-2-ylthio)-N-{[4-(3,4-dichlorobenzyl)morpholin-2-yl]methyl}acetamide

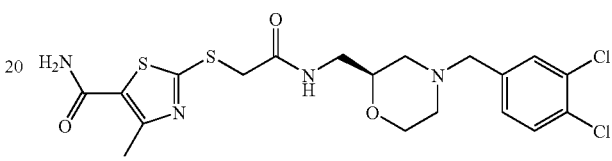

By a similar method as in Example 16, the title compound (245 mg) was obtained as a white solid from a free form (901 mg) of the resultant product of (54-3) and ammonium chloride (588 mg).

¹H-NMR (DMSO-d₆) δ 1.72-1.86 (1H, m), 1.97-2.09 (1H, m), 2.22 (3H, s), 2.55 (1H, d, J=10.5 Hz), 2.65 (1H, d, J=10.5 Hz), 3.11-3.17 (2H, m), 3.38-3.55 (4H, m), 3.76 (1H, d, J=11.1 Hz), 3.96 (2H, s), 7.29 (1H, d, J=8.4 Hz), 7.41-7.60 (4H, m), 8.30 (1H, dd, J=5.4, 5.4 Hz).

MS (ESI) m/z: 489 [M+H].

Example 64

Synthesis of (2S)-N-{[4-(3,4-dichlorobenzyl)morpholin-2-yl]methyl}-([1,3]thiazolo[5,4-b]pyridin-2-ylthio)acetamide

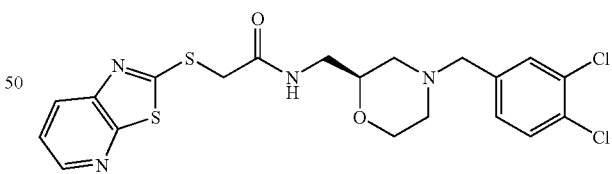

By a similar method as in (1-4), the title compound (405 mg) was obtained as a pale-yellow oil from the resultant product (388 mg) of (1-2) and 2-mercapto-[1,3]thiazolo[5,4-b]pyridine (168 mg).

¹H-NMR (DMSO-d₆) δ 1.72-1.86 (1H, m), 1.93-2.07 (1H, m), 2.53 (1H, d, J=11.1 Hz), 2.65 (1H, d, J=11.1 Hz), 3.13-3.19 (2H, m), 3.37-3.52 (4H, m), 3.74 (1H, d, J=11.1 Hz), 4.16 (2H, s), 7.26 (1H, dd, J=1.8, 8.1 Hz), 7.49-7.58 (3H, m), 8.20 (1H, dd, J=1.2, 8.1 Hz), 8.40 (1H, dd, J=5.7, 5.7 Hz), 8.50 (1H, dd, J=1.5, 4.5 Hz).

MS (ESI) m/z: 483 [M+H].

Example 65

Synthesis of (2S)-(6-aminobenzothiazol-2-ylthio)-N-{[4-(3,4-dichlorobenzyl)morpholin-2-yl]methyl}acetamide

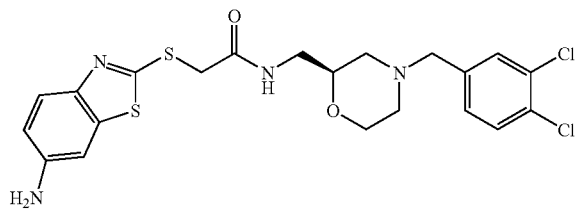

By a similar method as in (1-4), the title compound (371 mg) was obtained as a white amorphous solid from the resultant product (388 mg) of (1-2) and 6-amino-2-mercaptobenzothiazole (191 mg).

$^1$H-NMR (DMSO-d$_6$) δ 1.68-1.82 (1H, m), 1.90-2.07 (1H, m), 2.50-2.60 (1H, m), 2.62 (1H, d, J=10.3 Hz), 3.05-3.19 (2H, m), 3.35-3.52 (4H, m), 3.74 (1H, d, J=10.9 Hz), 3.99 (2H, s), 5.35 (2H, s), 6.70 (1H, d, J=8.5 Hz), 7.00 (1H, s), 7.25 (1H, d, J=7.8 Hz), 7.43-7.58 (3H, m), 8.21-8.35 (1H, m).

MS (ESI) m/z: 497 [M+H].

Example 66

Synthesis of (2S)-N-{[4-(3,4-dichlorobenzyl)morpholin-2-yl]methyl}-(4,5,6,7-tetrahydro[1,3]thiazolo[5,4-c]pyridin-2-ylthio)acetamide

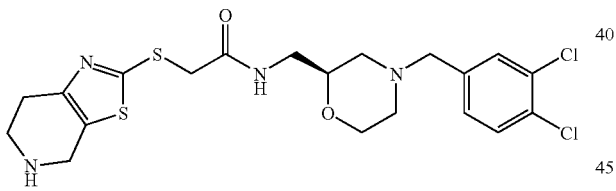

(66-1) Synthesis of 6-tertiary butoxycarbonyl-2-mercapto-4,5,6,7-tetrahydro[1,3]thiazolo[5,4-c]pyridine N-tertiary butoxycarbonyl-4-piperidone (996 mg) was dissolved in THF (15 mL), phenyltrimethylammonium tribromide (2.07 g) was added, and the mixture was stirred at room temperature for 30 min. Saturated aqueous sodium hydrogen carbonate was added to the reaction mixture, and the mixture was extracted with chloroform. The extract was washed with saturated brine, dried over anhydrous sodium sulfate, and the solvent was evaporated under reduced pressure. By a similar method as in (1-3), the title compound (310 mg) was obtained as a colorless oil from obtained residue (1.33 g) and ammonium dithiocarbamate (551 mg).

(66-2) Synthesis of (2S)-(6-tertiary butoxycarbonyl-4,5,6,7-tetrahydro[1,3]thiazolo[5,4-c]pyridin-2-ylthio)-N-{[4-(3,4-dichlorobenzyl)morpholin-2-yl]methyl}acetamide By a similar method as in (1-4), the title compound (558 mg) was obtained as a pale-yellow oil from the resultant product (442 mg) of (1-2) and the resultant product (310 mg) of (66-1).

(66-3) Synthesis of (2S)-N-{[4-(3,4-dichlorobenzyl)morpholin-2-yl]methyl}-(4,5,6,7-tetrahydro[1,3]thiazolo[5,4-c]pyridin-2-ylthio)acetamide By a similar method as in (42-2), the title compound (286 mg) was obtained as a colorless oil from the resultant product (558 mg) of (66-2).

$^1$H-NMR (DMSO-d$_6$) δ 1.72-1.86 (1H, m), 1.93-2.10 (1H, m), 2.50-2.70 (4H, m), 2.93 (2H, d, J=5.7 Hz), 3.09-3.15 (2H, m), 3.32-3.52 (4H, m), 3.74-3.80 (3H, m), 3.88 (2H, s), 7.29 (1H, dd, J=1.7, 6.4 Hz), 7.53-7.60 (2H, m), 8.27 (1H, dd, J=5.7, 5.7 Hz).

MS (ESI) m/z: 487 [M+H].

Example 67

Synthesis of (2S)-[4-(3-carbamoylisoxazol-5-yl)thiazol-2-ylthio]-N-{[4-(3,4-dichlorobenzyl)morpholin-2-yl]methyl}acetamide

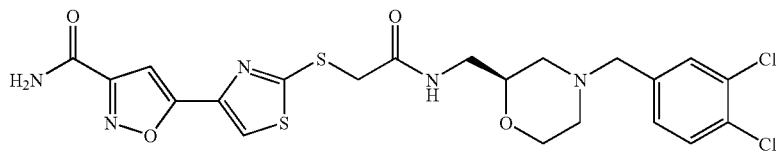

(67-1) Synthesis of 4-(3-ethoxycarbonylisoxazol-5-yl)-2-mercaptothiazole

By a similar method as in (1-3), the title compound (1.12 g) was obtained as a yellow solid from 5-bromoacetyl-3-ethoxycarbonylisoxazole (2.00 g) and ammonium dithiocarbamate (841 mg).

(67-2) Synthesis of (2S)-N-{[4-(3,4-dichlorobenzyl)morpholin-2-yl]methyl}-[4-(3-ethoxycarbonylisoxazol-5-yl)thiazol-2-ylthio]acetamide By a similar method as in (1-4), the title compound (1.70 g) was obtained as an orange amorphous solid from the resultant product (1.16 g) of (1-2) and the resultant product (769 mg) of (67-1).

(67-3) Synthesis of (2S)-[4-(3-carbamoylisoxazol-5-yl)thiazol-2-ylthio]-N-{[4-(3,4-dichlorobenzyl)morpholin-2-yl]methyl}acetamide By a similar method as in Example 25, the title compound (270 mg) was obtained as white crystals from the resultant product (572 mg) of (67-2).

¹H-NMR (DMSO-d₆) δ 1.69-1.83 (1H, m), 1.96-2.07 (1H, m), 2.52 (1H, d, J=11.1 Hz), 2.62 (1H, d, J=11.1 Hz), 3.11-3.17 (2H, m), 3.34-3.53 (4H, m), 3.72 (1H, d, J=11.1 Hz), 4.04 (2H, s), 7.14 (1H, s), 7.25 (1H, dd, J=1.8, 8.1 Hz), 7.50 (1H, d, J=1.8 Hz), 7.56 (1H, d, J=8.1 Hz), 7.90 (1H, brs), 8.20 (1H, brs), 8.33 (1H, s), 8.37 (1H, dd, J=5.7, 5.7 Hz).

MS (ESI) m/z: 542 [M+H].

Example 68

Synthesis of (2S)-N-{[4-(3,4-dichlorobenzyl)morpholin-2-yl]methyl}-[4-(2-methoxycarbonylpropan-2-yl)thiazol-2-ylthio]acetamide

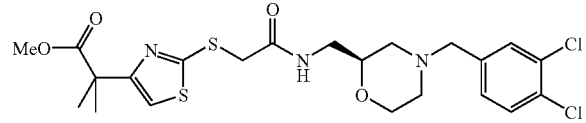

(68-1) Synthesis of 4-(2-methoxycarbonylpropan-2-yl)-2-mercaptothiazole

By a similar method as in (66-1), the title compound (782 mg) was obtained as a pale-yellow oil from methyl 2,2-dimethylacetoacetate (1.44 g).

(68-2) Synthesis of (2S)-N-{[4-(3,4-dichlorobenzyl)morpholin-2-yl]methyl}-[4-(2-methoxycarbonylpropan-2-yl)thiazol-2-ylthio]acetamide By a similar method as in (1-4), the title compound (1.51 g) was obtained as a pale-yellow oil from the resultant product (1.33 g) of (1-2) and the resultant product (782 mg) of (68-1).

¹H-NMR (DMSO-d₆) δ 1.48 (6H, s), 1.72-1.86 (1H, m), 1.98-2.11 (1H, m), 2.56 (1H, d, J=11.1 Hz), 2.65 (1H, d, J=11.1 Hz), 3.09-3.15 (2H, m), 3.38-3.52 (4H, m), 3.58 (3H, s), 3.76 (1H, d, J=11.1 Hz), 3.90 (2H, s), 7.29 (1H, dd, J=1.5, 8.1 Hz), 7.37 (1H, s), 7.54 (1H, d, J=1.5 Hz), 7.58 (1H, d, J=8.1 Hz), 8.29 (1H, dd, J=5.7, 5.7 Hz).

MS (ESI) m/z: 532 [M+H].

Example 69

Synthesis of (2S)-[4-(2-carboxypropan-2-yl)thiazol-2-ylthio]-N-{[4-(3,4-dichlorobenzyl)morpholin-2-yl]methyl}acetamide

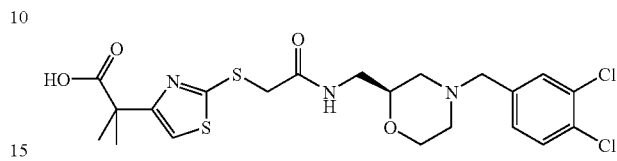

By a similar method as in (1-5), the title compound (183 mg) was obtained as a white amorphous solid from the resultant product (440 mg) of (68-2).

¹H-NMR (DMSO-d₆) δ 1.46 (6H, s), 1.73-1.87 (1H, m), 2.00-2.11 (1H, m), 2.56 (1H, d, J=11.1 Hz), 2.66 (1H, d, J=11.1 Hz), 3.10-3.16 (2H, m), 3.38-3.52 (4H, m), 3.76 (1H, d, J=11.1 Hz), 3.91 (2H, s), 7.30 (1H, dd, J=1.5, 8.2 Hz), 7.34 (1H, s), 7.54 (1H, d, J=1.5 Hz), 7.58 (1H, d, J=8.2 Hz), 8.29 (1H, dd, J=5.7 Hz).

MS (ESI) m/z: 518 [M+H].

Example 70

Synthesis of (2S)-(E)-[4-(2-carboxyethen-1-yl)thiazol-2-ylthio]-N-{[4-(3,4-dichlorobenzyl)morpholin-2-yl]methyl}acetamide

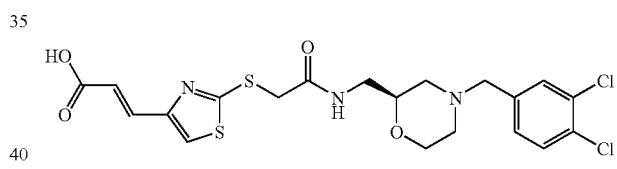

(70-1) Synthesis of (2S)-N-{[4-(3,4-dichlorobenzyl)morpholin-2-yl]methyl}-[4-(hydroxymethyl)thiazol-2-ylthio]acetamide The resultant product (2.09 g) of (1-4) was dissolved in ethanol (40 mL) and tetrahydrofuran (40 mL), sodium borohydride (454 mg) was added, lithium chloride (509 mg) was further added, and the mixture was stirred at room temperature for 4.5 hrs. Water was poured into the reaction mixture, the organic solvent alone was evaporated under reduced pressure, and the mixture was extracted with ethyl acetate. The extract was washed with saturated brine, dried over anhydrous sodium sulfate, and the solvent was evaporated under reduced pressure. The obtained residue was purified by silica gel column chromatography using a mixed solvent of chloroform and methanol as an eluent. The solvent was evaporated from the eluent to give the title compound (1.53 g) as a colorless oil.

(70-2) Synthesis of (2S)-N-{[4-(3,4-dichlorobenzyl)morpholin-2-yl]methyl}-(4-formylthiazol-2-ylthio)acetamide The resultant product (1.53 g) of (70-1) was dissolved in chloroform (10 mL), magnesium sulfate (500 mg) was added, manganese dioxide (1.35 g) was further added, and the mixture was stirred overnight at room temperature. Magnesium sulfate (500 mg) and manganese dioxide (1.35 g) were further added and the mixture was stirred at room temperature for 7 hrs. The reaction mixture was filtered through celite, and the solvent was evaporated under reduced pressure. The obtained residue was purified by silica gel column chromatography using a mixed solvent of chloroform and methanol as an eluent. The solvent was evaporated from the eluent to give the title compound (643 mg) as a colorless oil.

(70-3) Synthesis of (2S)-(E)-[4-(2-carboxyethen-1-yl)thiazol-2-ylthio]-N-{[4-(3,4-dichlorobenzyl)morpholin-2-yl]methyl}acetamide The resultant product (643 mg) of (70-2) was dissolved in pyridine (5 mL), malonic acid (291 mg) and piperidine (14 μL) were added, and the mixture was stirred at 100° C. for 3.5 hrs. The reaction mixture was poured into water, 1M hydrochloric acid was added to adjust to pH=4, and the mixture was extracted with ethyl acetate. The extract was washed with saturated brine, dried over anhydrous sodium sulfate, and the solvent was evaporated under reduced pressure. The obtained residue was purified by silica gel column chromatography using a mixed solvent of chloroform and methanol as an eluent. The solvent was evaporated from the eluent to give the title compound (618 mg) as a white amorphous solid.

$^1$H-NMR (DMSO-d$_6$) δ 1.70-1.84 (1H, m), 1.98-2.10 (1H, m), 2.53 (1H, d, J=11.1 Hz), 2.63 (1H, d, J=11.1 Hz), 3.11-3.17 (2H, m), 3.38-3.52 (4H, m), 3.75 (1H, d, J=11.1 Hz), 4.01 (2H, s), 6.54 (1H, d, J=15.3 Hz), 7.28 (1H, dd, J=1.5, 8.1 Hz), 7.45-7.58 (3H, m), 7.96 (1H, s), 8.34 (1H, dd, J=5.7, 5.7 Hz), 12.4 (1H, brs).

MS (ESI) m/z: 502 [M+H]

Example 71

Synthesis of (2S)-(E)-[4-(2-carbamoylethen-1-yl)thiazol-2-ylthio]-N-{[4-(3,4-dichlorobenzyl)morpholin-2-yl]methyl}acetamide

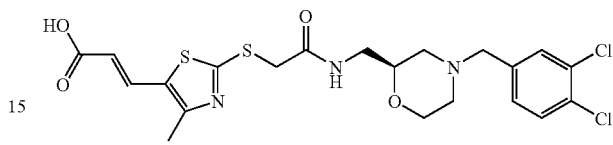

By a similar method as in Example 16, the title compound (173 mg) was obtained as a colorless oil from the resultant product (301 mg) of Example 70 and ammonium chloride (193 mg).

$^1$H-NMR (DMSO-d$_6$) δ 1.71-1.84 (1H, m), 1.98-2.10 (1H, m), 2.53 (1H, d, J=11.7 Hz), 2.63 (1H, d, J=11.9 Hz), 3.11-3.17 (2H, m), 3.38-3.52 (4H, m), 3.75 (1H, d, J=11.7 Hz), 3.98 (2H, s), 6.74 (1H, d, J=15.6 Hz), 7.11 (1H, brs), 7.27-7.33 (2H, m), 7.52-7.60 (3H, m), 7.82 (1H, s), 8.31 (1H, dd, J=5.7, 5.7 Hz).

MS (ESI) m/z: 501 [M+H].

Example 72

Synthesis of (2S)-(E)-[5-(2-carboxyethen-1-yl)-4-ethylthiazol-2-ylthio]-N-{[4-(3,4-dichlorobenzyl)morpholin-2-yl]methyl}acetamide (72-1) Synthesis of (2S)-N-{[4-(3,4-dichlorobenzyl)morpholin-2-yl]methyl}-[5-(hydroxymethyl)-4-methylthiazol-2-ylthio]acetamide By a similar method as in (70-1), the title compound (450 mg) was obtained as a colorless oil from the resultant product (1.70 g) of (54-2).

(72-2) Synthesis of (2S)-N-{[4-(3,4-dichlorobenzyl)morpholin-2-yl]methyl}-(5-formyl-4-methylthiazol-2-ylthio)acetamide By a similar method as in (70-2), the title compound (361 mg) was obtained as a white amorphous solid from the resultant product (450 mg) of (72-1).

(72-3) Synthesis of (2S)-(E)-[5-(2-carboxyethen-1-yl)-4-methylthiazol-2-ylthio]-N-{[4-(3,4-dichlorobenzyl)morpholin-2-yl]methyl}acetamide By a similar method as in (70-3), the title compound (140 mg) was obtained as a pale-yellow solid from the resultant product (361 mg) of (72-2).

$^1$H-NMR (DMSO-d$_6$) δ 1.72-1.86 (1H, m), 1.98-2.10 (1H, m), 2.41 (3H, s), 2.55 (1H, d, J=10.8 Hz), 2.65 (1H, d, J=10.8 Hz), 3.11-3.17 (2H, m), 3.38-3.52 (4H, m), 3.77 (1H, d, J=10.8 Hz), 4.00 (2H, s), 5.91 (1H, d, J=15.6 Hz), 7.28 (1H, d, J=8.1 Hz), 7.51-7.66 (3H, m), 8.37 (1H, dd, J=5.7, 5.7 Hz), 12.5 (1H, brs).

MS (ESI) m/z: 516 [M+H].

Example 73

Synthesis of (2S)-N-{[4-(3,4-dichlorobenzyl)morpholin-2-yl]methyl}-[4-(1-ethoxycarbonylcyclopropan-1-yl)thiazol-2-ylthio]acetamide

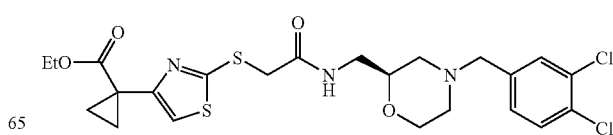

(73-1) Synthesis of 4-(1-ethoxycarbonylcyclopropan-1-yl)-2-mercaptothiazole

By a similar method as in (1-3), the title compound (7.56 g) was obtained as a yellow oil from ethyl 1-bromoacetylcyclopropanecarboxylate (13.1 g) and ammonium dithiocarbamate (5.93 g).

(73-2) Synthesis of [4-(1-ethoxycarbonylcyclopropan-1-yl)thiazol-2-ylthio]methyl acetate By a similar method as in (1-4), the title compound (1.61 g) was obtained as a yellow oil from the resultant product (7.56 g) of (73-1) and methyl bromoacetate (3.04 mL).

(73-3) Synthesis of [4-(1-ethoxycarbonylcyclopropan-1-yl)thiazol-2-ylthio]acetic acid By a similar method as in (1-5), the title compound (1.06 g) was obtained as a pale-yellow oil from the resultant product (1.61 g) of (73-2).

(73-4) Synthesis of (2S)-N-{[4-(3,4-dichlorobenzyl)morpholin-2-yl]methyl}-[4-(1-ethoxycarbonylcyclopropan-1-yl)thiazol-2-ylthio]acetamide By a similar method as in Example 16, the title compound (675 mg) was obtained as a colorless oil from the resultant product (1.06 g) of (73-3) and (2S)-2-aminomethyl-4-(3,4-dichlorobenzyl)morpholine dihydrochloride (1.17 g).

$^1$H-NMR (DMSO-$d_6$) δ 1.15 (3H, t, J=8.1 Hz), 1.30-1.41 (2H, m), 1.42-1.53 (2H, m), 1.70-1.83 (1H, m), 1.92-2.08 (1H, m), 2.55 (1H, d, J=10.5 Hz), 2.63 (1H, d, J=10.5 Hz), 3.08-3.16 (2H, m), 3.38-3.51 (4H, m), 3.75 (1H, d, J=10.5 Hz), 3.90 (2H, s), 3.98-4.10 (2H, m), 7.29 (1H, d, J=8.4 Hz), 7.43-7.60 (3H, m), 8.27 (1H, dd, J=5.7, 5.7 Hz).

MS (ESI) m/z: 544 [M+H].

Example 74

Synthesis of (2S)-N-{[4-(3,4-dichlorobenzyl)morpholin-2-yl]methyl}-[4-(1-carboxycyclopropan-1-yl)thiazol-2-ylthio]acetamide

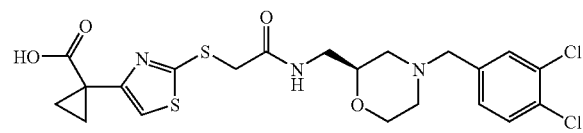

By a similar method as in (1-5), the title compound (594 mg) was obtained as a white amorphous solid from the resultant product (615 mg) of (73-4).

$^1$H-NMR (DMSO-$d_6$) δ 1.34-1.38 (2H, m), 1.47-1.52 (2H, m), 1.70-1.84 (1H, m), 1.95-2.09 (1H, m), 2.52 (1H, d, J=10.5 Hz), 2.63 (1H, d, J=10.5 Hz), 3.09-3.15 (2H, m), 3.38-3.52 (4H, m), 3.76 (1H, d, J=10.5 Hz), 3.90 (2H, s), 7.29 (1H, dd, J=1.5, 8.4 Hz), 7.53-7.60 (3H, m), 8.27 (1H, dd, J=5.7, 5.7 Hz), 12.5 (1H, s).

MS (ESI) m/z: 516 [M+H].

Example 75

Synthesis of (2S)-[4-(carboxymethyl)thiazol-2-ylthio]-N-{[4-(3,4-difluorobenzyl)morpholin-2-yl]methyl}acetamide

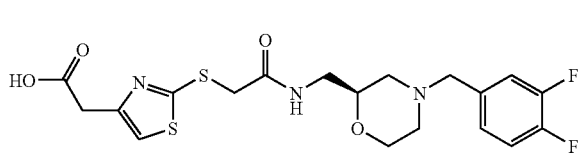

(75-1) Synthesis of (2S)-N-[(4-tertiary butoxycarbonylmorpholin-2-yl)methyl]chloroacetamide By a similar method as in (1-1), the title compound (6.15 g) was obtained as a colorless oil from 2-aminomethyl-4-tertiary butoxycarbonylmorpholine (4.65 g).

(75-2) Synthesis of (2S)-N-[(4-tertiary butoxycarbonylmorpholin-2-yl)methyl]-[4-(ethoxycarbonylmethyl)thiazol-2-ylthio]acetamide By a similar method as in (1-4), the title compound (6.80 g) was obtained as a yellow oil from the resultant product (6.15 g) of (75-1) and the resultant product (4.48 g) of (2-1).

(75-3) Synthesis of (2S)-[4-(ethoxycarbonylmethyl)thiazol-2-ylthio]-N-[(morpholin-2-yl)methyl]acetamide By a similar method as in (42-2), the title compound (3.96 g) was obtained as a pale-yellow oil from the resultant product (6.80 g) of (75-2).

(75-4) Synthesis of (2S)-[4-(ethoxycarbonylmethyl)thiazol-2-ylthio]-N-[(morpholin-2-yl)methyl]acetamide hydrochloride By a similar method as in (1-2), the title compound (4.40 g) was obtained as a white amorphous solid from the resultant product (3.96 g) of (75-3).

(75-5) Synthesis of (2S)-N-{[4-(3,4-difluorobenzyl)morpholin-2-yl]methyl}-[4-(ethoxycarbonylmethyl)thiazol-2-ylthio]acetamide Saturated aqueous sodium hydrogen carbonate was added to the resultant product (1.10 g) of (75-4), and the mixture was extracted with chloroform. The extract was washed with saturated brine, dried over anhydrous sodium sulfate, and the solvent was evaporated under reduced pressure. The obtained residue was dissolved in methylene chloride (15 mL), 3,4-difluorobenzaldehyde (332 μL) and acetic acid (159 μL) were added and the mixture was stirred at room temperature for 1 hr. Sodium triacetoxyborohydride (1.18 g) was added to the reaction mixture, and the mixture was stirred overnight at room temperature. Saturated aqueous sodium hydrogen carbonate was added to the reaction mixture, and the mixture was extracted with chloroform. The extract was washed with saturated brine, dried over anhydrous sodium sulfate, and the solvent was evaporated under reduced pressure. The obtained (75-6) Synthesis of (2S)-[4-(carboxymethyl)thiazol-2-ylthio]-N-{[4-(3,4-difluorobenzyl)morpholin-2-yl]methyl}acetamide By a similar method as in (1-5), the title compound (260 mg) was obtained as a white amorphous solid from the resultant product (291 mg) of (75-5).

¹H-NMR (DMSO-$d_6$) δ 1.71-1.85 (1H, m), 1.95-2.10 (1H, m), 2.56 (1H, d, J=11.1 Hz), 2.65 (1H, d, J=11.1 Hz), 3.10-3.16 (2H, m), 3.34-3.52 (4H, m), 3.67 (2H, s), 3.77 (1H, d, J=11.1 Hz), 3.92 (2H, s), 7.13-7.16 (1H, m), 7.29-7.42 (3H, m), 8.29-8.33 (1H, m).

MS (ESI) m/z: 458 [M+H].

Example 76

Synthesis of (2S)-[4-(carboxymethyl)thiazol-2-ylthio]-N-{[4-(3-chloro-4-fluorobenzyl)morpholin-2-yl]methyl}acetamide

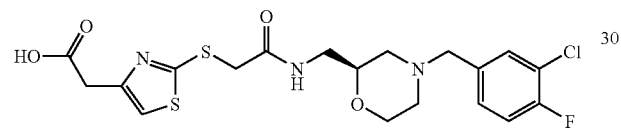

(76-1) Synthesis of (2S)-N-{[4-(3-chloro-4-fluorobenzyl)morpholin-2-yl]methyl}-[4-(ethoxycarbonylmethyl)thiazol-2-ylthio]acetamide By a similar method as in (75-5), the title compound (719 mg) was obtained as a colorless oil from the resultant product (792 mg) of (75-4) and 3-chloro-4-fluorobenzaldehyde (349 mg).

(76-2) Synthesis of (2S)-[4-(carboxymethyl)thiazol-2-ylthio]-N-{[4-(3-chloro-4-fluorobenzyl)morpholin-2-yl]methyl}acetamide By a similar method as in (1-5), the title compound (633 mg) was obtained as a white amorphous solid from the resultant product (719 mg) of (76-1).

¹H-NMR (DMSO-$d_6$) δ 1.73-1.89 (1H, m), 1.92-2.11 (1H, m), 2.50-2.69 (2H, m), 3.10-3.16 (2H, m), 3.34-3.52 (4H, m), 3.67 (2H, s), 3.77 (1H, d, J=11.1 Hz), 3.93 (2H, s), 7.25-7.60 (4H, m), 8.29-8.35 (1H, m).

MS (ESI) m/z: 474 [M+H].

Example 77

Synthesis of (2S)-[4-(carboxymethyl)thiazol-2-ylthio]-N-{[4-(4-chloro-3-fluorobenzyl)morpholin-2-yl]methyl}acetamide

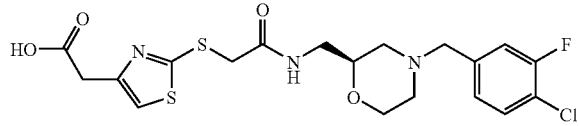

(77-1) Synthesis of (2S)-N-{[4-(4-chloro-3-fluorobenzyl)morpholin-2-yl]methyl}-[4-(ethoxycarbonylmethyl)thiazol-2-ylthio]acetamide By a similar method as in (75-5), the title compound (735 mg) was obtained as a colorless oil from the resultant product (792 mg) of (75-4) and 4-chloro-3-fluorobenzaldehyde (349 mg).

(77-2) Synthesis of (2S)-[4-(carboxymethyl)thiazol-2-ylthio]-N-{[4-(4-chloro-3-fluorobenzyl)morpholin-2-yl]methyl}acetamide By a similar method as in (1-5), the title compound (621 mg) was obtained as a white amorphous solid from the resultant product (735 mg) of (77-1).

¹H-NMR (DMSO-$d_6$) δ 1.70-1.88 (1H, m), 1.95-2.11 (1H, m), 2.56 (1H, d, J=11.1 Hz), 2.65 (1H, d, J=11.1 Hz), 3.10-3.16 (2H, m), 3.34-3.52 (4H, m), 3.67 (2H, s), 3.77 (1H, d, J=11.1 Hz), 3.92 (2H, s), 7.17 (1H, d, J=8.1 Hz), 7.33 (1H, d, J=10.5 Hz), 7.38 (1H, s), 7.53 (1H, t, J=8.1 Hz), 8.29-8.32 (1H, m).

MS (ESI) m/z: 474 [M+H].

Example 78

Synthesis of (2S)-[4-(carboxymethyl)thiazol-2-ylthio]-N-{[4-(6-fluoronaphthyl-2-ylmethyl)morpholin-2-yl]methyl}acetamide

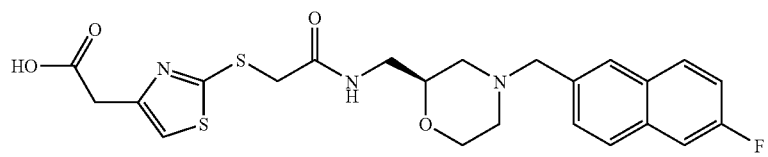

(78-1) Synthesis of (2S)-[4-(ethoxycarbonylmethyl)thiazol-2-ylthio]-N-{[4-(6-fluoronaphthyl-2-ylmethyl)morpholin-2-yl]methyl}acetamide By a similar method as in (75-5), the title compound (762 mg) was obtained as a colorless oil from the resultant product (792 mg) of (75-4) and 6-fluoro-2-naphtoaldehyde (383 mg).

(78-2) Synthesis of (2S)-[4-(carboxymethyl)thiazol-2-ylthio]-N-{[4-(6-fluoronaphthyl-2-ylmethyl)morpholin-2-yl]methyl}acetamide By a similar method as in (1-5), the title compound (686 mg) was obtained as a white amorphous solid from the resultant product (762 mg) of (78-1).
$^1$H-NMR (DMSO-$d_6$) δ 1.73-1.89 (1H, m), 1.92-2.11 (1H, m), 2.52-2.76 (2H, m), 3.10-3.16 (2H, m), 3.34-3.52 (4H, m), 3.67 (2H, s), 3.77 (1H, d, J=11.1 Hz), 3.91 (2H, s), 7.36 (1H, s), 7.37-7.44 (1H, m), 7.53 (1H, d, J=8.4 Hz), 7.68 (1H, d, J=8.4 Hz), 7.83-7.90 (2H, m), 7.95-8.01 (1H, m), 8.29-8.32 (1H, m).
MS (ESI) m/z: 490 [M+H].

Example 79

Synthesis of (2S)-[4-(carbamoylmethyl)thiazol-2-ylthio]-N-{[4-(3,4-difluorobenzyl)morpholin-2-yl]methyl}acetamide

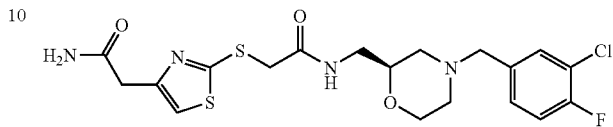

By a similar method as in Example 16, the title compound (301 mg) was obtained as white crystals from the resultant product (458 mg) of (75-6) and ammonium chloride (321 mg).
$^1$H-NMR(DMSO-$d_6$) δ 1.71-1.84(1H, m), 1.94-2.09(1H, m), 2.55(1H, d, J=11.1 Hz), 2.64(1H, d, J=11.1Hz), 3.10-3.17 (2H, m), 3.38-3.52(6H, m), 3.76(1H, d, J=11.1 Hz), 3.92(2H, s), 6.99(1H, brs), 7.10-7.16(1H, m), 7.31-7.42(4H, m), 8.30 (1H, dd, J=5.7, 5.7 Hz).

MS(ESI)m/z:457[M+H].

Example 80

Synthesis of (2S)-[4-(carbamoylmethyl)thiazol-2-ylthio]-N-{[4-(3-chloro-4-fluorobenzyl)morpholin-2-yl]methyl}acetamide

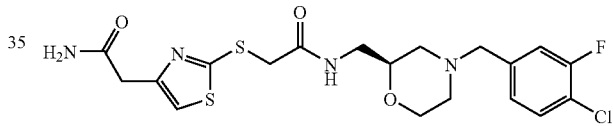

By a similar method as in Example 16, the title compound (409 mg) was obtained as a colorless oil from the resultant product (443 mg) of (76-2) and ammonium chloride (300 mg).
$^1$H-NMR (DMSO-$d_6$) δ 1.71-1.85 (1H, m), 1.94-2.09 (1H, m), 2.55 (1H, d, J=11.1 Hz), 2.64 (1H, d, J=11.1 Hz), 3.09-3.17 (2H, m), 3.38-3.52 (6H, m), 3.76 (1H, d, J=11.1 Hz), 3.92 (2H, s), 6.99 (1H, brs), 7.27-7.41 (4H, m), 7.48 (1H, dd, J=1.8, 7.2 Hz), 8.30 (1H, dd, J=5.7, 5.7 Hz).
MS (ESI) m/z: 473 [M+H].

Example 81

Synthesis of (2S)-[4-(carbamoylmethyl)thiazol-2-ylthio]-N-{[4-(4-chloro-3-fluorobenzyl)morpholin-2-yl]methyl}acetamide

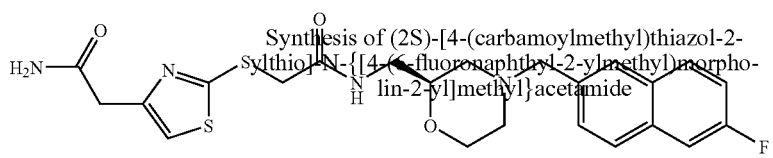

By a similar method as in Example 16, the title compound (403 mg) was obtained as a white solid from the resultant product (424 mg) of (77-2) and ammonium chloride (287 mg).
$^1$H-NMR (DMSO-$d_6$) δ 1.71-1.84 (1H, m), 1.94-2.09 (1H, m), 2.56 (1H, d, J=11.1 Hz), 2.64 (1H, d, J=11.1 Hz), 3.10-3.17 (2H, m), 3.38-3.52 (6H, m), 3.76 (1H, d, J=11.1 Hz), 3.92 (2H, s), 6.99 (1H, brs), 7.17 (1H, dd, J=1.4, 8.2 Hz), 7.31 (1H, s), 7.34 (1H, d, J=1.4 Hz), 7.39 (1H, brs), 7.53 (1H, t, J=8.2 Hz), 8.29 (1H, dd, J=5.7, 5.7 Hz).
MS (ESI) m/z: 473 [M+H].

Example 82

Synthesis of (2S)-[4-(carbamoylmethyl)thiazol-2-ylthio]-N-{[4-(6-fluoronaphthyl-2-ylmethyl)morpholin-2-yl]methyl}acetamide By a similar method as in Example 16, the title compound (387 mg) was obtained as a white amorphous solid from the resultant product (462 mg) of (78-2) and ammonium chloride (303 mg).
$^1$H-NMR (DMSO-$d_6$) δ 1.76-1.90 (1H, m), 1.99-2.13 (1H, m), 2.60 (1H, d, J=11.2 Hz), 2.70 (1H, d, J=11.2 Hz), 3.09-3.17 (2H, m), 3.40-3.54 (4H, m), 3.59 (2H, s), 3.76 (1H, d, J=11.2 Hz), 3.91 (2H, s), 6.98 (1H, brs), 7.30 (1H, s), 7.32-

7.43 (2H, m), 7.52 (1H, d, J=8.5 Hz), 7.68 (1H, dd, J=2.6, 10.4 Hz), 7.78-7.89 (2H, m), 7.91-8.02 (1H, m), 8.29 (1H, dd, J=5.7, 5.7 Hz).
MS (ESI) m/z: 489 [M+H].

Example 83

Synthesis of (2S)-[4-(carboxymethyl)thiazol-2-ylthio]-N-{[4-(3-chlorobenzyl)morpholin-2-yl]methyl}acetamide

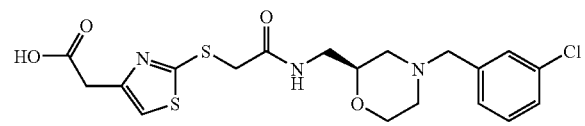

(83-1) Synthesis of (2S)-N-{[4-(3-chlorobenzyl)morpholin-2-yl]methyl}chloroacetamide By a similar method as in (1-1), the title compound (13.4 g) was obtained as a yellow oil from (2S)-2-aminomethyl-4-(3-chlorobenzyl)morpholine dihydrochloride (12.5 g).

(83-2) Synthesis of (2S)-N-{[4-(3-chlorobenzyl)morpholin-2-yl]methyl}-[4-(ethoxycarbonylmethyl)thiazol-2-ylthio]acetamide By a similar method as in (1-4), the title compound (1.01 g) was obtained as a pale-yellow oil from the resultant product (1.27 g) of (83-1) and the resultant product (813 mg) of (2-1).

(83-3) Synthesis of (2S)-[4-(carboxymethyl)thiazol-2-ylthio]-N-{[4-(3-chlorobenzyl)morpholin-2-yl]methyl}acetamide By a similar method as in (1-5), the title compound (850 mg) was obtained as a white amorphous solid from the resultant product (1.01 g) of (83-2).
$^1$H-NMR (DMSO-$d_6$) δ 1.71-2.20 (2H, m), 2.53-2.79 (2H, m), 3.10-3.17 (2H, m), 3.34-3.52 (4H, m), 3.67 (2H, s), 3.79 (1H, d, J=10.7 Hz), 3.93 (2H, s), 7.20-7.42 (5H, m), 8.25-8.36 (1H, m).
MS (ESI) m/z: 456 [M+H].

Example 84

Synthesis of (2S)-[4-(carbamoylmethyl)thiazol-2-ylthio]-N-{[4-(3-chlorobenzyl)morpholin-2-yl]methyl}acetamide

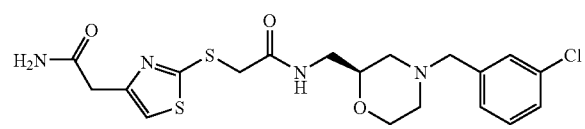

By a similar method as in Example 16, the title compound (425 mg) was obtained as a colorless oil from the resultant product (456 mg) of (83-3) and ammonium chloride (321 mg).

$^1$H-NMR (DMSO-$d_6$) δ 1.71-1.85 (1H, m), 1.94-2.09 (1H, m), 2.55 (1H, d, J=11.1 Hz), 2.65 (1H, d, J=11.1 Hz), 3.09-3.17 (2H, m), 3.38-3.52 (6H, m), 3.76 (1H, d, J=11.1 Hz), 3.91 (2H, s), 6.97 (1H, brs), 7.20-7.41 (6H, m), 8.28 (1H, dd, J=5.7, 5.7 Hz).
MS (ESI) m/z: 455 [M+H].

Example 85

Synthesis of (2S)-[4-(carboxymethyl)thiazol-2-ylthio]-N-{[4-(4-chlorobenzyl)morpholin-2-yl]methyl}acetamide

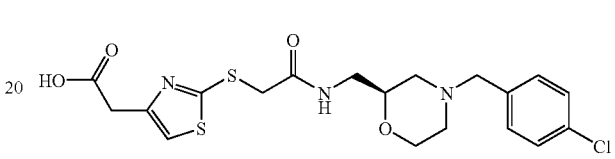

(85-1) Synthesis of (2S)-N-{[4-(4-chlorobenzyl)morpholin-2-yl]methyl}-[4-(ethoxycarbonylmethyl)thiazol-2-ylthio]acetamide The resultant product (899 mg) of (75-3) was dissolved in methylene chloride (12.5 mL), 4-chlorobenzaldehyde (387 mg) and acetic acid (143 μL) were added and the mixture was stirred at room temperature for 1 hr. Sodium triacetoxyborohydride (1.06 g) was added to the reaction mixture and the mixture was further stirred overnight at room temperature. Saturated aqueous sodium hydrogen carbonate was added to the reaction mixture, and the mixture was extracted with chloroform. The extract was washed with saturated brine, dried over anhydrous sodium sulfate, and the solvent was evaporated under reduced pressure. The obtained residue was purified by silica gel column chromatography using a mixed solvent of chloroform and acetone as an eluent. The solvent was evaporated from the eluent to give the title compound (1.16 g) as a pale-yellow oil.

(85-2) Synthesis of (2S)-[4-(carboxymethyl)thiazol-2-ylthio]-N-{[4-(4-chlorobenzyl)morpholin-2-yl]methyl}acetamide By a similar method as in (1-5), the title compound (904 mg) was obtained as a white amorphous solid from the resultant product (1.16 g) of (85-1).
$^1$H-NMR (DMSO-$d_6$) δ 1.68-1.88 (1H, m), 1.95-2.10 (1H, m), 2.50-2.70 (2H, m), 3.09-3.17 (2H, m), 3.34-3.52 (4H, m), 3.67 (2H, s), 3.77 (1H, d, J=11.2 Hz), 3.92 (2H, s), 7.28-7.42 (5H, m), 8.32 (1H, dd, J=5.5, 5.5 Hz).

MS (ESI) m/z: 456 [M+H].

Example 86

Synthesis of (2S)-[4-(carboxymethyl)thiazol-2-ylthio]-N-{[4-(2,3-dichlorobenzyl)morpholin-2-yl]methyl}acetamide

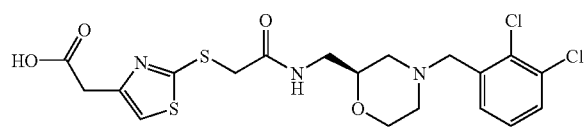

(86-1) Synthesis of (2S)-N-{[4-(2,3-dichlorobenzyl)morpholin-2-yl]methyl}-[4-(ethoxycarbonylmethyl)thiazol-2-ylthio]acetamide By a similar method as in (85-1), the title compound (908 mg) was obtained as a colorless oil from the resultant product (899 mg) of (75-3) and 2,3-dichlorobenzaldehyde (481 mg).

(86-2) Synthesis of (2S)-[4-(carboxymethyl)thiazol-2-ylthio]-N-{[4-(2,3-dichlorobenzyl)morpholin-2-yl]methyl}acetamide By a similar method as in (1-5), the title compound (650 mg) was obtained as a white amorphous solid from the resultant product (908 mg) of (86-1).
$^1$H-NMR (DMSO-$d_6$) δ 1.81-1.96 (1H, m), 2.07-2.21 (1H, m), 2.53-2.75 (2H, m), 3.10-3.19 (2H, m), 3.34-3.52 (4H, m), 3.67 (2H, s), 3.70-3.80 (1H, m), 3.93 (2H, s), 7.32-7.38 (2H, m), 7.46 (1H, dd, J=1.5, 7.8 Hz), 7.56 (1H, dd, J=1.5, 7.8 Hz), 8.32 (1H, dd, J=5.7, 5.7 Hz), 12.3 (1H, brs).
MS (ESI) m/z: 490 [M+H].

Example 87

Synthesis of (2S)-[4-(carboxymethyl)thiazol-2-ylthio]-N-{[4-(2,4-dichlorobenzyl)morpholin-2-yl]methyl}acetamide

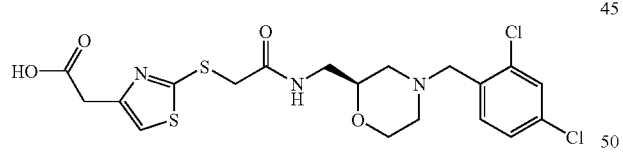

(87-1) Synthesis of (2S)-N-{[4-(2,4-dichlorobenzyl)morpholin-2-yl]methyl}-[4-(ethoxycarbonylmethyl)thiazol-2-ylthio]acetamide By a similar method as in (85-1), the title compound (1.13 g) was obtained as a colorless oil from the resultant product (899 mg) of (75-3) and 2,4-dichlorobenzaldehyde (481 mg).

(87-2) Synthesis of (2S)-[4-(carboxymethyl)thiazol-2-ylthio]-N-{[4-(2,4-dichlorobenzyl)morpholin-2-yl]methyl}acetamide By a similar method as in (1-5), the title compound (799 mg) was obtained as a white amorphous solid from the resultant product (1.13 g) of (87-1).

$^1$H-NMR (DMSO-$d_6$) δ 1.80-1.93 (1H, m), 2.07-2.21 (1H, m), 2.59 (1H, d, J=10.8 Hz), 2.68 (1H, d, J=10.8 Hz), 3.09-3.19 (2H, m), 3.34-3.52 (4H, m), 3.67 (2H, s), 3.78 (1H, d, J=10.8 Hz), 3.93 (2H, s), 7.36-7.44 (2H, m), 7.49 (1H, d, J=8.4 Hz), 7.59 (1H, d, J=2.1 Hz), 8.31 (1H, dd, J=5.7, 5.7 Hz), 12.4 (1H, brs).
MS (ESI) m/z: 490 [M+H].

Example 88

Synthesis of (2S)-[4-(carboxymethyl)thiazol-2-ylthio]-N-{[4-(3,5-dichlorobenzyl)morpholin-2-yl]methyl}acetamide

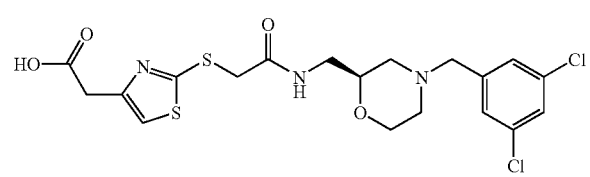

(88-1) Synthesis of (2S)-N-{[4-(3,5-dichlorobenzyl)morpholin-2-yl]methyl}-[4-(ethoxycarbonylmethyl)thiazol-2-ylthio]acetamide By a similar method as in (0.85-1), the title compound (874 mg) was obtained as a colorless oil from the resultant product (899 mg) of (75-3) and 3,5-dichlorobenzaldehyde (481 mg).

(88-2) Synthesis of (2S)-[4-(carboxymethyl)thiazol-2-ylthio]-N-{[4-(3,5-dichlorobenzyl)morpholin-2-yl]methyl}acetamide By a similar method as in (1-5), the title compound (615 mg) was obtained as a white amorphous solid from the resultant product (874 mg) of (88-1).
$^1$H-NMR (DMSO-$d_6$) δ 1.71-1.89 (1H, m), 1.96-2.11 (1H, m), 2.55 (1H, d, J=11.1 Hz), 2.65 (1H, d, J=11.1 Hz), 3.09-3.17 (2H, m), 3.34-3.52 (4H, m), 3.67 (2H, s), 3.77 (1H, d, J=11.1 Hz), 3.92 (2H, s), 7.34-7.38 (3H, m), 7.49 (1H, dd, J=1.5, 1.5 Hz), 8.30 (1H, dd, J=5.7, 5.7 Hz), 12.4 (1H, brs).
MS (ESI) m/z: 490 [M+H].

Example 89

Synthesis of (2S)-[4-(carboxymethyl)thiazol-2-ylthio]—N-{[4-(3-chloro-2-fluorobenzyl)morpholin-2-yl]methyl}acetamide

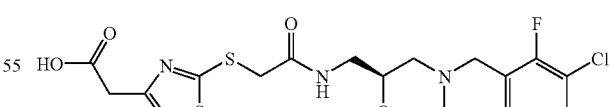

(89-1) Synthesis of (2S)-N-{[4-(3-chloro-2-fluorobenzyl)morpholin-2-yl]methyl}-[4-(ethoxycarbonylmethyl)thiazol-2-ylthio]acetamide By a similar method as in (85-1), the title compound (980 mg) was obtained as a colorless oil from the resultant product (899 mg) of (75-3) and 3-chloro-2-fluorobenzaldehyde (436 mg).

(89-2) Synthesis of (2S)-[4-(carboxymethyl)thiazol-2-ylthio]-N-{[4-(3-chloro-2-fluorobenzyl)morpholin-2-yl]methyl}acetamide By a similar method as in (1-5), the title compound (823 mg) was obtained as a white amorphous solid from the resultant product (980 mg) of (89-1).

$^1$H-NMR (DMSO-$d_6$) δ 1.75-1.90 (1H, m), 1.99-2.16 (1H, m), 2.57 (1H, d, J=11.1 Hz), 2.68 (1H, d, J=11.1 Hz), 3.09-3.18 (2H, m), 3.34-3.52 (4H, m), 3.67 (2H, s), 3.76 (1H, d, J=11.1 Hz), 3.92 (2H, s), 7.16-7.24 (1H, m), 7.33-7.40 (2H, m), 7.45-7.53 (1H, m), 8.30 (1H, dd, J=5.7, 5.7 Hz), 12.4 (1H, brs).

MS (ESI) m/z: 474 [M+H].

Example 90

Synthesis of (2S)-[4-(carboxymethyl)thiazol-2-ylthio]-N-{[4-(3-chloro-4-methylbenzyl)morpholin-2-yl]methyl}acetamide

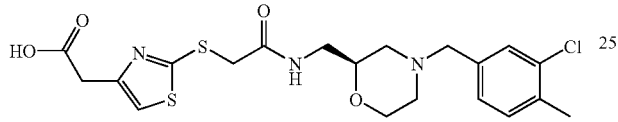

(90-1) Synthesis of (2S)-N-{[4-(3-chloro-4-methylbenzyl)morpholin-2-yl]methyl}-[4-(ethoxycarbonylmethyl)thiazol-2-ylthio]acetamide By a similar method as in (85-1), the title compound (1.15 g) was obtained as a colorless oil from the resultant product (899 mg) of (75-3) and 3-chloro-4-methylbenzaldehyde (425 mg).

(90-2) Synthesis of (2S)-[4-(carboxymethyl)thiazol-2-ylthio]-N-{[4-(3-chloro-4-methylbenzyl)morpholin-2-yl]methyl}acetamide By a similar method as in (1-5), the title compound (884 mg) was obtained as a white amorphous solid from the resultant product (1.15 g) of (90-1).

$^1$H-NMR (DMSO-$d_6$) δ 1.70-1.83 (1H, m), 1.92-2.10 (1H, m), 2.30 (3H, s), 2.55 (1H, d, J=11.1 Hz), 2.65 (1H, d, J=11.1 Hz), 3.08-3.18 (2H, m), 3.34-3.52 (4H, m), 3.67 (2H, s), 3.76 (1H, d, J=11.1 Hz), 3.92 (2H, s), 7.12-7.18 (1H, m), 7.26-7.32 (2H, m), 7.37 (1H, s), 8.30 (1H, dd, J=5.7, 5.7 Hz).

MS (ESI) m/z: 470 [M+H].

Example 91

Synthesis of (2S)-[4-(carboxymethyl)thiazol-2-ylthio]-N-{[4-(3-chloro-4-methoxybenzyl)morpholin-2-yl]methyl}acetamide

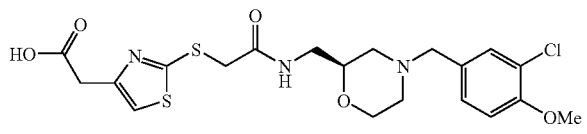

(91-1) Synthesis of (2S)-N-{[4-(3-chloro-4-methoxybenzyl)morpholin-2-yl]methyl}-[4-(ethoxycarbonylmethyl)thiazol-2-ylthio]acetamide By a similar method as in (85-1), the title compound (1.28 g) was obtained as a colorless oil from the resultant product (899 mg) of (75-3) and 3-chloro-4-methoxybenzaldehyde (469 mg).

(91-2) Synthesis of (2S)-[4-(carboxymethyl)thiazol-2-ylthio]-N-{[4-(3-chloro-4-methoxybenzyl)morpholin-2-yl]methyl}acetamide By a similar method as in (1-5), the title compound (1.01 g) was obtained as a white amorphous solid from the resultant product (1.28 g) of (91-1).

$^1$H-NMR (DMSO-$d_6$) δ 1.67-1.80 (1H, m), 1.92-2.10 (1H, m), 2.50-2.65 (2H, m), 3.09-3.17 (2H, m), 3.34-3.52 (4H, m), 3.67 (2H, s), 3.73-3.77 (1H, m), 3.83 (3H, s), 3.92 (2H, s), 7.09 (1H, d, J=8.4 Hz), 7.21 (1H, dd, J=1.8, 8.4 Hz), 7.32 (1H, d, J=1.8 Hz), 7.37 (1H, s), 8.30 (1H, dd, J=5.7, 5.7 Hz).

MS (ESI) m/z: 486 [M+H].

Example 92

Synthesis of (2S)-[4-(carboxymethyl)thiazol-2-ylthio]-N-{[4-(4-chloro-3-trifluoromethylbenzyl)morpholin-2-yl]methyl}acetamide

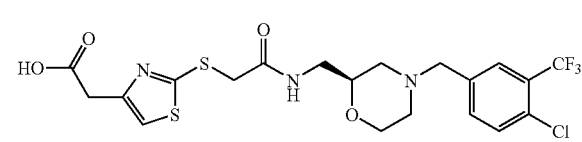

(92-1) Synthesis of (2S)-N-{[4-(4-chloro-3-trifluoromethylbenzyl)morpholin-2-yl]methyl}-[4-(ethoxycarbonylmethyl)thiazol-2-ylthio]acetamide By a similar method as in (85-1), the title compound (663 mg) was obtained as a colorless oil from the resultant product (899 mg) of (75-3) and 4-chloro-3-trifluoromethylbenzaldehyde (396 µL).

(92-2) Synthesis of (2S)-[4-(carboxymethyl)thiazol-2-ylthio]-N-{[4-(4-chloro-3-trifluoromethylbenzyl)morpholin-2-yl]methyl}acetamide By a similar method as in (1-5), the title compound (419 mg) was obtained as a white amorphous solid from the resultant product (663 mg) of (92-1).

$^1$H-NMR (DMSO-$d_6$) δ 1.72-1.88 (1H, m), 1.99-2.14 (1H, m), 2.50-2.66 (2H, m), 3.09-3.17 (2H, m), 3.34-3.52 (4H, m), 3.67 (2H, s), 3.73-3.77 (1H, m), 3.92 (2H, s), 7.37 (1H, s), 7.62 (1H, dd, J=1.5, 8.1 Hz), 7.68 (1H, d, J=8.1 Hz), 7.75 (1H, d, J=1.5 Hz), 8.30 (1H, dd, J=5.7, 5.7 Hz), 12.3 (1H, brs).

MS (ESI) m/z: 524 [M+H].

Example 93

Synthesis of (2S)-[4-(carboxymethyl)thiazol-2-ylthio]-N-{[4-(2,4-difluorobenzyl)morpholin-2-yl]methyl}acetamide

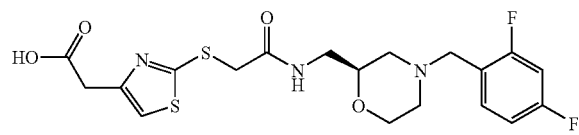

(93-1) Synthesis of (2S)-N-{[4-(2,4-difluorobenzyl)morpholin-2-yl]methyl}-[4-(ethoxycarbonylmethyl)thiazol-2-ylthio]acetamide By a similar method as in (85-1), the title compound (1.02 g) was obtained as a colorless oil from the resultant product (899 mg) of (75-3) and 2,4-difluorobenzaldehyde (301 μL).

(93-2) Synthesis of (2S)-[4-(carboxymethyl)thiazol-2-ylthio]-N-{[4-(2,4-difluorobenzyl)morpholin-2-yl]methyl}acetamide By a similar method as in (1-5), the title compound (791 mg) was obtained as a white amorphous solid from the resultant product (1.02 g) of (93-1).
$^1$H-NMR (DMSO-$d_6$) δ 1.71-1.88 (1H, m), 1.99-2.11 (1H, m), 2.51-2.66 (2H, m), 3.06-3.18 (2H, m), 3.34-3.52 (4H, m), 3.67 (2H, s), 3.73-3.78 (1H, m), 3.92 (2H, s), 6.98-7.10 (1H, m), 7.12-7.23 (1H, m), 7.37 (1H, s), 7.38-7.46 (1H, m), 8.30 (1H, dd, J=5.4, 5.4 Hz), 12.4 (1H, brs).
MS (ESI) m/z: 458 [M+H].

Example 94

Synthesis of (2S)-[4-(carboxymethyl)thiazol-2-ylthio]-N-{[4-(3-fluorobenzyl)morpholin-2-yl]methyl}acetamide

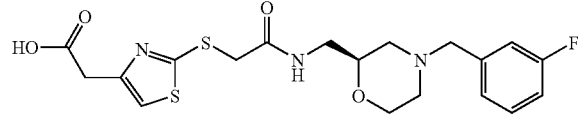

(94-1) Synthesis of (2S)-[4-(ethoxycarbonylmethyl)thiazol-2-ylthio]-N-{[4-(3-fluorobenzyl)morpholin-2-yl]methyl}acetamide By a similar method as in (85-1), the title compound (1.05 g) was obtained as a colorless oil from the resultant product (899 mg) of (75-3) and 3-fluorobenzaldehyde (292 μL).

(94-2) Synthesis of (2S)-[4-(carboxymethyl)thiazol-2-ylthio]-N-{[4-(3-fluorobenzyl)morpholin-2-yl]methyl}acetamide By a similar method as in (1-5), the title compound (768 mg) was obtained as a white amorphous solid from the resultant product (1.05 g) of (94-1).
$^1$H-NMR (DMSO-$d_6$) δ 1.70-1.91 (1H, m), 1.92-2.10 (1H, m), 2.50-2.78 (2H, m), 3.07-3.19 (2H, m), 3.34-3.52 (4H, m), 3.67 (2H, s), 3.77 (1H, d, J=11.0 Hz), 3.93 (2H, s), 7.00-7.21 (3H, m), 7.29-7.41 (2H, m), 8.29-8.35 (1H, m).
MS (ESI) m/z: 440 [M+H].

Example 95

Synthesis of (2S)-[4-(carboxymethyl)thiazol-2-ylthio]-N-{[4-(4-fluorobenzyl)morpholin-2-yl]methyl}acetamide

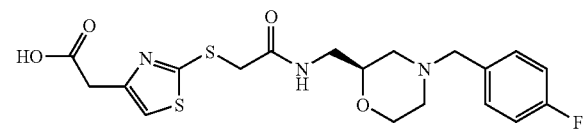

(95-1) Synthesis of (2S)-[4-(ethoxycarbonylmethyl)thiazol-2-ylthio]-N-{[4-(4-fluorobenzyl)morpholin-2-yl]methyl}acetamide By a similar method as in (85-1), the title compound (999 mg) was obtained as a colorless oil from the resultant product (899 mg) of (75-3) and 4-fluorobenzaldehyde (294 μL).

(95-2) Synthesis of (2S)-[4-(carboxymethyl)thiazol-2-ylthio]-N-{[4-(4-fluorobenzyl)morpholin-2-yl]methyl}acetamide By a similar method as in (1-5), the title compound (753 mg) was obtained as a white amorphous solid from the resultant product (999 mg) of (95-1).
$^1$H-NMR (DMSO-$d_6$) δ 1.70-1.89 (1H, m), 1.92-2.11 (1H, m), 2.56 (1H, d, J=10.8 Hz), 2.66 (1H, d, J=10.8 Hz), 3.08-3.16 (2H, m), 3.34-3.52 (4H, m), 3.67 (2H, s), 3.76 (1H, d, J=10.8 Hz), 3.93 (2H, s), 7.10-7.18 (2H, m), 7.30-7.38 (3H, m), 8.31 (1H, dd, J=5.7, 5.7 Hz).
MS (ESI) m/z: 440 [M+H].

Example 96

Synthesis of (2S)-[4-(carboxymethyl)thiazol-2-ylthio]-N-{[4-(4-fluoro-3-trifluoromethylbenzyl)morpholin-2-yl]methyl}acetamide

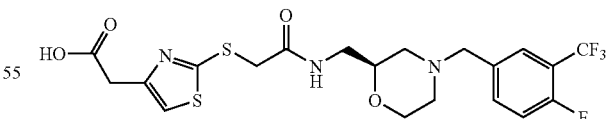

(96-1) Synthesis of (2S)-N-{[4-(4-fluoro-3-trifluoromethylbenzyl)morpholin-2-yl]methyl}-[4-(ethoxycarbonylmethyl)thiazol-2-ylthio]acetamide By a similar method as in (85-1), the title compound (690 mg) was obtained as a colorless oil from the resultant product (899 mg) of (75-3) and 4-fluoro-3-trifluoromethylbenzaldehyde (528 mg).

(96-2) Synthesis of (2S)-[4-(carboxymethyl)thiazol-2-ylthio]-N-{[4-(4-fluoro-3-trifluoromethylbenzyl)morpholin-2-yl]methyl}acetamide By a similar method as in (1-5), the title compound (616 mg) was obtained as a white amorphous solid from the resultant product (690 mg) of (96-1).

$^1$H-NMR (DMSO-d$_6$) δ 1.71-1.91 (1H, m), 1.92-2.09 (1H, m), 2.50-2.79 (2H, m), 3.06-3.18 (2H, m), 3.34-3.52 (4H, m), 3.67 (2H, s), 3.78 (1H, d, J=10.8 Hz), 3.93 (2H, s), 7.37 (1H, s), 7.43-7.52 (1H, m), 7.58-7.77 (2H, m), 8.23-8.35 (1H, m).

MS (ESI) m/z: 508 [M+H].

Example 97

Synthesis of (2S)-[4-(carbamoylmethyl)thiazol-2-ylthio]-N-{[4-(4-chlorobenzyl)morpholin-2-yl]methyl}acetamide

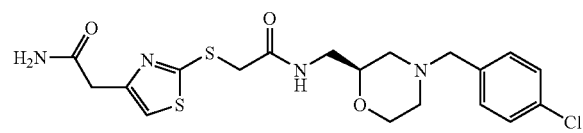

By a similar method as in Example 16, the title compound (573 mg) was obtained as a white amorphous solid from the resultant product (751 mg) of (85-2) and ammonium chloride (528 mg).

$^1$H-NMR (DMSO-d$_6$) δ 1.69-1.82 (1H, m), 1.94-2.09 (1H, m), 2.54 (1H, d, J=11.1 Hz), 2.64 (1H, d, J=11.1 Hz), 3.08-3.18 (2H, m), 3.38-3.52 (6H, m), 3.76 (1H, d, J=11.1 Hz), 3.91 (2H, s), 6.97 (1H, brs), 7.25-7.41 (6H, m), 8.28 (1H, dd, J=5.7, 5.7 Hz).

MS (ESI) m/z: 455 [M+H].

Example 98

Synthesis of (2S)-[4-(carbamoylmethyl)thiazol-2-ylthio]-N-{[4-(2,3-dichlorobenzyl)morpholin-2-yl]methyl}acetamide

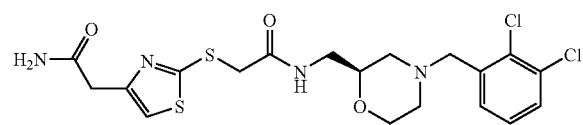

By a similar method as in Example 16, the title compound (402 mg) was obtained as a white amorphous solid from the resultant product (517 mg) of (86-2) and ammonium chloride (338 mg).

$^1$H-NMR (DMSO-d$_6$) δ 1.81-1.95 (1H, m), 2.06-2.20 (1H, m), 2.59 (1H, d, J=11.4 Hz), 2.68 (1H, d, J=11.4 Hz), 3.09-3.18 (2H, m), 3.38-3.52 (4H, m), 3.57 (2H, s), 3.78 (1H, d, J=11.4 Hz), 3.92 (2H, s), 6.97 (1H, brs), 7.27-7.40 (3H, m), 7.46 (1H, d, J=7.2 Hz), 7.55 (1H, d, J=7.2 Hz), 8.28 (1H, dd, J=5.7, 5.7 Hz).

MS (ESI) m/z: 489 [M+H].

Example 99

Synthesis of (2S)-[4-(carbamoylmethyl)thiazol-2-ylthio]-N-{[4-(2,4-dichlorobenzyl)morpholin-2-yl]methyl}acetamide

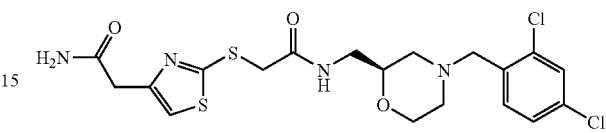

By a similar method as in Example 16, the title compound (347 mg) was obtained as white crystals from the resultant product (440 mg) of (87-2) and ammonium chloride (288 mg).

$^1$H-NMR (DMSO-d$_6$) δ 1.80-1.91 (1H, m), 2.04-2.19 (1H, m), 2.58 (1H, d, J=11.2 Hz), 2.67 (1H, d, J=11.2 Hz), 3.09-3.18 (2H, m), 3.38-3.55 (6H, m), 3.77 (1H, d, J=11.2 Hz), 3.92 (2H, s), 6.97 (1H, brs), 7.30 (1H, s), 7.32-7.42 (2H, m), 7.49 (1H, d, J=8.3 Hz), 7.58 (1H, d, J=2.0 Hz), 8.28 (1H, dd, J=5.7, 5.7 Hz).

MS (ESI) m/z: 489 [M+H].

Example 100

Synthesis of (2S)-[4-(carbamoylmethyl)thiazol-2-ylthio]-N-{[4-(3,5-dichlorobenzyl)morpholin-2-yl]methyl}acetamide

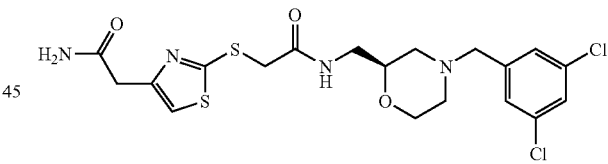

By a similar method as in Example 16, the title compound (372 mg) was obtained as a colorless oil from the resultant product (615 mg) of (88-2) and ammonium chloride (402 mg).

$^1$H-NMR (DMSO-d$_6$) δ 1.74-1.85 (1H, m), 1.97-2.10 (1H, m), 2.55 (1H, d, J=11.1 Hz), 2.65 (1H, d, J=11.1 Hz), 3.10-3.18 (2H, m), 3.38-3.56 (6H, m), 3.76 (1H, d, J=11.1 Hz), 3.92 (2H, s), 6.97 (1H, brs), 7.30-7.41 (4H, m), 7.48 (1H, d, J=1.9 Hz), 8.28 (1H, dd, J=5.7, 5.7 Hz).

MS (ESI) m/z: 489 [M+H].

Example 101

Synthesis of (2S)-[4-(carbamoylmethyl)thiazol-2-ylthio]-N-{[4-(3-chloro-2-fluorobenzyl)morpholin-2-yl]methyl}acetamide

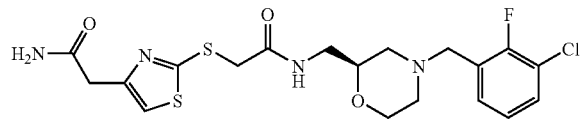

By a similar method as in Example 16, the title compound (470 mg) was obtained as a pale-yellow oil from the resultant product (547 mg) of (89-2) and ammonium chloride (370 mg).

$^1$H-NMR (DMSO-$d_6$) δ 1.77-1.89 (1H, m), 1.99-2.10 (1H, m), 2.57 (1H, d, J=11.1 Hz), 2.67 (1H, d, J=11.1 Hz), 3.09-3.18 (2H, m), 3.38-3.55 (6H, m), 3.76 (1H, d, J=11.1 Hz), 3.92 (2H, s), 6.97 (1H, brs), 7.17-7.24 (1H, m), 7.30 (1H, s), 7.32-7.41 (2H, m), 7.42-7.51 (1H, m), 8.28 (1H, dd, J=5.7, 5.7 Hz).

MS (ESI) m/z: 473 [M+H].

Example 102

Synthesis of (2S)-[4-(carbamoylmethyl)thiazol-2-ylthio]-N-{[4-(3-chloro-4-methylbenzyl)morpholin-2-yl]methyl}acetamide

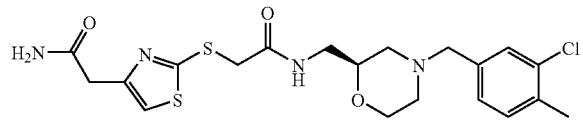

By a similar method as in Example 16, the title compound (438 mg) was obtained as a colorless oil from the resultant product (589 mg) of (90-2) and ammonium chloride (402 mg).

$^1$H-NMR (DMSO-$d_6$) δ 1.69-1.81 (1H, m), 1.94-2.08 (1H, m), 2.30 (3H, s), 2.55 (1H, d, J=11.1 Hz), 2.64 (1H, d, J=11.1 Hz), 3.08-3.16 (2H, m), 3.38-3.52 (6H, m), 3.75 (1H, d, J=11.1 Hz), 3.91 (2H, s), 6.96 (1H, brs), 7.15 (1H, d, J=7.5 Hz), 7.21-7.31 (3H, m), 7.37 (1H, brs), 8.28 (1H, dd, J=5.7, 5.7 Hz).

MS (ESI) m/z: 469 [M+H].

Example 103

Synthesis of (2S)-[4-(carbamoylmethyl)thiazol-2-ylthio]-N-{[4-(3-chloro-4-methoxybenzyl)morpholin-2-yl]methyl}acetamide

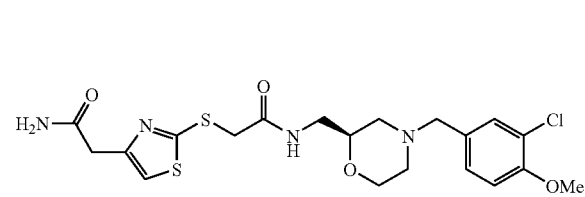

By a similar method as in Example 16, the title compound (590 mg) was obtained as a colorless oil from the resultant product (587 mg) of (91-2) and ammonium chloride (388 mg).

$^1$H-NMR (DMSO-$d_6$) δ 1.69-1.80 (1H, m), 1.94-2.06 (1H, m), 2.54 (1H, d, J=11.1 Hz), 2.64 (1H, d, J=11.1 Hz), 3.08-3.15 (2H, m), 3.38-3.52 (6H, m), 3.75 (1H, d, J=11.1 Hz), 3.83 (3H, s), 3.92 (2H, s), 6.98 (1H, brs), 7.09 (1H, d, J=8.4 Hz), 7.21 (1H, dd, J=1.8, 8.4 Hz), 7.30-7.33 (2H, m), 7.38 (1H, brs), 8.29 (1H, dd, J=5.7, 5.7 Hz).

MS (ESI) m/z: 485 [M+H].

Example 104

Synthesis of (2S)-[4-(carbamoylmethyl)thiazol-2-ylthio]-N-{[4-(4-chloro-3-trifluoromethylbenzyl)morpholin-2-yl]methyl}acetamide

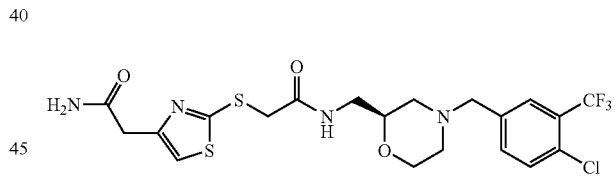

By a similar method as in Example 16, the title compound (207 mg) was obtained as a white amorphous solid from the resultant product (254 mg) of (92-2) and ammonium chloride (156 mg).

$^1$H-NMR (DMSO-$d_6$) δ 1.75-1.86 (1H, m), 2.00-2.11 (1H, m), 2.55 (1H, d, J=11.1 Hz), 2.65 (1H, d, J=11.1 Hz), 3.09-3.16 (2H, m), 3.40-3.52 (6H, m), 3.77 (1H, d, J=11.1 Hz), 3.91 (2H, s), 6.98 (1H, brs), 7.31 (1H, s), 7.38 (1H, brs), 7.62 (1H, d, J=8.1 Hz), 7.69 (1H, d, J=8.1 Hz), 7.75 (1H, s) 8.29 (1H, dd, J=5.7, 5.7 Hz).

MS (ESI) m/z: 523 [M+H].

Example 105

Synthesis of (2S)-[4-(carbamoylmethyl)thiazol-2-ylthio]-N-{[4-(2,4-difluorobenzyl)morpholin-2-yl]methyl}acetamide

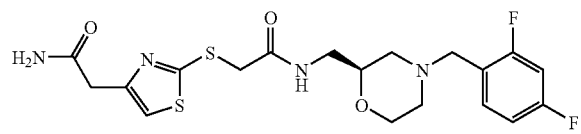

By a similar method as in Example 16, the title compound (581 mg) was obtained as a pale-yellow oil from the resultant product (651 mg) of (93-2) and ammonium chloride (457 mg).

$^1$H-NMR (DMSO-$d_6$) δ 1.73-1.83 (1H, m), 1.99-2.10 (1H, m), 2.56 (1H, d, J=11.4 Hz), 2.66 (1H, d, J=11.4 Hz), 3.08-3.16 (2H, m), 3.39-3.52 (6H, m), 3.76 (1H, d, J=11.4 Hz), 3.92 (2H, s), 6.98 (1H, brs), 7.01-7.11 (1H, m), 7.15-7.23 (1H, m), 7.31 (1H, s), 7.32-7.48 (2H, m), 8.29 (1H, dd, J=5.7, 5.7 Hz).

MS (ESI) m/z: 457 [M+H].

Example 106

Synthesis of (2S)-[4-(carbamoylmethyl)thiazol-2-ylthio]-N-{[4-(3-fluorobenzyl)morpholin-2-yl]methyl}acetamide

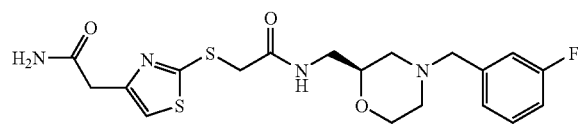

By a similar method as in Example 16, the title compound (379 mg) was obtained as a white amorphous solid from the resultant product (450 mg) of (94-2) and ammonium chloride (329 mg).

$^1$H-NMR (DMSO-$d_6$) δ 1.71-1.83 (1H, m), 1.94-2.09 (1H, m), 2.56 (1H, d, J=10.8 Hz), 2.66 (1H, d, J=10.8 Hz), 3.07-3.17 (2H, m), 3.39-3.53 (6H, m), 3.76 (1H, d, J=10.8 Hz), 3.92 (2H, s), 6.98 (1H, brs), 7.02-7.16 (3H, m), 7.30-7.41 (3H, m), 8.29 (1H, dd, J=5.7, 5.7 Hz).

MS (ESI) m/z: 439 [M+H].

Example 107

Synthesis of (2S)-[4-(carbamoylmethyl)thiazol-2-ylthio]-N-{[4-(4-fluorobenzyl)morpholin-2-yl]methyl}acetamide

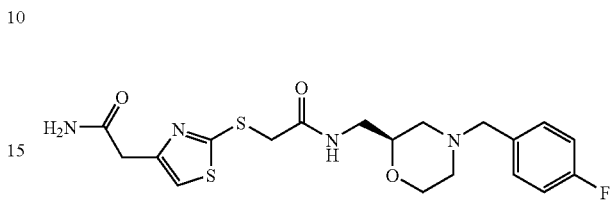

By a similar method as in Example 16, the title compound (410 mg) was obtained as a pale-yellow oil from the resultant product (522 mg) of (95-2) and ammonium chloride (381 mg).

$^1$H-NMR (DMSO-$d_6$) δ 1.69-1.80 (1H, m), 1.93-2.07 (1H, m), 2.54 (1H, d, J=11.1 Hz), 2.64 (1H, d, J=11.1 Hz), 3.05-3.16 (2H, m), 3.38-3.52 (6H, m), 3.75 (1H, d, J=11.1 Hz), 3.92 (2H, s), 6.98 (1H, brs), 7.08-7.18 (2H, m), 7.28-7.37 (3H, m), 7.39 (1H, brs), 8.29 (1H, dd, J=5.7, 5.7 Hz).

MS (ESI) m/z: 439 [M+H].

Example 108

Synthesis of (2S)-[4-(carbamoylmethyl)thiazol-2-ylthio]-N-{[4-(4-fluoro-3-trifluoromethylbenzyl)morpholin-2-yl]methyl}acetamide

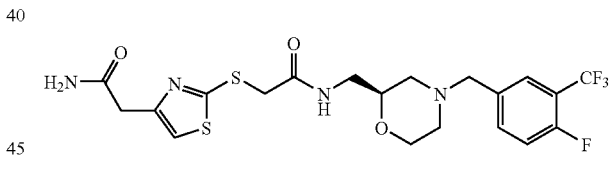

By a similar method as in Example 1.6, the title compound (389 mg) was obtained as a pale-yellow oil from the resultant product (489 mg) of (96-2) and ammonium chloride (309 mg).

$^1$H-NMR (DMSO-$d_6$) δ 1.72-1.84 (1H, m), 2.00-2.09 (1H, m), 2.54 (1H, d, J=11.1 Hz), 2.65 (1H, d, J=11.1 Hz), 3.07-3.17 (2H, m), 3.40-3.54 (6H, m), 3.76 (1H, d, J=11.1 Hz), 3.91 (2H, s), 6.98 (1H, brs), 7.31 (1H, s), 7.38 (1H, brs), 7.40-7.51 (1H, m), 7.62-7.68 (2H, m), 8.29 (1H, dd, J=5.7, 5.7 Hz).

MS (ESI) m/z: 507 [M+H].

Example 109

Synthesis of (2S)-(4-carboxy-5-methylthiazol-2-ylthio)-N-{[4-(3,4-dichlorobenzyl)morpholin-2-yl]methyl}acetamide

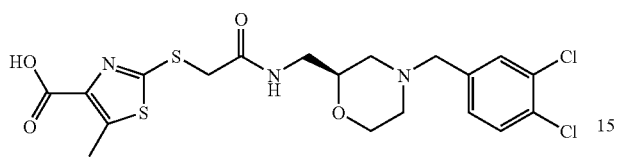

(109-1) Synthesis of 4-ethoxycarbonyl-5-methyl-2-mercaptothiazole

By a similar method as in (1-3), the title compound (2.10 g) was obtained as white crystals from ethyl 3-bromo-2-oxobutyrate (8.55 g) and ammonium dithiocarbamate (4.23 g).

(109-2) Synthesis of (2S)-N-{[4-(3,4-dichlorobenzyl)morpholin-2-yl]methyl}-(4-ethoxycarbonyl-5-methylthiazol-2-ylthio)acetamide By a similar method as in (1-4), the title compound (2.32 g) was obtained as a brown oil from the resultant product (1.55 g) of (1-2) and the resultant product (813 mg) of (109-1).

(109-3) Synthesis of (2S)-(4-carboxy-5-methylthiazol-2-ylthio)-N-{[4-(3,4-dichlorobenzyl)morpholin-2-yl]methyl}acetamide By a similar method as in (1-5), the title compound (1.94 g) was obtained as a white amorphous solid from the resultant product (2.32 g) of (109-2).
$^1$H-NMR (DMSO-$d_6$) δ 1.70-1.85 (1H, m), 1.95-2.11 (1H, m), 2.55 (1H, d, J=11.4 Hz), 2.64 (3H, s), 2.65 (1H, d, J=11.4 Hz), 3.08-3.16 (2H, m), 3.34-3.52 (4H, m), 3.75 (1H, d, J=11.4 Hz), 3.92 (2H, s), 7.28 (1H, dd, J=1.5, 8.1 Hz), 7.52-7.60 (2H, m), 8.31 (1H, dd, J=5.7, 5.7 Hz).
MS (ESI) m/z: 490 [M+H].

Example 110

Synthesis of (2S)-(4-carbamoyl-5-methylthiazol-2-ylthio)-N-{[4-(3,4-dichlorobenzyl)morpholin-2-yl]methyl}acetamide

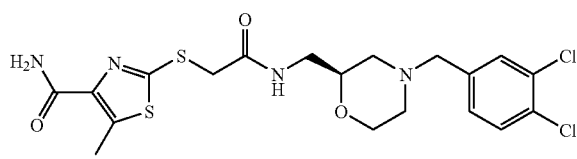

By a similar method as in Example 16, the title compound (250 mg) was obtained as white crystals from the resultant product (490 mg) of (109-3) and ammonium chloride (321 mg).
$^1$H-NMR (DMSO-$d_6$) δ 1.69-1.80 (1H, m), 1.94-2.07 (1H, m), 2.52 (1H, d, J=12.0 Hz), 2.59 (1H, d, J=12.0 Hz), 2.66 (3H, s), 3.09-3.17 (2H, m), 3.38-3.52 (4H, m), 3.75 (1H, d, J=12.0 Hz), 3.92 (2H, d, J=5.1 Hz), 7.28 (1H, dd, J=1.5, 8.1 Hz), 7.49-7.59 (3H, m), 7.65 (1H, brs), 8.27 (1H, dd, J=5.7, 5.7 Hz).
MS (ESI) m/z: 489 [M+H].

Example 111

Synthesis of (2S)-(4-carboxythiazol-2-ylthio)-N-{[4-(3-chloro-4-fluorobenzyl)morpholin-2-yl]methyl}acetamide

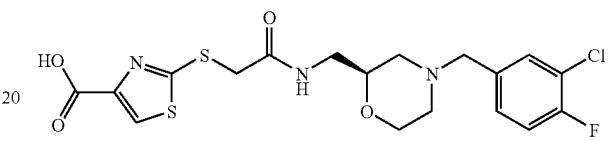

(111-1) Synthesis of (2S)-N-{[4-(3-chloro-4-fluorobenzyl)morpholin-2-yl]methyl}chloroacetamide By a similar method as in (1-1), the title compound (2.76 g) was obtained as a brown oil from (2S)-2-aminomethyl-4-(3-chloro-4-fluorobenzyl)morpholine dihydrochloride (2.32 g).

(111-2) Synthesis of (2S)-N-{[4-(3-chloro-4-fluorobenzyl)morpholin-2-yl]methyl}-(4-ethoxycarbonylthiazol-2-ylthio)acetamide By a similar method as in (1-4), the title compound (2.80 g) was obtained as a brown oil from the resultant product (2.76 g) of (111-1) and the resultant product (1.46 g) of (1-3).

(111-3) Synthesis of (2S)-(4-carboxythiazol-2-ylthio)-N-{[4-(3-chloro-4-fluorobenzyl)morpholin-2-yl]methyl}acetamide By a similar method as in (1-5), the title compound (1.88 g) was obtained as a white amorphous solid from the resultant product (2.80 g) of (111-2).
$^1$H-NMR (DMSO-$d_6$) δ 1.70-1.89 (1H, m), 1.95-2.15 (1H, m), 2.57 (1H, d, J=11.1 Hz), 2.66 (1H, d, J=11.1 Hz), 3.08-3.19 (2H, m), 3.34-3.52 (4H, m), 3.76 (1H, d, J=10.5 Hz), 3.99 (2H, s), 7.21-7.42 (2H, m), 7.43-7.52 (1H, m), 8.27-8.38 (2H, m).
MS (ESI) m/z: 460 [M+H].

Example 112

Synthesis of (2S)-(4-carbamoylthiazol-2-ylthio)-N-{[4-(3-chloro-4-fluorobenzyl)morpholin-2-yl]methyl}acetamide

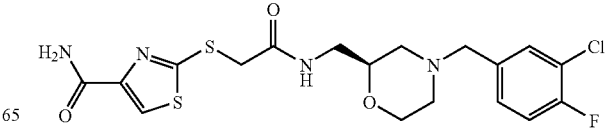

By a similar method as in Example 16, the title compound (1.47 g) was obtained as a white amorphous solid from the resultant product (1.65 g) of (111-3) and ammonium chloride (1.15 g).

¹H-NMR (DMSO-d₆) δ 1.66-1.78 (1H, m), 1.91-2.08 (1H, m), 2.51 (1H, d, J=11.1 Hz), 2.59 (1H, d, J=11.1 Hz), 3.09-3.17 (2H, m), 3.36-3.52 (4H, m), 3.74 (1H, d, J=11.1 Hz), 3.96 (1H, d, J=11.7 Hz), 4.04 (1H, d, J=11.7 Hz), 7.21-7.39 (2H, m), 7.48 (1H, dd, J=1.8, 7.2 Hz), 7.65 (1H, brs), 7.77 (1H, brs), 8.14 (1H, s), 8.26-8.39 (1H, m).

MS (ESI) m/z: 459 [M+H].

Example 113

Synthesis of (2S)-(4-carboxythiazol-2-ylthio)-N-{[4-(3,4-difluorobenzyl)morpholin-2-yl]methyl}acetamide

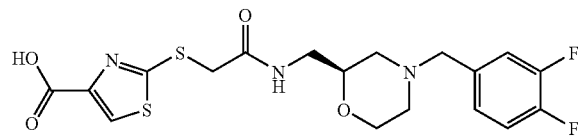

(113-1) Synthesis of (2S)-N-{[4-(3,4-difluorobenzyl)morpholin-2-yl]methyl}chloroacetamide By a similar method as in (1-1), the title compound (6.88 g) was obtained as a brown oil from (2S)-2-aminomethyl-4-(3,4-difluorobenzyl)morpholine dihydrochloride (6.30 g).

(113-2) Synthesis of (2S)-N-{[4-(3,4-difluorobenzyl)morpholin-2-yl]methyl}-(4-ethoxycarbonylthiazol-2-ylthio)acetamide By a similar method as in (1-4), the title compound (9.05 g) was obtained as a yellow oil from the resultant product (6.88 g) of (113-1) and the resultant product (4.16 g) of (1-3).

(113-3) Synthesis of (2S)-(4-carboxythiazol-2-ylthio)-N-{[4-(3,4-difluorobenzyl)morpholin-2-yl]methyl}acetamide By a similar method as in (1-5), the title compound (3.53 g) was obtained as a white amorphous solid from the resultant product (9.05 g) of (113-2).

¹H-NMR (DMSO-d₆) δ 1.70-1.87 (1H, m), 1.93-2.12 (1H, m), 2.56 (1H, d, J=11.1 Hz), 2.66 (1H, d, J=11.1 Hz), 3.08-3.19 (2H, m), 3.34-3.52 (4H, m), 3.76 (1H, d, J=11.1 Hz), 4.00 (2H, s), 7.03-7.19 (1H, m), 7.22-7.43 (2H, m), 8.24-8.37 (2H, m).

MS (ESI) m/z: 444 [M+H].

Example 114

Synthesis of (2S)-(4-carbamoylthiazol-2-ylthio)-N-{[4-(3,4-difluorobenzyl)morpholin-2-yl]methyl}acetamide

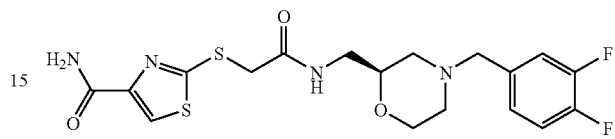

By a similar method as in Example 16, the title compound (1.32 g) was obtained as a white amorphous solid from the resultant product (2.09 g) of (113-3) and ammonium chloride (1.51 g).

¹H-NMR (DMSO-d₆) δ 1.68-1.79 (1H, m), 1.90-2.06 (1H, m), 2.51 (1H, d, J=11.1 Hz), 2.58 (1H, d, J=11.1 Hz), 3.08-3.17 (2H, m), 3.38-3.52 (4H, m), 3.74 (1H, d, J=11.1 Hz), 3.92-4.09 (2H, m), 7.04-7.17 (1H, m), 7.23-7.42 (2H, m), 7.66 (1H, brs), 7.76 (1H, brs), 8.14 (1H, s), 8.27-8.39 (1H, m).

MS (ESI) m/z: 443 [M+H].

Example 115

Synthesis of (2S)-[4-(2-amino-2-oxoethyl)aminocarbonylthiazol-2-ylthio]-N-{[4-(3,4-difluorobenzyl)morpholin-2-yl]methyl}acetamide

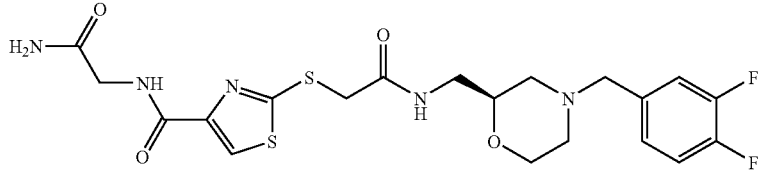

By a similar method as in Example 16, the title compound (133 mg) was obtained as a white solid from the resultant product (222 mg) of (113-3) and glycinamide hydrochloride (66 mg).

¹H-NMR (DMSO-d₆) δ 1.66-1.79 (1H, m), 1.92-2.05 (1H, m), 2.52 (1H, d, J=11.1 Hz), 2.60 (1H, d, J=11.1 Hz), 3.10-

3.18 (2H, m), 3.36-3.50 (4H, m), 3.74 (1H, d, J=11.1 Hz), 3.83 (2H, d, J=6.0 Hz), 3.96-4.08 (2H, m), 7.04-7.17 (2H, m), 7.28-7.42 (3H, m), 8.18 (1H, s), 8.34 (1H, dd, J=5.7, 5.7 Hz), 8.41 (1H, t, J=6.0 Hz).
MS (ESI) m/z: 500 [M+H].

Example 116

Synthesis of (2S)-[4-(4-carboxyphenyl)thiazol-2-ylthio]-N-{[4-(3,4-difluorobenzyl)morpholin-2-yl]methyl}acetamide

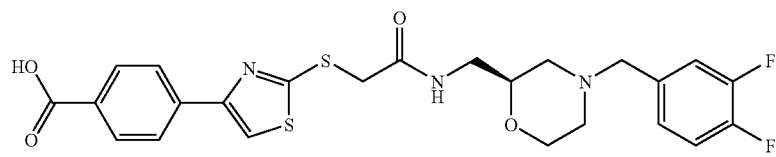

(116-1) Synthesis of (2S)-N-{[4-(3,4-difluorobenzyl)morpholin-2-yl]methyl}-[4-(4-methoxycarbonylphenyl)thiazol-2-ylthio]acetamide By a similar method as in (1-4), the title compound (1.46 g) was obtained as a yellow oil from the resultant product (1.02 g) of (113-1) and the resultant product (1.61 g) of (5-1).

(116-2) Synthesis of (2S)-[4-(4-carboxyphenyl)thiazol-2-ylthio]-N-{[4-(3,4-difluorobenzyl)morpholin-2-yl]methyl}acetamide By a similar method as in (1-5), the title compound (1.10 g) was obtained as a white amorphous solid from the resultant product (1.46 g) of (116-1).
$^1$H-NMR (DMSO-d$_6$) δ 1.69-1.80 (1H, m), 1.91-2.03 (1H, m), 2.50 (1H, d, J=11.1 Hz), 2.61 (1H, d, J=11.1 Hz), 3.10-3.20 (2H, m), 3.33-3.55 (4H, m), 3.71 (1H, d, J=11.1 Hz), 4.04 (2H, s), 7.04-7.10 (1H, m), 7.18-7.39 (2H, m), 7.99 (2H, d, J=8.4 Hz), 8.06 (2H, d, J=8.4 Hz), 8.21 (1H, s), 8.34 (1H, dd, J=5.7, 5.7 Hz), 12.9 (1H, brs).
MS (ESI) m/z: 520 [M+H]

Example 117

Synthesis of (2S)-[4-(4-carbamoylphenyl)thiazol-2-ylthio]-N-{[4-(3,4-difluorobenzyl)morpholin-2-yl]methyl}acetamide

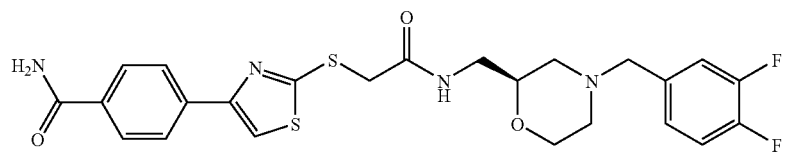

By a similar method as in Example 16, the title compound (152 mg) was obtained as a white solid from the resultant product (260 mg) of (116-2) and ammonium chloride (160 mg).
$^1$H-NMR (DMSO-d$_6$) δ 1.70-1.81 (1H, m), 1.91-2.02 (1H, m), 2.50 (1H, d, J=11.1 Hz), 2.61 (1H, d, J=11.1 Hz), 3.10-3.19 (2H, m), 3.34-3.52 (4H, m), 3.72 (1H, d, J=11.1 Hz), 4.04 (2H, s), 7.02-7.10 (1H, m), 7.18-7.41 (3H, m), 7.91-8.04 (5H, m), 8.17 (1H, s), 8.34 (1H, dd, J=5.7, 5.7 Hz).

MS (ESI) m/z: 519 [M+H].

Example 118

Synthesis of (2S)-N-{[4-(3,4-difluorobenzyl)morpholin-2-yl]methyl}-[4-(5-methyl-4H-1,2,4-triazol-3-yl)thiazol-2-ylthio]acetamide hydrochloride

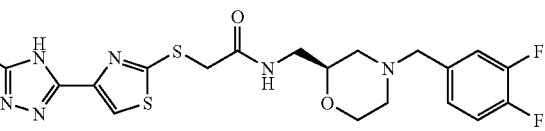

(118-1) Synthesis of (2S)-[4-(N'-tertiary butoxycarbonylhydrazinocarbonyl)thiazol-2-ylthio]-N-{[4-(3,4-difluorobenzyl)morpholin-2-yl]methyl}acetamide By a similar method as in Example 16, the title compound (1.10 g) was obtained as a white solid from the resultant product (1.11 g) of (113-3) and tertiary butoxycarbonyl hydrazide (396 mg).

(118-2) Synthesis of (2S)-N-{[4-(3,4-difluorobenzyl)morpholin-2-yl]methyl}-[4-(hydrazinocarbonyl)thiazol-2-ylthio]acetamide By a similar method as in (42-2), the title compound (565 mg) was obtained as a white amorphous solid from the resultant product (1.10 g) of (118-1).

(118-3) Synthesis of (2S)-N-{[4-(3,4-difluorobenzyl)morpholin-2-yl]methyl}-[4-(5-methyl-4H-1,2,4-triazol-3-yl)thiazol-2-ylthio]acetamide hydrochloride By a similar method as in Example 43, trifluoroacetic acid salt of the title compound was obtained as a colorless oil from the resultant product (565 mg) of (118-2) and ethyl imidoacetate hydrochloride (229 mg). By a similar method as in (1-2), the title compound (53 mg) was obtained as a white powder from the obtained residue.

$^1$H-NMR (DMSO-$d_6$) δ 2.42 (3H, s), 2.68-2.80 (1H, m), 2.88-3.05 (1H, m), 3.10-3.30 (4H, m), 3.72-4.10 (6H, m), 4.29 (2H, brs), 7.36-7.59 (2H, m), 7.75 (1H, t, J=8.7 Hz), 8.13 (1H, s), 8.58 (1H, m), 11.5 (1H, brs).

MS (ESI) m/z: 481 [M+H].

Example 119

Synthesis of (2S)-N-{[4-(3-chloro-4-fluorobenzyl)morpholin-2-yl]methyl}-[4-(1H-tetrazol-5-yl)thiazol-2-ylthio]acetamide

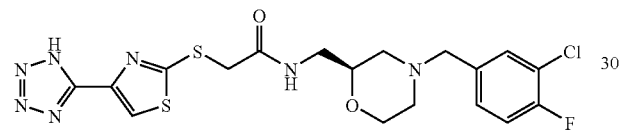

(119-1) Synthesis of (2S)-N-{[4-(3-chloro-4-fluorobenzyl)morpholin-2-yl]methyl}-(4-cyanothiazol-2-ylthio)acetamide By a similar method as in (22-1), the title compound (995 mg) was obtained as a colorless oil from the resultant product (1.32 g) of Example 112.

(119-2) Synthesis of (2S)-N-{[4-(3-chloro-4-fluorobenzyl)morpholin-2-yl]methyl}-[4-(1H-tetrazol-5-yl)thiazol-2-ylthio]acetamide By a similar method as in Example 59, the title compound (195 mg) was obtained as a pale-yellow amorphous solid from the resultant product (995 mg) of (119-1).

$^1$H-NMR (DMSO-$d_6$) δ 1.80-1.95 (1H, m), 2.02-2.19 (1H, m), 2.66 (1H, d, J=11.4 Hz), 2.78 (1H, d, J=11.4 Hz), 3.09-3.19 (2H, m), 3.39-3.57 (4H, m), 3.74 (1H, d, J=11.7 Hz), 3.92 (1H, d, J=14.6 Hz), 4.00 (1H, d, J=14.6 Hz), 7.18-7.39 (2H, m), 7.44 (1H, dd, J=1.9, 7.3 Hz), 8.22 (1H, s), 8.36 (1H, dd, J=5.8, 5.8 Hz).

MS (ESI) m/z: 484 [M+H].

Example 120

Synthesis of (2S)-N-{[4-(3,4-difluorobenzyl)morpholin-2-yl]methyl}-[4-(1H-tetrazol-5-yl)thiazol-2-ylthio]acetamide

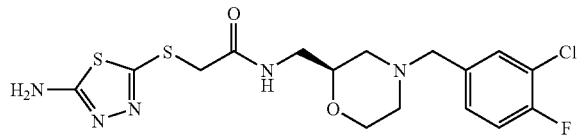

(120-1) Synthesis of (2S)-N-{[4-(3,4-difluorobenzyl)morpholin-2-yl]methyl}-(4-cyanothiazol-2-ylthio)acetamide By a similar method as in (22-1), the title compound (796 mg) was obtained as a colorless oil from the resultant product (1.14 g) of Example 114.

(120-2) Synthesis of (2S)-N-{[4-(3,4-difluorobenzyl)morpholin-2-yl]methyl}-[4-(1H-tetrazol-5-yl)thiazol-2-ylthio]acetamide By a similar method as in Example 59, the title compound (305 mg) was obtained as a yellow amorphous solid from the resultant product (796 mg) of (120-1).

$^1$H-NMR (DMSO-$d_6$) δ 1.80-1.95 (1H, m), 2.04-2.18 (1H, m), 2.66 (1H, d, J=12.3 Hz), 2.78 (1H, d, J=11.4 Hz), 3.10-3.19 (2H, m), 3.37-3.59 (4H, m), 3.73 (1H, d, J=12.3 Hz), 3.93 (1H, d, J=14.6 Hz), 4.00 (1H, d, J=14.6 Hz), 7.01-7.16 (1H, m), 7.22-7.40 (2H, m), 8.28 (1H, s), 8.35 (1H, dd, J=5.7, 5.7 Hz).

MS (ESI) m/z: 468 [M+H].

Example 121

Synthesis of (2S)-(5-amino-1,3,4-thiadiazol-2-ylthio)-N-{[4-(3-chloro-4-fluorobenzyl)morpholin-2-yl]methyl}acetamide (121-1) Synthesis of (2S)-N-{[4-(3-chloro-4-fluorobenzyl)morpholin-2-yl]methyl}chloroacetamide hydrochloride By a similar method as in (1-2), the title compound (3.50 g) was obtained as a pale-yellow amorphous solid from the resultant product (3.37 g) of (111-1).

(121-2) Synthesis of (2S)-(5-amino-1,3,4-thiadiazol-2-ylthio)-N-{[4-(3-chloro-4-fluorobenzyl)morpholin-2-yl]methyl}acetamide By a similar method as in (1-4), the title compound (435 mg) was obtained as a white solid from the resultant product (743 mg) of (121-1) and 2-amino-5-mercapto-1,3,4-thiadiazole (266 mg).

$^1$H-NMR (DMSO-d$_6$) δ 1.71-1.83 (1H, m), 1.98-2.09 (1H, m), 2.54 (1H, d, J=11.1 Hz), 2.65 (1H, d, J=11.1 Hz), 3.08-3.18 (2H, m), 3.41-3.51 (4H, m), 3.70-3.82 (3H, m), 7.23-7.39 (4H, m), 7.49 (1H, dd, J=1.8, 7.2 Hz), 8.23 (1H, dd, J=5.7, 5.7 Hz).

MS (ESI) m/z: 432 [M+H].

Example 122

Synthesis of (2S)-(5-acetamino-1,3,4-thiadiazol-2-ylthio)-N-{[4-(3-chloro-4-fluorobenzyl)morpholin-2-yl]methyl}acetamide

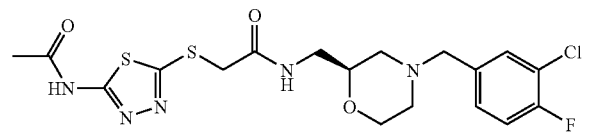

By a similar method as in Example 14, the title compound (125 mg) was obtained as white crystals from the resultant product (130 mg) of (121-2).

$^1$H-NMR (DMSO-d$_6$) δ 1.73-1.81 (1H, m), 1.96-2.09 (1H, m), 2.16 (3H, s), 2.54 (1H, d, J=11.1 Hz), 2.64 (1H, d, J=11.1 Hz), 3.08-3.18 (2H, m), 3.38-3.54 (4H, m), 3.75 (1H, d, J=11.1 Hz), 3.94 (2H, s), 7.27-7.40 (2H, m), 7.48 (1H, d, J=7.2 Hz), 8.31 (1H, dd, J=5.7, 5.7 Hz), 12.6 (1H, s).

MS (ESI) m/z: 474 [M+H].

Example 123

Synthesis of (2S)-(5-amino-1,3,4-thiadiazol-2-ylthio)-N-{[4-(3-chlorobenzyl)morpholin-2-yl]methyl}acetamide

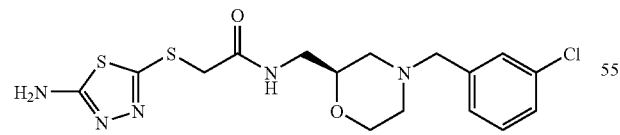

By a similar method as in (1-4), the title compound (723 mg) was obtained as white crystals from the resultant product (1.27 g) of (83-1) and 2-amino-5-mercapto-1,3,4-thiadiazole (533 mg).

$^1$H-NMR (DMSO-d$_6$) δ 1.71-1.83 (1H, m), 1.98-2.10 (1H, m), 2.55 (1H, d, J=11.4 Hz), 2.66 (1H, d, J=11.4 Hz), 3.07-3.17 (2H, m), 3.38-3.54 (4H, m), 3.70-3.81 (3H, m), 7.21-7.39 (6H, m), 8.21 (1H, dd, J=5.7, 5.7 Hz).

MS (ESI) m/z: 414 [M+H].

Example 124

Synthesis of (2S)-(5-acetamino-1,3,4-thiadiazol-2-ylthio)-N-{[4-(3-chlorobenzyl)morpholin-2-yl]methyl}acetamide

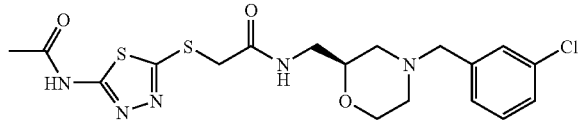

By a similar method as in Example 14, the title compound (405 mg) was obtained as white crystals from the resultant product (414 mg) of Example 123.

$^1$H-NMR (DMSO-d$_6$) δ 1.71-1.80 (1H, m), 1.96-2.09 (1H, m), 2.16 (3H, s), 2.54 (1H, d, J=10.8 Hz), 2.64 (1H, d, J=10.8 Hz), 3.08-3.13 (2H, m), 3.38-3.51 (4H, m), 3.75 (1H, d, J=10.8 Hz), 3.94 (2H, s), 7.23-7.38 (4H, m), 8.31 (1H, dd, J=5.7, 5.7 Hz), 12.6 (1H, s).

MS (ESI) m/z: 456 [M+H].

Example 125

Synthesis of (2S)-(5-amino-1,3,4-thiadiazol-2-ylthio)-N-{[4-(3,4-difluorobenzyl)morpholin-2-yl]methyl}acetamide

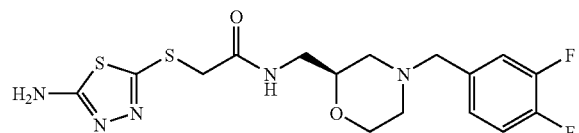

By a similar method as in (1-4), the title compound (333 mg) was obtained as white crystals from the resultant product (638 mg) of (113-1) and 2-amino-5-mercapto-1,3,4-thiadiazole (266 mg).

$^1$H-NMR (DMSO-d$_6$) δ 1.71-1.82 (1H, m), 1.98-2.08 (1H, m), 2.55 (1H, d, J=11.1 Hz), 2.65 (1H, d, J=11.1 Hz), 3.07-3.16 (2H, m), 3.39-3.52 (4H, m), 3.70-3.91 (3H, m), 7.11-7.18 (1H, m), 7.21-7.40 (4H, m), 8.23 (1H, dd, J=5.7, 5.7 Hz).

MS (ESI) m/z: 416 [M+H].

Example 126

Synthesis of (2S)-(5-acetamino-1,3,4-thiadiazol-2-ylthio)-N-{[4-(3,4-difluorobenzyl)morpholin-2-yl]methyl}acetamide

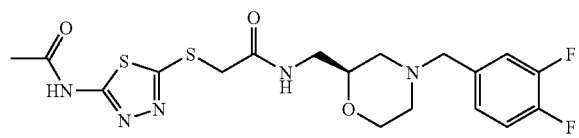

By a similar method as in Example 14, the title compound (220 mg) was obtained as white crystals from the resultant product (208 mg) of Example 125.

¹H-NMR (DMSO-d₆) δ 1.70-1.82 (1H, m), 1.96-2.08 (1H, m), 2.16 (3H, s), 2.54 (1H, d, J=10.8 Hz), 2.64 (1H, d, J=10.8 Hz), 3.07-3.16 (2H, m), 3.38-3.52 (4H, m), 3.75 (1H, d, J=11.1 Hz), 3.94 (2H, s), 7.10-7.16 (1H, m), 7.27-7.42 (2H, m), 8.30 (1H, dd, J=5.7, 5.7 Hz), 12.6 (1H, s).

MS (ESI) m/z: 458 [M+H].

Example 127

Synthesis of (2S)-N-{[4-(3,4-dichlorobenzyl)morpholin-2-yl]methyl}-(5-methyl-1,3,4-thiadiazol-2-ylthio)acetamide

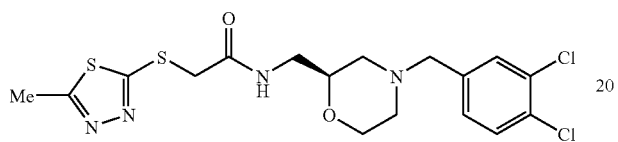

By a similar method as in (1-4), the title compound (3.38 g) was obtained as a pale-yellow solid from the resultant product (3.49 g) of (1-2) and 2-mercapto-5-methyl-1,3,4-thiadiazole (1.19 g).
¹H-NMR (DMSO-d₆) δ 1.72-1.87 (1H, m), 1.99-2.10 (1H, m), 2.54 (1H, d, J=11.1 Hz), 2.65-2.68 (4H, m), 3.09-3.18 (2H, m), 3.41-3.52 (4H, m), 3.75 (1H, d, J=11.1 Hz), 4.00 (2H, s), 7.30 (1H, dd, J=1.9, 8.3 Hz), 7.53-7.60 (2H, m), 8.32 (1H, dd, J=5.7, 5.7 Hz).

MS (ESI) m/z: 447 [M+H].

Example 128

Synthesis of (2S)-N-{[4-(3,4-dichlorobenzyl)morpholin-2-yl]methyl}-{2-[(3-ethoxy-1,3-dioxopropyl)amino]-1,3,4-thiadiazol-5-ylthio}acetamide

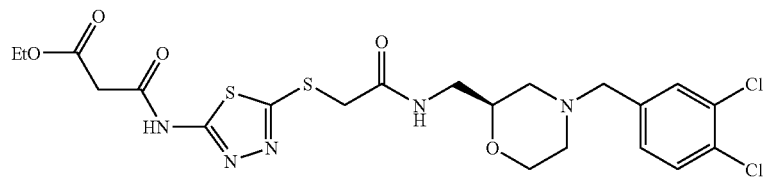

The resultant product (902 mg) of Example 52 was dissolved in dimethylformamide (5 mL) and, under ice-cooling, ethyl malonyl chloride (255 µL) was added, and the mixture was stirred for 40 min. Triethylamine (280 µL) and ethyl malonyl chloride (255 µL) were added to the reaction mixture, and the mixture was further stirred for 30 min. Saturated aqueous sodium hydrogen carbonate was added to the reaction mixture, and the mixture was extracted with chloroform. The extract was washed with saturated brine, dried, and the solvent was evaporated under reduced pressure. The residue was washed with ethyl acetate to give the title compound (773 mg) as a white solid.
¹H-NMR (DMSO-d₆) δ 1.19 (3H, t, J=7.2 Hz), 1.74-1.86 (1H, m), 1.96-2.09 (1H, m), 2.53 (1H, d, J=10.8 Hz), 2.63 (1H, d, J=10.8 Hz), 3.10-3.16 (2H, m), 3.38-3.52 (4H, m), 3.63 (2H, s), 3.75 (1H, d, J=10.8 Hz), 3.95 (2H, s), 4.11 (2H, q, J=7.2 Hz), 7.29 (1H, dd, J11.5, 8.1 Hz), 7.53-7.59 (2H, m), 8.29 (1H, dd, J=5.7, 5.7 Hz), 12.8 (1H, s).

MS (ESI) m/z: 562 [M+H]

Example 129

Synthesis of (2S)-{[2-(3-amino-1,3-dioxopropyl)amino]-1,3,4-thiadiazol-5-ylthio}-N-{[4-(3,4-dichlorobenzyl)morpholin-2-yl]methyl}acetamide

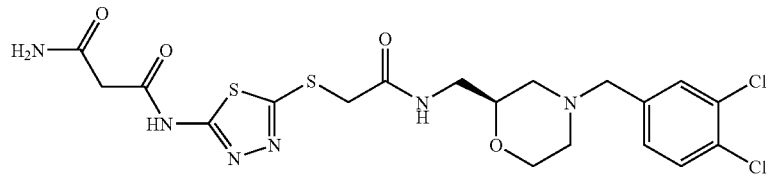

By a similar method as in Example 25, the title compound (112 mg) was obtained as a white solid from the resultant product (562 mg) of Example 128.
¹H-NMR (DMSO-d₆) δ 1.74-1.83 (1H, m), 1.94-2.09 (1H, m), 2.54 (1H, d, J=10.5 Hz), 2.65 (1H, d, J=10.5 Hz), 3.08-3.18 (2H, m), 3.38 (2H, s), 3.39-3.52 (4H, m), 3.75 (1H, d, J=10.5 Hz), 3.94 (2H, s), 7.18 (1H, brs), 7.29 (1H, d, J=8.4 Hz), 7.53-7.59 (3H, m), 8.28 (1H, dd, J=5.7, 5.7 Hz), 12.7 (1H, s).

MS (ESI) m/z: 533 [M+H].

Example 130

Synthesis of (2S)-{[2-(4-amino-1,4-dioxobutyl)amino]-1,3,4-thiadiazol-5-ylthio}-N-{[4-(3,4-dichlorobenzyl)morpholin-2-yl]methyl}acetamide

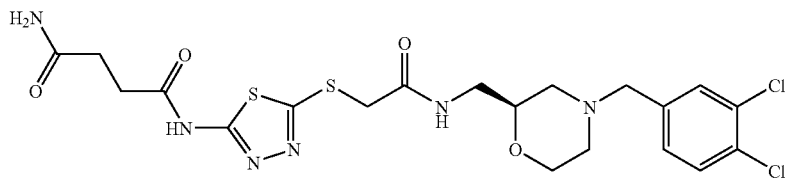

By a similar method as in Example 16, the title compound (123 mg) was obtained as a white solid from the resultant product (448 mg) of Example 52 and succinamic acid (141 mg).
$^1$H-NMR (DMSO-$d_6$) δ 1.73-1.85 (1H, m), 1.95-2.09 (1H, m), 2.42 (2H, t, J=6.9 Hz), 2.54 (1H, d, J=11.1 Hz), 2.60-2.70 (3H, m), 3.10-3.17 (2H, m), 3.38-3.52 (4H, m), 3.75 (1H, d, J=11.1 Hz), 3.93 (2H, s), 6.79 (1H, brs), 7.28-7.38 (2H, m), 7.53-7.60 (2H, m), 8.28 (1H, dd, J=5.7, 5.7 Hz), 12.6 (1H, s).
MS (ESI) m/z: 547 [M+H].

Example 131

Synthesis of (2S)-N-{[4-(3,4-dichlorobenzyl)morpholin-2-yl]methyl}-{2-[((5S)-2-oxopyrrolidin-5-yl)carbonylamino]-1,3,4-thiadiazol-5-ylthio}acetamide

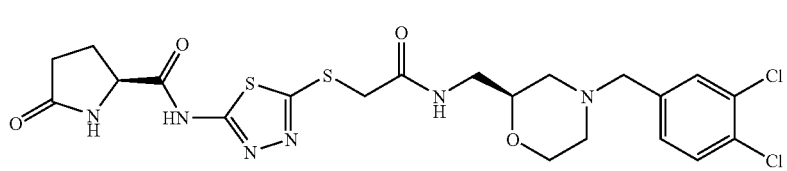

By a similar method as in Example 16, the title compound (252 mg) was obtained as a white amorphous solid from the resultant product (448 mg) of Example 52 and L-pyroglutamic acid (155 mg).
$^1$H-NMR (DMSO-$d_6$) δ 1.74-1.85 (1H, m), 1.90-2.10 (2H, m), 2.11-2.21 (2H, m), 2.29-2.43 (1H, m), 2.54 (1H, d, J=10.8 Hz), 2.64 (1H, d, J=10.8 Hz), 3.08-3.18 (2H, m), 3.38-3.52 (4H, m), 3.74-3.76 (1H, m), 3.95 (2H, s), 4.29-4.38 (1H, m), 7.29 (1H, dd, J=1.2, 8.1 Hz), 7.53 (1H, d, J=1.2 Hz), 7.58 (1H, d, J=8.1 Hz), 7.89 (1H, s), 8.29 (1H, dd, J=5.7, 5.7 Hz), 12.8 (1H, s).
MS (ESI) m/z: 559 [M+H].

Example 132

Synthesis of (2S)-N-{[4-(3,4-dichlorobenzyl)morpholin-2-yl]methyl}-{2-[((5R)-2-oxopyrrolidin-5-yl)carbonylamino]-1,3,4-thiadiazol-5-ylthio}acetamide By a similar method as in Example 16, the title compound (297 mg) was obtained as a white amorphous solid from the resultant product (448 mg) of Example 52 and D-pyroglutamic acid (155 mg).
$^1$H-NMR (DMSO-$d_6$) δ 1.74-1.85 (1H, m), 1.90-2.10 (2H, m), 2.11-2.21 (2H, m), 2.29-2.43 (1H, m), 2.54 (1H, d, J=10.8 Hz), 2.64 (1H, d, J=10.8 Hz), 3.09-3.19 (2H, m), 3.40-3.55 (4H, m), 3.74-3.76 (1H, m), 3.95 (2H, s), 4.30-4.40 (1H, m), 7.29 (1H, dd, J=1.5, 8.4 Hz), 7.53 (1H, d, J=1.5 Hz), 7.58 (1H, d, J=8.4 Hz), 7.89 (1H, s), 8.29 (1H, dd, J=5.7, 5.7 Hz), 12.8 (1H, s).
MS (ESI) m/z: 559 [M+H].

Example 133

Synthesis of (2S)-N-{[4-(3,4-dichlorobenzyl)morpholin-2-yl]methyl}-(1,3,4-thiadiazol-2-ylthio)acetamide

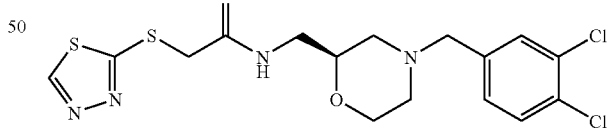

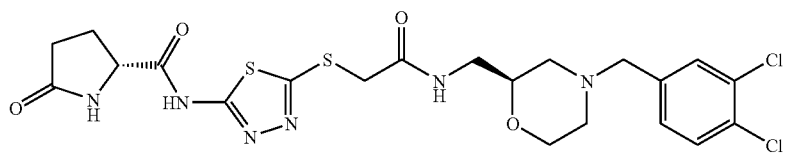

By a similar method as in (1-4), the title compound (240 mg) was obtained as white crystals from the resultant product (300 mg) of (1-2) and 2-mercapto-1,3,4-thiadiazole (100 mg).

$^1$H-NMR (DMSO-$d_6$) δ 1.74-1.80 (1H, m), 1.98-2.06 (1H, m), 2.53 (1H, d, J=11.1 Hz), 2.64 (1H, d, J=11.1 Hz), 3.10-3.14 (2H, m), 3.41-3.48 (4H, m), 3.74 (1H, d, J=11.1 Hz), 4.05 (2H, s), 7.28 (1H, dd, J=8.4, 1.5 Hz), 7.52 (1H, d, J=1.5 Hz), 7.57 (1H, d, J=8.4 Hz), 8.36 (1H, dd, J=5.7, 5.7 Hz), 9.50 (1H, s).

MS (ESI) m/z: 433 [M+H].

Example 134

Synthesis of (2S)-N-{[4-(3,4-dichlorobenzyl)morpholin-2-yl]methyl}-[2-(3-ethylureido)-1,3,4-thiadiazol-5-ylthio]acetamide

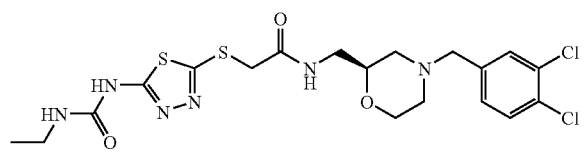

The resultant product (250 mg) of Example 52 was dissolved in tetrahydrofuran (1.8 mL), ethyl isocyanate (50 μL) was added, and the mixture was stirred at room temperature for 4.5 hrs. The reaction mixture was poured into water, and the mixture was extracted with ethyl acetate. The extract was washed with water and saturated brine, dried over anhydrous sodium sulfate, and the solvent was evaporated under reduced pressure. The obtained residue was washed with ethyl acetate to give the title compound (200 mg) as white crystals.

$^1$H-NMR (DMSO-$d_6$) δ 1.01 (3H, t, J=7.2 Hz), 1.72-1.79 (1H, m), 1.95-2.04 (1H, m), 2.50 (1H, d, J=11.1 Hz), 2.62 (1H, d, J=11.1 Hz), 3.08-3.12 (4H, m), 3.32-3.48 (4H, m), 3.72 (1H, d, J=11.1 Hz), 3.85 (2H, s), 6.57 (1H, brs), 7.26 (1H, dd, J=8.4, 1.5 Hz), 7.50 (1H, d, J=1.5 Hz), 7.55 (1H, d, J=8.4 Hz), 8.24 (1H, dd, J=5.7, 5.7 Hz), 10.92 (1H, s).

MS (ESI) m/z: 519 [M+H].

Example 135

Synthesis of (2S)-N-{[4-(3,4-dichlorobenzyl)morpholin-2-yl]methyl}-[2-(2-hydroxyacetamino)-1,3,4-thiadiazol-5-ylthio]acetamide

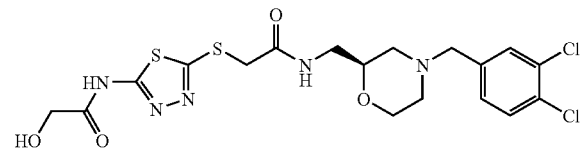

(135-1) Synthesis of (2S)-[2-(2-acetoxyacetamino)-1,3,4-thiadiazol-5-ylthio]-N-{[4-(3,4-dichlorobenzyl)morpholin-2-yl]methyl}acetamide The resultant product (250 mg) of Example 52 dissolved in dimethylformamide (1.6 mL), acetoxyacetyl chloride (60 μL) and triethylamine (80 μL) were added, and the mixture was stirred at room temperature for 1.5 hrs. The reaction mixture was poured into water, and the mixture was extracted with ethyl acetate. The extract was washed with water and saturated brine, dried over anhydrous sodium sulfate, and the solvent was evaporated under reduced pressure. The obtained residue was washed with ethyl acetate to give the title compound (270 mg) as a white solid.

(135-2) Synthesis of (2S)-N-{[4-(3,4-dichlorobenzyl)morpholin-2-yl]methyl}-[2-(2-hydroxyacetylamino)-1,3,4-thiadiazol-5-ylthio]acetamide The resultant product (170 mg) of (135-1) was dissolved in methanol (3.0 mL), potassium carbonate (45 mg) was added, and the mixture was stirred at room temperature for 2 hrs. The reaction mixture was poured into ice water, the mixture was neutralized with a 4N hydrochloric acid, and extracted with ethyl acetate. The extract was dried over anhydrous sodium sulfate, and the solvent was evaporated under reduced pressure. The obtained crystal was washed with ethyl acetate to give the title compound (125 mg) as white crystals.

$^1$H-NMR (DMSO-$d_6$) δ 1.72-1.79 (1H, m), 1.96-2.04 (1H, m), 2.52 (1H, d, J=11.1 Hz), 2.62 (1H, d, J=11.1 Hz), 3.08-3.12 (2H, m), 3.3-3.5 (4H, m), 3.73 (1H, d, J=11.1 Hz), 3.92 (2H, s), 4.14 (2H, d, J=4.5 Hz), 5.51 (1H, brs), 7.27 (1H, d, J=8.1 Hz), 7.51 (1H, s), 7.55 (1H, d, J=8.1 Hz), 8.28 (1H, dd, J=5.7, 5.7 Hz), 12.34 (1H, brs).

MS (ESI) m/z: 506 [M+H].

Example 136

Synthesis of (2S)-(5-carboxymethylthio-1,3,4-thiadiazol-2-ylthio)-N-{[4-(3,4-dichlorobenzyl)morpholin-2-yl]methyl}acetamide

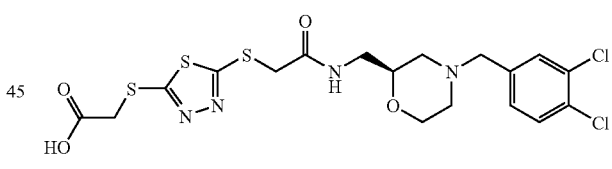

By a similar method as in (1-4), the title compound (970 mg) was obtained as a white amorphous solid from the resultant product (1.0 g) of (1-2) and (5-mercapto-1,3,4-thiadiazol-2-yl)thioacetic acid (600 mg).

$^1$H-NMR (DMSO-$d_6$) δ 1.77-1.84 (1H, m), 2.01-2.09 (1H, m), 2.55 (1H, d, J=11.1 Hz), 2.66 (1H, d, J=11.1 Hz), 3.09-3.13 (2H, m), 3.41-3.51 (4H, m), 3.75 (1H, d, J=11.1 Hz), 3.97 (2H, s), 4.09 (2H, s), 7.28 (1H, dd, J=8.1, 1.5 Hz), 7.53 (1H, d, J=1.5 Hz), 7.56 (1H, d, J=8.1 Hz), 8.33 (1H, dd, J=5.7, 5.7 Hz).

MS (ESI) m/z: 523 [M+H].

Example 137

Synthesis of (2S)-[5-(2-amino-2-oxoethylthio)-1,3,4-thiadiazol-2-ylthio]-N-{[4-(3,4-dichlorobenzyl)morpholin-2-yl]methyl}acetamide

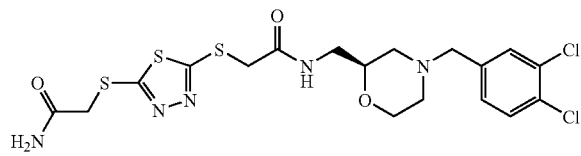

By a similar method as in Example 16, the title compound (100 mg) was obtained as white crystals from the resultant product (300 mg) of Example 136 and ammonium chloride (185 mg).

$^1$H-NMR (DMSO-d$_6$) δ 1.74-1.81 (1H, m), 1.99-2.06 (1H, m), 2.54 (1H, d, J=11.1 Hz), 2.64 (1H, d, J=11.1 Hz), 3.09-3.13 (2H, m), 3.27-3.49 (4H, m), 3.75 (1H, d, J=11.1 Hz), 3.98 (4H, s), 7.27-7.30 (2H, m), 7.53 (1H, s), 7.56 (1H, d, J=8.1 Hz), 7.69 (1H, brs) 8.34 (1H, dd, J=5.4, 5.4 Hz).

MS (ESI) m/z: 522 [M+H].

Example 138

Synthesis of (2S)-[5-(2-methylamino-2-oxoethylthio)-1,3,4-thiadiazol-2-ylthio]-N-{[4-(3,4-dichlorobenzyl)morpholin-2-yl]methyl}acetamide

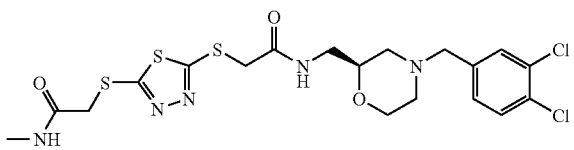

By a similar method as in Example 16, the title compound (240 mg) was obtained as white crystals from the resultant product (250 mg) of Example 136 and methylamine hydrochloride (120 mg).

$^1$H-NMR (DMSO-d$_6$) δ 1.74-1.81 (1H, m), 1.98-2.06 (1H, m), 2.53 (1H, d, J=11.1 Hz), 2.59 (3H, d, J=4.8 Hz), 2.64 (1H, d, J=11.1 Hz), 3.09-3.13 (2H, m), 3.42-3.48 (4H, m), 3.74 (1H, d, J=11.1 Hz), 3.96 (2H, s), 3.97 (2H, s), 7.28 (1H, dd, J=8.4, 1.8 Hz), 7.52 (1H, d, J=11.8 Hz), 7.56 (1H, d, J=8.4 Hz), 8.16 (1H, brs) 8.32 (1H, dd, J=5.7, 5.7 Hz).

MS (ESI) m/z: 536 [M+H].

Example 139

Synthesis of (2S)-N-{[4-(3,4-dichlorobenzyl)morpholin-2-yl]methyl}-(5-mercapto-1,3,4-thiadiazol-2-ylthio)acetamide

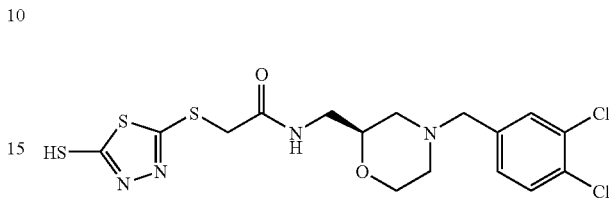

By a similar method as in Example 16, the title compound (550 mg) was obtained as a yellow amorphous solid from (2S)-2-aminomethyl-4-(3,4-dichlorobenzyl)morpholine dihydrochloride (1.0 g) and (5-mercapto-1,3,4-thiadiazol-2-yl)thioacetic acid (600 mg).

$^1$H-NMR (DMSO-d$_6$) δ 1.79-1.86 (1H, m), 2.05-2.12 (1H, m), 2.57 (1H, d, J=11.1 Hz), 2.67 (1H, d, J=11.1 Hz), 3.10-3.13 (2H, m), 3.42-3.50 (4H, m), 3.76 (1H, d, J=11.1 Hz), 3.86 (2H, s), 7.29 (1H, d, J=8.4 Hz), 7.54 (1H, s), 7.57 (1H, d, J=8.4 Hz), 8.30 (1H, dd, J=5.4, 5.4 Hz).

MS (ESI) m/z: 465 [M+H].

Example 140

Synthesis of (2S)-[5-(2-carboxypropan-2-ylthio)-1,3,4-thiadiazol-2-ylthio]-N-{[4-(3,4-dichlorobenzyl)morpholin-2-yl]methyl}acetamide

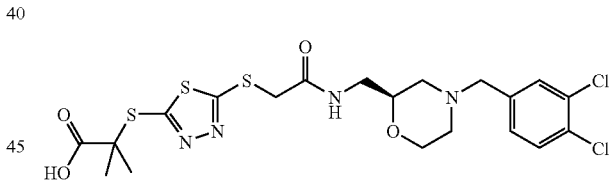

The resultant product (150 mg) of Example 139 and potassium carbonate (130 mg) were dissolved in dimethylformamide (1.0 mL), bromoisobutyric acid (65 mg) was added, and the mixture was stirred at room temperature for 4.5 hrs. Thereafter, bromoisobutyric acid (65 mg) was further added, and the mixture was stirred overnight at room temperature. The reaction mixture was poured into water, and the mixture was neutralized with a 1N hydrochloric acid and extracted with chloroform. The extract was dried over anhydrous sodium sulfate, and the solvent was evaporated under reduced pressure. The obtained residue was purified by silica gel column chromatography using a mixed solvent of chloroform and methanol as an eluent. The solvent was evaporated from the eluent to give the title compound (50 mg) as a white solid.

$^1$H-NMR (DMSO-d$_6$) δ 1.52 (6H, s), 1.83-1.89 (1H, m), 2.06-2.13 (1H, m), 2.58 (1H, d, J=11.1 Hz), 2.71 (1H, d, J=11.1 Hz), 3.10-3.14 (2H, m), 3.44-3.51 (4H, m), 3.75 (1H, d, J=11.1 Hz), 4.02 (2H, s), 7.29 (1H, d, J=8.4 Hz), 7.54 (1H, s), 7.57 (1H, dd, J=8.1, 2.7 Hz), 8.38 (1H, dd, J=5.7, 5.7 Hz).

MS (ESI) m/z: 551 [M+H].

Example 141

Synthesis of (2S)-N-{[4-(3,4-dichlorobenzyl)morpholin-2-yl]methyl}-[4-(1-oxoethyl)phenylthio]acetamide

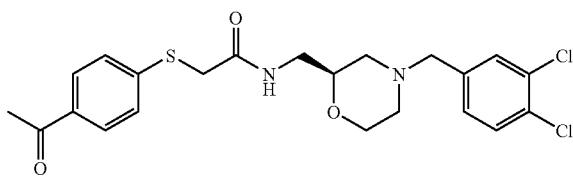

By a similar method as in Example 16, the title compound (477 mg) was obtained as a colorless oil from (4-acetylphenyl)thioacetic acid (252 mg) and (2S)-2-aminomethyl-4-(3,4-dichlorobenzyl)morpholine dihydrochloride (348 mg).

$^1$H-NMR (DMSO-$d_6$) δ 1.70-1.80 (1H, m), 1.94-2.08 (1H, m), 2.52 (3H, s), 2.52-2.62 (2H, m), 3.08-3.17 (2H, m), 3.38-3.52 (4H, m), 3.72-3.80 (3H, m), 7.26 (1H, dd, J=1.8, 8.1 Hz), 7.42 (2H, dd, J=1.8, 6.9 Hz), 7.51 (1H, d, J=1.8 Hz), 7.58 (1H, d, J=8.1 Hz), 7.87 (2H, dd, J=1.8, 6.9 Hz), 8.28 (1H, dd, J=5.7, 5.7 Hz).

MS (ESI) m/z: 467 [M+H]

Example 142

Synthesis of (2S)-N-{[4-(3,4-dichlorobenzyl)morpholin-2-yl]methyl}-(4-methoxycarbonylphenylthio)acetamide

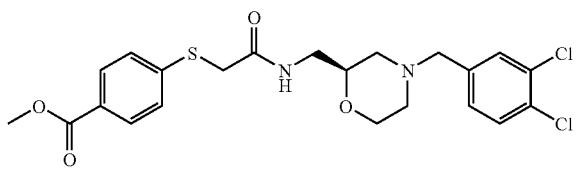

The resultant product (220 mg) of Example 37 was dissolved in dimethylformamide (3 mL), potassium carbonate (130 mg) and methyl iodide (22 μL) were added, and the mixture was stirred at room temperature for 4 hrs. The reaction mixture was extracted with ethyl acetate. The extract was washed with saturated brine, dried over anhydrous sodium sulfate, and the solvent was evaporated under reduced pressure. The obtained residue was purified by silica gel column chromatography using a mixed solvent of chloroform and methanol as an eluent. The solvent was evaporated from the eluent to give the title compound (150 mg) as a white amorphous solid.

$^1$H-NMR (DMSO-$d_6$) δ 1.76-1.71 (1H, m), 1.97-2.03 (1H, m), 2.52-2.59 (2H, m), 3.11-3.14 (2H, m), 3.38 (2H, s), 3.40-3.47 (2H, m), 3.73-3.77 (3H, m), 3.81 (3H, s), 7.26 (1H, dd, J=1.6, 8.0 Hz), 7.42 (2H, d, J=8.4 Hz), 7.49 (1H, d, J=1.6 Hz), 7.56 (1H, d, J=8.0 Hz), 7.85 (2H, d, J=8.4 Hz), 8.24 (1H, dd, J=5.8, 5.8 Hz).

MS (ESI) m/z: 483 [M+H].

Example 143

Synthesis of (2 S)-(5-carboxypyridin-2-ylthio)-N-{[4-(3,4-dichlorobenzyl)morpholin-2-yl]methyl}acetamide

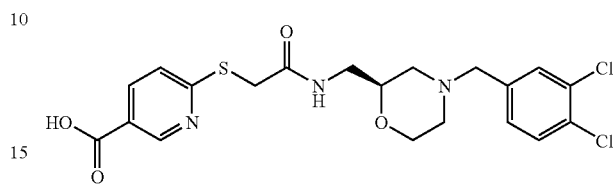

By a similar method as in (1-4), the title compound (580 mg) was obtained as a white amorphous solid from the resultant product (990 mg) of (1-2) and 6-mercaptonicotinic acid (440 mg).

$^1$H-NMR (DMSO-$d_6$) δ 1.73-1.79 (1H, m), 1.95-2.02 (1H, m), 2.52-2.54 (1H, m), 2.59-2.63 (1H, m), 3.06-3.17 (2H, m), 3.43-3.47 (4H, m), 3.72-3.76 (1H, m), 3.83-3.92 (2H, m), 7.28 (1H, dd, J=1.6, 8.4 Hz), 7.38 (1H, d, J=8.4 Hz), 7.51 (1H, d, J=1.6 Hz), 7.57 (1H, d, J=8.4 Hz), 8.05 (1H, dd, J=1.9, 8.4 Hz), 8.18 (1H, dd, J=5.7, 5.7 Hz), 8.86 (1H, d, J=1.9 Hz).

MS (ESI) m/z: 470 [M+H]

Example 144

Synthesis of (2S)-N-{[(4-(3,4-dichlorobenzyl)morpholin-2-yl]methyl}-[4-(morpholin-4-ylsulfonyl)phenylthio]acetamide (144-1) Synthesis of methyl 4-(morpholin-4-ylsulfonyl)phenylthioacetate

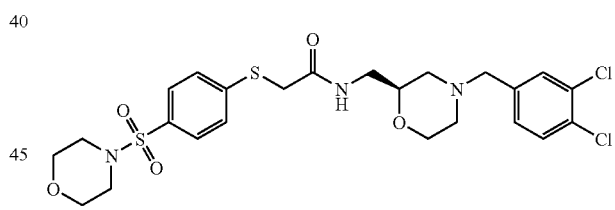

Dichloromethane (15 mL) and potassium carbonate (1.3 g) dissolved in water (15 mL) were added to 4-fluorobenzenesulfonyl chloride (1 g). Then, morpholine (530 μL) was added, and the mixture was stirred at room temperature for 1.5 hrs. After completion of the reaction, the mixture was extracted with chloroform, then the extract was washed with saturated brine, dried over anhydrous sodium sulfate, and the solvent was evaporated under reduced pressure to give a white solid (1.3 g). By a similar method as in (1-4), the title compound (0.93 g) was obtained as a white solid from the obtained white solid (1.3 g) and methyl thioglycolate (0.6 mL).

(144-2) Synthesis of (2S)-N-{[4-(3,4-dichlorobenzyl)morpholin-2-yl]methyl}-[4-(morpholin-4-ylsulfonyl)phenylthio]acetamide The resultant product (400 mg) of (144-1) was dissolved in methanol (10 mL) and tetrahydrofuran (10 mL), a 1 mol/L aqueous sodium hydroxide solution (2 mL) was added, and the mixture was stirred overnight at room temperature. 1 mol/L hydrochloric acid (2 mL) was added to the reaction mixture, and the solvent was evaporated under reduced pressure. By a similar method as in Example 16, the title compound (400 mg) was obtained as a white amorphous solid from the obtained residue and (2S)-2-aminomethyl-4-(3,4-dichlorobenzyl)morpholine dihydrochloride (280 mg).

$^1$H-NMR (DMSO-$d_6$) δ 1.73-1.79 (1H, m), 2.00-2.06 (1H, m), 2.52-2.57 (1H, m), 2.59-2.64 (1H, m), 2.86 (4H, t, J=4.6 Hz), 3.11-3.15 (2H, m), 3.40-3.49 (4H, m), 3.61 (4H, t, J=4.6 Hz), 3.74-3.78 (1H, m), 3.79 (2H, s), 7.28 (1H, dd, J=1.6, 8.3 Hz), 7.51-7.58 (4H, m), 7.60-7.64 (2H, m), 8.27 (1H, dd, J=, 5.6, 5.6 Hz).

MS (ESI) m/z: 574 [M+H].

Example 145

Synthesis of (2S)-N-{[4-(3,4-dichlorobenzyl)morpholin-2-yl]methyl}-(4-sulfamoylphenylthio)acetamide

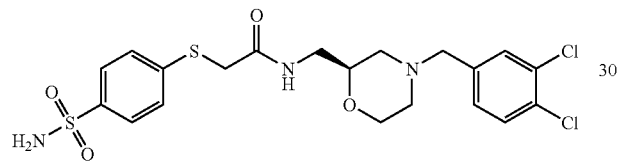

(145-1) Synthesis of methyl 4-sulfamoylphenylthioacetate

By a similar method as in (1-4), the title compound (150 mg) was obtained as a white solid from 4-fluorobenzenesulfonamide (1 g) and methyl thioglycolate (0.62 mL).

(145-2) Synthesis of (2S)-N-{[4-(3,4-dichlorobenzyl)morpholin-2-yl]methyl}-(4-sulfamoylphenylthio)acetamide By a similar method as in (144-2), the title compound (260 mg) was obtained as a white amorphous solid from the resultant product (190 mg) of (145-1) and (2S)-2-aminomethyl-4-(3,4-dichlorobenzyl)morpholine dihydrochloride (220 mg).

$^1$H-NMR (DMSO-$d_6$) δ 1.73-1.79 (1H, m), 1.99-2.07 (1H, m), 2.53-2.57 (1H, m), 2.60-2.63 (1H, m), 3.10-3.14 (2H, m), 3.41-3.49 (4H, m), 3.74-3.78 (3H, m), 7.26-7.31 (3H, m), 7.44-7.49 (2H, m), 7.53 (1H, d, J=1.5 Hz), 7.57 (1H, d, J=8.4 Hz), 7.68-7.73 (2H, m), 8.24 (1H, dd, J=5.6, 5.6 Hz)

MS (ESI) m/z: 504 [M+H].

Example 146

Synthesis of (2S)-N-{[4-(3,4-dichlorobenzyl)morpholin-2-yl]methyl}-(pyrimidin-2-ylthio)acetamide

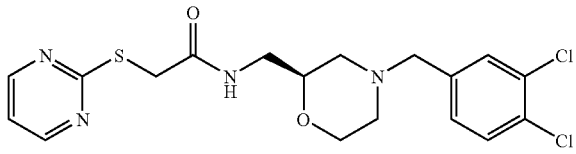

By a similar method as in (1-4), the title compound (240 mg) was obtained as a white amorphous solid from the resultant product (200 mg) of (1-2) and 2-mercaptopyrimidine (70 mg).

$^1$H-NMR (DMSO-$d_6$) δ 1.74-1.81 (1H, m), 1.97-2.05 (1H, m), 2.52-2.56 (1H, m), 2.61-2.66 (1H, m), 3.09-3.14 (2H, m), 3.41-3.49 (4H, m), 3.72-3.77 (1H, m), 3.83 (2H, s), 7.21 (1H, t, J=4.9 Hz), 7.29 (1H, dd, J=1.8, 8.3 Hz), 7.53 (1H, d, J=1.8 Hz), 7.57 (1H, d, J=8.3 Hz), 8.14 (1H, dd, J=5.7, 5.7 Hz), 8.60 (2H, d, J=4.9 Hz).

MS (ESI) m/z: 427 [M+H].

Example 147

Synthesis of (2S)-N-{[4-(3,4-dichlorobenzyl)morpholin-2-yl]methyl}-(4-methoxypyrimidin-2-ylthio)acetamide

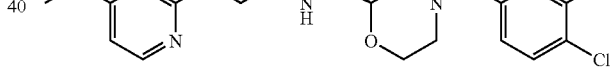

(147-1) Synthesis of methyl 4-methoxypyrimidin-2-ylthioacetate

By a similar method as in (1-4), the title compound (310 mg) was obtained as a colorless oil from 2-chloro-4-methoxypyrimidine (0.5 g) and methyl thioglycolate (320 μL.

(147-2) Synthesis of (2S)-N-{[4-(3,4-dichlorobenzyl)morpholin-2-yl]methyl}-(4-methoxypyrimidin-2-ylthio)acetamide By a similar method as in (144-2), the title compound (400 mg) was obtained as a yellow amorphous solid from the resultant product (310 mg) of (147-1) and (2S)-2-aminomethyl-4-(3,4-dichlorobenzyl)morpholine dihydrochloride (450 mg).

$^1$H-NMR (DMSO-$d_6$) δ 1.73-1.80 (1H, m), 1.96-2.04 (1H, m), 2.51-2.56 (1H, m), 2.59-2.64 (1H, m), 3.09-3.14 (2H, m), 3.41-3.48 (4H, m), 3.71-3.76 (1H, m), 3.82 (2H, s), 3.90 (3H, s), 6.62 (1H, d, J=5.5 Hz), 7.28 (1H, dd, J=11.5, 8.1 Hz), 7.52 (1H, d, J=1.5 Hz), 7.57 (1H, d, J=8.1 Hz), 8.11 (1H, dd, J=5.7, 5.7 Hz), 8.29 (1H, d, J=5.5 Hz).

MS (ESI) m/z: 457 [M+H].

Example 148

Synthesis of (2S)-N-{[4-(3,4-dichlorobenzyl)morpholin-2-yl]methyl}-(4,6-dimethoxypyrimidin-2-ylthio)acetamide

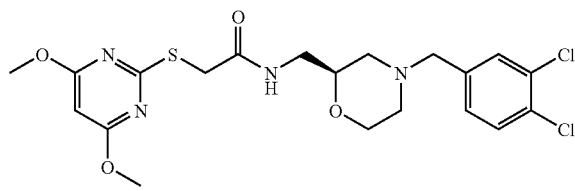

(148-1) Synthesis of methyl 4,6-dimethoxypyrimidin-2-ylthioacetate

By a similar method as in (1-4), the title compound (370 mg) was obtained as a white powder from 2-chloro-4,6-dimethoxypyrimidine (0.6 g) and methyl thioglycolate (320 μL).

(148-2) Synthesis of (2S)-N-{[4-(3,4-dichlorobenzyl)morpholin-2-yl]methyl}-(4,6-dimethoxypyrimidin-2-ylthio)acetamide By a similar method as in (144-2), the title compound (300 mg) was obtained as a white powder from the resultant product (370 mg) of (148-1) and (2S)-2-aminomethyl-4-(3,4-dichlorobenzyl)morpholine dihydrochloride (450 mg).

$^1$H-NMR (DMSO-$d_6$) δ 1.72-1.78 (1H, m), 1.95-2.04 (1H, m), 2.52-2.56 (1H, m), 2.58-2.63 (1H, m), 3.09-3.14 (2H, m), 3.40-3.47 (4H, m), 3.71-3.76 (1H, m), 3.81 (2H, s), 3.85 (6H, s), 5.92 (1H, s), 7.28 (1H, dd, J=11.6, 8.0 Hz), 7.52 (1H, d, J=1.6 Hz), 7.57 (1H, d, J=8.0 Hz), 8.09 (1H, dd, J=5.7, 5.7 Hz).

MS (ESI) m/z: 487 [M+H].

Example 149

Synthesis of (2S)-N-{[4-(3,4-dichlorobenzyl)morpholin-2-yl]methyl}-(2,4-dimethoxypyrimidin-6-ylthio)acetamide

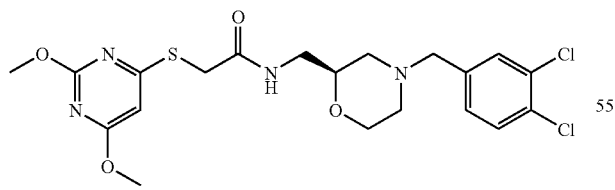

(149-1) Synthesis of methyl 2,4-dimethoxypyrimidin-6-ylthioacetate

By a similar method as in (1-4), the title compound (600 mg) was obtained as a colorless oil from 4-chloro-2,6-dimethoxypyrimidine (550 mg) and methyl thioglycolate (300 μL).

(149-2) Synthesis of (2S)-N-{[4-(3,4-dichlorobenzyl)morpholin-2-yl]methyl}-(2,4-dimethoxypyrimidin-6-ylthio)acetamide By a similar method as in (144-2), the title compound (510 mg) was obtained as a white amorphous solid from the resultant product (300 mg) of (149-1) and (2S)-2-aminomethyl-4-(3,4-dichlorobenzyl)morpholine dihydrochloride (380 mg).

$^1$H-NMR (DMSO-$d_6$) δ 1.73-1.80 (1H, m), 1.96-2.04 (1H, m), 2.51-2.56 (1H, m), 2.58-2.63 (1H, m), 3.09-3.15 (2H, m), 3.40-3.48 (4H, m), 3.72-3.76 (1H, m), 3.83 (2H, s), 3.84 (3H, s), 3.87 (3H, s), 6.49 (1H, s), 7.28 (1H, dd, J=1.7, 8.1 Hz), 7.52 (1H, d, J=1.7 Hz), 7.57 (1H, d, J=8.1 Hz), 8.15 (1H, dd, J=5.8, 5.8 Hz).

MS (ESI) m/z: 487 [M+H].

Example 150

Synthesis of (2S)-N-{[4-(3,4-dichlorobenzyl)morpholin-2-yl]methyl}-(pyrimidin-5-ylthio)acetamide

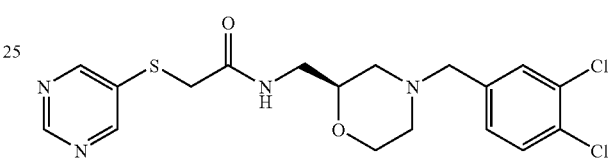

(150-1) Synthesis of methylpyrimidin-5-ylthioacetate

By a similar method as in (1-4), the title compound (50 mg) was obtained as a colorless oil from 5-bromopyrimidine (1 g) and methyl thioglycolate (600 μL).

(150-2) Synthesis of ((2S)-N-{[4-(3,4-dichlorobenzyl)morpholin-2-yl]methyl}-(pyrimidin-5-ylthio)acetamide By a similar method as in (144-2), the title compound (90 mg) was obtained as a white amorphous solid from the resultant product (50 mg) of (150-1) and (2S)-2-aminomethyl-4-(3,4-dichlorobenzyl)morpholine dihydrochloride (97 mg).

$^1$H-NMR (DMSO-$d_6$) δ 1.71-1.78 (1H, m), 2.00-2.08 (1H, m), 2.52-2.62 (2H, m), 3.08-3.12 (2H, m), 3.36-3.49 (4H, m), 3.72-3.78 (3H, m), 7.27-7.31 (1H, m), 7.52-7.59 (2H, m), 8.22 (1H, dd, J=5.4, 5.4 Hz), 8.79 (2H, s), 9.01 (1H, s).

MS (ESI) m/z: 427 [M+H].

Example 151

Synthesis of (2S)-N-{[4-(3,4-dichlorobenzyl)morpholin-2-yl]methyl}-(4-methylpyrimidin-2-ylthio)acetamide

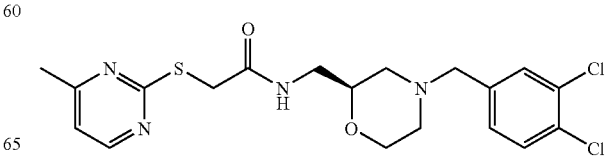

By a similar method as in (1-4), the title compound (210 mg) was obtained as a white amorphous solid from the resultant product (230 mg) of (1-2) and 2-mercapto-4-methylpyrimidine monohydrochloride (100 mg).

$^1$H-NMR (DMSO-$d_6$) δ 1.73-1.80 (1H, m), 1.96-2.03 (1H, m), 2.39 (3H, s), 2.51-2.56 (1H, m), 2.61-2.65 (1H, m), 3.09-3.14 (2H, m), 3.42-3.48 (4H, m), 3.72-3.77 (1H, m), 3.79-3.82 (2H, m), 7.09 (1H, d, J=5.0 Hz), 7.29 (1H, dd, J=1.4, 8.2 Hz), 7.53 (1H, d, J=1.4 Hz), 7.58 (1H, d, J=8.2 Hz), 8.15 (1H, dd, J=5.7, 5.7 Hz), 8.44 (1H, d, J=5.0 Hz).

MS (ESI) m/z: 441 [M+H].

Example 152

Synthesis of (2S)-N-{[4-(3,4-dichlorobenzyl)morpholin-2-yl]methyl}-(4-trifluoromethylpyrimidin-2-ylthio)acetamide

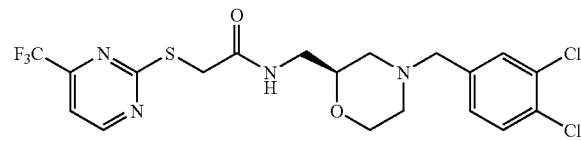

By a similar method as in (1-4), the title compound (180 mg) was obtained as a white amorphous solid from the resultant product (230 mg) of (1-2) and 2-mercapto-4-trifluoromethylpyrimidine (110 mg).

$^1$H-NMR (DMSO-$d_6$) δ 1.76-1.82 (1H, m), 1.98-2.07 (1H, m), 2.52-2.56 (1H, m), 2.63-2.67 (1H, m), 3.09-3.14 (2H, m), 3.42-3.50 (4H, m), 3.73-3.77 (1H, m), 3.92 (2H, s), 7.29 (1H, dd, J=1.5, 8.1 Hz), 7.54 (1H, d, J=1.5 Hz), 7.58 (1H, d, J=8.1 Hz), 7.71 (1H, d, J=5.0 Hz), 8.26 (1H, dd, J=5.7, 5.7 Hz), 8.96 (1H, d, J=5.0 Hz).

MS (ESI) m/z: 495 [M+H].

Example 153

Synthesis of (2S)-N-{[4-(3,4-dichlorobenzyl)morpholin-2-yl]methyl}-(5-ethoxycarbonyl-4-trifluoromethylpyrimidin-2-ylthio)acetamide

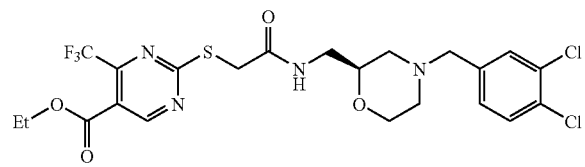

(153-1) Synthesis of 5-ethoxycarbonyl-4-trifluoromethylpyrimidin-2-ylthioacetic acid By a similar method as in (1-4), the title compound (1.1 g) was obtained as an orange oil from 2-chloro-5-ethoxycarbonyl-4-trifluoromethylpyrimidine (1 g) and thioglycol acid (300 μL).

(153-2) Synthesis of (2S)-N-{[4-(3,4-dichlorobenzyl)morpholin-2-yl]methyl}-(5-ethoxycarbonyl-4-trifluoromethylpyrimidin-2-ylthio)acetamide By a similar method as in Example 16, the title compound (240 mg) was obtained as a white amorphous solid from the resultant product (1 g) of (153-1) and (2S)-2-aminomethyl-4-(3,4-dichlorobenzyl)morpholine dihydrochloride (1.3 g).

$^1$H-NMR (DMSO-$d_6$) δ 1.29 (3H, t, J=7.1 Hz), 1.75-1.82 (1H, m), 1.98-2.07 (1H, m), 2.51-2.57 (1H, m), 2.63-2.68 (1H, m), 3.09-3.17 (2H, m), 3.43-3.50 (4H, m), 3.73-3.78 (1H, m), 3.98 (2H, s), 4.34 (2H, q, J=7.1 Hz), 7.29 (1H, dd, J=1.6, 8.4 Hz), 7.53 (1H, d, J=1.6 Hz), 7.57 (1H, d, J=8.4 Hz), 8.29 (1H, dd, J=5.7, 5.7 Hz), 9.16 (1H, s).

MS (ESI) m/z: 567 [M+H].

Example 154

Synthesis of (2S)-(3-carbamoylpyridin-6-ylthio)-N-{[4-(3,4-dichlorobenzyl)morpholin-2-yl]methyl}acetamide

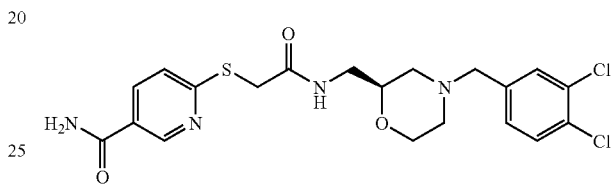

By a similar method as in Example 8, the title compound (270 mg) was obtained as a white powder from the resultant product (450 mg) of Example 143.

$^1$H-NMR (DMSO-$d_6$) δ 1.71-1.78 (1H, m), 1.94-2.01 (1H, m), 2.51-2.55 (1H, m), 2.59-2.63 (1H, m), 3.09-3.14 (2H, m), 3.40-3.48 (4H, m), 3.72-3.76 (1H, m), 3.86-3.90 (2H, m), 7.28 (1H, dd, J=1.6, 8.2 Hz), 7.42 (1H, d, J=8.4 Hz), 7.52 (1H, d, J=1.6 Hz), 7.53 (1H, brs), 7.57 (1H, d, J=8.2 Hz), 8.06 (1H, dd, J=2.0, 8.4 Hz), 8.09 (1H, brs), 8.20 (1H, dd, J=5.8, 5.8 Hz), 8.86 (1H, d, J=2.0 Hz).

MS (ESI) m/z: 469 [M+H].

Example 155

Synthesis of (2S)-N-{[4-(3,4-dichlorobenzyl)morpholin-2-yl]methyl}-(4-hydroxy-6-trifluoromethylpyrimidin-2-ylthio)acetamide

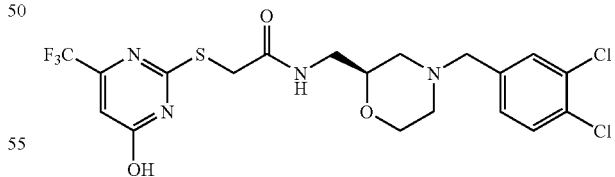

By a similar method as in (1-4), the title compound (390 mg) was obtained as a white powder from the resultant product (380 mg) of (1-2) and 4-hydroxy-2-mercapto-6-trifluoromethylpyrimidine (200 mg).

$^1$H-NMR (DMSO-$d_6$) δ 1.85-1.91 (1H, m), 2.08-2.15 (1H, m), 2.58-2.62 (1H, m), 2.70-2.74 (1H, m), 3.10-3.14 (2H, m), 3.43-3.52 (4H, m), 3.75-3.79 (1H, m), 3.89 (2H, s), 6.60 (1H, s), 7.31 (1H, dd, J=1.4, 8.3 Hz), 7.55 (1H, d, J=1.4 Hz), 7.59 (1H, d, J=8.3 Hz), 8.26 (1H, dd, J=5.7, 5.7 Hz).

MS (ESI) m/z: 511 [M+H].

Example 156

Synthesis of (2S)-N-{[4-(3,4-dichlorobenzyl)morpholin-2-yl]methyl}-(5-methoxycarbonylpyrimidin-2-ylthio)acetamide

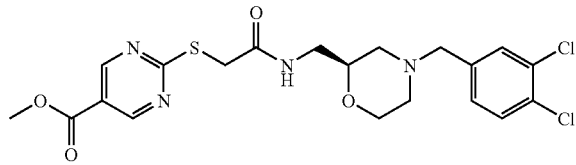

(156-1) Synthesis of 5-methoxycarbonylpyrimidin-2-ylthioacetic acid

2-Benzylthio-5-methoxycarbonylpyrimidine (400 mg) was dissolved in dichloromethane (10 mL). Then, m-chloroperbenzoic acid (350 mg) was added, and the mixture was stirred at room temperature for 2 hrs. After evaporation of the solvent under reduced pressure, by a similar method as in (1-4), the title compound (200 mg) was obtained as a white solid from the obtained residue and thioglycol acid (105 μL).

(156-2) Synthesis of (2S)-N-{[4-(3,4-dichlorobenzyl)morpholin-2-yl]methyl}-(5-methoxycarbonylpyrimidin-2-ylthio)acetamide By a similar method as in Example 16, the title compound (220 mg) was obtained as a white solid from the resultant product (240 mg) of (156-1) and (2S)-2-aminomethyl-4-(3,4-dichlorobenzyl)morpholine dihydrochloride (440 mg).

$^1$H-NMR (DMSO-$d_6$) δ 1.77-1.82 (1H, m), 2.00-2.05 (1H, m), 2.53-2.56 (1H, m), 2.65-2.67 (1H, m), 3.10-3.15 (2H, m), 3.42-3.49 (4H, m), 3.73-3.77 (1H, m), 3.86 (3H, s), 3.93 (2H, s), 7.29 (1H, dd, J=1.6, 8.1 Hz), 7.52 (1H, d, J=1.6 Hz), 7.57 (1H, d, J=8.1 Hz), 8.22 (1H, dd, J=5.8, 5.8 Hz), 9.00 (2H, s).

MS (ESI) m/z: 485 [M+H].

Example 157

Synthesis of (2S)-N-{[4-(3,4-dichlorobenzyl)morpholin-2-yl]methyl}-(5-ethoxycarbonyl-4-methylpyrimidin-2-ylthio)acetamide

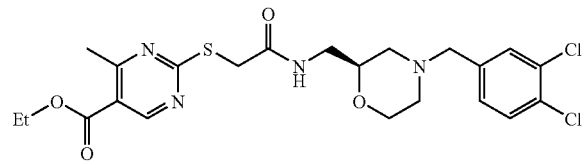

(157-1) Synthesis of 5-ethoxycarbonyl-4-methylpyrimidin-2-ylthioacetic acid

By a similar method as in (156-1), the title compound (200 mg) was obtained as a white solid from 2-benzylthio-5-methoxycarbonyl-4-methylpyrimidine (400 mg) and thioglycol acid (100 μL).

(157-2) Synthesis of (2S)-N-{[4-(3,4-dichlorobenzyl)morpholin-2-yl]methyl}-[(5-ethoxycarbonyl-4-methyl)pyrimidin-2-ylthio]acetamide By a similar method as in Example 16, the title compound (420 mg) was obtained as a white amorphous solid from the resultant product (200 mg) of (157-1) and (2S)-2-aminomethyl-4-(3,4-dichlorobenzyl)morpholine dihydrochloride (330 mg).

$^1$H-NMR (DMSO-$d_6$) δ 1.29 (3H, t, J=7.1 Hz), 1.76-1.81 (1H, m), 1.97-2.04 (1H, m), 2.52-2.55 (1H, m), 2.61-2.65 (1H, m), 2.66 (3H, s), 3.11-3.15 (2H, m), 3.41-3.49 (4H, m), 3.72-3.77 (1H, m), 3.89 (2H, s), 4.29 (2H, q, J=7.1 Hz), 7.28 (1H, dd, J=1.4, 8.3 Hz), 7.52 (1H, d, J=1.4 Hz), 7.56 (1H, d, J=8.3 Hz), 8.19 (1H, dd, J=5.8, 5.8 Hz), 8.88 (1H, s).

MS (ESI) m/z: 513 [M+H].

Example 158

Synthesis of (2S)-[4-(2-carboxyethyl)phenylthio]-N-{[4-(3,4-dichlorobenzyl)morpholin-2-yl]methyl}acetamide

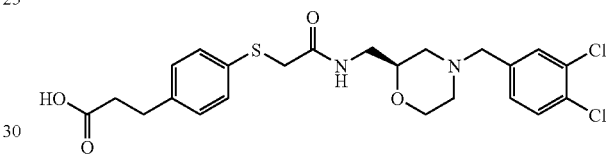

By a similar method as in (1-4), the title compound (350 mg) was obtained as a white amorphous solid from 3-(4-mercaptophenyl)propionic acid (200 mg) and the resultant product (400 mg) of (1-2).

$^1$H-NMR (DMSO-$d_6$) δ 1.73-1.78 (1H, m), 1.98-2.06 (1H, m), 2.47-2.67 (4H, m), 2.77 (2H, t, J=7.6 Hz), 3.08-3.12 (2H, m), 3.38-3.48 (4H, m), 3.58 (2H, s), 3.74-3.78 (1H, m), 7.14-7.18 (2H, m), 7.22-7.30 (3H, m), 7.51-7.53 (1H, m), 7.56 (1H, d, J=8.0 Hz), 8.12 (1H, dd, J=5.8, 5.8 Hz), 12.08 (1H, brs).

MS (ESI) m/z: 497 [M+H].

Example 159

Synthesis of (2S)-[4-(2-carbamoylethyl)phenylthio]-N-{[4-(3,4-dichlorobenzyl)morpholin-2-yl]methyl}acetamide

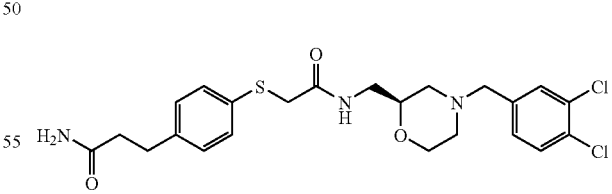

By a similar method as in Example 8, the title compound (220 mg) was obtained as a white solid from the resultant product (230 mg) of Example 158.

$^1$H-NMR (DMSO-$d_6$) δ 1.72-1.78 (1H, m), 2.00-2.05 (1H, m), 2.31 (2H, t, J=7.8 Hz), 2.52-2.62 (2H, m), 2.75 (2H, t, J=7.8 Hz), 3.08-3.12 (2H, m), 3.38-3.48 (4H, m), 3.58 (2H, s), 3.73-3.78 (1H, m), 6.72 (1H, brs), 7.12-7.17 (2H, m), 7.23-7.30 (4H, m), 7.52 (1H, d, J=1.5 Hz), 7.57 (1H, d, J=8.4 Hz), 8.11 (1H, dd, J=5.9, 5.9 Hz).

MS (ESI) m/z: 496 [M+H].

Example 160

Synthesis of (2S)-N-{[4-(3,4-dichlorobenzyl)morpholin-2-yl]methyl}-(4-methyl-2-oxo-2H-chromen-7-ylthio)acetamide

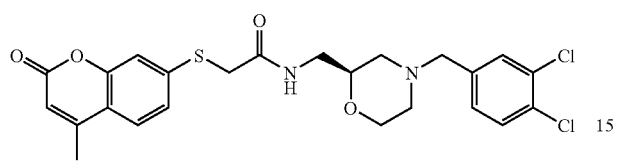

By a similar method as in (1-4), the title compound (450 mg) was obtained as a white amorphous solid from 7-mercapto-4-methyl-2H-chromen-2-one (200 mg) and the resultant product (380 mg) of (1-2).

$^1$H-NMR (DMSO-d$_6$) δ 1.72-1.77 (1H, m), 1.95-2.02 (1H, m), 2.39 (3H, s), 2.50-2.52 (1H, m), 2.56-2.59 (1H, m), 3.12-3.15 (2H, m), 3.36 (2H, s), 3.40-3.47 (2H, m), 3.72-3.84 (3H, m), 6.30 (1H, s), 7.21-7.29 (2H, m), 7.35 (1H, d, J=1.5 Hz), 7.46-7.47 (1H, m), 7.55 (1H, d, J=8.1 Hz), 7.66 (1H, d, J=8.4 Hz), 8.29 (1H, dd, J=5.8, 5.8 Hz).

MS (ESI) m/z: 507 [M+H].

Example 161

Synthesis of (2S)-N-{[4-(3,4-dichlorobenzyl)morpholin-2-yl]methyl}-(4-ethoxycarbonylmethylphenylthio)acetamide

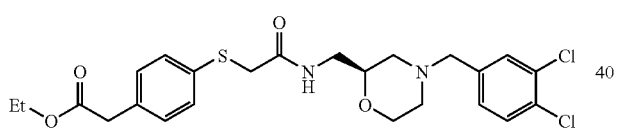

(161-1) Synthesis of 4-ethoxycarbonylmethylphenylthioacetic acid

Ethyl 4-bromophenylacetate (500 mg), diisopropylethylamine (700 μL), tris(dibenzylideneacetone)dipalladium(0) (46 mg) and 4,5-bis(diphenylphosphino)-9,9-dimethylxanthene (Xantphos) (58 mg) were dissolved in dioxane (5 mL). Then, thioglycol acid (140 μL) was added, and the mixture was heated under reflux for 4 hrs. The reaction mixture was poured into water, the aqueous phase was washed with ethyl acetate and acidified with 1 mol/L hydrochloric acid. Then, and the mixture was extracted with ethyl acetate. The extract was washed with saturated brine, dried over anhydrous sodium sulfate, and the solvent was evaporated under reduced pressure to give the title compound (260 mg) as a colorless oil.

(161-2) Synthesis of (2S)-N-{[4-(3,4-dichlorobenzyl)morpholin-2-yl]methyl}-(4-ethoxycarbonylmethylphenylthio)acetamide By a similar method as in Example 16, the title compound (220 mg) was obtained as a white amorphous solid from the resultant product (260 mg) of (161-1) and (2S)-2-aminomethyl-4-(3,4-dichlorobenzyl)morpholine dihydrochloride (350 mg).

$^1$H-NMR (DMSO-d$_6$) δ 1.16 (3H, t, J=7.1 Hz), 1.73-1.80 (1H, m), 1.98-2.07 (1H, m), 2.52-2.63 (2H, m), 3.08-3.15 (2H, m), 3.40-3.49 (4H, m), 3.61 (2H, s), 3.62 (2H, s), 3.73-3.78 (1H, m), 4.05 (2H, q, J=7.1 Hz), 7.19 (2H, d, J=8.3 Hz), 7.26-7.30 (3H, m), 7.53 (1H, d, J=1.9 Hz), 7.57 (1H, d, J=8.5 Hz), 8.15 (1H, dd, J=5.8, 5.8 Hz).

MS (ESI) m/z: 511 [M+H].

Example 162

Synthesis of (2S)-(4-carboxymethylphenylthio)-N-{[4-(3,4-dichlorobenzyl)morpholin-2-yl]methyl}acetamide

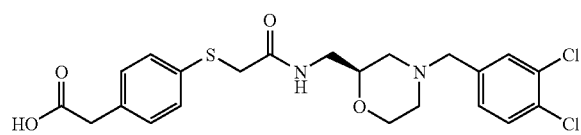

By a similar method as in (1-5), the title compound (130 mg) was obtained as a white amorphous solid from the resultant product (180 mg) of (161-2).

$^1$H-NMR (DMSO-d$_6$) δ 1.73-1.79 (1H, m), 2.00-2.06 (1H, m), 2.52-2.68 (2H, m), 3.08-3.12 (2H, m), 3.40-3.49 (4H, m), 3.52 (2H, s), 3.61 (2H, s), 3.74-3.78 (1H, m), 7.17-7.21 (2H, m), 7.26-7.31 (3H, m), 7.53 (1H, d, J=1.2 Hz), 7.57 (1H, d, J=8.3 Hz), 8.15 (1H, dd, J=5.8, 5.8 Hz).

MS (ESI) m/z: 483 [M+H].

Example 163

Synthesis of (2S)-N-{[4-(3,4-dichlorobenzyl)morpholin-2-yl]methyl}-(4-hydroxy-5-methyl-pyrimidin-2-ylthio)acetamide

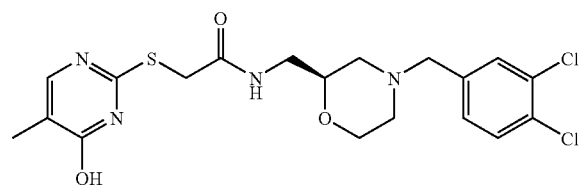

By a similar method as in (1-4), the title compound (270 mg) was obtained as a white solid from 4-hydroxy-2-mercapto-5-methylpyrimidine (150 mg) and the resultant product (380 mg) of (1-2).

$^1$H-NMR (DMSO-d$_6$) δ 1.76-1.82 (1H, m), 1.85 (3H, s), 1.97-2.06 (1H, m), 2.51-2.56 (1H, m), 2.63-2.67 (1H, m), 3.08-3.12 (2H, m), 3.42-3.49 (4H, m), 3.72-3.78 (1H, m), 3.80-3.83 (2H, m), 7.29 (1H, dd, J=1.5, 8.0 Hz), 7.53 (1H, d, J=1.5 Hz), 7.58 (1H, d, J=8.0 Hz), 7.69 (1H, brs), 8.17 (1H, dd, J=5.8, 5.8 Hz), 12.71 (1H, brs).

MS (ESI) m/z: 457 [M+H].

Example 164

Synthesis of (2S)-N-{[4-(3,4-dichlorobenzyl)morpholin-2-yl]methyl}-(4-hydroxypyrimidin-2-ylthio)acetamide

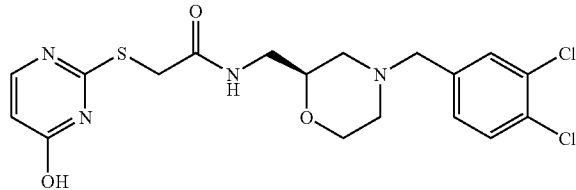

By a similar method as in (1-4), the title compound (130 mg) was obtained as a white solid from 2-thiouracil (130 mg) and the resultant product (380 mg) of (1-2).

$^1$H-NMR (DMSO-d$_6$) δ 1.76-1.83 (1H, m), 2.00-2.07 (1H, m), 2.51-2.57 (1H, m), 2.63-2.67 (1H, m), 3.09-3.13 (2H, m), 3.42-3.49 (4H, m), 3.73-3.85 (3H, m), 6.13 (1H, brs), 7.29 (1H, dd, J=1.6, 8.0 Hz), 7.53 (1H, d, J=1.6 Hz), 7.58 (1H, d, J=8.0 Hz), 7.81 (1H, brs), 8.15-8.21 (1H, m), 12.74 (1H, brs).

MS (ESI) m/z: 443 [M+H].

Example 165

Synthesis of (2S)-N-{[4-(3,4-dichlorobenzyl)morpholin-2-yl]methyl}-(4-hydroxy-5-ethoxycarbonylpyrimidin-2-ylthio)acetamide

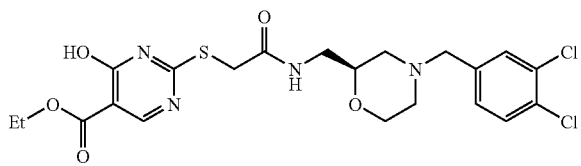

By a similar method as in (1-4), the title compound (380 mg) was obtained as a yellow solid from 5-ethoxycarbonyl-2-thiouracil (210 mg) and the resultant product (400 mg) of (1-2).

$^1$H-NMR (DMSO-d$_6$) δ 1.21 (3H, t, J=7.0 Hz), 1.76-1.82 (1H, m), 1.97-2.03 (1H, m), 2.51-2.53 (1H, m), 2.63-2.66 (1H, m), 3.05-3.16 (2H, m), 3.37-3.47 (4H, m), 3.67-3.77 (3H, m), 4.15 (2H, q, J=7.0 Hz), 7.28 (1H, dd, J=1.3, 8.4 Hz), 7.52 (1H, d, J=1.3 Hz), 7.56 (1H, d, J=8.4 Hz), 8.24-8.29 (1H, m), 8.32 (1H, s).

MS (ESI) m/z: 515 [M+H].

Example 166

Synthesis of (2S)-N-{[4-(3,4-dichlorobenzyl)morpholin-2-yl]methyl}-(4-ethoxycarbonylmethyl-6,7-dimethoxyquinazolin-2-ylthio)acetamide

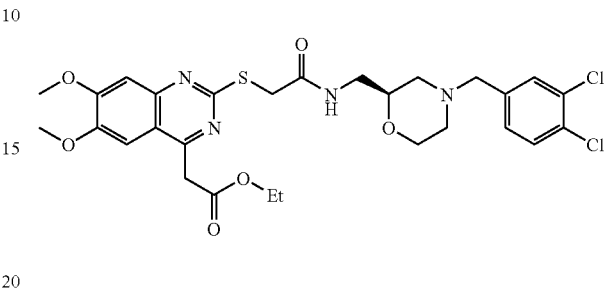

(166-1) Synthesis of 2-chloro-4-[bis(ethoxycarbonyl)methyl]-6,7-dimethoxyquinazoline Diethyl malonate (0.76 mL) was dissolved in dioxane (25 mL), sodium hydride (200 mg) was added, and the mixture was stirred at room temperature for 30 min. Then, 2,4-dichloro-6,7-dimethoxyquinazoline (1.3 g) was added, and the mixture was heated under reflux for 3.5 hrs. Water was added to the reaction mixture, and the mixture was extracted with ethyl acetate. The extract was washed with saturated brine, dried over anhydrous sodium sulfate, and the solvent was evaporated under reduced pressure. The obtained residue was recrystallized from a mixed solvent of ethyl acetate and hexane to give the title compound (840 mg) as a white solid.

(166-2) Synthesis of 4-[bis(ethoxycarbonyl)methyl]-2-mercapto-6,7-dimethoxyquinazoline The resultant product (600 mg) of (166-1) and thiourea (250 mg) were dissolved in ethanol (100 mL), and the mixture was heated under reflux for 48 hrs. The yellow solid precipitated in the reaction mixture was collected by filtration and washed with water and ethyl acetate to give the title compound (500 mg) as a yellow solid.

(166-3) Synthesis of 4-ethoxycarbonylmethyl-2-mercapto-6,7-dimethoxyquinazoline

By a similar method as in (1-5), the title compound (71 mg) was obtained as a white amorphous solid from the resultant product (180 mg) of (166-2).

(166-4) Synthesis of (2S)-N-{[4-(3,4-dichlorobenzyl)morpholin-2-yl]methyl}-[(4-ethoxycarbonylmethyl-6,7-dimethoxyquinazoline)-2-ylthio]acetamide By a similar method as in (1-4), the title compound (18 mg) was obtained as a white solid from the resultant product (71 mg) of (166-3) and the resultant product (77 mg) of (1-2).

$^1$H-NMR (DMSO-d$_6$) δ 1.17 (3H, t, J=7.1 Hz), 1.68-1.76 (1H, m), 1.85-1.89 (1H, m), 2.42-2.46 (1H, m), 2.54-2.56 (1H, m), 3.11-3.16 (2H, m), 3.24 (2H, s), 3.35-3.50 (2H, m), 3.63-3.68 (1H, m), 3.86-3.91 (5H, m), 3.97 (3H, s), 4.12 (2H, q, J=7.1 Hz), 4.30 (2H, s), 7.16-7.22 (2H, m), 7.38 (1H, s), 7.43 (1H, s), 7.54 (1H, d, J=8.0 Hz), 8.11-8.17 (1H, m).

MS (ESI) m/z: 623 [M+H].

Example 167

Synthesis of (2S)-N-{[4-(3,4-dichlorobenzyl)morpholin-2-yl]methyl}-(4-methoxycarbonyl-1-methyl-2,3-dihydro-1H-benzo[b]azepin-7-ylthio)acetamide

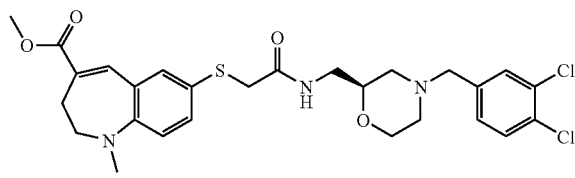

(167-1) Synthesis of 4-methoxycarbonyl-1-methyl-2,3-dihydro-1H-benzo[b]azepin-7-ylthioacetic acid By a similar method as in (161-1), the title compound (430 mg) was obtained as a yellow oil from 7-bromo-4-methoxycarbonyl-1-methyl-2,3-dihydro-1H-benzo[b]azepine (600 mg) and thioglycol acid (140 μL).

(167-2) Synthesis of (2S)-N-{[4-(3,4-dichlorobenzyl)morpholin-2-yl]methyl}-(4-methoxycarbonyl-1-methyl-2,3-dihydro-1H-benzo[b]azepin-7-ylthio)acetamide By a similar method as in Example 16, the title compound (350 mg) was obtained as a yellow amorphous solid from the resultant product (420 mg) of (167-1) and (2S)-2-aminomethyl-4-(3,4-dichlorobenzyl)morpholine dihydrochloride (480 mg).
$^1$H-NMR (DMSO-d$_6$) δ 1.69-1.76 (1H, m), 1.95-2.03 (1H, m), 2.51-2.59 (2H, m), 2.68-2.72 (2H, m), 2.96 (3H, s), 3.05-3.10 (2H, m), 3.16-3.21 (2H, m) 3.36-3.49 (6H, m), 3.69-3.76 (4H, m), 6.78 (1H, d, J=8.7 Hz), 7.23-7.27 (2H, m), 7.40 (1H, d, J=2.0 Hz), 7.48-7.57 (3H, m), 8.01 (1H, dd, J=5.6, 5.6 Hz).
MS(ESI) m/z: 564 [M+H]

Example 168

Synthesis of (2S)-(4-carboxy-1-methyl-2,3-dihydro-1H-benzo[b]azepin-7-ylthio)-N-{[4-(3,4-dichlorobenzyl)morpholin-2-yl]methyl}acetamide

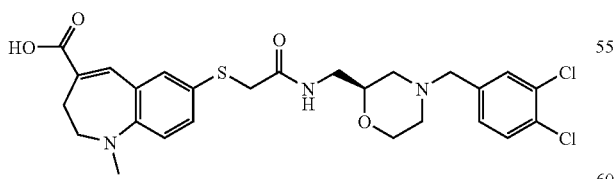

By a similar method as in (1-5), the title compound (170 mg) was obtained as a white amorphous solid from the resultant product (330 mg) of (167-2).
$^1$H-NMR (DMSO-d$_6$) δ 1.70-1.77 (1H, m), 1.95-2.03 (1H, m), 2.53-2.59 (2H, m), 2.65-2.69 (2H, m), 2.95 (3H, s), 3.05-3.10 (2H, m), 3.14-3.20 (2H, m) 3.39-3.49 (6H, m), 3.71-3.76 (1H, m), 6.76 (1H, d, J=8.6 Hz), 7.20-7.28 (2H, m), 7.37 (1H, d, J=1.1 Hz), 7.48-7.57 (3H, m), 8.01 (1H, dd, J=5.3, 5.3 Hz), 12.43 (1H, brs).
MS (ESI) m/z: 550 [M+H].

Example 169

Synthesis of (2S)-N-{[4-(3,4-dichlorobenzyl)morpholin-2-yl]methyl}-(pyridin-4-ylthio)acetamide

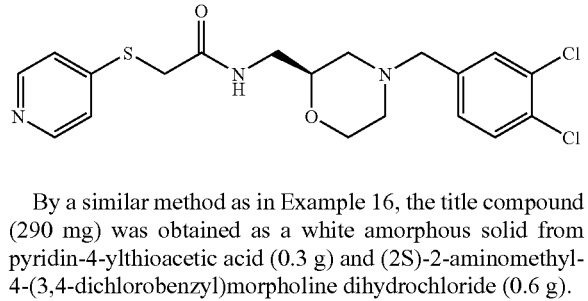

By a similar method as in Example 16, the title compound (290 mg) was obtained as a white amorphous solid from pyridin-4-ylthioacetic acid (0.3 g) and (2S)-2-aminomethyl-4-(3,4-dichlorobenzyl)morpholine dihydrochloride (0.6 g).
$^1$H-NMR (DMSO-d$_6$) δ 1.72-1.79 (1H, m), 1.98-2.06 (1H, m), 2.52-2.62 (2H, m), 3.10-3.15 (2H, m), 3.40-3.49 (4H, m), 3.74-3.80 (3H, m), 7.25-7.29 (3H, m), 7.52 (1H, d, J=1.3 Hz), 7.57 (1H, d, J=8.4 Hz), 8.27-8.32 (1H, m), 8.36 (2H, d, J=6.1 Hz).
MS (ESI) m/z: 426 [M+H].

Example 170

Synthesis of (2S)-N-{[4-(3,4-dichlorobenzyl)morpholin-2-yl]methyl}-(thieno[3,2-c]pyridin-4-ylthio)acetamide

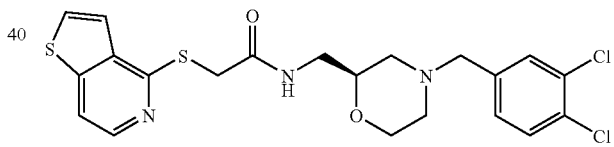

(170-1) Synthesis of 4-mercaptothieno[3,2-c]pyridine

By a similar method as in (166-2), the title compound (240 mg) was obtained as a brown solid from 4-chlorothieno[3,2-c]pyridine (0.5 g) and thiourea (350 mg).

(170-1) Synthesis of (2S)-N-{[4-(3,4-dichlorobenzyl)morpholin-2-yl]methyl}-(thieno[3,2-c]pyridin-4-ylthio)acetamide By a similar method as in (1-4), the title compound (250 mg) was obtained as a white amorphous solid from the resultant product (230 mg) of (170-1) and the resultant product (500 mg) of (1-2).
$^1$H-NMR (DMSO-d$_6$) δ 1.70-1.77 (1H, m), 1.90-1.98 (1H, m), 2.49-2.55 (1H, m), 2.58-2.63 (1H, m), 3.07-3.16 (2H, m), 3.36-3.46 (4H, m), 3.69-3.74 (1H, m), 3.98-4.02 (2H, m), 7.24-7.29 (1H, m), 7.49-7.53 (2H, m), 7.56 (1H, d, J=8.1 Hz), 7.84 (1H, d, J=5.5 Hz), 7.93 (1H, d, J=5.5 Hz), 8.18 (1H, dd, J=5.6, 5.6 Hz), 8.23 (1H, d, J=5.7 Hz).

MS (ESI) m/z: 482 [M+H].

Example 171

Synthesis of (2S)-N-{[4-(3,4-dichlorobenzyl)morpholin-2-yl]methyl}-(1-oxoindan-5-ylthio)acetamide

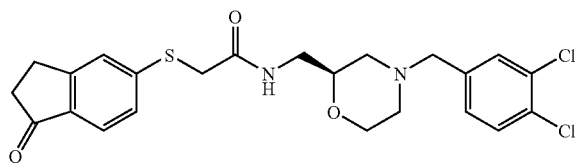

(171-1) Synthesis of 1-oxoindan-5-ylthioacetic acid

By a similar method as in (161-1), the title compound (100 mg) was obtained as a yellow solid from 5-bromo-1-indanone (450 mg) and thioglycol acid (140

(171-2) Synthesis of (2S)-N-{[4-(3,4-dichlorobenzyl)morpholin-2-yl]methyl}-(1-oxoindan-5-ylthio)-acetamide By a similar method as in Example 16, the title compound (90 mg) was obtained as a white amorphous solid from the resultant product (100 mg) of (171-1) and (2S)-2-aminomethyl-4-(3,4-dichlorobenzyl)morpholine dihydrochloride (160 mg).
$^1$H-NMR (DMSO-$d_6$) δ 1.72-1.79 (1H, m), 1.98-2.04 (1H, m), 2.51-2.63 (4H, m), 3.04 (2H, t, J=5.4 Hz), 3.11-3.15 (2H, m), 3.38-3.49 (4H, m), 3.72-3.80 (3H, m), 7.24-7.33 (2H, m), 7.46-7.59 (4H, m), 8.25-8.30 (1H, m).
MS (ESI) m/z: 479 [M+H].

Example 172

Synthesis of (2S)-N-{[4-(3,4-dichlorobenzyl)morpholin-2-yl]methyl}-(2-methoxycarbonylfuran-5-ylthio)acetamide

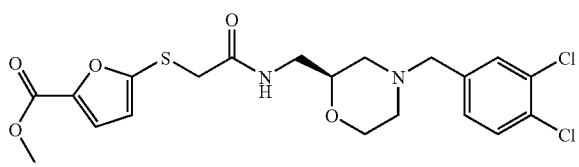

(172-1) Synthesis of 2-methoxycarbonylfuran-5-ylthioacetic acid

By a similar method as in (161-1), the title compound (750 mg) was obtained as a white solid from 5-bromo-2-methoxycarbonylfuran (820 mg) and thioglycol acid (300 μL).

(172-2) Synthesis of (2S)-N-{[4-(3,4-dichlorobenzyl)morpholin-2-yl]methyl}-(2-methoxycarbonylfuran-5-ylthio)acetamide By a similar method as in Example 16, the title compound (1.6 g) was obtained as a white amorphous solid from the resultant product (750 mg) of (172-1) and (2S)-2-aminomethyl-4-(3,4-dichlorobenzyl)morpholine dihydrochloride (1.2 g).
$^1$H-NMR (DMSO-$d_6$) δ 1.72-1.79 (1H, m), 1.99-2.06 (1H, m), 2.53-2.58 (1H, m), 2.59-2.64 (1H, m), 3.05-3.13 (2H, m), 3.39-3.49 (4H, m), 3.63 (2H, s), 3.73-3.80 (4H, m), 6.69 (1H, d, J=3.6H), 7.30 (1H, dd, J=1.3, 8.4 Hz), 7.32 (1H, d, J=3.6 Hz), 7.53-7.56 (1H, m), 7.58 (1H, d, J=8.4 Hz), 8.21 (1H, dd, J=5.7, 5.7 Hz).
MS (ESI) m/z: 473 [M+H].

Example 173

Synthesis of (2S)-N-{[4-(3,4-dichlorobenzyl)morpholin-2-yl]methyl}-(1-oxoindan-6-ylthio)acetamide

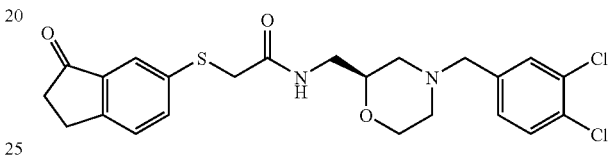

(173-1) Synthesis of 1-oxoindan-6-ylthioacetic acid

By a similar method as in (161-1), the title compound (90 mg) was obtained as a white solid from 6-bromo-1-indanone (420 mg) and thioglycol acid (140 μL).

(173-2) Synthesis of (2S)-N-{[4-(3,4-dichlorobenzyl)morpholin-2-yl]methyl}-(1-oxoindan-6-ylthio)acetamide By a similar method as in Example 16, the title compound (180 mg) was obtained as a white amorphous solid from the resultant product (90 mg) of (173-1) and (2S)-2-aminomethyl-4-(3,4-dichlorobenzyl)morpholine dihydrochloride (140 mg).
$^1$H-NMR (DMSO-$d_6$) δ 1.71-1.78 (1H, m), 1.97-2.05 (1H, m), 2.51-2.61 (2H, m), 2.62 (2H, t, J=5.8 Hz), 3.04 (2H, t, J=5.8 Hz), 3.07-3.12 (2H, m), 3.38-3.47 (4H, m), 3.69 (2H, s), 3.72-3.76 (1H, m), 7.27 (1H, dd, J=1.5, 8.3 Hz), 7.50-7.53 (2H, m), 7.54-7.58 (2H, m), 7.60-7.64 (1H, m), 8.18 (1H, dd, J=5.7, 5.7 Hz).
MS (ESI) m/z: 479 [M+H].

Example 174

Synthesis of (2S)-(3-acetyl-2-oxo-2H-chromen-6-ylthio)-N-{[4-(3,4-dichlorobenzyl)morpholin-2-yl]methyl}acetamide

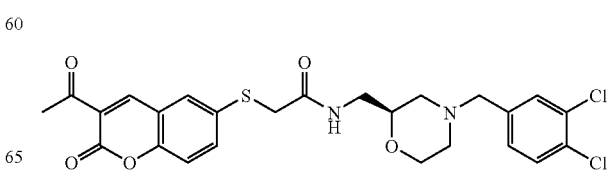

(174-1) Synthesis of 3-acetyl-2-oxo-2H-chromen-6-ylthioacetic acid

By a similar method as in (161-1), the title compound (300 mg) was obtained as a yellow solid from 6-bromo-3-acetyl-2H-chromen-2-one (520 mg) and thioglycol acid (140 μL).

(174-2) Synthesis of (2S)-(3-acetyl-2-oxo-2H-chromen-6-ylthio)-N-{[4-(3,4-dichlorobenzyl)morpholin-2-yl]methyl}acetamide By a similar method as in Example 16, the title compound (100 mg) was obtained as a yellow solid from the resultant product (300 mg) of (174-1) and (2S)-2-aminomethyl-4-(3,4-dichlorobenzyl)morpholine dihydrochloride (340 mg).
$^1$H-NMR (DMSO-d$_6$) δ 1.68-1.76 (1H, m), 1.94-2.02 (1H, m), 2.51-2.58 (5H, m), 3.08-3.12 (2H, m), 3.35-3.45 (4H, m), 3.68 (2H, s), 3.71-3.75 (1H, m), 7.25 (1H, dd, J=1.6, 8.3 Hz), 7.43 (1H, d, J=8.6 Hz), 7.49 (1H, d, J=1.6 Hz), 7.55 (1H, d, J=8.3 Hz), 7.72 (1H, dd, J=2.2, 8.6 Hz), 7.94 (1H, d, J=2.2 Hz), 8.18 (1H, dd, J=5.7, 5.7 Hz), 8.55 (1H, s).
MS (ESI) m/z: 535 [M+H].

Example 175

Synthesis of (2S)-N-{[4-(3,4-dichlorobenzyl)morpholin-2-yl]methyl}-{4-[bis(ethoxycarbonyl)methyl]pyrimidin-2-ylthio}acetamide

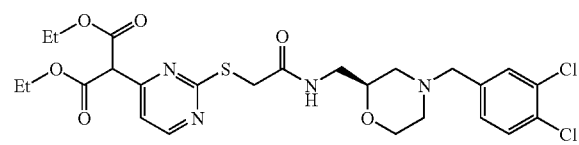

(175-1) Synthesis of 2-chloro-4-[bis(ethoxycarbonyl)methyl]pyrimidine

By a similar method as in (166-1), the title compound (1.3 g) was obtained as a yellow solid from 2,4-dichloropyrimidine (2 g) and diethyl malonate (480 mg).

(175-2) Synthesis of 4-[bis(ethoxycarbonyl)methyl]-2-mercaptopyrimidine

By a similar method as in (166-2), the title compound (510 mg) was obtained as a yellow solid from the resultant product (530 mg) of (175-1) and thiourea (150 mg).

(175-3) Synthesis of (2S)-N-{[4-(3,4-dichlorobenzyl)morpholin-2-yl]methyl}-{4-[bis(ethoxycarbonyl)methyl]pyrimidin-2-ylthio}acetamide By a similar method as in (1-4), the title compound (370 mg) was obtained as a white amorphous solid from the resultant product (210 mg) of (175-2) and the resultant product (300 mg) of (1-2).
$^1$H-NMR (DMSO-d$_6$) δ 1.14-1.24 (6H, m), 1.75-1.81 (1H, m), 1.97-2.06 (1H, m), 2.51-2.56 (1H, m), 2.62-2.67 (1H, m), 3.08-3.13 (2H, m), 3.40-3.49 (4H, m), 3.72-3.76 (1H, m), 3.81 (2H, s), 4.13-4.20 (4H, m), 5.14 (1H, s), 7.25-7.31 (2H, m), 7.53 (1H, d, J=1.8 Hz), 7.57 (1H, d, J=8.4 Hz), 8.11 (1H, dd, J=5.7, 5.7 Hz), 8.63 (1H, d, J=5.3 Hz).

MS (ESI) m/z: 585 [M+H].

Example 176

Synthesis of (2S)-N-{[4-(3,4-dichlorobenzyl)morpholin-2-yl]methyl}-(3-methoxycarbonyl-2-oxo-2H-chromen-6-ylthio)acetamide

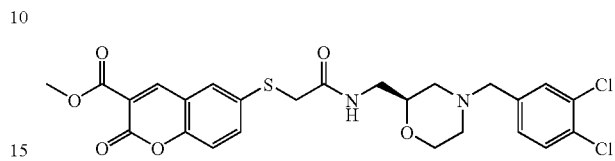

(176-1) Synthesis of 3-methoxycarbonyl-2-oxo-2H-chromen-6-ylthioacetic acid

By a similar method as in (161-1), the title compound (830 mg) was obtained as a yellow solid from 6-bromo-3-methoxycarbonyl-2H-chromen-2-one (1 g) and thioglycol acid (700 μL).

(176-2) Synthesis of (2S)-N-{[4-(3,4-dichlorobenzyl)morpholin-2-yl]methyl}-(3-methoxycarbonyl-2-oxo-2H-chromen-6-ylthio)acetamide By a similar method as in Example 16, the title compound (1.1 g) was obtained as a yellow solid from the resultant product (820 mg) of (176-1) and (2S)-2-aminomethyl-4-(3,4-dichlorobenzyl)morpholine dihydrochloride (970 mg).
$^1$H-NMR (DMSO-d$_6$) δ 1.68-1.73 (1H, m), 1.93-2.01 (1H, m), 2.51-2.58 (2H, m), 3.07-3.12 (2H, m), 3.35-3.45 (4H, m), 3.68 (2H, s), 3.71-3.75 (1H, m), 3.82 (3H, s), 7.25 (1H, dd, J=1.7, 8.0 Hz), 7.42 (1H, d, J=8.7 Hz), 7.49 (1H, d, J=1.7 Hz), 7.56 (1H, d, J=8.0 Hz), 7.73 (1H, dd, J=2.2, 8.7 Hz), 7.92 (1H, d, J=2.2 Hz), 8.22 (1H, dd, J=5.8, 5.8 Hz), 8.70 (1H, s).
MS (ESI) m/z: 551 [M+H].

Example 177

Synthesis of (2S)-N-{[4-(3,4-dichlorobenzyl)morpholin-2-yl]methyl}-(4-methoxycarbonylphenylsulfinyl)acetamide

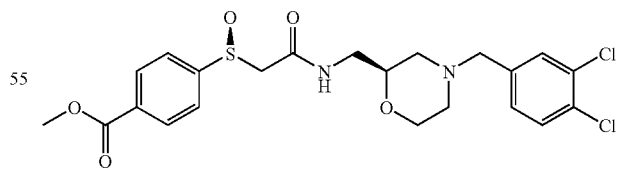

(177-1) Synthesis of 4-methoxycarbonylphenylthioacetic acid

By a similar method as in (161-1), the title compound (2.1 g) was obtained as a white solid from methyl 4-bromobenzoate (3 g) and thioglycol acid (1 mL).

(177-2) Synthesis of 4-methoxycarbonylphenylsulfinylacetic acid

The resultant product (300 mg) of (177-1) was dissolved in dichloromethane (10 mL), and m-chloroperbenzoic acid (290 mg) was added. The mixture was stirred at room temperature 2 hrs, and the solid precipitated in the reaction mixture was collected by filtration to give the title compound (230 mg) as a white solid.

(177-3) Synthesis of (2S)-N-{[4-(3,4-dichlorobenzyl)morpholin-2-yl]methyl}-(4-methoxycarbonylphenylsulfinyl)acetamide By a similar method as in Example 16, the title compound (410 mg) was obtained as a white amorphous solid from the resultant product (230 mg) of (177-2) and (2S)-2-aminomethyl-4-(3,4-dichlorobenzyl)morpholine dihydrochloride (330 mg).

$^1$H-NMR (DMSO-$d_6$) δ 1.72-1.82 (1H, m), 1.98-2.08 (1H, m), 2.52-2.58 (1H, m), 2.61-2.66 (1H, m), 3.02-3.17 (2H, m), 3.30-3.50 (4H, m), 3.72-3.83 (2H, m), 3.86-3.93 (4H, m), 7.27-7.33 (1H, m), 7.53-7.57 (1H, m), 7.59 (1H, d, J=8.3 Hz), 7.81 (2H, d, J=8.4 Hz), 8.13 (2H, d, J=8.4 Hz), 8.24-8.29 (1H, m).

MS (ESI) m/z: 499 [M+H].

Example 178

Synthesis of (2S)-(4-carboxyphenylsulfinyl)-N-{[4-(3,4-dichlorobenzyl)morpholin-2-yl]methyl}acetamide

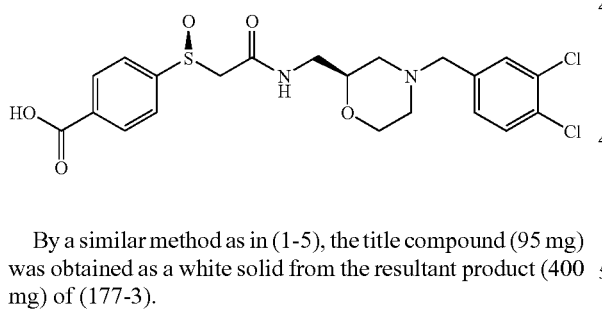

By a similar method as in (1-5), the title compound (95 mg) was obtained as a white solid from the resultant product (400 mg) of (177-3).

$^1$H-NMR (DMSO-$d_6$) δ 1.73-1.84 (1H, m), 2.02-2.10 (1H, m), 2.53-2.58 (1H, m), 2.62-2.67 (1H, m), 3.01-3.19 (2H, m), 3.42-3.49 (4H, m), 3.73-3.91 (3H, m), 7.31 (1H, d, J=8.1 Hz), 7.54 (1H, s), 7.58 (1H, d, J=8.1 Hz), 7.78 (2H, d, J=8.2 Hz), 8.10 (2H, d, J=8.2 Hz), 8.20-8.25 (1H, m), 13.21 (1H, brs).

MS (ESI) m/z: 485 [M+H].

Example 179

Synthesis of (2S)-N-{[4-(3,4-dichlorobenzyl)morpholin-2-yl]methyl}-(2-methoxycarbonylnaphthalen-6-ylthio)acetamide

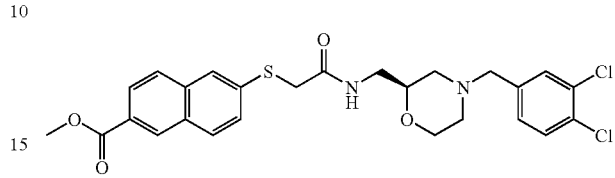

(179-1) Synthesis of 2-methoxycarbonylnaphthalen-6-ylthioacetic acid

By a similar method as in (161-1), the title compound (460 mg) was obtained as a white solid from methyl 6-bromo-2-naphtoate (1 g) and thioglycol acid (300 μL).

(179-2) Synthesis of (2S)-N-{[4-(3,4-dichlorobenzyl)morpholin-2-yl]methyl}-(2-methoxycarbonylnaphthalen-6-ylthio)acetamide By a similar method as in Example 16, the title compound (870 mg) was obtained as a white amorphous solid from the resultant product (460 mg) of (179-1) and (2S)-2-aminomethyl-4-(3,4-dichlorobenzyl)morpholine dihydrochloride (570 mg).

$^1$H-NMR (DMSO-$d_6$) δ 1.62-1.69 (1H, m), 1.83-1.92 (1H, m), 2.41-2.49 (2H, m), 3.09-3.20 (4H, m), 3.36-3.44 (2H, m), 3.68-3.73 (1H, m), 3.83-3.86 (2H, m), 3.89 (3H, s), 7.15 (1H, dd, J=1.1, 8.4 Hz), 7.37 (1H, d, J=1.1 Hz), 7.52 (1H, d, J=8.4 Hz), 7.53-7.57 (1H, m), 7.87-7.91 (2H, m), 7.93-7.98 (1H, m), 8.07 (1H, d, J=8.7 Hz), 8.32 (1H, dd, J=5.7, 5.7 Hz), 8.56 (1H, s).

MS (ESI) m/z: 533 [M+H].

Example 180

Synthesis of (2S)-(2-carboxynaphthalen-6-ylthio)-N-{[4-(3,4-dichlorobenzyl)morpholin-2-yl]methyl}acetamide

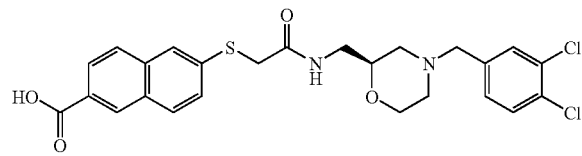

By a similar method as in (1-5), the title compound (430 mg) was obtained as a white solid from the resultant product (750 mg) of (179-2).

$^1$H-NMR (DMSO-$d_6$) δ 1.64-1.72 (1H, m), 1.86-1.95 (1H, m), 2.43-2.54 (2H, m), 3.10-3.16 (2H, m), 3.23 (2H, s), 3.36-3.45 (2H, m), 3.69-3.74 (1H, m), 3.78-3.85 (2H, m), 7.17 (1H, dd, J=1.3, 8.3 Hz), 7.41 (1H, d, J=1.3 Hz), 7.50-7.55 (2H, m), 7.84-7.88 (2H, m), 7.96 (1H, d, J=8.6 Hz), 8.03 (1H, d, J=8.7 Hz), 8.26 (1H, dd, J=5.8, 5.8 Hz), 8.54 (1H, s), 12.99 (1H, brs).

MS (ESI) m/z: 519 [M+H].

Example 181

Synthesis of (2S)-(2-carboxyfuran-5-ylthio)-N-{[4-(3,4-dichlorobenzyl)morpholin-2-yl]methyl}acetamide

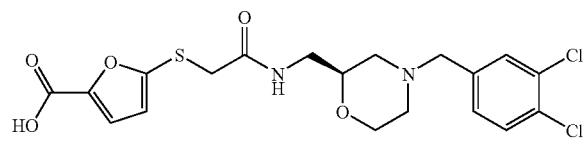

By a similar method as in (1-5), the title compound (210 mg) was obtained as a white solid from the resultant product (1.6 g) of (172-2).

$^1$H-NMR (DMSO-d$_6$) δ 1.77-1.84 (1H, m), 2.04-2.11 (1H, m), 2.55-2.60 (1H, m), 2.63-2.68 (1H, m), 3.08-3.12 (2H, m), 3.43-3.51 (4H, m), 3.60 (2H, s), 3.74-3.79 (1H, m), 6.65 (1H, d, J=3.2H), 7.19 (1H, d, J=3.2 Hz), 7.28-7.32 (1H, m), 7.53-7.59 (2H, m), 8.14-8.20 (1H, m).

MS (ESI) m/z: 459 [M+H].

Example 182

Synthesis of (2S)-(3-carboxy-2-oxo-2H-chromen-6-ylthio)-N-{[4-(3,4-dichlorobenzyl)morpholin-2-yl]methyl}acetamide

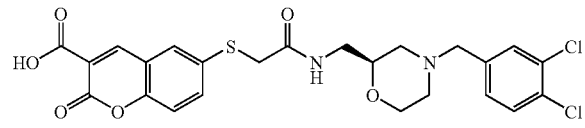

By a similar method as in (1-5), the title compound (270 mg) was obtained as a yellow amorphous solid from the resultant product (780 mg) of (176-2).

$^1$H-NMR (DMSO-d$_6$) δ 1.69-1.76 (1H, m), 1.95-2.04 (1H, m), 2.51-2.60 (2H, m), 3.07-3.12 (2H, m), 3.37-3.46 (4H, m), 3.66-3.76 (3H, m), 7.26 (1H, dd, J=1.4, 8.4 Hz), 7.40 (1H, d, J=8.7 Hz), 7.50 (1H, d, J=1.4 Hz), 7.55 (1H, d, J=8.4 Hz), 7.71 (1H, dd, J=2.2, 8.7 Hz), 7.90 (1H, d, J=2.2 Hz), 8.18 (1H, dd, J=5.7, 5.7 Hz), 8.64 (1H, s).

MS (ESI) m/z: 537 [M+H].

Example 183

Synthesis of (2S)-(3-carboxyphenylthio)-N-{[4-(3,4-dichlorobenzyl)morpholin-2-yl]methyl}acetamide

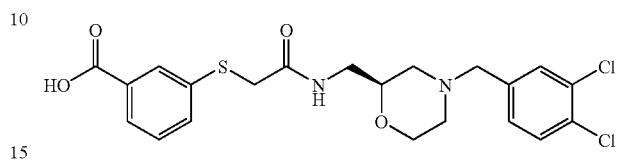

By a similar method as in (1-4), the title compound (3 g) was obtained as a white amorphous solid from 3-mercaptobenzoic acid (1.26 g) and the resultant product (3.2 g) of (1-2).

$^1$H-NMR (DMSO-d$_6$) δ 1.69-1.77 (1H, m), 1.98-2.04 (1H, m), 2.52-2.59 (2H, m), 3.08-3.13 (2H, m), 3.39-3.47 (4H, m), 3.68-3.76 (3H, m), 7.27 (1H, dd, J=1.2, 8.3 Hz), 7.42 (1H, t, J=7.8 Hz), 7.51 (1H, d, J=1.2 Hz), 7.55-7.60 (2H, m), 7.74 (1H, d, J=7.8 Hz), 7.86 (1H, s), 8.24 (1H, dd, J=5.8, 5.8 Hz).

MS (ESI) m/z: 469 [M+H].

Example 184

Synthesis of (2S)-(3-carbamoylphenylthio)-N-{[4-(3,4-dichlorobenzyl)morpholin-2-yl]methyl}acetamide

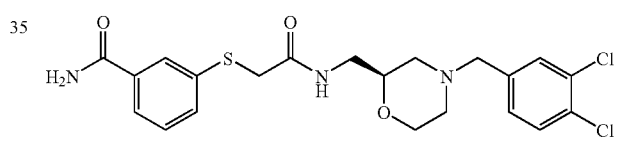

By a similar method as in Example 8, the title compound (200 mg) was obtained as a white amorphous solid from the resultant product (250 mg) of Example 183.

$^1$H-NMR (DMSO-d$_6$) δ 1.69-1.76 (1H, m), 1.96-2.04 (1H, m), 2.51-2.60 (2H, m), 3.08-3.13 (2H, m), 3.38-3.47 (4H, m), 3.69-3.76 (3H, m), 7.27 (1H, dd, J=1.5, 8.0 Hz), 7.34-7.42 (2H, m), 7.45-7.50 (1H, m), 7.52 (1H, d, J=1.5 Hz), 7.56 (1H, d, J=8.0 Hz), 7.64-7.70 (1H, m), 7.81 (1H, s), 7.96 (1H, brs), 8.15 (1H, dd, J=5.8, 5.8 Hz).

MS (ESI) m/z: 468 [M+H].

Example 185

Synthesis of (2S)-N-{[4-(3,4-dichlorobenzyl)morpholin-2-yl]methyl}-(3-methoxycarbonylmethylphenylthio)acetamide

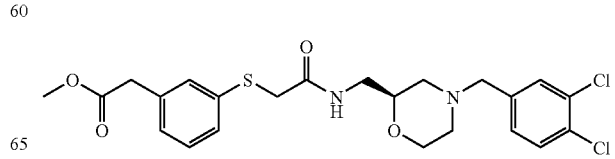

(185-1) Synthesis of 3-ethoxycarbonylmethylphenylthioacetic acid

By a similar method as in (161-1), the title compound (450 mg) was obtained as a colorless oil from ethyl 3-bromophenylacetate (1 g) and thioglycol acid (900 μL).

(185-2) Synthesis of (2S)-N-{[4-(3,4-dichlorobenzyl)morpholin-2-yl]methyl}-(3-ethoxycarbonylmethylphenylthio)acetamide By a similar method as in Example 16, the title compound (170 mg) was obtained as a white amorphous solid from the resultant product (450 mg) of (185-1) and (2S)-2-aminomethyl-4-(3,4-dichlorobenzyl)morpholine dihydrochloride (600 mg).

$^1$H-NMR (DMSO-$d_6$) δ 1.72-1.79 (1H, m), 1.98-2.06 (1H, m), 2.52-2.62 (2H, m), 3.08-3.13 (2H, m), 3.40-3.48 (4H, m), 3.60 (3H, s), 3.63 (2H, s), 3.64 (2H, s), 3.73-3.78 (1H, m), 7.05-7.10 (1H, m), 7.19-7.30 (4H, m), 7.52 (1H, d, J=1.6 Hz), 7.57 (1H, d, J=8.0 Hz), 8.15 (1H, dd, J=5.7, 5.7 Hz).

MS (ESI) m/z: 497 [M+H].

Example 186

Synthesis of (2S)-(3-carboxymethylphenylthio)-N-{[4-(3,4-dichlorobenzyl)morpholin-2-yl]methyl}acetamide

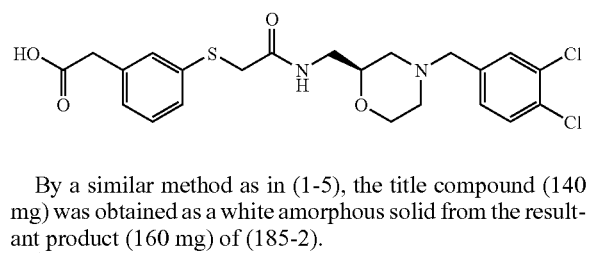

By a similar method as in (1-5), the title compound (140 mg) was obtained as a white amorphous solid from the resultant product (160 mg) of (185-2).

$^1$H-NMR (DMSO-$d_6$) δ 1.73-1.79 (1H, m), 1.99-2.06 (1H, m), 2.52-2.62 (2H, m), 3.09-3.13 (2H, m), 3.41-3.49 (4H, m), 3.53 (2H, s), 3.63 (2H, s), 3.74-3.78 (1H, m), 7.05-7.09 (1H, m), 7.19-7.30 (4H, m), 7.52 (1H, d, J=1.2 Hz), 7.57 (1H, d, J=8.3 Hz), 8.15 (1H, dd, J=5.6, 5.6 Hz).

MS (ESI) m/z: 483 [M+H].

Example 187

Synthesis of (2S)-N-{[4-(3-chloro-4-fluorobenzyl)morpholin-2-yl]methyl}-(4-hydroxypyrimidin-2-ylthio)acetamide

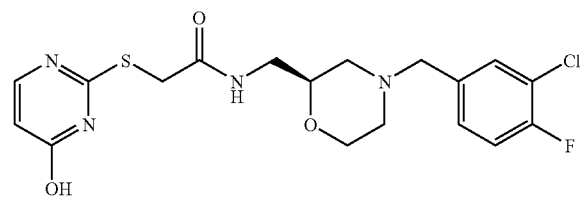

By a similar method as in (1-4), the title compound (80 mg) was obtained as a white solid from 2-mercaptouracil (135 mg) and the resultant product (400 mg) of (111-1).

$^1$H-NMR (DMSO-$d_6$) δ 1.75-1.82 (1H, m), 1.97-2.06 (1H, m), 2.51-2.57 (1H, m), 2.63-2.68 (1H, m), 3.09-3.14 (2H, m), 3.39-3.50 (4H, m), 3.73-3.77 (1H, m), 3.79-3.87 (2H, m), 6.12 (1H, brs), 7.27-7.41 (2H, m), 7.46-7.50 (1H, m), 7.82 (1H, brs), 8.15-8.22 (1H, m), 12.74 (1H, brs).

MS (ESI) m/z: 427 [M+H].

Example 188

Synthesis of (2S)-N-{[4-(3-chloro-4-fluorobenzyl)morpholin-2-yl]methyl}-(4-methoxycarbonylphenylthio)acetamide

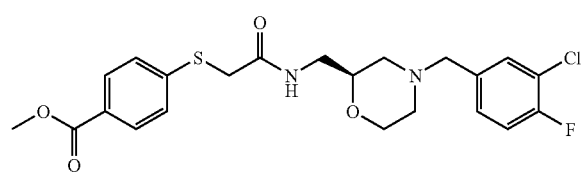

By a similar method as in Example 16, the title compound (640 mg) was obtained as a white amorphous solid from the resultant product (330 mg) of (177-1) and (2S)-2-aminomethyl-4-(3-chloro-4-fluorobenzyl)morpholine dihydrochloride (490 mg).

$^1$H-NMR (DMSO-$d_6$) δ 1.69-1.76 (1H, m), 1.95-2.03 (1H, m), 2.51-2.59 (2H, m), 3.09-3.14 (2H, m), 3.36 (2H, s), 3.39-3.48 (2H, m), 3.72-3.77 (3H, m), 3.83 (3H, s), 7.23-7.29 (1H, m), 7.34 (1H, dd, J=8.7, 9.1 Hz), 7.40-7.46 (3H, m), 7.83-7.87 (2H, m), 8.24 (1H, dd, J=5.8, 5.8 Hz).

MS (ESI) m/z: 467 [M+H].

Example 189

Synthesis of (2S)-(4-carboxyphenylthio)-N-{[4-(3-chloro-4-fluorobenzyl)morpholin-2-yl]methyl}acetamide

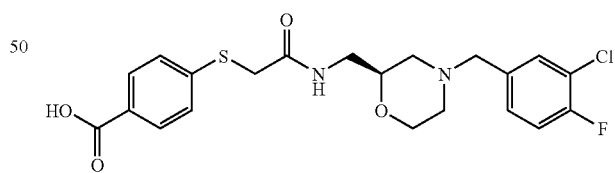

By a similar method as in (1-5), the title compound (340 mg) was obtained as a white amorphous solid from the resultant product (420 mg) of Example 188.

$^1$H-NMR (DMSO-$d_6$) δ 1.70-1.75 (1H, m), 1.96-2.02 (1H, m), 2.51-2.59 (2H, m), 3.10-3.14 (2H, m), 3.37 (2H, s), 3.43-3.47 (2H, m), 3.71-3.79 (3H, m), 7.24-7.29 (1H, m), 7.33 (1H, dd, J=8.7, 9.1 Hz), 7.40 (2H, d, J=8.5 Hz), 7.43-7.46 (1H, m), 7.83 (2H, d, J=8.5 Hz), 8.23 (1H, dd, J=5.7, 5.7 Hz), 12.85 (1H, brs).

MS (ESI) m/z: 453 [M+H].

Example 190

Synthesis of (2S)-(4-carbamoylphenylthio)-N-{[4-(3-chloro-4-fluorobenzyl)morpholin-2-yl]methyl}acetamide

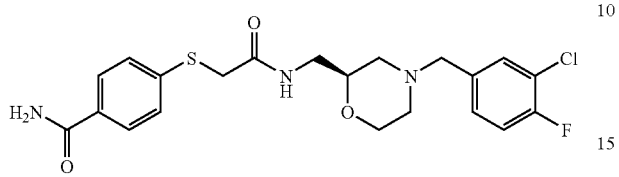

By a similar method as in Example 8, the title compound (130 mg) was obtained as a white solid from the resultant product (220 mg) of Example 189.
$^1$H-NMR (DMSO-$d_6$) δ 1.69-1.75 (1H, m), 1.96-2.03 (1H, m), 2.51-2.60 (2H, m), 3.10-3.14 (2H, m), 3.37 (2H, s), 3.40-3.47 (2H, m), 3.71-3.78 (3H, m), 7.24-7.38 (5H, m), 7.44-7.47 (1H, m), 7.80 (2H, d, J=8.2 Hz), 7.91 (1H, brs), 8.20 (1H, dd, J=5.7, 5.7 Hz).
MS (ESI) m/z: 452 [M+H].

Example 191

Synthesis of (2S)-(4-carboxyphenylsulfonyl)-N-{[4-(3,4-dichlorobenzyl)morpholin-2-yl]methyl}acetamide

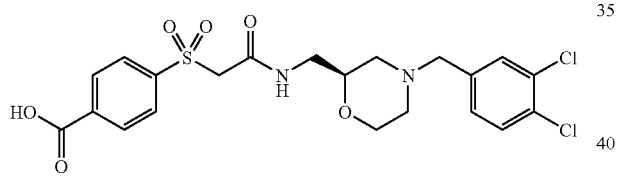

(191-1) Synthesis of 4-methoxycarbonylphenylsulfonylacetic acid

By a similar method as in (177-2), the title compound (310 mg) was obtained as a white amorphous solid from the resultant product (450 mg) of (177-1).

(191-2) Synthesis of (2S)-N-{[4-(3,4-dichlorobenzyl)morpholin-2-yl]methyl}-(4-methoxycarbonylphenylsulfonyl)acetamide By a similar method as in Example 16, the title compound (140 mg) was obtained as a white amorphous solid from the resultant product (310 mg) of (191-1) and (2S)-2-aminomethyl-4-(3,4-dichlorobenzyl)morpholine dihydrochloride (420 mg).

(191-3) Synthesis of (2S)-(4-carboxyphenylsulfonyl)-N-{[4-(3,4-dichlorobenzyl)morpholin-2-yl]methyl}acetamide By a similar method as in (1-5), the title compound (70 mg) was obtained as a white solid from the resultant product (140 mg) of (191-2).

$^1$H-NMR (DMSO-$d_6$) δ 1.73-1.78 (1H, m), 2.00-2.07 (1H, m), 2.54-2.62 (2H, m), 2.99-3.11 (2H, m), 3.40-3.50 (4H, m), 3.73-3.77 (1H, m), 4.36 (2H, s), 7.28-7.32 (1H, m), 7.53-7.59 (2H, m), 7.96 (2H, d, J=8.1 Hz), 8.15 (2H, d, J=8.1 Hz), 8.29 (1H, dd, J=5.4, 5.4 Hz).
MS (ESI) m/z: 501 [M+H].

Example 192

Synthesis of (2S)-N-{[4-(3,4-dichlorobenzyl)morpholin-2-yl]methyl}-(1-methyl-1H-imidazol-2-ylthio)acetamide

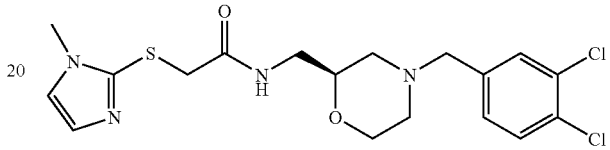

By a similar method as in (1-4), the title compound (250 mg) was obtained as a white amorphous solid from 2-mercapto-1-methyl-1H-imidazole (180 mg) and the resultant product (610 mg) of (1-2).
$^1$H-NMR (DMSO-$d_6$) δ 1.74-1.79 (1H, m), 2.00-2.07 (1H, m), 2.50-2.56 (1H, m), 2.62-2.65 (1H, m), 3.07-3.10 (2H, m), 3.40-3.49 (4H, m), 3.57 (3H, s), 3.62 (2H, s), 3.74-3.77 (1H, m), 6.90 (1H, s), 7.22 (1H, s), 7.30 (1H, dd, J=1.8, 8.2 Hz), 7.54 (1H, d, J=1.8 Hz), 7.57 (1H, d, J=8.2 Hz), 8.23 (1H, dd, J=5.6, 5.6 Hz).
MS (ESI) m/z: 429 [M+H].

Example 193

Synthesis of (2S)-N-{[4-(3,4-dichlorobenzyl)morpholin-2-yl]methyl}-[4-(2-methoxycarbonyl-2-propoxy)phenylthio]acetamide

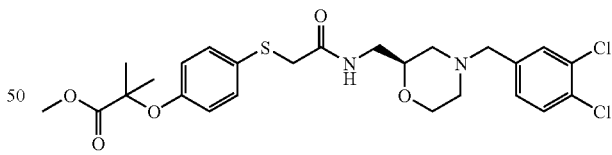

(193-1) Synthesis of methyl 2-(4-bromophenoxy)-2-methylpropionate 2-(4-Bromophenoxy)-2-methylpropionic acid (1 g) was dissolved in methanol (5 mL), a catalytic amount of thionyl chloride was added, and the mixture was stirred at room temperature for 7 hrs. Saturated brine was added to the reaction mixture, and the mixture was extracted with a mixed solvent of chloroform-methanol. The extract was dried over anhydrous sodium sulfate, and the solvent was evaporated under reduced pressure to give the title compound (920 mg) as a colorless oil.

(193-2) Synthesis of 4-(2-methoxycarbonyl-2-propoxy)phenylthioacetic acid

By a similar method as in (161-1), the title compound (430 mg) was obtained as a colorless oil from the resultant product (440 mg) of (193-1) and thioglycol acid (120 µL).

(193-3) Synthesis of (2S)-N-{[4-(3,4-dichlorobenzyl)morpholin-2-yl]methyl}-[4-(2-methoxycarbonyl-2-propoxy)phenylthio]acetamide By a similar method as in Example 16, the title compound (630 mg) was obtained as a white amorphous solid from the resultant product (420 mg) of (193-2) and (2S)-2-aminomethyl-4-(3,4-dichlorobenzyl)morpholine dihydrochloride (510 mg).

$^1$H-NMR (DMSO-d$_6$) δ 1.49 (6H, s), 1.72-1.78 (1H, m), 1.98-2.07 (1H, m), 2.52-2.62 (2H, m), 3.07-3.11 (2H, m), 3.38-3.48 (4H, m), 3.52 (2H, s), 3.68 (3H, s), 3.73-3.77 (1H, m), 6.73 (2H, d, J=8.6 Hz), 7.25-7.31 (3H, m), 7.53 (1H, d, J=1.3 Hz), 7.57 (1H, d, J=8.1 Hz), 8.05-8.09 (1H, m).

MS (ESI) m/z: 541 [M+H].

Example 194

Synthesis of (2S)-[4-(2-carboxy-2-propoxy)phenylthio]-N-{[4-(3,4-dichlorobenzyl)morpholin-2-yl]methyl}acetamide

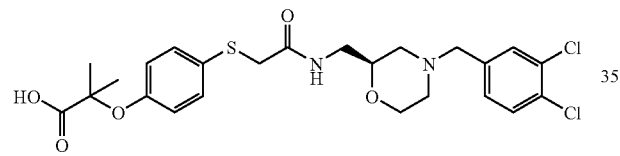

By a similar method as in (1-5), the title compound (360 mg) was obtained as a white amorphous solid from the resultant product (500 mg) of (193-3).

$^1$H-NMR (DMSO-d$_6$) δ 1.48 (6H, s), 1.74-1.79 (1H, m), 2.00-2.07 (1H, m), 2.54-2.57 (1H, m), 2.60-2.62 (1H, m), 3.07-3.10 (2H, m), 3.38-3.49 (4H, m), 3.51 (2H, s), 3.74-3.77 (1H, m), 6.77 (2H, d, J=8.9 Hz), 7.25-7.31 (3H, m), 7.53-7.58 (2H, m), 8.06 (1H, dd, J=5.7, 5.7 Hz).

MS (ESI) m/z: 527 [M+H]

Example 195

Synthesis of (2S)-[4-(2-carbamoyl-2-propoxy)phenylthio]-N-{[4-(3,4-dichlorobenzyl)morpholin-2-yl]methyl}acetamide

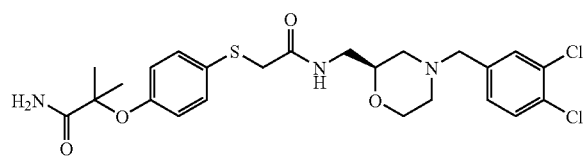

By a similar method as in Example 8, the title compound (180 mg) was obtained as a white amorphous solid from the resultant product (240 mg) of Example 194.

$^1$H-NMR (DMSO-d$_6$) δ 1.40 (6H, s), 1.75-1.80 (1H, m), 2.01-2.07 (1H, m), 2.54-2.57 (1H, m), 2.61-2.64 (1H, m), 3.07-3.13 (2H, m), 3.40-3.50 (4H, m), 3.53 (2H, s), 3.74-3.78 (1H, m), 6.82-6.86 (2H, m), 7.22-7.32 (4H, m), 7.47 (1H, brs), 7.52-7.59 (2H, m), 8.06-8.12 (1H, m).

MS (ESI) m/z: 526 [M+H].

Example 196

Synthesis of (2S)-N-{[4-(3-chloro-4-fluorobenzyl)morpholin-2-yl]methyl}-(6-oxo-1,6-dihydropyridazin-3-ylthio)acetamide

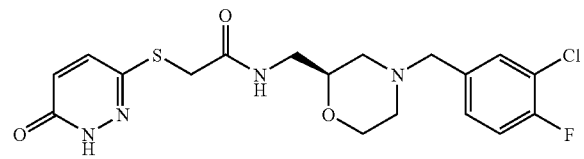

(196-1) Synthesis of 3-mercapto-6-methoxypyridazine

By a similar method as in (166-2), the title compound (1.4 g) was obtained as a yellow solid from 3-chloro-6-methoxypyridazine (2.1 g) and thiourea (1.7 g).

(196-2) Synthesis of ethyl 6-oxo-1,6-dihydropyridazin-3-ylthioacetate

By a similar method as in (1-4), a white powder was obtained from the resultant product (1.4 g) of (196-1) and ethyl bromoacetate (1.3 mL), and the powder was dissolved in a 1 mol/L hydrogen chloride-ethanol solution (20 mL), and the mixture was heated under reflux for 5 hrs. The solid precipitated in the reaction mixture was collected by filtration to give the title compound (950 mg) as a white solid.

(196-3) Synthesis of 6-oxo-1,6-dihydropyridazin-3-ylthioacetic acid

By a similar method as in (1-5), the title compound (280 mg) was obtained as a white solid from the resultant product (790 mg) of (196-2).

(196-4) Synthesis of (2S)-N-{[4-(3-chloro-4-fluorobenzyl)morpholin-2-yl]methyl}-(6-oxo-1,6-dihydropyridazin-3-ylthio)acetamide By a similar method as in Example 16, the title compound (260 mg) was obtained as a white solid from the resultant product (280 mg) of (196-3) and (2S)-2-aminomethyl-4-(3-chloro-4-fluorobenzyl)morpholine dihydrochloride (520 mg).

$^1$H-NMR (DMSO-d$_6$) δ 1.73-1.79 (1H, m), 1.97-2.04 (1H, m), 2.51-2.55 (1H, m), 2.61-2.64 (1H, m), 3.09-3.12 (2H, m), 3.40-3.48 (4H, m), 3.72-3.76 (3H, m), 6.81-6.84 (1H, m), 7.27-7.40 (3H, m), 7.47-7.50 (1H, m), 8.13 (1H, dd, J=5.8, 5.8 Hz), 12.97 (1H, s).

MS (ESI) m/z: 427 [M+H].

Example 197

Synthesis of (2S)-N-{[4-(3-chlorobenzyl)morpholin-2-yl]methyl}-(6-oxo-1,6-dihydropyridazin-3-ylthio)acetamide

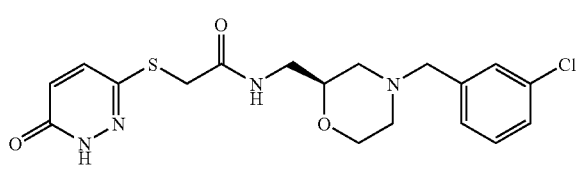

By a similar method as in (144-2), the title compound (150 mg) was obtained as a white solid from the resultant product (300 mg) of (196-2) and (2S)-2-aminomethyl-4-(3-chlorobenzyl)morpholine dihydrochloride (400 mg).

$^1$H-NMR (DMSO-$d_6$) δ 1.74-1.79 (1H, m), 1.98-2.04 (1H, m), 2.52-2.55 (1H, m), 2.62-2.65 (1H, m), 3.09-3.12 (2H, m), 3.40-3.49 (4H, m), 3.72-3.76 (3H, m), 6.82 (1H, d, J=9.8 Hz), 7.24-7.36 (4H, m), 7.39 (1H, d, J=9.8 Hz), 8.13 (1H, dd, J=5.7, 5.7 Hz), 12.96 (1H, s).

MS (ESI) m/z: 409 [M+H].

Example 198

Synthesis of (2S)-N-{[4-(3,4-difluorobenzyl)morpholin-2-yl]methyl}-(6-oxo-1,6-dihydropyridazin-3-ylthio)acetamide

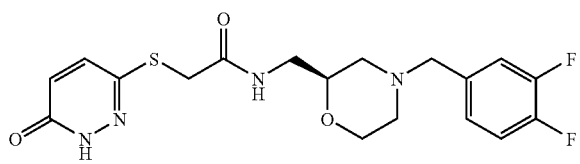

By a similar method as in (144-2), the title compound (110 mg) was obtained as a white solid from the resultant product (300 mg) of (196-2) and (2S)-2-aminomethyl-4-(3,4-difluorobenzyl)morpholine dihydrochloride (400 mg).

$^1$H-NMR (DMSO-$d_6$) δ 1.73-1.79 (1H, m), 1.98-2.04 (1H, m), 2.51-2.55 (1H, m), 2.61-2.64 (1H, m), 3.09-3.12 (2H, m), 3.41-3.49 (4H, m), 3.71-3.77 (3H, m), 6.82 (1H, d, J=9.8 Hz), 7.12-7.16 (1H, m), 7.29-7.41 (3H, m), 8.13 (1H, dd, J=5.5, 5.5 Hz), 12.97 (1H, s).

MS (ESI) m/z: 411 [M+H].

Example 199

Synthesis of (2S)-4-(4-carboxyphenylthio)-N-{[4-(3,4-dichlorobenzyl)morpholin-2-yl]methyl}butyramide

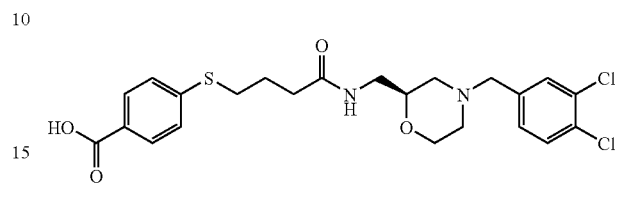

(199-1) Synthesis of (2S)-N-{[4-(3,4-dichlorobenzyl)morpholin-2-yl]methyl}-4-chlorobutyramide By a similar method as in (1-1), the title compound (1.4 g) was obtained as a colorless oil from (2S)-2-aminomethyl-4-(3,4-dichlorobenzyl)morpholine dihydrochloride (2 g) and 4-chlorobutyryl chloride (680 μL).

(199-2) Synthesis of (2S)-4-(4-carboxyphenylthio)-N-{[4-(3,4-dichlorobenzyl)morpholin-2-yl]methyl}butyramide By a similar method as in (1-4), the title compound (190 mg) was obtained as a white amorphous solid from 4-mercaptobenzoic acid (160 mg) and the resultant product (410 mg) of (199-1).

$^1$H-NMR (DMSO-$d_6$) δ 1.75-1.84 (3H, m), 2.02-2.09 (1H, m), 2.23 (2H, t, J=7.1 Hz), 2.54-2.58 (1H, m), 2.64-2.68 (1H, m), 3.01 (2H, t, J=7.1 Hz), 3.08-3.11 (2H, m), 3.44-3.51 (4H, m), 3.74-3.78 (1H, m), 7.28 (1H, dd, J=1.5, 8.1 Hz), 7.37 (2H, d, J=8.4 Hz), 7.52 (1H, d, J=1.5 Hz), 7.57 (1H, d, J=8.1 Hz), 7.85 (2H, d, J=8.4 Hz), 7.93 (1H, dd, J=5.7, 5.7 Hz).

MS (ESI) m/z: 497 [M+H].

Example 200

Synthesis of (2S)-3-(4-carboxyphenylthio)-N-{[4-(3,4-dichlorobenzyl)morpholin-2-yl]methyl}propionamide

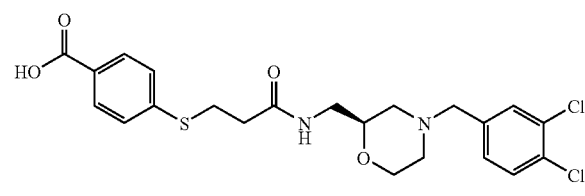

(200-1) Synthesis of (2S)-N-{[4-(3,4-dichlorobenzyl)morpholin-2-yl]methyl}-3-chloropropionamide By a similar method as in (1-1), the title compound (600 mg) was obtained as a colorless oil from (2S)-2-aminomethyl-4-(3,4-dichlorobenzyl)morpholine dihydrochloride (500 mg) and 3-chloropropionyl chloride (160 μL).

(200-2) Synthesis of (2S)-3-(4-carboxyphenylthio)-N-{[4-(3,4-dichlorobenzyl)morpholin-2-yl]methyl}propionamide By a similar method as in (1-4), the title compound (240 mg) was obtained as a white amorphous solid from 4-mercaptobenzoic acid (200 mg) and the resultant product (600 mg) of (200-1).

$^1$H-NMR (DMSO-$d_6$) δ 1.77-1.83 (1H, m), 2.02-2.09 (1H, m), 2.45 (2H, t, J=6.9 Hz), 2.55-2.58 (1H, m), 2.66-2.69 (1H, m), 3.08-3.11 (2H, m), 3.20 (2H, t, J=6.9 Hz), 3.42-3.52 (4H, m), 3.74-3.78 (1H, m), 7.28-7.31 (1H, m), 7.35 (2H, d, J=8.2 Hz), 7.53-7.58 (2H, m), 7.84 (2H, d, J=8.2 Hz), 8.01 (1H, dd, J=5.4, 5.4 Hz), 12.85 (1H, m)

MS (ESI) m/z: 483 [M+H].

Example 201

Synthesis of (2S)-N-{[4-(3,4-dichlorobenzyl)morpholin-2-yl]methyl}-4-(6-oxo-1,6-dihydropyridazin-3-ylthio)butyramide

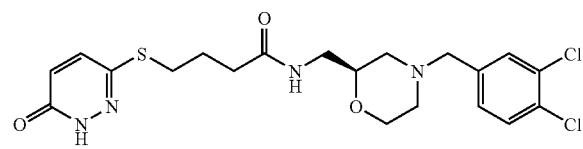

(201-1) Synthesis of methyl 4-(6-oxo-1,6-dihydropyridazin-3-ylthio)butyrate

By a similar method as in (196-2), the title compound (350 mg) was obtained as a yellow solid from the resultant product (300 mg) of (196-1) and methyl 4-chlorobutyrate.

(201-2) Synthesis of (2S)-N-{[4-(3,4-dichlorobenzyl)morpholin-2-yl]methyl}-4-(6-oxo-1,6-dihydropyridazin-3-ylthio)butyramide By a similar method as in (144-2), the title compound (460 mg) was obtained as a white amorphous solid from the resultant product (350 mg) of (201-1) and (2S)-2-aminomethyl-4-(3,4-dichlorobenzyl)morpholine dihydrochloride (340 mg).

$^1$H-NMR (DMSO-$d_6$) δ 1.74-1.83 (3H, m), 2.02-2.08 (1H, m), 2.18 (2H, t, J=7.2 Hz), 2.55-2.58 (1H, m), 2.63-2.66 (1H, m), 2.95 (2H, t, J=7.2 Hz), 3.05-3.09 (2H, m), 3.39-3.51 (4H, m), 3.74-3.78 (1H, m), 6.80 (1H, d, J=9.8 Hz), 7.28-7.33 (2H, m), 7.53 (1H, d, J=1.7 Hz), 7.57 (1H, d, J=8.1 Hz), 7.93 (1H, dd, J=5.8, 5.8 Hz), 12.95 (1H, s).

MS (ESI) m/z: 471 [M+H].

Example 202

Synthesis of (2S)-N-{[4-(3,4-dichlorobenzyl)morpholin-2-yl]methyl}-(2-ethoxycarbonylpyridin-5-ylthio)acetamide

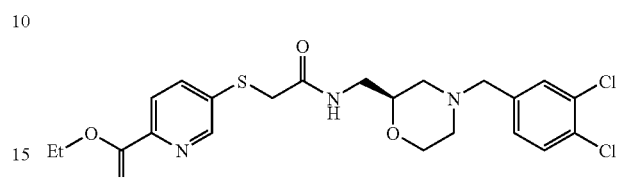

(202-1) Synthesis of 2-ethoxycarbonylpyridin-5-ylthioacetic acid

By a similar method as in (161-1), the title compound (600 mg) was obtained as a colorless oil from 5-bromo-2-ethoxycarbonylpyridine (970 mg) and thioglycol acid (350 μL).

(202-2) Synthesis of (2S)-N-{[4-(3,4-dichlorobenzyl)morpholin-2-yl]methyl}-(2-ethoxycarbonylpyridin-5-ylthio)acetamide By a similar method as in Example 16, the title compound (730 mg) was obtained as a white amorphous solid from the resultant product (600 mg) of (202-1) and (2S)-2-aminomethyl-4-(3,4-dichlorobenzyl)morpholine dihydrochloride (550 mg).

$^1$H-NMR (DMSO-$d_6$) δ 1.29 (3H, t, J=7.1 Hz), 1.70-1.75 (1H, m), 1.97-2.03 (1H, m), 2.52-2.59 (2H, m), 3.10-3.14 (2H, m), 3.39-3.48 (4H, m), 3.73-3.77 (1H, m), 3.83 (2H, s), 4.00 (2H, q, J=7.1 Hz), 7.27 (1H, dd, J=1.5, 8.4 Hz), 7.51 (1H, d, J=1.5 Hz), 7.57 (1H, d, J=8.4 Hz), 7.91 (1H, dd, J=2.2, 8.4 Hz), 7.96 (1H, d, J=8.4 Hz), 8.31 (1H, dd, J=5.7, 5.7 Hz), 8.62 (1H, d, J=2.2 Hz).

MS (ESI) m/z: 498 [M+H].

Example 203

Synthesis of (2S)-(2-carboxypyridin-5-ylthio)-N-{[4-(3,4-dichlorobenzyl)morpholin-2-yl]methyl}acetamide

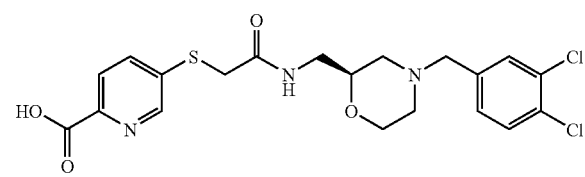

By a similar method as in (1-5), the title compound (460 mg) was obtained as a white solid from the resultant product (620 mg) of (202-2).

$^1$H-NMR (DMSO-$d_6$) δ 1.69-1.84 (1H, m), 1.95-2.10 (1H, m), 2.51-2.69 (2H, m), 3.10-3.15 (2H, m), 3.40-3.51 (4H, m), 3.75-3.86 (3H, m), 7.28-7.31 (1H, m), 7.53-7.60 (2H, m), 7.90 (1H, dd, J=2.2, 8.1 Hz), 7.94 (1H, d, J=8.1 Hz), 8.30-8.34 (1H, m), 8.60 (1H, d, J=2.2 Hz).

Example 204

Synthesis of (2S)-(2-carbamoylpyridin-5-ylthio)-N-{[4-(3,4-dichlorobenzyl)morpholin-2-yl]methyl}acetamide

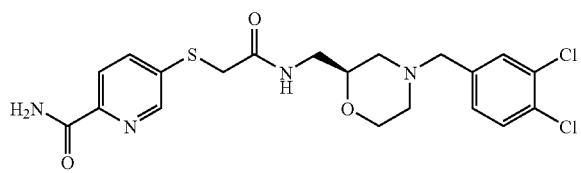

By a similar method as in Example 8, the title compound (230 mg) was obtained as a white amorphous solid from the resultant product (270 mg) of Example 203.

$^1$H-NMR (DMSO-$d_6$) δ 1.69-1.74 (1H, m), 1.97-2.04 (1H, m), 2.52-2.60 (2H, m), 3.10-3.13 (2H, m), 3.39-3.47 (4H, m), 3.74-3.83 (3H, m), 7.27 (1H, dd, J=1.6, 8.4 Hz), 7.52 (1H, d, J=1.6 Hz), 7.57 (1H, d, J=8.4 Hz), 7.61 (1H, brs), 7.91-7.96 (2H, m), 8.04 (1H, brs), 8.27 (1H, dd, J=5.7, 5.7 Hz), 8.54 (1H, s).

MS (ESI) m/z: 469 [M+H].

Example 205

Synthesis of (2S)-N-{[4-(3,4-dichlorobenzyl)morpholin-2-yl]methyl}-(3-ethoxycarbonylpyridin-5-ylthio)acetamide

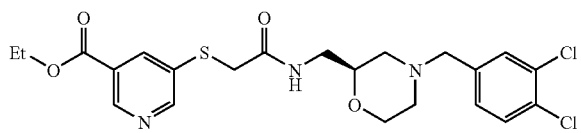

(205-1) Synthesis of 3-ethoxycarbonylpyridin-5-ylthioacetic acid

By a similar method as in (161-1), the title compound (580 mg) was obtained as a colorless oil from 5-bromo-3-ethoxycarbonylpyridine (670 mg) and thioglycol acid (300 μL).

(205-2) Synthesis of (2S)-N-{[4-(3,4-dichlorobenzyl)morpholin-2-yl]methyl}-(3-ethoxycarbonylpyridin-5-ylthio)acetamide By a similar method as in Example 16, the title compound (480 mg) was obtained as a white amorphous solid from the resultant product (260 mg) of (205-1) and (2S)-2-aminomethyl-4-(3,4-dichlorobenzyl)morpholine dihydrochloride (350 mg).

$^1$H-NMR (DMSO-$d_6$) δ 1.32 (3H, t, J=7.1 Hz), 1.70-1.75 (1H, m), 1.97-2.04 (1H, m), 2.52-2.59 (2H, m), 3.08-3.11 (2H, m), 3.39-3.47 (4H, m), 3.72-3.77 (3H, m), 4.34 (2H, q, J=7.1 Hz), 7.27 (1H, dd, J=1.5, 8.3 Hz), 7.51 (1H, d, J=1.5 Hz), 7.56 (1H, d, J=8.3 Hz), 8.22-8.28 (2H, m), 8.77 (1H, d, J=2.3 Hz), 8.88 (1H, d, J=1.8 Hz).

MS (ESI) m/z: 470 [M+H].

Example 206

Synthesis of (2S)-(3-carboxypyridin-5-ylthio)-N-{[4-(3,4-dichlorobenzyl)morpholin-2-yl]methyl}acetamide

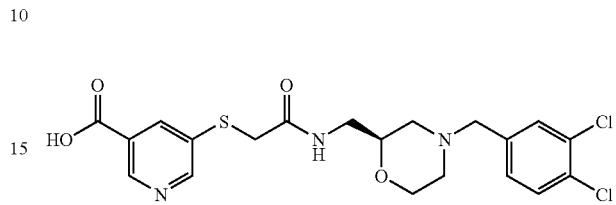

By a similar method as in (1-5), the title compound (240 mg) was obtained as a white amorphous solid from the resultant product (410 mg) of (205-2).

$^1$H-NMR (DMSO-$d_6$) δ 1.70-1.76 (1H, m), 1.98-2.05 (1H, m), 2.52-2.60 (2H, m), 3.08-3.12 (2H, m), 3.38-3.47 (4H, m), 3.72-3.77 (3H, m), 7.28 (1H, dd, J=1.8, 8.4 Hz), 7.52 (1H, d, J=1.8 Hz), 7.56 (1H, d, J=8.4 Hz), 8.21-8.22 (1H, m), 8.25 (1H, dd, J=5.8, 5.8 Hz), 8.73 (1H, d, J=2.2 Hz), 8.86 (1H, d, J=1.6 Hz).

MS (ESI) m/z: 470 [M+H].

Example 207

Synthesis of (2S)-(3-carbamoylpyridin-5-ylthio)-N-{[4-(3,4-dichlorobenzyl)morpholin-2-yl]methyl}acetamide

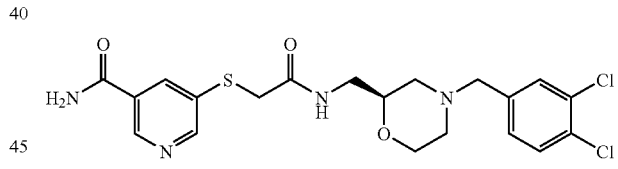

By a similar method as in Example 8, the title compound (150 mg) was obtained as a white amorphous solid from the resultant product (180 mg) of Example 206.

$^1$H-NMR (DMSO-$d_6$) δ 1.69-1.75 (1H, m), 1.97-2.04 (1H, m), 2.51-2.60 (2H, m), 3.08-3.12 (2H, m), 3.37-3.47 (4H, m), 3.71-3.79 (3H, m), 7.28 (1H, dd, J=1.5, 8.2 Hz), 7.53 (1H, d, J=1.5 Hz), 7.57 (1H, d, J=8.2 Hz), 7.66 (1H, brs), 8.16 (1H, brs), 8.18-8.20 (1H, m), 8.22 (1H, dd, J=5.7, 5.7 Hz), 8.65 (1H, d, J=2.2 Hz), 8.33 (1H, d, J=1.5 Hz).

MS (ESI) m/z: 469 [M+H].

Example 208

Synthesis of (2S)-(E)-N-{[4-(3,4-dichlorobenzyl)morpholin-2-yl]methyl}-[5-(2-carboxyethen-1-yl)pyridin-2-ylthio]acetamide

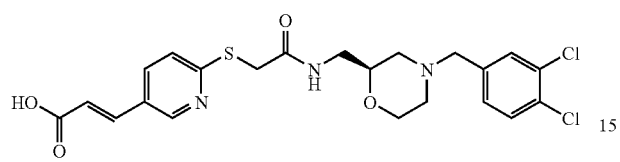

(208-1) Synthesis of methyl (E)-5-(2-tertiary butoxycarbonylethen-1-yl)pyridin-2-ylthioacetate By a similar method as in (1-4), the title compound (600 mg) was obtained as a white amorphous solid from (E)-2-chloro-5-(2-tertiary butoxycarbonylethen-1-yl)pyridine (800 mg) and methyl thioglycolate (290 μL).

(208-2) Synthesis of (2S)-(E)-N-{[4-(3,4-dichlorobenzyl)morpholin-2-yl]methyl}-[5-(2-carboxyethen-1-yl)pyridin-2-ylthio]acetamide By a similar method as in (144-2), a white amorphous solid was obtained from the resultant product (440 mg) of (208-1) and (2S)-2-aminomethyl-4-(3,4-dichlorobenzyl)morpholine dihydrochloride (420 mg). The solid was dissolved in trifluoroacetic acid (3 mL) and the mixture was stirred for 1 hr. The solvent was evaporated, and the obtained residue was purified by silica gel column chromatography using a mixed solvent of chloroform and methanol as an eluent. The solvent was evaporated from the eluent to give the title compound (310 mg) as a white amorphous solid.

$^1$H-NMR (DMSO-d$_6$) δ 1.70-1.82 (1H, m), 1.93-2.10 (1H, m), 2.51-2.70 (2H, m), 3.10-3.20 (2H, m), 3.40-3.60 (4H, m), 3.75-3.92 (3H, m), 6.60 (1H, d, J=16.2 Hz), 7.30-7.36 (1H, m), 7.38 (1H, d, J=8.4 Hz), 7.58 (1H, d, J=16.2 Hz), 7.59-7.63 (2H, m), 8.03 (1H, dd, J=2.0, 8.4 Hz), 8.17-8.26 (1H, m), 8.64 (1H, d, J=2.0 Hz), 12.44 (1H, brs).
MS (ESI) m/z: 496 [M+H].

Example 209

Synthesis of (2S)-(3-chloropyridazin-6-ylthio)-N-{[4-(3,4-dichlorobenzyl)morpholin-2-yl]methyl}acetamide

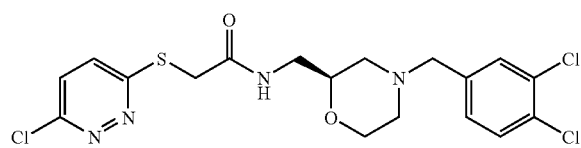

By a similar method as in (144-2), the title compound (220 mg) was obtained as a white solid from methyl 3-chloropyridazin-6-ylthioacetate (219 mg).

$^1$H-NMR (DMSO-d$_6$) δ 1.77-1.82 (1H, m), 1.99-2.06 (1H, m), 2.52-2.55 (1H, m), 2.65-2.68 (1H, m), 3.11-3.14 (2H, m), 3.45-3.50 (4H, m), 3.73-3.76 (1H, m), 3.98 (2H, s), 7.28-7.30 (1H, m), 7.53 (1H, s), 7.56 (1H, d, J=8.0 Hz), 7.74 (1H, d, J=9.3 Hz), 7.80 (1H, d, J=9.3 Hz), 8.26 (1H, dd, J=5.7, 5.7 Hz).
MS (ESI) m/z: 461 [M+H].

Example 210

Synthesis of (2S)-N-{[4-(3,4-dichlorobenzyl)morpholin-2-yl]methyl}-[3-(methoxycarbonyl)methylthiopyridazin-6-ylthio]acetamide

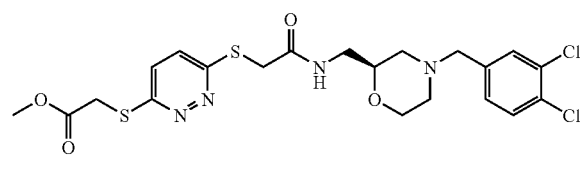

By a similar method as in (1-4), the title compound (54 mg) was obtained as a yellow oil from the resultant product (462 mg) of Example 209 and methyl thioglycolate (91 μL).

$^1$H-NMR (DMSO-d$_6$) δ 1.75-1.80 (1H, m), 1.99-2.04 (1H, m), 2.53-2.55 (1H, m), 2.62-2.65 (1H, m), 3.10-3.13 (2H, m), 3.43-3.48 (4H, m), 3.64 (3H, s), 3.73-3.76 (1H, m), 3.96 (2H, s), 4.15 (2H, s), 7.28-7.30 (1H, m), 7.53-7.59 (4H, m), 8.24-8.27 (1H, m).
MS (ESI) m/z: 531 [M+H].

Example 211

Synthesis of (2S)-N-{[4-(3,4-dichlorobenzyl)morpholin-2-yl]methyl}-(3-methoxypyridazin-6-ylthio)acetamide

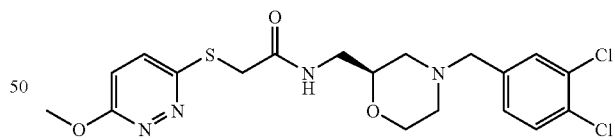

By a similar method as in (144-2), the title compound (109 mg) was obtained as a brown oil from methyl 3-methoxypyridazin-6-ylthioacetate (214 mg) and (2S)-2-aminomethyl-4-(3,4-dichlorobenzyl)morpholine dihydrochloride (348 mg).

$^1$H-NMR (DMSO-d$_6$) δ 1.75-1.81 (1H, m), 1.99-2.04 (1H, m), 2.52-2.55 (1H, m), 2.62-2.65 (1H, m), 3.11-3.14 (2H, m), 3.44-3.48 (4H, m), 3.73-3.76 (1H, m), 3.91 (2H, s), 3.95 (3H, s), 7.13 (1H, d, J=9.0 Hz), 7.27-7.29 (1H, m), 7.52 (1H, d, J=1.6 Hz), 7.59 (2H, t, J=9.4 Hz), 8.19 (1H, dd, J=5.8, 5.8 Hz).

MS (ESI) m/z: 457 [M+H].

Example 212

Synthesis of (2S)-(3-acetaminopyridazin-6-ylthio)-N-{[4-(3,4-dichlorobenzyl)morpholin-2-yl]methyl}acetamide

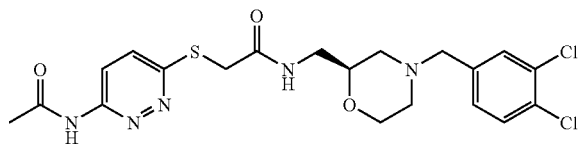

By a similar method as in (144-2), the title compound (55 mg) was obtained as a brown solid from methyl 3-acetaminopyridazin-6-ylthioacetate (483 mg) and (2S)-2-aminomethyl-4-(3,4-dichlorobenzyl)morpholine dihydrochloride (696 mg).

$^1$H-NMR (DMSO-d$_6$) δ 1.73-1.78 (1H, m), 2.00-2.02 (1H, m), 2.11 (3H, s), 2.50-2.63 (2H, m), 3.12 (2H, brs), 3.37-3.43 (4H, m), 3.72-3.75 (1H, m), 3.94 (2H, s), 7.27-7.29 (1H, m), 7.52-7.66 (3H, m), 8.15-8.20 (2H, m), 10.99 (1H, s).

MS (ESI) m/z: 484 [M+H].

Example 213

Synthesis of (2S)-(2-chloropyrazin-3-ylthio)-N-{[4-(3,4-dichlorobenzyl)morpholin-2-yl]methyl}acetamide

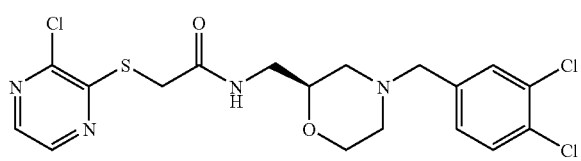

By a similar method as in (144-2), the title compound (170 mg) was obtained as a pale-yellow amorphous solid from methyl 2-chloropyrazin-3-ylthioacetate (981 mg) and (2S)-2-aminomethyl-4-(3,4-dichlorobenzyl)morpholine dihydrochloride (1.57 g).

$^1$H-NMR (DMSO-d$_6$) δ 1.76-1.81 (1H, m), 2.00-2.07 (1H, m), 2.50-2.57 (1H, m), 2.63-2.66 (1H, m), 3.09-3.13 (2H, m), 3.31-49 (4H, m), 3.74-3.77 (1H, m), 3.91 (2H, s), 7.28-7.31 (1H, m), 7.54-7.59 (2H, m), 8.20-8.23 (2H, m), 8.45 (1H, d, J=2.4 Hz).

MS (ESI) m/z: 461 [M+H].

Example 214

Synthesis of (2S)-N-{[4-(3,4-dichlorobenzyl)morpholin-2-yl]methyl}-(6-oxo-1,6-dihydropyridazin-3-ylthio)acetamide

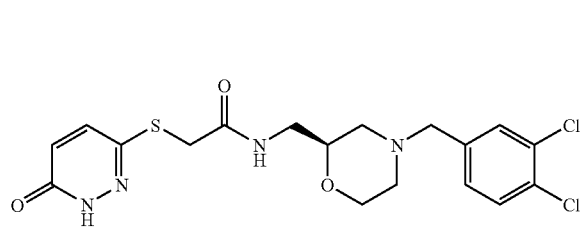

By a similar method as in (144-2), the title compound (108 mg) was obtained as a brown solid from methyl 6-oxo-1,6-dihydropyridazin-3-ylthioacetate (203 mg) and (2S)-2-aminomethyl-4-(3,4-dichlorobenzyl)morpholine dihydrochloride (348 mg).

$^1$H-NMR (DMSO-d$_6$) δ 1.75-1.80 (1H, m), 2.00-2.05 (1H, m), 2.50-2.65 (2H, m), 3.11 (2H, brs), 3.45 (4H, brs), 3.72 (3H, brs), 6.81-6.83 (1H, m), 7.29-7.31 (1H, m), 7.37-7.40 (1H, m), 7.54-7.59 (2H, m), 8.13 (1H, brs), 12.97 (1H, brs).

MS (ESI) m/z: 443 [M+H].

Example 215

Synthesis of (2S)-N-{[4-(3,4-dichlorobenzyl)morpholin-2-yl]methyl}-(pyrazin-2-ylthio)acetamide

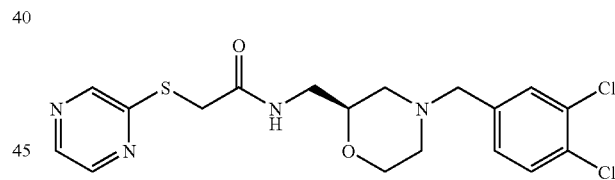

By a similar method as in (144-2), the title compound (1.0 g) was obtained as a white solid from methylpyrazin-2-ylthioacetate (829 mg) and (2S)-2-aminomethyl-4-(3,4-dichlorobenzyl)morpholine dihydrochloride (1.57 g).

$^1$H-NMR (DMSO-d$_6$) δ 1.74-1.80 (1H, m), 2.02-2.03 (1H, m), 2.54-2.56 (1H, m), 2.61-2.64 (1H, m), 3.10-3.13 (2H, m), 3.45-3.48 (4H, m), 3.74-3.76 (1H, m), 3.88 (2H, s), 7.28-7.30 (1H, m), 7.53 (1H, s), 7.58 (1H, d, J=8.0 Hz), 8.20 (1H, brs), 8.33 (1H, s), 8.42 (1H, s), 8.62 (1H, s).

MS (ESI) m/z: 427 [M+H].

Example 216

Synthesis of (2S)-N-{[4-(3,4-dichlorobenzyl)morpholin-2-yl]methyl}-(3,6-dimethylpyrazin-2-ylthio)acetamide

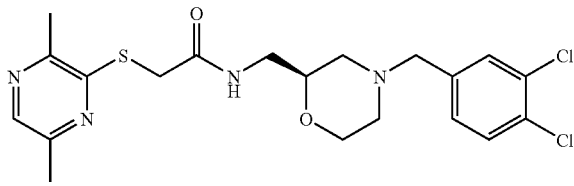

By a similar method as in (144-2), the title compound (330 mg) was obtained as a white solid from methyl 3,6-dimethylpyrazin-2-ylthioacetate (488 mg) and (2S)-2-aminomethyl-4-(3,4-dichlorobenzyl)morpholine dihydrochloride (800 mg).

$^1$H-NMR (DMSO-$d_6$) δ 1.73-1.78 (1H, m), 1.95-2.02 (1H, m), 2.38 (3H, s), 2.40 (3H, s), 2.49-2.55 (1H, m), 2.60-2.63 (1H, m), 3.10-3.13 (2H, m), 3.41-3.48 (4H, m), 3.72-3.75 (1H, m), 3.85-3.90 (2H, m), 7.27-7.29 (1H, m), 7.52 (1H, d, J=1.7 Hz), 7.57 (1H, d, J=8.4 Hz), 8.09 (1H, s), 8.12 (1H, dd, J=5.8, 5.8 Hz).

MS (ESI) m/z: 455 [M+H].

Example 217

Synthesis of (2S)-N-{[4-(3,4-dichlorobenzyl)morpholin-2-yl]methyl}-(6-methylpyridazin-3-ylthio)acetamide

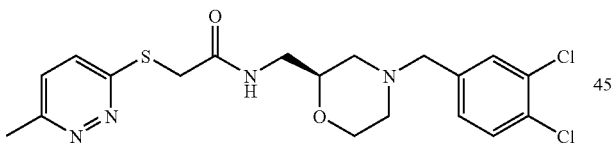

(217-1) Synthesis of 3-chloro-6-di-(tertiary butoxycarbonyl)methylpyridazine

Sodium hydride (60%, 333 mg) was suspended in dioxane (20 mL), di(tert-butyl)malonate (1.13 mL) was added, and the mixture was stirred at room temperature for 30 min. 3,6-Dichloropyridazine (0.75 g) was added to the reaction mixture and the mixture was heated under reflux for 1 hr. The reaction mixture was poured into water, and the mixture was extracted with ethyl acetate. The extract was washed with a saturated aqueous sodium hydrogen carbonate solution and saturated brine, dried over anhydrous sodium sulfate, and the solvent was evaporated under reduced pressure. The obtained residue was purified by silica gel column chromatography using a mixed solvent of ethyl acetate and hexane as an eluent. The solvent was evaporated from the eluent to give the title compound (1.44 g) as a yellow solid.

(217-2) Synthesis of methyl 6-di-(tertiary butoxycarbonyl)methylpyridazin-3-ylthioacetate By a similar method as in (1-4), the title compound (1.64 g) was obtained as a yellow oil from the resultant product (1.82 g) of (217-1) and methyl thioglycolate (499 μL).

(217-3) Synthesis of (2S)-[6-di-(tertiary butoxycarbonyl)methylpyridazin-3-ylthio]-N-{[4-(3,4-dichlorobenzyl)morpholin-2-yl]methyl}acetamide By a similar method as in (144-2), the title compound (940 mg) was obtained as a red-brown oil from the resultant product (1.21 g) of (217-2) and (2S)-2-aminomethyl-4-(3,4-dichlorobenzyl)morpholine dihydrochloride (1.04 g).

(217-4) Synthesis of (2S)-N-{[4-(3,4-dichlorobenzyl)morpholin-2-yl]methyl}-(6-methylpyridazin-3-ylthio)acetamide The resultant product (940 mg) of (217-3) was dissolved in trifluoroacetic acid (6 mL), and the mixture was stirred at room temperature for 1 hr. The reaction mixture was adjusted to pH=4 with a 1 mol/L aqueous sodium hydroxide solution. Saturated brine was added to the obtained solution, and the mixture was extracted with a mixed solvent of chloroform-methanol. The extract was dried over anhydrous sodium sulfate, and the solvent was evaporated under reduced pressure. The obtained residue was purified by silica gel column chromatography using a mixed solvent of chloroform and methanol as an eluent. The solvent was evaporated from the eluent to give the title compound (265 mg) as a white solid.

$^1$H-NMR (DMSO-$d_6$) δ 1.79-1.82 (1H, m), 1.99-2.03 (1H, m), 2.52-2.56 (4H, m), 2.68-2.70 (1H, m), 3.12-3.15 (2H, m), 3.41-3.48 (4H, m), 3.73-3.76 (1H, m), 3.95 (2H, s), 7.28 (1H, d, J=7.9 Hz), 7.41 (1H, d, J=8.8 Hz), 7.52-7.58 (3H, m), 8.23 (1H, dd, J=5.6, 5.6 Hz).

MS (ESI) m/z: 441 [M+H].

Example 218

Synthesis of (2S)-N-{[4-(3,4-dichlorobenzyl)morpholin-2-yl]methyl}-(3-methoxycarbonylpyridazin-6-ylthio)acetamide

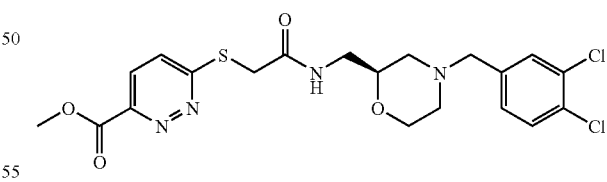

By a similar method as in Example 16, the title compound (388 mg) was obtained as a white solid from 3-methoxycarbonylpyridazin-6-ylthioacetic acid (799 mg) and (2S)-2-aminomethyl-4-(3,4-dichlorobenzyl)morpholine dihydrochloride (1.22 g).

$^1$H-NMR (DMSO-$d_6$) δ 1.77-1.82 (1H, m), 1.98-2.05 (1H, m), 2.49-2.54 (1H, m), 2.66-2.69 (1H, m), 3.12-3.15 (2H, m), 3.45-3.51 (4H, m), 3.73-3.76 (1H, m), 3.88 (3H, s), 4.07 (2H, s), 7.27-7.29 (1H, m), 7.51 (1H, s), 7.57 (1H, d, J=8.0 Hz), 7.87 (1H, d, J=9.0 Hz), 8.00 (1H, d, J=9.0 Hz), 8.30 (1H, dd, J=5.7, 5.7 Hz).

MS (ESI) m/z: 485 [M+H].

Example 219

Synthesis of (2S)-(3-carboxypyridazin-6-ylthio)-N-{[4-(3,4-dichlorobenzyl)morpholin-2-yl]methyl}acetamide

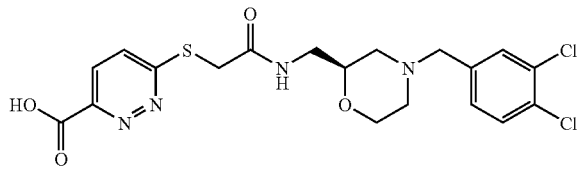

By a similar method as in (1-5), the title compound (164 mg) was obtained as a white solid from the resultant product (270 mg) of Example 218.

$^1$H-NMR (DMSO-$d_6$) δ 1.81-1.87 (1H, m), 2.04-2.10 (1H, m), 2.55-2.58 (1H, m), 2.70-2.73 (1H, m), 3.10-3.18 (2H, m), 3.43-3.55 (4H, m), 3.74-3.77 (1H, m), 4.06 (2H, s), 7.28-7.30 (1H, m), 7.53 (1H, d, J=1.3 Hz), 7.57 (1H, d, J=8.2 Hz), 7.83 (1H, d, J=9.0 Hz), 7.97 (1H, d, J=9.0 Hz), 8.29 (1H, dd, J=5.6, 5.6 Hz).

MS (ESI) m/z: 471 [M+H].

Example 220

Synthesis of (2S)-(3-carbamoylpyridazin-6-ylthio)-N-{[4-(3,4-dichlorobenzyl)morpholin-2-yl]methyl}acetamide

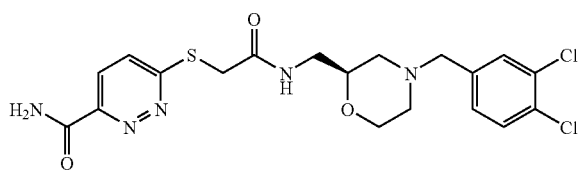

By a similar method as in Example 16, the title compound (46 mg) was obtained as a pale-yellow solid from the resultant product (67 mg) of Example 219 and ammonium chloride (46 mg).

$^1$H-NMR (DMSO-$d_6$) δ 1.74-1.80 (1H, m), 1.98-2.04 (1H, m), 2.50-2.55 (1H, m), 2.62-2.65 (1H, m), 3.12-3.14 (2H, m), 3.42-3.48 (4H, m), 3.73-3.76 (1H, m), 4.06 (2H, s), 7.27-7.29 (1H, m), 7.52 (1H, d, J=1.2 Hz), 7.57 (1H, d, J=8.4 Hz) 7.85 (2H, d, J=9.0 Hz), 7.99 (1H, d, J=9.0 Hz), 8.24 (1H, dd, J=5.6, 5.6 Hz), 8.40 (1H, brs).

MS (ESI) m/z: 470 [M+H].

Example 221

Synthesis of (2S)-[6-(carboxymethyl)pyrazin-2-ylthio]-N-{[4-(3,4-dichlorobenzyl)morpholin-2-yl]methyl}acetamide

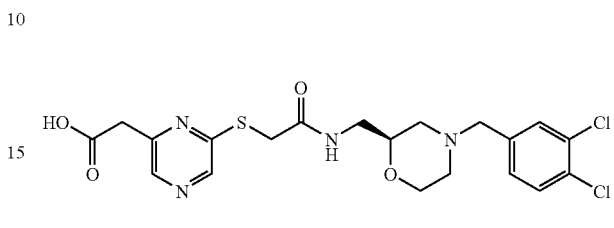

(221-1) Synthesis of 2-chloro-6-di-(tertiary butoxycarbonyl)methylpyrazine

By a similar method as in (217-1), the title compound (2.11 g) was obtained as a white solid from di-(tertiary butoxycarbonyl)malonic acid (2.26 mL) and 2,6-dichloropyrazine (1.49 g).

(221-2) Synthesis of methyl 6-di-(tertiary butoxycarbonyl)methylpyrazin-2-ylthioacetate By a similar method as in (1-4), the title compound (1.92 g) was obtained as a yellow oil from the resultant product (2.11 g) of (221-1) and methyl thioglycolate (581 μL).

(221-3) Synthesis of (2S)-[6-di-(tertiary butoxycarbonyl)methylpyrazin-2-ylthio]-N-{[4-(3,4-dichlorobenzyl)morpholin-2-yl]methyl}acetamide By a similar method as in (144-2), the title compound (1.57 g) was obtained as a white solid from the resultant product (1.20 g) of (221-2) and (2S)-2-aminomethyl-4-(3,4-dichlorobenzyl)morpholine dihydrochloride (1.04 g).

(221-4) Synthesis of (2S)-[6-(carboxymethyl)pyrazin-2-ylthio]-N-{[4-(3,4-dichlorobenzyl)morpholin-2-yl]methyl}acetamide By a similar method as in (217-4), the title compound (707 mg) was obtained as a white solid from the resultant product (1.57 g) of (221-3).

$^1$H-NMR (DMSO-$d_6$) δ 1.91 (1H, brs), 1.99 (1H, brs), 2.49-2.51 (1H, m), 2.67 (1H, brs), 3.11-3.14 (2H, m), 3.49-3.57 (4H, m), 3.79-3.82 (3H, m), 3.86 (2H, s), 7.31-7.33 (1H, m), 7.59-7.61 (2H, m), 8.21 (1H, brs), 8.31 (1H, s), 8.49 (1H, s) 11.43 (1H, brs).

MS (ESI) m/z: 485 [M+H].

Example 222

Synthesis of (2S)-(3-aminopyridazin-6-ylthio)-N-{[4-(3,4-dichlorobenzyl)morpholin-2-yl]methyl}acetamide

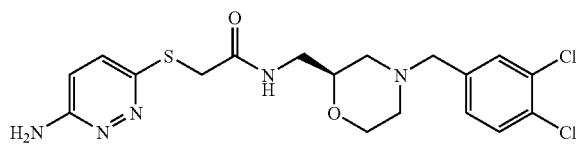

The resultant product (270 mg) of Example 212 was dissolved in a 1 mol/L hydrochloric acid, and the mixture was heated under reflux for 1 hr. The reaction mixture was adjusted to pH=9 with a 1 mol/L aqueous sodium hydroxide solution. The obtained solution was extracted with ethyl acetate. The extract was washed with saturated brine, dried over anhydrous sodium sulfate, and the solvent was evaporated under reduced pressure. The obtained residue was purified by silica gel column chromatography using a mixed solvent of chloroform and methanol as an eluent. The solvent was evaporated from the eluent to give the title compound (58 mg) as a white solid.

$^1$H-NMR (DMSO-$d_6$) δ 1.79-1.84 (1H, m), 2.06-2.08 (1H, m), 2.55-2.58 (1H, m), 2.64-2.67 (1H, m), 3.09-3.12 (2H, m), 3.43-3.52 (4H, m), 3.74-3.82 (3H, m), 6.32 (2H, s), 6.74 (1H, d, J=9.4 Hz), 7.25-7.31 (2H, m), 7.54-7.59 (2H, m), 8.13 (1H, dd, J=5.8, 5.8 Hz).

MS (ESI) m/z: 442 [M+H].

Example 223

Synthesis of (2S)-[6-(carbamoylmethyl)pyrazin-2-ylthio]-N-{[4-(3,4-dichlorobenzyl)morpholin-2-yl]methyl}acetamide

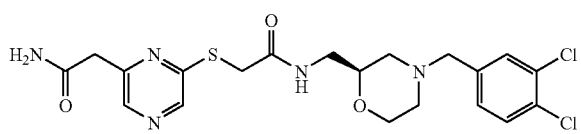

By a similar method as in Example 16, the title compound (200 mg) was obtained as a white solid from the resultant product (700 mg) of Example 221 and ammonium chloride (430 mg).

$^1$H-NMR (DMSO-$d_6$) δ 1.72-1.78 (1H, m), 1.99-2.03 (1H, m), 2.50-2.54 (1H, m), 2.58-2.61 (1H, m), 3.10-3.13 (2H, m), 3.42-3.47 (4H, m), 3.61 (2H, s), 3.72-3.75 (1H, m), 3.85 (2H, s), 7.07 (1H, brs), 7.28 (1H, d, J=7.9 Hz), 7.52-7.58 (3H, m), 8.15-8.16 (1H, m), 8.27 (1H, s), 8.46 (1H, s).

MS (ESI) m/z: 484 [M+H].

Example 224

Synthesis of (2S)-N-{[4-(3,4-dichlorobenzyl)morpholin-2-yl]methyl}-[6-(methoxycarbonyl)methylpyridazin-3-ylthio]acetamide

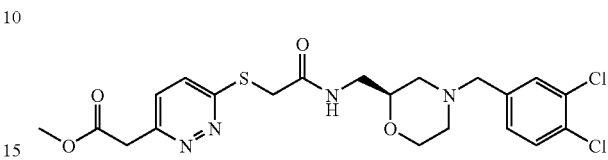

By a similar method as in (1-4), the title compound (88 mg) was obtained as a white solid from the resultant product (388 mg) of (1-2) and 3-mercapto-6-methoxycarbonylmethylpyridazine (190 mg).

$^1$H-NMR (DMSO-$d_6$) δ 1.77-1.82 (1H, m), 1.99-2.02 (1H, m), 2.51-2.54 (1H, m), 2.67-2.69 (1H, m), 3.11-3.14 (2H, m), 3.42-3.49 (4H, m), 3.62 (3H, s), 3.73-3.75 (1H, m), 3.97 (2H, s), 4.06 (2H, s), 7.28-7.30 (1H, m), 7.51-7.54 (2H, m), 7.58 (1H, d, J=8.4 Hz), 7.67 (1H, d, J=8.4 Hz), 8.24 (1H, brs).

MS (ESI) m/z: 499 [M+H].

Example 225

Synthesis of (2S)-(E)-[6-(2-carboxyethen-1-yl)pyridazin-3-ylthio]-N-{[4-(3,4-dichlorobenzyl)morpholin-2-yl]methyl}acetamide

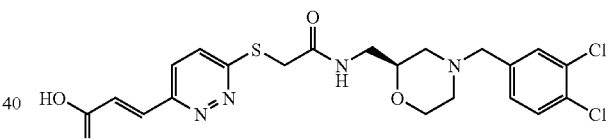

(225-1) Synthesis of (2S)-N-{[4-(3,4-dichlorobenzyl)morpholin-2-yl]methyl}-[6-(hydroxymethyl)pyridazin-3-ylthio]acetamide By a similar method as in (70-1), the title compound (310 mg) was obtained as a colorless oil from the resultant product (815 mg) of Example 218.

(225-2) Synthesis of (2S)-N-{[4-(3,4-dichlorobenzyl)morpholin-2-yl]methyl}-(3-formylpyridazin-6-ylthio)acetamide By a similar method as in (70-2), the title compound (134 mg) was obtained as a colorless oil from the resultant product (310 mg) of (225-1).

(225-3) Synthesis of (2S)-(E)-[6-(2-carboxyethen-1-yl)pyridazin-3-ylthio]-N-{[4-(3,4-dichlorobenzyl)morpholin-2-yl]methyl}acetamide By a similar method as in (70-3), the title compound (16 mg) was obtained as a white amorphous solid from the resultant product (134 mg) of (225-2) and malonic acid (61 mg).

¹H-NMR (DMSO-d₆) δ 1.76-1.82 (1H, m), 1.98-2.03 (1H, m), 2.50-2.54 (1H, m), 2.64-2.67 (1H, m), 3.12-3.15 (2H, m), 3.37-3.48 (4H, m), 3.73-3.76 (1H, m), 4.00 (2H, s), 6.91 (1H, d, J=16.2 Hz), 7.27 (1H, d, J=7.7 Hz), 7.50-7.57 (2H, m), 7.65 (1H, d, J=16.2 Hz), 7.75 (1H, d, J=9.0 Hz), 7.99 (1H, d, J=9.0 Hz), 8.26 (1H, dd, J=5.5, 5.5 Hz), 12.74 (1H, brs).

MS (ESI) m/z: 497 [M+H].

Example 226

Synthesis of (2S)-[6-(carbamoylmethyl)pyridazin-3-ylthio]-N-{[4-(3,4-dichlorobenzyl)morpholin-2-yl]methyl}acetamide

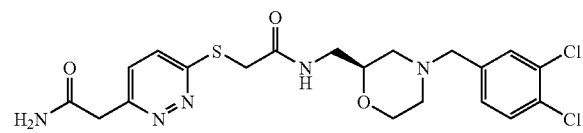

By a similar method as in Example 25, the title compound (415 mg) was obtained as a white solid from the resultant product (720 mg) of Example 224.

¹H-NMR (400 MHz, DMSO-d₆) δ:1.76-1.82 (1H, m), 1.99-2.02 (1H, m), 2.52-2.55 (1H, m), 2.65-2.67 (1H, m), 3.11-3.14 (2H, m), 3.43-3.49 (4H, m), 3.72-3.76 (3H, m), 3.96 (2H, s), 7.04 (1H, brs), 7.28-7.30 (1H, m), 7.47 (1H, d, J=8.8 Hz), 7.53 (1H, d, J=1.9 Hz), 7.56-7.62 (3H, m), 8.23 (1H, brs)

MS (ESI) m/z: 484 [M+H].

Example 227

Synthesis of (2S)-N-{[4-(3,4-dichlorobenzyl)morpholin-2-yl]methyl}-(6-thioxo-1,6-dihydropyridazin-3-ylthio)acetamide

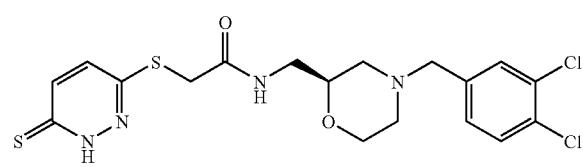

By a similar method as in (144-2), the title compound (157 mg) was obtained as a yellow solid from methyl 6-thioxo-1,6-dihydropyridazin-3-ylthioacetate (432 mg) and (2S)-2-aminomethyl-4-(3,4-dichlorobenzyl)morpholine dihydrochloride (696 mg).

¹H-NMR (DMSO-d₆) δ 1.74-1.79 (1H, m), 1.99-2.02 (1H, m), 2.05-2.56 (1H, m), 2.63-2.66 (1H, m), 3.10-3.13 (2H, m), 3.44-3.49 (4H, m), 3.74-3.80 (3H, m), 7.28-7.32 (2H, m), 7.47 (1H, d, J=9.5 Hz), 7.55-7.60 (2H, m), 8.22-8.25 (1H, m), 14.68 (1H, brs).

MS (ESI) m/z: 459 [M+H].

Example 228

Synthesis of (2S)-N-{[4-(3,4-dichlorobenzyl)morpholin-2-yl]methyl}-(6-oxo-1-methyl-1,6-dihydropyridazin-3-ylthio)acetamide

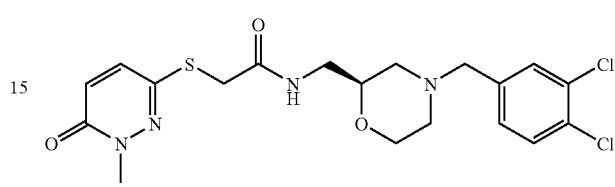

By a similar method as in (144-2), the title compound (143 mg) was obtained as a white solid from methyl 6-oxo-1-methyl-1,6-dihydropyridazin-3-ylthioacetate (100 mg) and (2S)-2-aminomethyl-4-(3,4-dichlorobenzyl)morpholine dihydrochloride (163 mg).

¹H-NMR (DMSO-d₆) δ 1.75-1.80 (1H, m), 2.00-2.05 (1H, m), 2.50-2.56 (1H, m), 2.62-2.65 (1H, m), 3.11-3.14 (2H, m), 3.43-3.47 (4H, m), 3.59 (3H, s), 3.72-3.77 (3H, m), 6.87-6.89 (1H, m), 7.28-7.32 (1H, m), 7.40-7.42 (1H, m), 7.53-7.59 (2H, m), 8.15-8.18 (1H, m).

MS (ESI) m/z: 457 [M+H].

Example 229

Synthesis of (2S)-(cyclopentylthio)-N-{[4-(3,4-dichlorobenzyl)morpholin-2-yl]methyl}acetamide

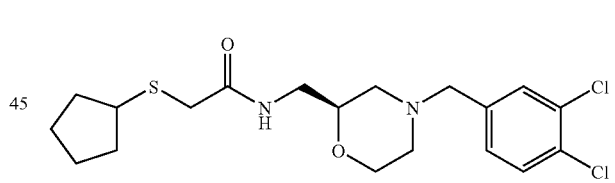

By a similar method as in (1-4), the title compound (150 mg) was obtained as white crystals from the resultant product (388 mg) of (1-2) and cyclopentylmercaptan (118 μL).

¹H-NMR (DMSO-d₆) δ 1.30-1.71 (6H, m), 1.71-1.95 (3H, m), 2.02-2.13 (1H, m), 2.53-2.69 (2H, m), 3.01-3.14 (5H, m), 3.39-3.54 (4H, m), 3.78 (1H, d, J=11.4 Hz), 7.30 (1H, dd, J=1.8, 8.4 Hz), 7.55 (1H, d, J=1.8 Hz), 7.58 (1H, d, J=8.4 Hz), 8.04 (1H, t, J=5.8 Hz).

MS (ESI) m/z: 417 [M+H].

Example 230

Synthesis of (2S)-4-(cyclopentylthio)-N-{[4-(3,4-dichlorobenzyl)morpholin-2-yl]methyl}butyramide

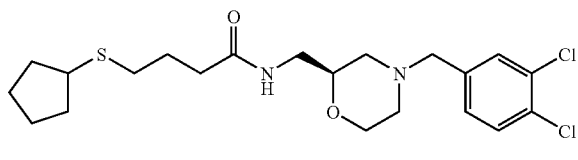

By a similar method as in Example 16, the title compound (325 mg) was obtained as white crystals from 4-cyclopentylthiobutyric acid (244 mg) and (2S)-2-aminomethyl-4-(3,4-dichlorobenzyl)morpholine dihydrochloride (348 mg).

$^1$H-NMR (DMSO-d$_6$) δ 1.30-1.82 (9H, m), 1.84-2.10 (5H, m), 2.45 (2H, t, J=7.2 Hz), 2.52-2.69 (2H, m), 2.98-3.12 (3H, m), 3.38-3.52 (4H, m), 3.72-3.80 (1H, m), 7.30 (1H, dd, J=1.9, 8.3 Hz), 7.54 (1H, d, J=1.9 Hz), 7.59 (1H, d, J=8.3 Hz), 7.91 (1H, t, J=5.8 Hz).

MS (ESI) m/z: 445 [M+H].

Example 231

Synthesis of (2S)-4-(cyclopentanesulfonyl)-N-{[4-(3,4-dichlorobenzyl)morpholin-2-yl]methyl}butyramide

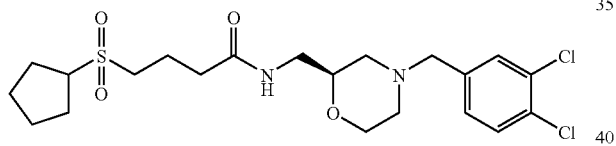

By a similar method as in Example 16, the title compound (39 mg) was obtained as white crystals from 4-cyclopentanesulfonylbutyric acid (264 mg) and (2S)-2-aminomethyl-4-(3,4-dichlorobenzyl)morpholine dihydrochloride (348 mg).

$^1$H-NMR (DMSO-d$_6$) δ 1.50-1.72 (4H, m), 1.73-1.99 (7H, m), 2.00-2.10 (1H, m), 2.23 (2H, t, J=7.2 Hz), 2.52-2.70 (2H, m), 2.95-3.12 (4H, m), 3.38-3.62 (5H, m), 3.72-3.80 (1H, m), 7.30 (1H, dd, J=1.2, 8.4 Hz), 7.55 (1H, d, J=1.2 Hz), 7.59 (1H, d, J=8.4 Hz), 7.96 (1H, t, J=5.7 Hz).

MS (ESI) m/z: 477 [M+H].

Example 232

Synthesis of (2S)-4-(cyclopentanesulfonyl)-N-{[4-(3-chloro-4-fluorobenzyl)morpholin-2-yl]methyl}butyramide

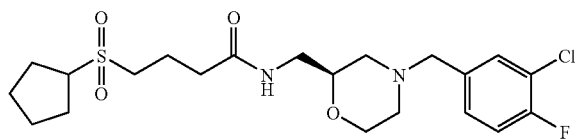

By a similar method as in Example 16, the title compound (317 mg) was obtained as white crystals from 4-cyclopentanesulfonylbutyric acid (264 mg) and (2S)-2-aminomethyl-4-(3-chloro-4-fluorobenzyl)morpholine dihydrochloride (332 mg).

$^1$H-NMR (DMSO-d$_6$) δ 1.50-1.72 (4H, m), 1.73-1.99 (7H, m), 2.00-2.10 (1H, m), 2.23 (2H, t, J=7.2 Hz), 2.52-2.70 (2H, m), 2.95-3.12 (4H, m), 3.38-3.62 (5H, m), 3.70-3.80 (1H, m), 7.27-7.39 (2H, m), 7.49 (1H, dd, J=1.8, 7.2 Hz), 7.96 (1H, t, J=5.7 Hz).

MS (ESI) m/z: 461 [M+H]

Example 233

Synthesis of (2S)-4-(cyclopentanesulfonyl)-N-{[4-(3-chlorobenzyl)morpholin-2-yl]methyl}butyramide

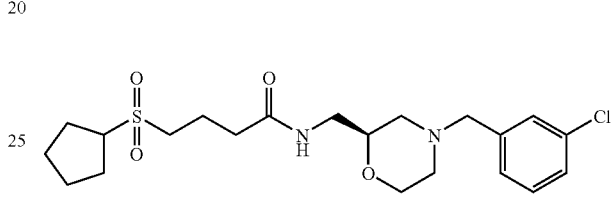

By a similar method as in Example 16, the title compound (290 mg) was obtained as white crystals from 4-cyclopentanesulfonylbutyric acid (264 mg) and (2S)-2-aminomethyl-4-(3-chlorobenzyl)morpholine dihydrochloride (314 mg).

$^1$H-NMR (DMSO-d$_6$) δ 1.50-1.72 (4H, m), 1.73-1.99 (7H, m), 2.00-2.10 (1H, m), 2.23 (2H, t, J=7.2 Hz), 2.52-2.70 (2H, m), 2.95-3.12 (4H, m), 3.39-3.62 (5H, m), 3.70-3.80 (1H, m), 7.21-7.39 (4H, m), 7.96 (1H, t, J=5.7 Hz).

MS (ESI) m/z: 443 [M+H].

Example 234

Synthesis of (2S)-4-(cyclopentanesulfonyl)-N-{[4-(3,4-difluorobenzyl)morpholin-2-yl]methyl}butyramide

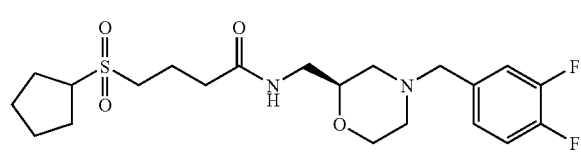

By a similar method as in Example 16, the title compound (336 mg) was obtained as white crystals from 4-cyclopentanesulfonylbutyric acid (264 mg) and (2S)-2-aminomethyl-4-(3,4-difluorobenzyl)morpholine dihydrochloride (315 mg).

$^1$H-NMR (DMSO-d$_6$) δ 1.50-1.72 (4H, m), 1.73-1.99 (7H, m), 2.00-2.10 (1H, m), 2.23 (2H, t, J=7.2 Hz), 2.52-2.69 (2H, m), 2.95-3.12 (4H, m), 3.38-3.62 (5H, m), 3.70-3.80 (1H, m), 7.07-7.18 (1H, m), 7.28-7.44 (2H, m), 7.96 (1H, t, J=5.7 Hz).

MS (ESI) m/z: 445 [M+H].

Example 235

Synthesis of (2S)-4-(cyclopentylthio)-N-{[4-(3,4-difluorobenzyl)morpholin-2-yl]methyl}butyramide

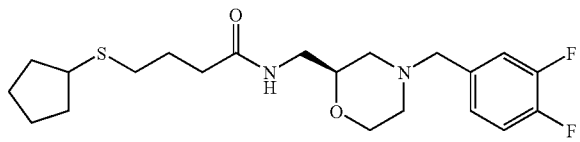

By a similar method as in Example 16, the title compound (351 mg) was obtained as a colorless oil from 4-cyclopentylthiobutyric acid (244 mg) and (2S)-2-aminomethyl-4-(3,4-difluorobenzyl)morpholine dihydrochloride (315 mg).
$^1$H-NMR (DMSO-$d_6$) δ 1.30-1.80 (9H, m), 1.83-2.09 (5H, m), 2.44 (2H, t, J=7.2 Hz), 2.52-2.69 (2H, m), 2.98-3.12 (3H, m), 3.38-3.52 (4H, m), 3.72-3.80 (1H, m), 7.09-7.18 (1H, m), 7.28-7.41 (2H, m), 7.89 (1H, t, J=5.7 Hz).
MS (ESI) m/z: 413 [M+H].

Example 236

Synthesis of (2S)-N-{[4-(3,4-dichlorobenzyl)morpholin-2-yl]methyl}-(1-methyl-1H-tetrazol-5-ylthio)acetamide

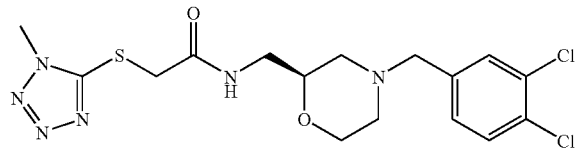

By a similar method as in (1-4), the title compound (367 mg) was obtained as a colorless oil from the resultant product (388 mg) of (1-2) and 5-mercapto-1-methyl-1H-tetrazole (122 mg).
$^1$H-NMR (DMSO-$d_6$) δ 1.71-1.87 (1H, m), 1.96-2.10 (1H, m), 2.51-2.69 (2H, m), 3.08-3.14 (2H, m), 3.39-3.52 (4H, m), 3.70-3.81 (1H, m), 3.96 (3H, s), 4.02 (2H, s), 7.30 (1H, dd, J=1.8, 8.4 Hz), 7.54 (1H, d, J=1.8 Hz), 7.59 (1H, d, J=8.4 Hz), 8.37 (1H, dd, J=5.7, 5.7 Hz).
MS (ESI) m/z: 431 [M+H].

Example 237

Synthesis of (2S)-(2-carboxythiophen-5-ylthio)-N-{[4-(3,4-dichlorobenzyl)morpholin-2-yl]methyl}acetamide

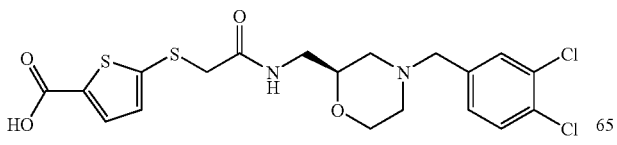

(237-1) Synthesis of 2-bromo-5-ethoxycarbonylthiophene

2-Bromo-5-thiophenecarboxylic acid (500 mg) was dissolved in ethanol (5 mL), conc. sulfuric acid (50 μL) was added and the mixture was heated under reflux for 4 hrs. Conc. sulfuric acid (50 μL) was further added and the mixture was heated under reflux for 5 hrs. Then, the mixture was allowed to return to room temperature. Water was added to the reaction mixture, and the mixture was extracted with ethyl acetate. The extract was washed with saturated brine, dried, and the solvent was evaporated under reduced pressure. The residue was purified by silica gel column chromatography using a mixed solvent of ethyl acetate and hexane as an eluent. The solvent was evaporated from the eluent to give the title compound (500 mg) as a yellow oil.

(237-2) Synthesis of 2-ethoxycarbonylthiophen-5-ylthioacetic acid

By a similar method as in (161-1), the title compound (390 mg) was obtained as a colorless oil from the resultant product (500 mg) of (237-1) and thioglycol acid (150 μL).

(237-3) Synthesis of (2S)-N-{[4-(3,4-dichlorobenzyl)morpholin-2-yl]methyl}-(2-ethoxycarbonylthiophen-5-ylthio)acetamide By a similar method as in Example 16, the title compound was obtained as a white solid from the resultant product (390 mg) of (237-2) and (2S)-2-aminomethyl-4-(3,4-dichlorobenzyl)morpholine dihydrochloride (550 mg).

(237-4) Synthesis of (2S)-(2-carboxythiophen-5-ylthio)-N-{[4-(3,4-dichlorobenzyl)morpholin-2-yl]methyl}acetamide The total amount of the resultant product of (237-3) was dissolved in ethanol (5 mL), a 1 mol/L aqueous sodium hydroxide solution (5 mL) was added, and the mixture was stirred overnight at room temperature. 1 mol/L hydrochloric acid was added to the reaction mixture, and the mixture was extracted with ethyl acetate. The extract was dried over anhydrous sodium sulfate, and the solvent was evaporated under reduced pressure. The obtained residue was purified by silica gel column chromatography using a mixed solvent of chloroform and methanol as an eluent. The solvent was evaporated from the eluent to give the title compound (485 mg) as a white solid.
$^1$H-NMR (DMSO-$d_6$) δ 1.74-1.79 (1H, m), 2.00-2.06 (1H, m), 2.54 (1H, d, J=11.4 Hz), 2.62 (1H, d, J=11.4 Hz), 3.10-3.13 (2H, m), 3.40-3.49 (4H, m), 3.65 (2H, d, J=1.8 Hz), 3.74-3.77 (1H, m), 7.15 (1H, d, J=3.9 Hz), 7.29 (1H, dd, J=2.0, 8.4 Hz), 7.53 (1H, d, J=2.0 Hz) 7.56-7.60 (2H, m), 8.17 (1H, dd, J=5.7, 5.7 Hz).
MS (ESI) m/z: 475 [M+H].

Example 238

Synthesis of (2S)-[5-(4-carboxyphenyl)thiophen-2-ylthio]-N-{[4-(3,4-dichlorobenzyl)morpholin-2-yl]methyl}acetamide

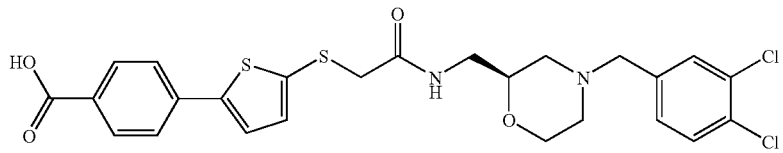

The resultant product (200 mg) of Example 31, tetrakistriphenylphosphinepalladium (25 mg), sodium carbonate (200 mg) and 4-methoxycarbonylphenylboronic acid (105 mg) were dissolved in a mixed solution of ethylene glycol dimethylether (4 mL) and water (250 μL), and the mixture was heated under reflux at 130° C. for 6 hrs. Then, water was added to the reaction mixture and the mixture was extracted with ethyl acetate. The extract was evaporated under reduced pressure, and the residue was purified by column chromatography using chloroform as an eluent. The eluent was evaporated and the obtained yellow oil was dissolved in ethanol (2 mL). A 1N aqueous sodium hydroxide solution (50 μL) was added and the mixture was stirred overnight at room temperature. The reaction mixture was adjusted to pH=5 with 1N hydrochloric acid, and the mixture was extracted with chloroform. The extract was dried, and the solvent was evaporated under reduced pressure. The obtained residue was purified by silica gel column chromatography using a mixed solvent of chloroform and methanol as an eluent. The solvent was evaporated from the eluent to give the title compound (90 mg) as a pale-yellow solid.

$^1$H-NMR (DMSO-$d_6$) δ 1.74-1.79 (1H, m), 1.96-2.03 (1H, m), 2.5 (1H, m), 2.62 (1H, d, J=11.0 Hz), 3.10-3.13 (2H, m), 3.3-3.4 (4H, m), 3.57 (2H, s), 3.73 (1H, d, J=11.0 Hz), 7.20-7.24 (2H, m), 7.45 (1H, s), 7.53 (1H, d, J=8.1 Hz), 7.57 (1H, d, J=3.4 Hz), 7.72 (2H, d, J=8.1 Hz), 7.94 (2H, d, J=8.1 Hz), 8.13 (1H, brs).

MS (ESI) m/z: 551 [M+H].

Example 239

Synthesis of (2S)-[5-(3-carboxyphenyl)thiophen-2-ylthio]-N-{[4-(3,4-dichlorobenzyl)morpholin-2-yl]methyl}acetamide

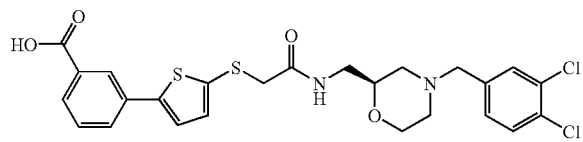

By a similar method as in Example 238, the title compound (45 mg) was obtained as a pale-yellow solid from the resultant product (200 mg) of Example 31 and 3-methoxycarbonylphenylboronic acid (105 mg).

$^1$H-NMR (DMSO-$d_6$) δ 1.74-1.79 (1H, m), 1.97-2.03 (1H, m), 2.5 (1H, m), 2.62 (1H, d, J=11.1 Hz), 3.10-3.13 (2H, m), 3.30-3.47 (4H, m), 3.55 (2H, s), 3.73 (1H, d, J=11.1 Hz), 7.19 (1H, d, J=3.7 Hz), 7.22 (1H, dd, J=1.4, 8.0 Hz), 7.45 (1H, d, J=1.4 Hz), 7.50-7.54 (3H, m), 7.86 (2H, dd, J=1.4, 8.0 Hz), 8.00-8.14 (2H, m).

MS (ESI) m/z: 551 [M+H].

Example 240

Synthesis of (2S)-N-{[4-(3,4-dichlorobenzyl)morpholin-2-yl]methyl}-[4-(5-oxo-4,5-dihydro-1,2,4-oxadiazol-3-yl)thiazol-2-ylthio]acetamide hydrochloride

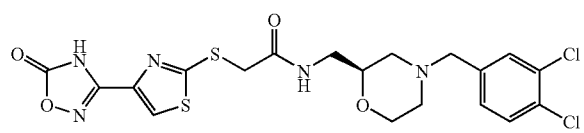

The resultant product (245 mg) of (22-2) was dissolved in 1,4-dioxane (5 mL), carbonyldiimidazole (122 mg) was added, and the mixture was heated under reflux for 2 hrs. After allowing to cool, carbonyldiimidazole (122 mg) was added, and the mixture was further heated under reflux for 2 hrs. Ethyl acetate was added to the reaction mixture, and the mixture was washed with saturated brine, dried over anhydrous sodium sulfate, and the solvent was evaporated under reduced pressure. The obtained residue was purified by silica gel column chromatography using a mixed solvent of chloroform and methanol as an eluent. The solvent was evaporated from the eluent to give the title compound (87 mg) as a white solid.

$^1$H-NMR (DMSO-$d_6$) δ 1.71-1.84 (1H, m), 1.98-2.10 (1H, m), 2.53-2.69 (2H, m), 3.07-3.18 (2H, m), 3.39-3.53 (4H, m), 3.69-3.78 (1H, m), 3.92-4.04 (2H, m), 7.28 (1H, dd, J=2.1, 8.1 Hz), 7.52 (1H, d, J=2.1 Hz), 7.57 (1H, d, J=8.1 Hz), 8.17 (1H, s), 8.33 (1H, dd, J=5.7, 5.7 Hz).

MS (ESI) m/z: 516 [M+H].

Example 241

Synthesis of (2S)-N-{[4-(3,4-dichlorobenzyl)morpholin-2-yl]methyl}acetamide

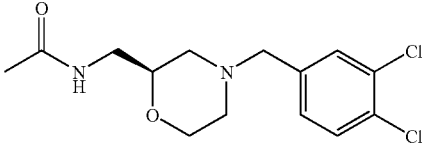

By a similar method as in Example 135, the title compound (530 mg) was obtained as a white amorphous solid from (2S)-2-aminomethyl-4-(3,4-dichlorobenzyl)morpholine (0.6 g) and acetyl chloride (370 μL).

$^1$H-NMR (DMSO-$d_6$) δ 1.75-1.81 (4H, m), 2.01-2.08 (1H, m), 2.54-2.58 (1H, m), 2.65-2.68 (1H, m), 3.03-3.08 (2H, m), 3.41-3.50 (4H, m), 3.74-3.78 (1H, m), 7.30 (1H, dd, J=1.6, 8.3 Hz), 7.55 (1H, d, J=1.6 Hz), 7.59 (1H, d, J=8.3 Hz), 7.93 (1H, dd, J=5.7, 5.7 Hz).

MS (ESI) m/z: 317 [M+H].

Experimental Example 1

Binding Inhibitory Test of Chemokine to Human Eosinophils

Human eosinophils were separated by the CD16 negative selection method from anticoagulation-treated peripheral blood of healthy subject (e.g., J. Immunol. Methods, vol. 145, pages 105-110, 1991). The separated eosinophils ($2 \times 10^5$ cells), 50 pmol/L[$^{125}$I]-eotaxin (2000 Ci/mmoL, manufactured by Amersham Pharmacia Biotech) and a test compounds were mixed in 0.1 mL of binding buffer (50 mmol/L HEPES, 1 mmol/L CaCl$_2$, 5 mmol/L MgCl$_2$, 0.5% bovine serum albumin (BSA), 0.1% sodium azide, pH 7.4), and the mixture was incubated in a multiscreen plate (manufactured by MILLIPORE) at 25° C. for 1 hr. After incubation, the reaction mixture in the multiscreen plate was filtered by vacuum manifold, and washed with 0.6 mL of a cold washing buffer (50 mmol/L HEPES, 1 mmol/L CaCl$_2$, 5 mmol/L MgCl$_2$, 0.5 mol/L NaCl, 0.1% sodium azide, pH 7.4), and the radioactivity maintained on the filter was measured. The compounds of the present invention showed a binding inhibitory activity against chemokine in this assay. The $IC_{50}$ values (concentration of test compound necessary for decreasing binding of [$^{125}$I]-eotaxin to human eosinophils by 50%) of some of the compounds of the present invention were as follows.

TABLE 1

| compounds | $IC_{50}$(nmol/L) |
|---|---|
| Example 2 | 2.4 |
| Example 9 | 12.7 |
| Example 10 | 2.4 |
| Example 11 | 0.8 |
| Example 13 | 0.4 |
| Example 15 | 0.4 |
| Example 17 | 0.9 |
| Example 23 | 1.0 |
| Example 27 | 2.3 |
| Example 37 | 34.3 |

Experimental Example 2

Effect on Intracellular Calcium Concentration

The effect of the compound of the present invention on intracellular calcium mobilization in peripheral blood eosinophils of healthy subject upon CCL11 stimulation was examined by the following method.

Eosinophils separated from peripheral blood of healthy subject were suspended in 0.5% bovine serum albumin-containing phosphate buffered saline, and incubated at 37° C. for 45 min in the presence of 5 µmol/L of Fura-2 AM (manufactured by DOJINDO LABORATORIES).

After incubation, the cells were washed 3 times with a measurement buffer (10 mmol/L HEPES, and 0.5% bovine serum albumin-containing hanks' balanced salt solution) to remove Fura-2 AM that was not incorporated into the cells.

Finally, the cells were adjusted to $1 \times 10^6$ cells/mL with the measurement buffer and preserved in a dark place until measurement. The intracellular calcium was measured using FDSS3000 manufactured by Hamamatsu Photonics K.K. In other words, the cell suspension (0.1 mL) loaded with Fura-2 AM was placed in a 96 well plate for measurement, the fluorescence intensity to the excitation light at wavelengths 340 nm and 380 nm was measured by FDSS3000, the ratio of the fluorescence intensity to the excitation light at these two wavelengths was determined, based on which the intracellular calcium concentration was calculated. As the agonist, used was CCL11 (1.0 nmol/L), which is a CCR3 selective ligand, and the antagonistic activity was determined as 50% suppression rate ($IC_{50}$ value) of the increase in the intracellular calcium concentration, when eosinophils were treated with various concentrations of the compound of the present invention at 3 min before agonist stimulation.

TABLE 2

| compounds | $IC_{50}$(nmol/L) |
|---|---|
| Example 2 | 1.8 |
| Example 15 | 1.6 |
| Example 17 | 2.5 |
| Example 23 | 0.8 |
| Example 37 | 4.9 |
| Example 40 | 2.0 |
| Example 46 | 3.1 |
| Example 53 | 5.3 |
| Example 55 | 1.1 |
| Example 59 | 2.1 |
| Example 64 | 0.3 |
| Example 71 | 0.5 |
| Example 79 | 0.9 |
| Example 107 | 2.5 |
| Example 109 | 22.3 |
| Example 110 | 1.5 |
| Example 112 | 0.9 |
| Example 115 | 2.6 |
| Example 123 | 2.6 |
| Example 125 | 3.6 |
| Example 146 | 2.5 |
| Example 174 | 16.2 |
| Example 198 | 3.9 |
| Example 207 | 2.4 |
| Example 223 | 0.1 |
| Example 232 | 38.5 |

3: Effect on Antigen Induced Allergic and Biphasic Ear Edema Model

The in vivo effect of the compound of the present invention was examined using a mouse ovalbumin (OVA) induced allergic and biphasic ear edema model. The model was prepared according to the method of Sugawara et al. (Allergy & Clinical Immunology International, Supplement No. 2, P 785, 2000). In other words, male BALB/c mice were immunized by intraperitoneal injection with 10 µg of OVA and 1 mg of aluminum hydroxide gel (Alum). At 14 days after immunization, OVA (5 µg) were subcutaneously injected to the both ears of the mouse, whereby ear edema was induced. The thickness of the ears was measured using a dial sickness gauge immediately before subcutaneous injection and 1 and 24 hrs after subcutaneous injection of OVA. The compound of the present invention was suspended in a vehicle, 0.5% hydroxypropylmethyl cellulose solution, and orally administered at 3 mg/kg or 10 mg/kg once a day using an orally gavage needle from 2 days before ear edema induction. The doses of some of the compounds of the present invention that showed a significant suppressive action as compared to a vehicle administration group are shown in the following Table.

TABLE 3

| compounds | Immediate phase (mg/kg) | Late phase (mg/kg) |
|---|---|---|
| Example 2 | 3 | 3 |
| Example 17 | 3 | 3 |
| Example 37 | 3 | 3 |
| Example 40 | 3 | 3 |
| Example 46 | 10 | 10 |
| Example 53 | 3 | 3 |
| Example 64 | 10 | 3 |
| Example 123 | 10 | 10 |
| Example 125 | 10 | 3 |
| Example 146 | 3 | 3 |
| Example 198 | 10 | 10 |

INDUSTRIAL APPLICABILITY

The compound of the present invention is an antagonist that inhibits binding of human eosinophils and CCL11, which is a CCR3 selective chemokine, and also inhibits an increase in the intracellular calcium mobilization, which is induced by CCL11. Therefore, the compound is considered to be useful as a pharmaceutical agent for the treatment and/or prevention of immune and inflammatory diseases.

This application is based on a patent application No. 2004-261655 filed in Japan, the contents of which are incorporated in full herein by this reference.

The invention claimed is:

1. A compound represented by the formula (1)

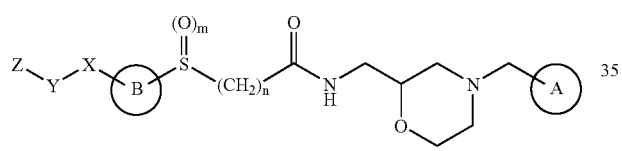

(1)

wherein ring A is aryl having substituent(s), or heteroaryl optionally having substituent(s), ring B is arylene optionally having substituent(s), divalent heterocyclic group optionally having substituent(s), or $C_{3-8}$ cycloalkylene optionally having substituent(s), m is an integer of 0 to 2, n is an integer of 1 to 5, X is a bond, —NH—, —NR$^1$— wherein R$^1$ is $C_{1-6}$ alkyl optionally having substituent(s), —CO—, —CO$_2$—, —OCO—, —CONR$^a$— wherein R$^a$ is hydrogen atom or $C_{1-6}$ alkyl optionally having substituent(s), hereinafter the same, —NR$^a$CO—, —NR$^2$CONR$^3$— wherein R$^2$ and R$^3$ may be the same or different and each is hydrogen atom or $C_{1-6}$ alkyl optionally having substituent(s), or R$^2$ and R$^3$ in combination optionally form, together with the atoms bonded thereto, a ring optionally having substituent(s), oxygen atom, sulfur atom, —SO—, —SO$_2$—, —NR$^a$SO$_2$—, —SO$_2$NR$^a$—, $C_{1-6}$ alkylene optionally having substituent(s), $C_{2-6}$ alkenylene optionally having substituent(s), $C_{2-6}$ alkynylene optionally having substituent(s), —O—X$^a$— wherein X$^a$ is $C_{1-6}$ alkylene optionally having substituent(s), hereinafter the same, —X$^a$—O—, —CO—X$^a$—, —X$^a$—CO—, —CONR$^a$—X$^a$—, —X$^a$—CONR$^a$—, —NR$^a$CO—X$^a$—, —X$^a$—NR$^a$CO—, —S—X$^a$—, —X$^a$—S—, —SO—X$^a$—, —X$^a$—SO—, —NR$^a$—X$^a$—, —X$^a$—NR$^a$—, —SO$_2$—X$^a$—, —X$^a$—SO$_2$—, —C(=N—CO$_2$—R$^1$)—, —C(=N—SO$_2$—R$^1$)—, —C(=N—SO$_2$NH$_2$)—, —C(=CH—NO$_2$)—, —C(=N—CN)— or $C_{3-8}$ cycloalkylidene group optionally having substituent(s), Y is a bond, —NH—, —NR$^4$— wherein R$^4$ is $C_{1-6}$ alkyl optionally having substituent(s), hereinafter the same, —CO—, —CO$_2$—, —OCO—, —CONR$^b$— wherein R$^b$ is hydrogen atom or $C_{1-6}$ alkyl optionally having substituent(s), hereinafter the same, —NR$^b$CO—, —NR$^5$CONR$^6$— wherein R$^5$ and R$^6$ may be the same or different and each is hydrogen atom or $C_{1-6}$ alkyl optionally having substituent(s), or R$^5$ and R$^6$ in combination optionally form, together with the atoms bonded thereto, a ring optionally having substituent(s), oxygen atom, sulfur atom, —SO—, —SO$_2$—, —NR$^b$SO$_2$—, —SO$_2$NR$^b$—, $C_{1-6}$ alkylene optionally having substituent(s), $C_{2-6}$ alkenylene optionally having substituent(s), $C_{2-6}$ alkynylene optionally having substituent(s), —O—X$^b$— wherein X$^b$ is $C_{1-6}$ alkylene optionally having substituent(s), hereinafter the same, —X$^b$—O—, —CO—X$^b$—, —X$^b$—CO—, —CONR$^b$—X$^b$—, —X$^b$—CONR$^b$—, —NR$^b$CO—X$^b$—, —X$^b$—NR$^b$CO—, —S—X$^b$—, —X$^b$—S—, —SO—X$^b$—, —X$^b$—SO—, —NR$^b$—X$^b$—, —X$^b$—NR$^b$—, —SO$_2$—X$^b$—, —X$^b$—SO$_2$—, —C(=N—CO$_2$—R$^4$)—, —C(=N—SO$_2$—R$^4$)—, —C(=N—SO$_2$NH$_2$)—, —C(=CH—NO$_2$)— or —C(=N—CN)—, and Z is hydrogen atom, halogen atom, $C_{1-6}$ alkyl optionally having substituent(s), $C_{3-8}$ cycloalkyl optionally having substituent(s), aryl optionally having substituent(s), heterocyclic group optionally having substituent(s), hydroxy, nitro, amino, cyano, $C_{1-6}$ alkoxy optionally having substituent(s), mono- or di-$C_{1-6}$ alkylamino optionally having substituent(s), $C_{1-7}$ acylamino optionally having substituent(s), sulfonylamino optionally having substituent(s), hydrazino optionally having substituent(s), guanidino optionally having substituent(s) or amidino optionally having substituent(s), or a pharmaceutically acceptable salt thereof.

2. The compound of claim 1, wherein ring B is arylene optionally having substituent(s), or divalent heterocyclic group optionally having substituent(s), and X is a bond, —NH—, —NR$^1$— wherein R$^1$ is $C_{1-6}$ alkyl optionally having substituent(s), —CO—, —CO$_2$—, —OCO—, —CONR$^a$— wherein R$^a$ is hydrogen atom or $C_{1-6}$ alkyl optionally having substituent(s), hereinafter the same, —NR$^a$CO—, —NR$^2$CONR$^3$— wherein R$^2$ and R$^3$ may be the same or different and each is hydrogen atom or $C_{1-6}$ alkyl optionally having substituent(s), or R$^2$ and R$^3$ in combination optionally form, together with the atoms bonded thereto, a ring optionally having substituent(s), oxygen atom, sulfur atom, —SO—, —SO$_2$—, —NR$^a$SO$_2$—, —SO$_2$NR$^a$—, $C_{1-6}$ alkylene optionally having substituent(s), $C_{2-6}$ alkenylene optionally having substituent(s), $C_{2-6}$ alkynylene optionally having substituent(s), —O—X$^a$— wherein X$^a$ is $C_{1-6}$ alkylene optionally having substituent(s), hereinafter the same, —X$^a$—O—, —CO—X$^a$—, —X$^a$—CO—, —CONR$^a$—X$^a$—, —X$^a$—CONR$^a$—, —NR$^a$CO—X$^a$—, —X$^a$—NR$^a$CO—, —S—X$^a$—, —X$^a$—S—, —SO—X$^a$—, —X$^a$—SO—, —NR$^a$—X$^a$—, —X$^a$—NR$^a$—, —SO$_2$—X$^a$—, —X$^a$—SO$_2$—, —C(=N—CO$_2$—R$^1$)—, —C(=N—SO$_2$—R$^1$)—, —C(=N—SO$_2$NH$_2$)—, —C(=CH—NO$_2$)— or —C(=N—CN)—, or a pharmaceutically acceptable salt thereof.

3. The compound of claim 1, wherein, in the formula (1), m is 0 or 2, or a pharmaceutically acceptable salt thereof.

4. The compound of claim 1, wherein, in the formula (1), m is 0, or a pharmaceutically acceptable salt thereof.

5. The compound of claim 1, wherein, in the formula (1), X is a bond, —NH—, —NR$^1$— wherein R$^1$ is C$_{1-6}$ alkyl optionally having substituent(s), —CO—, —CO$_2$—, —OCO—, —CONR$^a$— wherein R$^a$ is hydrogen atom or C$_{1-6}$ alkyl optionally having substituent(s), hereinafter the same, —NR$^a$CO—, —NR$^2$CONR$^3$— wherein R$^2$ and R$^3$ may be the same or different and each is hydrogen atom or C$_{1-6}$ alkyl optionally having substituent(s), oxygen atom, sulfur atom, —SO—, —SO$_2$—, —NR$^a$SO$_2$—, —SO$_2$NR$^a$—, C$_{2-6}$ alkenylene optionally having substituent(s), —CO—X$^a$— wherein X$^a$ is C$_{1-6}$ alkylene optionally having substituent(s), hereinafter the same, —X$^a$—CO—, —CONR$^a$—X$^a$—, —X$^a$—CONR$^a$—, —NR$^a$CO—X$^a$—, —X$^a$—NR$^a$CO— or C$_{3-8}$ cycloalkylidene optionally having substituent(s), or a pharmaceutically acceptable salt thereof.

6. The compound of claim 1, wherein, in the formula (1), X is a bond, —CO—, —CONR$^a$— wherein R$^a$ is hydrogen atom or C$_{1-6}$ alkyl optionally having substituent(s), hereinafter the same, —NR$^a$CO—, —CO—X$^a$— wherein X$^a$ is C$_{1-6}$ alkylene optionally having substituent(s), hereinafter the same, —X$^a$—CO—, —CONR$^a$—X$^a$—, —X$^a$—CONR$^a$—, —NR$^a$CO—X$^a$— or —X$^a$—NR$^a$CO—, or a pharmaceutically acceptable salt thereof.

7. The compound of claim 1, wherein, in the formula (1), Y is a bond, —NH—, —NR$^4$— wherein R$^4$ is C$_{1-6}$ alkyl optionally having substituent(s), —CO—, —CO$_2$—, —OCO—, —CONR$^b$— wherein R$^b$ is hydrogen atom or C$_{1-6}$ alkyl optionally having substituent(s), hereinafter the same, —NR$^b$CO—, —NR$^5$CONR$^6$— wherein R$^5$ and R$^6$ may be the same or different and each is hydrogen atom or C$_{1-6}$ alkyl optionally having substituent(s), oxygen atom, sulfur atom, —SO—, —SO$_2$—, —NR$^b$SO$_2$—, —SO$_2$NR$^b$—, —CO—X$^b$— wherein X$^b$ is C$_{1-6}$ alkylene optionally having substituent(s), hereinafter the same, —X$^b$—CO—, —CONR$^b$—X$^b$—, —X$^b$—CONR$^b$—, —NR$^b$CO—X$^b$— or —X$^b$—NR$^b$CO—, or a pharmaceutically acceptable salt thereof.

8. The compound of claim 1, wherein, in the formula (1), Y is a bond, —CO—, —CONR$^b$— wherein R$^b$ is hydrogen atom or C$_{1-6}$ alkyl optionally having substituent(s), hereinafter the same, —NR$^b$CO—, —CO—X$^b$— wherein X$^b$ is C$_{1-6}$ alkylene optionally having substituent(s), hereinafter the same, —X$^b$—CO—, —CONR$^b$—X$^b$—, —X$^b$—CONR$^b$—, —NR$^b$CO—X$^b$— or —X$^b$—NR$^b$CO—, or a pharmaceutically acceptable salt thereof.

9. The compound of claim 1, wherein, in the formula (1), Z is hydrogen atom, halogen atom, C$_{1-6}$ alkyl optionally having substituent(s), C$_{3-8}$ cycloalkyl optionally having substituent(s), aryl optionally having substituent(s), heterocyclic group optionally having substituent(s), hydroxy, nitro, amino, cyano, C$_{1-6}$ alkoxy optionally having substituent(s), mono- or di-C$_{1-6}$ alkylamino optionally having substituent(s), C$_{1-7}$ acylamino optionally having substituent(s), sulfonylamino optionally having substituent(s), hydrazino optionally having substituent(s), guanidino optionally having substituent(s), or amidino optionally having substituent(s), or a pharmaceutically acceptable salt thereof.

10. The compound of claim 1, wherein, in the formula (1), Z is hydrogen atom, hydroxy, amino, C$_{1-6}$ alkyl optionally having substituent(s), C$_{1-6}$ alkoxy optionally having substituent(s), aryl optionally having substituent(s) or heterocyclic group optionally having substituent(s), or a pharmaceutically acceptable salt thereof.

11. The compound of claim 1, which is represented by the formula (1a)

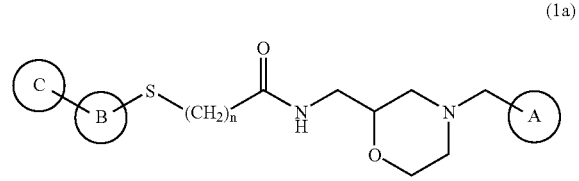

(1a)

wherein ring C is aryl optionally having substituent(s) or heteroaryl and other symbols are as defined in claim 1, or a pharmaceutically acceptable salt thereof.

12. The compound of claim 1, wherein, in the formula (1), ring A is phenyl having substituent(s), or a pharmaceutically acceptable salt thereof.

13. The compound of claim 1, wherein, in the formula (1), n is 1 to 3, or a pharmaceutically acceptable salt thereof.

14. The compound of claim 1, wherein, in the formula (1), the absolute configuration at the 2-position of morpholine is S configuration, or a pharmaceutically acceptable salt thereof.

15. The compound of claim 1, which is selected from the group consisting of
(2S)-[4-(carboxymethyl)thiazol-2-ylthio]-N-{[4-(3,4-dichlorobenzyl)morpholin-2-yl]methyl}acetamide,
(2S)-[4-(3-aminophenyl)thiazol-2-ylthio]-N-{[4-(3,4-dichlorobenzyl)morpholin-2-yl]methyl}acetamide,
(2S)-[4-(3-carbamoyl-4-hydroxyphenyl)thiazol-2-ylthio]-N-{[4-(3,4-dichlorobenzyl)morpholin-2-yl]methyl}acetamide,
(2S)-N-{[4-(3,4-dichlorobenzyl)morpholin-2-yl]methyl}-[4-(pyridin-4-yl)thiazol-2-ylthio]acetamide,
(2S)-N-{[4-(3,4-dichlorobenzyl)morpholin-2-yl]methyl}-[4-(3,4-dimethoxyphenyl)thiazol-2-ylthio]acetamide,
(2S)-(4-carbamoylthiazol-2-ylthio)-N-{[4-(3,4-dichlorobenzyl)morpholin-2-yl]methyl}acetamide,
(2S)- {4-[(2-amino-2-oxoethyl)aminocarbonyl]thiazol-2-ylthio}-N- {[4-(3,4-dichlorobenzyl)morpholin-2-yl]methyl}acetamide,
(2S)-N-{[4-(3,4-dichlorobenzyl)morpholin-2-yl]methyl}-[4-(5-methyl-1,2,4-oxadiazol-3-yl)thiazol-2-ylthio]acetamide,
(2S)-(5-amino-8H-indeno[1,2-d]thiazol-2-ylthio)-N-{[4-(3,4-dichlorobenzyl)morpholin-2-yl]methyl}acetamide,
(2S)-(4-carboxyphenylthio)-N-{[4-(3,4-dichlorobenzyl)morpholin -2-yl]methyl}acetamide,
(2S)-{4-[(2-amino-2-oxoethyl)aminocarbonyl]phenylthio}-N-{[4-(3,4-dichlorobenzyl)morpholin-2-yl]methyl}acetamide,
(2S)-{4-[(2-carboxyethyl)aminocarbonyl]thiazol-2-ylthio}-N-{[4-(3,4-dichlorobenzyl)morpholin-2-yl]methyl}acetamide,
(2S)-(5-acetamino-1,3,4-thiadiazol-2-ylthio)-N-{[4-(3,4-dichlorobenzyl)morpholin-2-yl]methyl}acetamide,
(2S)-4-(4-carbamoylthiazol-2-ylthio)-N-{[4-(3,4-dichlorobenzyl)morpholin-2-yl]methyl}butyramide,
(2S)-N-{[4-(3,4-dichlorobenzyl)morpholin-2-yl]methyl}-[4-(1H-tetrazol-5-yl)thiazol-2-ylthio]acetamide,
(2S)-N-{[4-(3,4-dichlorobenzyl)morpholin-2-yl]methyl}-([1,3]thiazolo[5,4-b]pyridin-2-ylthio)acetamide,
(2S)-(E)-[4-(2-carbamoylethen-1-yl)thiazol-2-ylthio]-N-{[4-(3,4-dichlorobenzyl)morpholin-2-yl]methyl}acetamide, 2S)-[4-(carbamoylmethyl)thiazol-2-ylthio]-N-{[4-(3,4-difluorobenzyl)morpholin-2-yl]methyl}acetamide,
(2S)-[4-(carbamoylmethyl)thiazol-2-ylthio]-N-{[4-(4-fluorobenzyl)morpholin-2-yl]methyl}acetamide,
(2S)-(4-carboxy-5-methylthiazol-2-ylthio)-N-{[4-(3,4-dichlorobenzyl)morpholin-2-yl]methyl}acetamide,
(2S)-(4-carbamoyl-5-methylthiazol-2-ylthio)-N-{[4-(3,4-dichlorobenzyl)morpholin-2-yl]methyl}acetamide,
(2S)-(4-carbamoylthiazol-2-ylthio)-N-{[4-(3-chloro-4-fluorobenzyl)morpholin-2-yl]methyl}acetamide,
(2S)-[4-(2-amino-2-oxoethyl)aminocarbonylthiazol-2-ylthio]-N-{[4-(3,4-difluorobenzyl)morpholin-2-yl]methyl}acetamide,
(2S)-(5-amino-1,3,4-thiadiazol-2-ylthio)-N-{[4-(3-chlorobenzyl)morpholin-2-yl]methyl}acetamide,
(2S)-(5-amino-1,3,4-thiadiazol-2-ylthio)-N-{[4-(3,4-difluorobenzyl)morpholin-2-yl]methyl}acetamide,
(2S)-N-{[4-(3,4-dichlorobenzyl)morpholin-2-yl]methyl}-(pyrimidin-2-ylthio)acetamide,
(2S)-(3-acetyl-2-oxo-2H-chromen-6-ylthio)-N-{[4-(3,4-dichlorobenzyl)morpholin-2-yl]methyl}acetamide,
(2S)-N-{[4-(3,4-difluorobenzyl)morpholin-2-yl]methyl}-(6-oxo-1,6-dihydropyridazin-3-ylthio)acetamide,
(2S)-[6-(carbamoylmethyl)pyrazin-2-ylthio]-N-{[4-(3,4-dichlorobenzyl)morpholin-2-yl]methyl}acetamide, and
(2S)-4-(cyclopentanesulfonyl)-N-{[4-(3-chloro-4-fluorobenzyl)morpholin-2-yl]methyl}butyramide, or a pharmaceutically acceptable salt thereof.

16. A CCR3 antagonist comprising, as an active ingredient, the compound of claim 1, or a pharmaceutically acceptable salt thereof.

17. A pharmaceutical composition comprising the compound of claim 1, or a pharmaceutically acceptable salt thereof, and a pharmaceutically acceptable carrier.

18. The pharmaceutical composition of claim 17, which is an agent for the treatment of asthma, sinusitis, allergic rhinitis, atopic dermatitis, allergic conjunctivitis, allergic myelitis, ulcerative colitis, Crohn's disease or rheumatoid arthritis.

19. A method for the treatment of a disease selected from the group consisting of asthma, sinusitis, allergic rhinitis, atopic dermatitis, allergic conjunctivitis, allergic myelitis, ulcerative colitis, Crohn's disease and rheumatoid arthritis, which comprises administering an effective amount of the compound of claim 1, or a pharmaceutically acceptable salt thereof to an animal having the disease.

20. A production method of a compound represented by the formula (1)

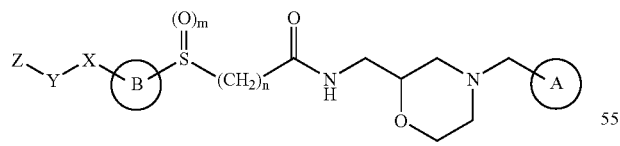

(1)

wherein
ring A is aryl having substituent(s), or heteroaryl optionally having substituent(s),
ring B is arylene optionally having substituent(s), divalent heterocyclic group optionally having substituent(s), or $C_{3-8}$ cycloalkylene optionally having substituent(s),
m is an integer of 0 to 2,
n is an integer of 1 to 5,
X is a bond, —NH—, —NR$^1$— wherein R$^1$ is $C_{1-6}$ alkyl optionally having substituent(s), —CO—, —CO$_2$—, —OCO—, —CONR$^a$— wherein R$^a$ is hydrogen atom or $C_{1-6}$ alkyl optionally having substituent(s), hereinafter the same, —NR$^a$CO—, —NR$^2$CONR$^3$— wherein R$^2$ and R$^3$ may be the same or different and each is hydrogen atom or $C_{1-6}$ alkyl optionally having substituent(s),
or R$^2$ and R$^3$ in combination optionally form, together with the atoms bonded thereto, a ring optionally having substituent(s), oxygen atom, sulfur atom, —SO—, —SO$_2$—, —NR$^a$SO$_2$—, —SO$_2$NR$^a$—, $C_{1-6}$ alkylene optionally having substituent(s), $C_{2-6}$ alkenylene optionally having substituent(s), $C_{2-6}$ alkynylene optionally having substituent(s), —O—X$^a$— wherein X$^a$ is $C_{1-6}$ alkylene optionally having substituent(s), hereinafter the same, —X$^a$—O—, —CO—X$^a$—, —X$^a$—CO—, —CONR$^a$—X$^a$—, —X$^a$—CONR$^a$—, —NR$^a$CO—X$^a$—, —X$^a$—NR$^a$CO—, —S—X$^a$—, —X$^a$—S—, —SO—X$^a$—, —X$^a$—SO—, —NR$^a$—X$^a$—, —X$^a$—NR$^a$—, —SO$_2$—X$^a$—, —X$^a$—SO$_2$—, —C(=N—CO$_2$—R$^1$)—, —C(=N—SO$_2$—R$^1$)—, —C(=N—SO$_2$NH$_2$)—, —C(=CH—NO$_2$)—, —C(=N—CN)— or $C_{3-8}$ cycloalkylidene optionally having substituent(s), Y is a bond, —NH—, —NR$^4$— wherein R$^4$ is $C_{1-6}$ alkyl optionally having substituent(s), hereinafter the same, —CO—, —CO$_2$—, —OCO—, —CONR$^b$— wherein R$^b$ is hydrogen atom or $C_{1-6}$ alkyl optionally having substituent(s), hereinafter the same, —NR$^b$CO—, —NR$^5$CONR$^6$— wherein R$^5$ and R$^6$ may be the same or different and each is hydrogen atom or $C_{1-6}$ alkyl optionally having substituent(s), or R$^5$ and R$^6$ in combination optionally form, together with the atoms bonded thereto, a ring optionally having substituent(s), oxygen atom, sulfur atom, —SO—, —SO$_2$—, —NR$^b$SO$_2$—, —SO$_2$NR$^b$—, $C_{1-6}$ alkylene optionally having substituent(s), $C_{2-6}$ alkenylene optionally having substituent(s), $C_{2-6}$ alkynylene optionally having substituent(s), —O—X$^b$— wherein X$^b$ is $C_{1-6}$ alkylene optionally having substituent(s), hereinafter the same, —X$^b$—O—, —CO—X$^b$—, —X$^b$—CO—, —CONR$^b$—X$^b$—, —X$^b$—CONR$^b$—, —NR$^b$CO—X$^b$—, —X$^b$—NR$^b$CO—, —S—X$^b$—, —X$^b$—S—, —SO—X$^b$—, —X$^b$—SO—, —NR$^b$—X$^b$—, —X$^b$—NR$^b$—, —SO$_2$—X$^b$—, —X$^b$—SO$_2$—, —C(=N—CO$_2$—R$^4$)—, —C(=N—SO$_2$—R$^4$)—, —C(=N—SO$_2$NH$_2$)—, —C(=CH—NO$_2$)— or —C(=N—CN)—, and Z is hydrogen atom, halogen atom, $C_{1-6}$ alkyl optionally having substituent(s), $C_{3-8}$ cycloalkyl optionally having substituent(s), aryl optionally having substituent(s), heterocyclic group optionally having substituent(s), hydroxy, nitro, amino, cyano, $C_{1-6}$ alkoxy optionally having substituent(s), mono- or di-$C_{1-6}$ alkylamino optionally having substituent(s), $C_{1-7}$ acylamino optionally having substituent(s), sulfonylamino optionally having substituent(s), hydrazino optionally having substituent(s), guanidino optionally having substituent(s) or amidino optionally having substituent(s), or a salt thereof, which comprises reacting a compound represented by the formula (6)

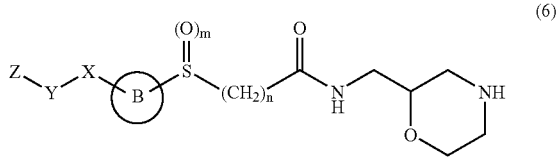
(6)

wherein each symbol is as defined above, or a salt thereof, with a compound represented by the formula (8)

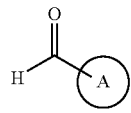
(8)

wherein ring A is as defined above, or a salt thereof.

21. (2S)-[4-(carboxymethyl)thiazol-2-ylthio]-N-{[4-(3,4-dichlorobenzyl)morpholin-2-yl]methyl}acetamide.

22. A pharmaceutical composition comprising the compound of claim 21, or a pharmaceutically acceptable salt thereof, and a pharmaceutically acceptable carrier.

23. The pharmaceutical composition of claim 22, which is an agent for the treatment of asthma, sinusitis, allergic rhinitis, atopic dermatitis, allergic conjunctivitis, allergic myelitis, ulcerative colitis, Crohn's disease or rheumatoid arthritis.

24. A method for the treatment of a disease selected from the group consisting of asthma, sinusitis, allergic rhinitis, atopic dermatitis, allergic conjunctivitis, allergic myelitis, ulcerative colitis, Crohn's disease and rheumatoid arthritis, which comprises administering an effective amount of the compound of claim 21, or a pharmaceutically acceptable salt thereof to an animal having the disease.

\* \* \* \* \*

UNITED STATES PATENT AND TRADEMARK OFFICE
CERTIFICATE OF CORRECTION

| | |
|---|---|
| PATENT NO. | : 7,935,700 B2 |
| APPLICATION NO. | : 11/662228 |
| DATED | : May 3, 2011 |
| INVENTOR(S) | : Yoshihito Tanaka et al. |

Page 1 of 1

It is certified that error appears in the above-identified patent and that said Letters Patent is hereby corrected as shown below:

Col. 174 - Claim 2, line 64, "-C(=N-CO$_2$-R$^1$-" should be changed to -- -C(=N-CO$_2$-R$^1$)- --; and
line 64 "-C(=N-SO$_2$-R$^1$-" should be changed to -- -C(=N-SO$_2$-R$^1$)- --.

Col. 176 - Claim 15, lines 45-46, "2S)-[4-(carbamoylmethyl)thiazol-2-ylthio]-N-{[4-(3,4-difluorobenzyl)morpholin-2-yl]methyl}acetamide" should be changed to -- (2S)-[4-(carbamoylmethyl)thiazol-2-ylthio]-N-{[4-(3,4-difluorobenzyl)morpholin-2-yl]methyl}acetamide --.

Signed and Sealed this
Eighteenth Day of October, 2011

David J. Kappos
*Director of the United States Patent and Trademark Office*

UNITED STATES PATENT AND TRADEMARK OFFICE
CERTIFICATE OF CORRECTION

PATENT NO. : 7,935,700 B2  
APPLICATION NO. : 11/662228  
DATED : May 3, 2011  
INVENTOR(S) : Yoshihito Tanaka et al.

Page 1 of 1

It is certified that error appears in the above-identified patent and that said Letters Patent is hereby corrected as shown below:

In the Claims:

Col. 174 - Claim 2, line 64, "-C(=N-CO$_2$-R$^1$-" should be changed to -- -C(=N-CO$_2$-R$^1$)- --; and line 64 "-C(=N-SO$_2$-R$^1$-" should be changed to -- -C(=N-SO$_2$-R$^1$)- --.

Col. 177, lines 1-2 (Claim 15, lines 45-46), "2S)-[4-(carbamoylmethyl)thiazol-2-ylthio]-N-{[4-(3,4-difluorobenzyl)morpholin-2-yl]methyl}acetamide" should be changed to -- (2S)-[4-(carbamoylmethyl)thiazol-2-ylthio]-N-{[4-(3,4-difluorobenzyl)morpholin-2-yl]methyl}acetamide --.

This certificate supersedes the Certificate of Correction issued October 18, 2011.

Signed and Sealed this  
Thirtieth Day of April, 2013

Teresa Stanek Rea  
*Acting Director of the United States Patent and Trademark Office*